US012656338B2

(12) United States Patent
Singamaneni et al.

(10) Patent No.: US 12,656,338 B2
(45) Date of Patent: Jun. 16, 2026

(54) ULTRABRIGHT FLUORESCENT NANOCONSTRUCTS AS UNIVERSAL ENHANCERS

(71) Applicant: Washington University, St. Louis, MO (US)

(72) Inventors: Srikanth Singamaneni, St. Louis, MO (US); Jingyi Luan, St. Louis, MO (US); Jeremiah J. Morrissey, St. Louis, MO (US)

(73) Assignee: Washington University, St. Louis, MO (US)

( * ) Notice: Subject to any disclaimer, the term of this patent is extended or adjusted under 35 U.S.C. 154(b) by 1441 days.

(21) Appl. No.: 17/281,480

(22) PCT Filed: Oct. 4, 2019

(86) PCT No.: PCT/US2019/054730
§ 371 (c)(1),
(2) Date: Mar. 30, 2021

(87) PCT Pub. No.: WO2020/072924
PCT Pub. Date: Apr. 9, 2020

(65) Prior Publication Data
US 2021/0396747 A1 Dec. 23, 2021

Related U.S. Application Data

(60) Provisional application No. 62/879,824, filed on Jul. 29, 2019, provisional application No. 62/741,237, filed on Oct. 4, 2018.

(51) Int. Cl.
*G01N 33/53* (2006.01)
*B82Y 15/00* (2011.01)
(Continued)

(52) U.S. Cl.
CPC .......... *G01N 33/5306* (2013.01); *B82Y 15/00* (2013.01); *G01N 21/648* (2013.01);
(Continued)

(58) Field of Classification Search
CPC ............. G01N 33/5306; G01N 21/648; G01N 33/533; G01N 33/54346; G01N 33/54373;
(Continued)

(56) References Cited

U.S. PATENT DOCUMENTS

2010/0135856 A1* 6/2010 Pyo .................. G01N 33/54346
422/69
2014/0106469 A1 4/2014 Wu et al.
(Continued)

FOREIGN PATENT DOCUMENTS

EP        1818668 A1      8/2007
JP      2011081002 A      4/2011
(Continued)

OTHER PUBLICATIONS

Luan et al. Add-on plasmonic patch as a universal fluorescence enhancer. Light Sci Appl 7, pp. 1-13. (Year: 2018).*
(Continued)

*Primary Examiner* — Shafiqul Haq
(74) *Attorney, Agent, or Firm* — Armstrong Teasdale LLP

(57) ABSTRACT

Disclosed herein is a fluorescent nanoconstruct that includes a plasmonic nanostructure having at least one localized surface plasmon resonance wavelength ($\lambda$LSPR), at least one spacer coating, at least one fluorescent agent having a maximum excitation wavelength ($\lambda$EX), and wherein the fluorescent nanoconstruct has a fluorescent intensity that is at least 500 times greater than a fluorescent intensity of the at least one fluorescent agent alone.

14 Claims, 127 Drawing Sheets

(51) Int. Cl.

| | |
|---|---|
| *G01N 21/64* | (2006.01) |
| *G01N 33/533* | (2006.01) |
| *G01N 33/543* | (2006.01) |
| *G01N 33/553* | (2006.01) |

(52) U.S. Cl.
CPC ..... *G01N 33/533* (2013.01); *G01N 33/54346* (2013.01); *G01N 33/54373* (2013.01); *G01N 33/553* (2013.01)

(58) Field of Classification Search
CPC ...... G01N 33/553; B82Y 15/00; B82Y 30/00; B82Y 5/00
See application file for complete search history.

(56) References Cited

U.S. PATENT DOCUMENTS

| | | |
|---|---|---|
| 2016/0322217 A1 | 11/2016 | Fukuda et al. |
| 2017/0084215 A1 | 3/2017 | Olson et al. |

FOREIGN PATENT DOCUMENTS

| | | |
|---|---|---|
| KR | 10-2011-0103009 A | 9/2011 |
| WO | 2007090666 A1 | 8/2007 |
| WO | 2011096394 A1 | 8/2011 |
| WO | 2013078452 A1 | 5/2013 |
| WO | 2015051465 A1 | 4/2015 |
| WO | 2015058046 A1 | 4/2015 |

OTHER PUBLICATIONS

Gandra et al. Probing Distance-Dependent Plasmon-Enhanced Near-Infrared Fluorescence Using Polyelectrolyte Multilayers as Dielectric Spacers. Angew. Chem. Int. Ed. 2014, 53, 866-870. (Year: 2014).*

Luan et al., "Ultrabright fluorescent nanoscale labels for the femtomolar detection of analytes with standard bioassays", Nature Biomedical Engineering, Oct. 2018, 17 pages.

International Search Report and Written Opinion for PCT/US2019/054730, mailed on Jan. 16, 2020, 9 pages.

Huang et al., "Core-shell plasmonic nanostructures to fine-tune long "Au nanoparticle-fluorophore" distance and radiative dynamics", Colloids and Surfaces A: Physicochem. Eng. Aspects, 2013, vol. 421, pp. 101-108.

Kawada, S., Prospects of advanced photonics, Plasmonics: new nanophotonics, academic trends, Sep. 2010, pp. 75-77.

Ribeiro et al., "Artefact-free Evaluation of Metal Enhanced Fluorescence in SIlica Coated Gold Nanoparticles", Scientific Reports, 2017, vol. 7, pp. 1-12.

* cited by examiner

FIG. 24

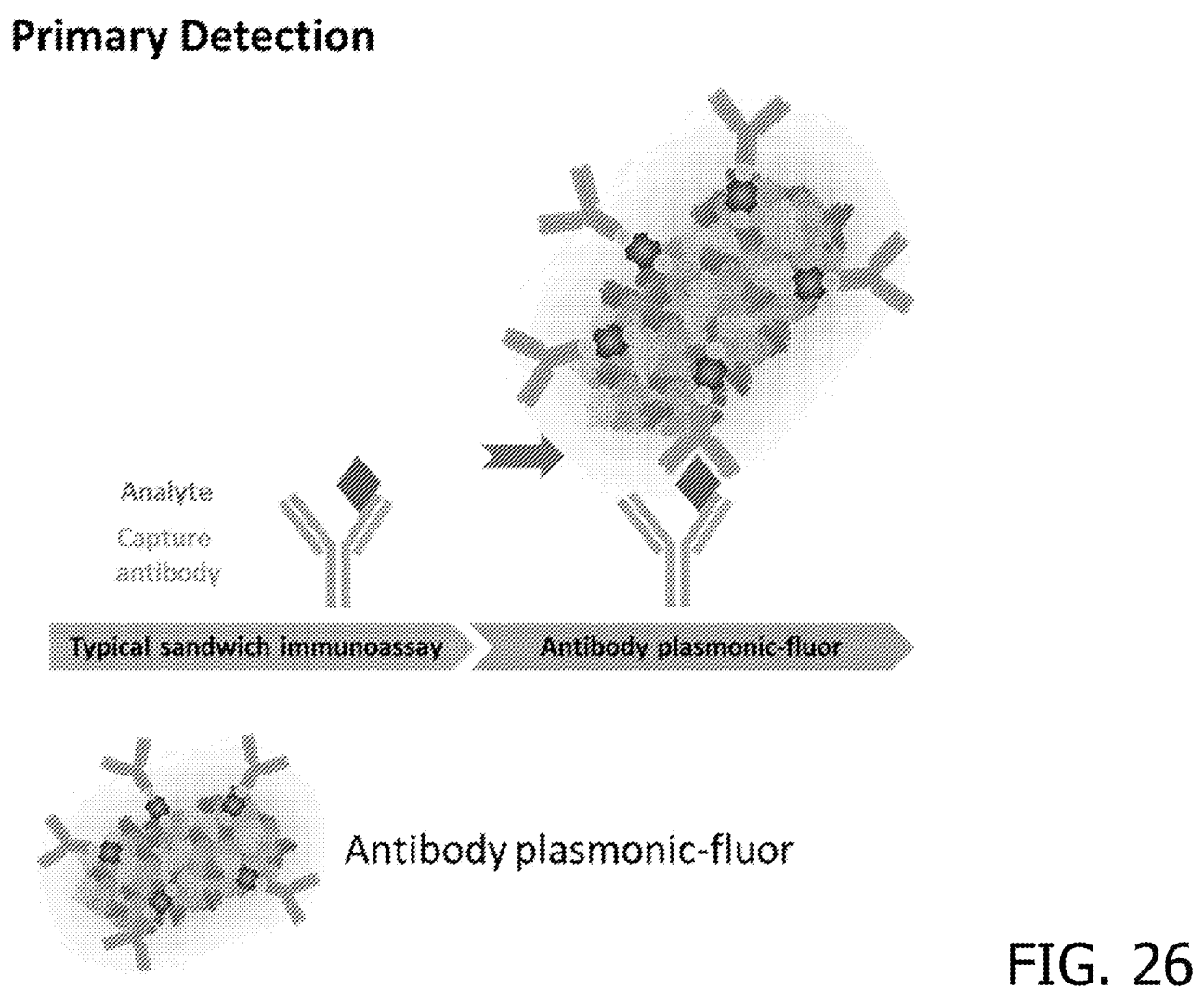

Primary Detection

Analyte
Capture antibody

Typical sandwich immunoassay

Antibody plasmonic-fluor

Antibody plasmonic-fluor

FIG. 26

| Seed Amount | AuNR Volume (nm^3) |
|---|---|
| 5 μL | 5.26E+04 |
| 10 μL | 3.78E+04 |
| 24 μL | 2.16E+04 |
| 48 μL * | 1.17E+04 |
| 96 μL | 9.64E+03 |

Human IL-6 ELISA

| | Data 1 | Data 2 | Mean | S.D. |
|---|---|---|---|---|
| 6ng/ml | 2.930 | 2.843 | 2.887 | 0.062 |
| 600pg/ml | 0.123 | 0.060 | 0.092 | 0.045 |
| 60pg/ml | 0.002 | 0.004 | 0.003 | 0.002 |
| 6pg/ml | 0.000 | 0.149 | 0.075 | 0.106 |
| 600fg/ml | 0.007 | 0.002 | 0.004 | 0.003 |
| 60fg/ml | 0.009 | 0.002 | 0.005 | 0.005 |
| 6fg/ml | 0.000 | 0.000 | 0.000 | 0.000 |
| 0 | 0.002 | 0.080 | 0.001 | 0.002 |

Human IL-6 p-ELISA

| | Data 1 | Data 2 | Mean | S.D. |
|---|---|---|---|---|
| 6ng/ml | 4060 | 4240 | 4150 | 127.28 |
| 600pg/ml | 2590 | 2780 | 2685 | 134.35 |
| 60pg/ml | 746 | 714 | 730 | 22.63 |
| 6pg/ml | 130 | 125 | 127.5 | 3.54 |
| 600fg/ml | 37.8 | 38.1 | 37.95 | 0.21 |
| 50fg/ml | 29.5 | 27.2 | 28.35 | 1.63 |
| 6fg/ml | 18.6 | 18.9 | 18.75 | 0.21 |
| 0 | 16.3 | 16.8 | 16.55 | 0.35 |

Human IL-6 ELISA

| | Data 1 | Data 2 | Mean | S.D. |
|---|---|---|---|---|
| 6ng/ml | 3.382 | 3.318 | 3.350 | 0.046 |
| 500pg/ml | 2.508 | 2.458 | 2.483 | 0.035 |
| 60pg/ml | 0.560 | 0.576 | 0.568 | 0.011 |
| 6pg/ml | 0.105 | 0.101 | 0.103 | 0.002 |
| 600fg/ml | 0.048 | 0.048 | 0.048 | 0.000 |
| 60fg/ml | 0.042 | 0.043 | 0.042 | 0.001 |
| 6fg/ml | 0.042 | 0.047 | 0.044 | 0.003 |
| 0 | 0.051 | 0.041 | 0.045 | 0.007 |

FIG. 46

With plasmonic-fluor-Cy3

With fluor-Cy3

Plasmonic-fluor enhanced mouse IL-6 Luminex assay

|  | Data 1 | Data 2 | Mean | S.D. |
|---|---|---|---|---|
| 0 | 330 | 333 | 331.5 | 2.12 |
| 0.359pg/ml | 360 | 393 | 376.5 | 23.33 |
| 3.59pg/ml | 536 | 518 | 527 | 12.73 |
| 35.9pg/ml | 815 | 848 | 831.5 | 23.33 |
| 359pg/ml | 2081 | 2356 | 2218.5 | 194.45 |

Plasmonic-fluor enhanced mouse TNF-α Luminex assay

|  | Data 1 | Data 2 | Mean | S.D. |
|---|---|---|---|---|
| 0 | 131 | 132.5 | 131.75 | 1.06 |
| 39.5fg/ml | 153.5 | 148.5 | 151 | 3.54 |
| 395fg/ml | 288.5 | 255.5 | 272 | 23.33 |
| 3950fg/ml | 568 | 859 | 713.5 | 205.77 |
| 39500fg/ml | 1906 | 2353 | 2129.5 | 316.08 |

Mouse IL-6 Luminex assay

|  | Data 1 | Data 2 | Mean | S.D. |
|---|---|---|---|---|
| 0 | 8 | 8 | 8 | 0.00 |
| 0.359pg/ml | 8 | 9 | 8.5 | 0.71 |
| 3.59pg/ml | 8.5 | 8 | 8.25 | 0.35 |
| 35.9pg/ml | 16.5 | 18 | 17.25 | 1.06 |
| 359pg/ml | 96 | 94 | 95 | 1.41 |

Mouse TNF-α Luminex assay

|  | Data 1 | Data 2 | Mean | S.D. |
|---|---|---|---|---|
| 0 | 12 | 15 | 13.5 | 2.12 |
| 39.5fg/ml | 13 | 14 | 13.5 | 0.71 |
| 395fg/ml | 14 | 14 | 14 | 0.00 |
| 3950fg/ml | 19 | 16 | 17.5 | 2.12 |
| 39500fg/ml | 75 | 70 | 72.5 | 3.54 |

FIG. 63

| Coordinate | Analyte/Control | Coordinate | Analyte/Control |
|---|---|---|---|
| A1, A2 | Reference spots | C15, C16 | Lipocalin-2 |
| A23, A24 | Reference spots | C17, C18 | MCP-1 |
| B1, B2 | Adiponectin | C19, C20 | MMP-9 |
| B3, B4 | ANPEP | C21,C22 | Neprilysin |
| B5, B6 | Angiotensinogen | C23, C24 | PSA |
| B7, B8 | Annexin V | D1, D2 | RAGE |
| B9, B10 | β2-Microglobulin | D3, D4 | RBP4 |
| B11, B12 | Clusterin | D5, D6 | Renin |
| B13, B14 | CXCL16 | D7, D8 | Resistin |
| B15, B16 | Cyr61 | D9, D10 | SCF |
| B17, B18 | Cystatin C | D11, D12 | Serpin A3 |
| B19, B20 | DPPIV | D13, D14 | TNF-α |
| B21,B22 | EGF | D15, D16 | TNF RI |
| B23, B24 | EGF R | D17, D18 | TFF3 |
| C1, C2 | FABP1 | D19, D20 | Thrombospondin-1 |
| C3, C4 | Fetuin A | D21, D22 | TWEAK |
| C5, C6 | GROα | D23, D24 | uPA |
| C7, C8 | IL-1ra | E1, E2 | VCAM-1 |
| C9, C10 | IL-6 | E3, E4 | VEGF |
| C11, C12 | IL-10 | F1, F2 | Reference Spots |
| C13, C14 | TIM-1 | F23, F24 | PBS (Negative Control) |

FIG. 67B

| | With fluor | | | |
|---|---|---|---|---|
| | Data 1 | Data 2 | Mean | S.D. |
| Adiponectin | 200 | 30 | 115 | 120.21 |
| ANPEP | 146 | 44 | 95 | 72.12 |
| Angiotensinogen | 134 | 240 | 187 | 74.95 |
| Annexin V | 46 | -4 | 21 | 35.36 |
| β2-Microglobulin | 2000 | 2030 | 2015 | 21.21 |
| Clusterin | -28 | -30 | -29 | 1.41 |
| CXCL16 | -24 | -22 | -23 | 1.41 |
| Cyr61 | -28 | -12 | -20 | 11.31 |
| Cystatin C | 268 | 262 | 265 | 4.24 |
| DPPIV | -38 | 144 | 53 | 128.69 |
| EGF | 584 | 602 | 593 | 12.73 |
| EGF R | 28 | 52 | 40 | 16.97 |
| FABP1 | 124 | 168 | 146 | 31.11 |
| fetuin A | 1290 | 1360 | 1325 | 49.50 |
| G80a | 130 | 10 | 70 | 84.85 |
| IL-1ra | 34 | -18 | 8 | 36.77 |
| IL-6 | -20 | -26 | -23 | 4.24 |
| IL-10 | -24 | -32 | -28 | 5.66 |
| TIM-1 | 16 | -2 | 7 | 12.73 |
| Lipocalin-2 | 152 | 150 | 151 | 1.41 |
| MCP-1 | -12 | -18 | -15 | 4.24 |
| MMP-9 | -28 | -30 | -29 | 1.41 |
| Neprilysin | -16 | -10 | -13 | 4.24 |
| PSA | 260 | 250 | 255 | 7.07 |
| RAGE | 258 | 290 | 274 | 22.63 |
| RBP4 | 478 | 554 | 516 | 53.74 |
| Renin | -16 | 100 | 42 | 82.02 |
| Resistin | 150 | 114 | 132 | 25.46 |
| SCF | -24 | -12 | -18 | 8.49 |
| Serpin A3 | 316 | 340 | 328 | 16.97 |
| TNF-α | -22 | -24 | -23 | 1.41 |
| TNF RI | 272 | 306 | 289 | 24.04 |
| TFF3 | 969 | 998 | 983.5 | 20.51 |
| Thrombospondin-1 | -32 | -52 | -42 | 14.14 |
| TWEAK | -16 | -30 | -23 | 9.90 |
| uPA | 42 | 38 | 40 | 2.83 |
| VCAM-1 | 667 | 677 | 672 | 7.07 |
| VEGF | 62 | 153 | 107 | 63.64 |

FIG. 73

| | With plasmonic-fluor | | | |
|---|---|---|---|---|
| | Data 1 | Data 2 | Mean | S.D. |
| Adiponectin | 55500 | 57800 | 56650 | 1626.35 |
| ANPEP | 55300 | 54100 | 54700 | 848.53 |
| Angiotensinogen | 46100 | 44400 | 45250 | 1202.08 |
| Annexin V | 29000 | 28000 | 28500 | 707.11 |
| β2-Microglobulin | 117000 | 110000 | 113500 | 4949.75 |
| Clusterin | 25500 | 24800 | 25150 | 494.97 |
| CXCL16 | 25300 | 25200 | 25250 | 70.71 |
| Cyr61 | 27700 | 26300 | 27000 | 989.95 |
| Cystatin C | 73900 | 73200 | 73550 | 494.97 |
| DPPIV | 10600 | 9550 | 10075 | 742.46 |
| EGF | 85700 | 91200 | 88450 | 3889.08 |
| EGF R | 25800 | 26600 | 26200 | 565.69 |
| FABP1 | 35600 | 38400 | 37000 | 1979.90 |
| Fetuin A | 141000 | 136000 | 138500 | 3535.53 |
| GROα | 29800 | 27800 | 28800 | 1414.21 |
| IL-1ra | 26100 | 26300 | 26250 | 70.71 |
| IL-6 | 24200 | 24500 | 24350 | 212.13 |
| IL-10 | 22100 | 21300 | 21700 | 565.69 |
| TIM-1 | 27100 | 28400 | 27750 | 919.24 |
| Lipocalin-2 | 72700 | 73300 | 73000 | 424.26 |
| MCP-1 | 28100 | 24500 | 26300 | 2545.58 |
| MMP-9 | 26500 | 23600 | 25050 | 2050.61 |
| Neprilysin | 20500 | 20700 | 20600 | 141.42 |
| PSA | 58200 | 65900 | 63050 | 5444.73 |
| RAGE | 75800 | 73700 | 74750 | 1484.92 |
| RBP4 | 105000 | 106000 | 105500 | 707.11 |
| Renin | 19600 | 19800 | 19700 | 141.42 |
| Resistin | 47400 | 49700 | 48550 | 1626.35 |
| SCF | 23300 | 22500 | 22900 | 565.69 |
| Serpin A3 | 78500 | 77500 | 78000 | 707.11 |
| TNF-α | 14000 | 16100 | 15050 | 1484.92 |
| TNF RI | 74600 | 80300 | 77450 | 4030.51 |
| TFF3 | 110000 | 104000 | 107000 | 4242.64 |
| Thrombospondin- | 11400 | 9070 | 10235 | 1647.56 |
| TWEAK | 9090 | 8830 | 8960 | 183.85 |
| uPA | 30300 | 31600 | 30950 | 919.24 |
| VCAM-1 | 121000 | 120000 | 120500 | 707.11 |
| VEGF | 43700 | 39600 | 41650 | 2899.14 |

With plasmonic-fluor-800CW

With fluor-800CW

10 µm

Mouse IL-12 ELISA

| | Abs. 1 | Abs. 2 | Conc. 1 | Conc. 2 | Mean | S.D. |
|---|---|---|---|---|---|---|
| Blank | 0.47 | 0.44 | 5.38 | -36.75 | 0.00 | 0.00 |
| LPS 0.01 µg/ml | 0.63 | 0.63 | 207.75 | 207.13 | 207.44 | 0.44 |
| LPS 0.05 µg/ml | 0.90 | 0.94 | 549.00 | 599.63 | 574.31 | 35.80 |
| LPS 0.1 µg/ml | 1.15 | 1.10 | 853.88 | 789.00 | 821.44 | 45.87 |
| LPS 0.2 µg/ml | 1.28 | 1.24 | 1017.25 | 969.25 | 993.25 | 33.94 |
| LPS 0.5 µg/ml | 1.26 | 1.23 | 994.63 | 955.00 | 974.81 | 28.02 |

Mouse TNF-α ELISA

| | Abs. 1 | Abs. 2 | Conc. 1 | Conc. 2 | Mean | S.D. |
|---|---|---|---|---|---|---|
| Blank | 0.07 | 0.07 | -40.50 | -27.50 | 0.00 | 0.00 |
| LPS 0.01 µg/ml | 0.07 | 0.08 | -10.00 | -0.50 | 0.00 | 0.00 |
| LPS 0.05 µg/ml | 0.16 | 0.15 | 438.00 | 360.50 | 399.25 | 54.80 |
| LPS 0.1 µg/ml | 0.27 | 0.30 | 953.00 | 1119.00 | 1036.00 | 117.38 |
| LPS 0.2 µg/ml | 0.40 | 0.39 | 1624.50 | 1571.50 | 1598.00 | 37.48 |
| LPS 0.5 µg/ml | 0.41 | 0.40 | 1690.00 | 1631.50 | 1660.75 | 41.37 |

ULTRABRIGHT FLUORESCENT NANOCONSTRUCTS AS UNIVERSAL ENHANCERS

CROSS-REFERENCE TO RELATED APPLICATIONS

This application is a US National Stage Entry of International Patent Application No. PCT/US2019/054730, filed Oct. 4, 2019, which claims the benefit of priority to U.S. Provisional Application No. 62/741,237, filed Oct. 4, 2018, and U.S. Provisional Application No. 62/879,824, filed Jul. 29, 2019, the entire contents of which are incorporated herein by reference in their entireties.

FEDERAL SUPPORT

This invention was made with government support under CBET1254399, awarded by the National Science Foundation and CA141521, awarded by the National Institutes of Health. The government has certain rights in the invention.

BACKGROUND OF THE DISCLOSURE

The field of the disclosure relates generally to ultrabright fluorescent nanoconstructs, plasmonic-fluors (PF), which can be used to enhance biological assays. Specifically, it relates to the use of a novel combination of a plasmonic nanostructure, spacer layer, and fluorophores which results in a nanoconstruct which is spectrally similar to the fluorophores but which is at least 500 fold brighter than the individual fluorophores alone. These ultrabright fluorescent nanoconstructs can be conjugated to at least one biorecognition element and used to enhance the performance of and improve the limits of detection of various biological assays and processes.

Relevant concentrations of biomolecules or biomarkers related to diseases such as cancer, heart disease, inflammation, and neurological disorders can range in many orders of magnitude from μg/ml levels to sub-fg/ml, some of which possibly still remain unidentified due to the lack of sensitive bioanalytical tools. It is also highly desirable to utilize small sample volume for multiplexed detection within precious biofluids such as breath condensates, ocular fluids, cerebrospinal fluid, or serum from neonates or small animal models, which necessitates sample dilutions, further lowering the concentration. As the cornerstone of biomedical science and clinical research, fluorescence-based bioanalytical methods are widely employed in the detection, quantification and imaging of a broad range of bioanalytes. Several methods, such as enhancing antibody affinity, reducing the background fluorescence, promoting mass transfer, and increasing the substrate surface area, have been explored to improve the sensitivity of fluoroimmunoassays. However, weak fluorescence signal and the associated poor signal-to-noise ratio of the fluorescence label remains a challenge, limiting the ultimate sensitivity of current fluorescence-based assays.

Most previous plasmon-enhanced fluorescence assays rely on engineering the substrate to be plasmonically active through either deposition of metal islands or adsorption of plasmonic nanostructures. These methods naturally require the utilization of special surfaces and possibly significant alterations of the read-out devices and the bioassay protocol. As such, they are not readily applied to a large variety of systems or bioassays.

Some plasmon enhanced fluorescence assays have tried to employ particles in the solution phase, but these particles have been plagued by issues of instability, high non-specific binding causing unacceptable background signals, and, most importantly, poor fluorescence enhancement. The degree of fluorescence enhancement has typically been less than 10-fold.

Fluorescence probes and fluorometric approaches have been employed in biomedical research, not only as imaging tools to visualize the location and dynamics of cells and various sub-cellular species and molecular interactions in cells and tissues, but also as labels in fluoroimmunoassays for detection and quantification of molecular biomarkers. Fluorescence-based techniques have radically transformed biology and life sciences by unravelling the genomic, transcriptomic, and proteomic signatures of disease development, progression, and response to therapy. However, "feeble signal" has been a persistent and recurring problem in a battery of detection and imaging techniques that rely on fluorescence. Overcoming this fundamental challenge without the use of specialized reagents, equipment, or significant modifications to well-established procedures has been the subject of extensive research in the field of biomedical optics. For example, there is an urgent need for ultrasensitive fluoroimmunoassays that can be broadly adopted by most biological and clinical laboratories for the detection of target biological species of low abundance.

While fluorescence provides a number of benefits (including multiplexing, high dynamic range, broad platform applicability (i.e. can be used in cells, on cells, tissues, plates, beads, solution, etc.)) over assay detection schemes such as colorimetric ELISA or chemiluminescence, fluorescence is fundamentally limited by poor signal. In plate-based assays, complicated schemes are employed like poly-HRP, PCR-ELISA, avidin-biotin-complex (ABC) ELISA, and tyramide signal amplification (TSA) to achieve improved fluorescence detection sensitivity. All of these are more complicated, more expensive, and generally have poorer dynamic range than the version of the assay they replace. For very high detection sensitivities, complicated technologies such as digital ELISA (Quanterix Simoa System) or electrochemiluminescence (Meso Scale Discovery) each require specialized substrates, equipment, and workflows.

Generally, if an assay uses an antibody or streptavidin labeled with HRP which catalyzes a reaction which converts a substrate to either a luminescent species (as in chemiluminescence) or a species which absorbs light at a certain wavelength (as in ELISA), this assay's performance can be improved by using an antibody or streptavidin-conjugated plasmonic fluor. Examples of such assays are ELISA (colorimetric and chemiluminescent) and membrane-based immunoassays such as Western blot (colorimetric and chemiluminescent).

Improving the signal-to-noise ratio of the assays without radically deviating from existing assay protocols will also relax the stringent requirements of high sensitivity and bulky photodetectors, drive down the cost of implementation, eliminate cross-laboratory, cross-platform inconsistency, and potentially propel these technologies to point-of-care, in-field and resource-limited settings. Various techniques, including multiple-fluorophore labels, rolling cycle amplification, and photonic crystal enhancement have been introduced to improve the signal-to-noise ratio of fluorescence-based imaging and sensing techniques. Despite the improved sensitivity, these technologies are not widely adopted in research and clinical settings. Most of these technologies require significant modifications to the existing practices such as additional steps that significantly prolong the overall operation time, specialized and expensive readout systems, non-traditional data processing and analysis, or temperature-sensitive reagents which require tightly-controlled transport and storage conditions.

Enhancement in the emission of fluorophores in close vicinity to plasmonic nanostructures is attributed to the enhanced electromagnetic field (local excitation field) at the surface of the plasmonic nanostructures and a decrease in the fluorescence lifetime due to the coupling between excited fluorophores and surface plasmons of the nanostructures. So far, various plasmonic substrates such as metal nano-islands have been shown to result in moderate fluorescence enhancement, but these plasmonically active surfaces require the use of pre-fabricated substrates, typically a glass slide deposited with metal nanostructures, instead of standard or, sometimes, irreplaceable bioanalytical and bioimaging platforms. The requirement of special substrates limits cross-platform and cross-laboratory consistency and seamless integration with widely employed bioanalytical procedures, which largely limits their extensive application in biomedical research and clinical settings. Non-traditional bioconjugation procedures and poor stability of biomolecules (e.g., antibodies) immobilized on metal surfaces impose further challenges in their widespread application. Solution-phase plasmon-enhanced fluorescence solutions have been limited by generally poor fluorescence enhancement and unstable particles.

Multiplexed microarrays based on fluorescence are employed in expression profiling, drug-target binding assays, and high throughput proteomics. Compared to single platform such as enzyme-linked immunosorbent assay (ELISA), this technique allows researchers and clinicians to examine a large number of biomarkers in parallel to achieve patient stratification and monitoring of multifactorial diseases with limited sample volume, thereby minimizing the assay cost and time to perform multiple individual biomarker assays. Moreover, high throughput profiling of biomarkers enables personalized medicine with holistic, molecular fingerprinting of diseases, accommodating greater diagnostic resolution between closely related disease phenotypes. The sensitivity and specificity for diagnosis of kidney disease, for example, has been proven to be significantly greater by combining the urinary levels of multiple biomarkers than an individual one. However, despite the availability of various commercialized products, this multiplexed methodology suffers from inferior sensitivity and relatively high limit of detection (LOD) compared to ELISA, which hinders its widespread application.

One approach to address the low sensitivity of various fluorescent assays is disclosed in U.S. Provisional Application 62/590,877 titled "Plasmonic Film as a Universal Fluorescent Enhancer" filed on Nov. 27, 2017, which is herein incorporated by reference in its entirety. In this approach, plasmonic nanostructures are deposited on a polymer film that is then placed, plasmonic structures facing down, across the top of a plate or assay to which fluorophores have already been applied. By placing the film in this orientation, the proximity of the plasmonic nanostructures to the fluorophores provides for excellent fluorescent enhancement and greatly increases the sensitivity of the assays. While extremely useful, some assay techniques are not compatible with this method (e.g., if the assay is not performed on a flat, rigid surface such as a microplate or glass slide). Thus, there is a need to develop a method that addresses each of these disadvantages while simultaneously being compatible with an even larger array of assay techniques.

BRIEF DESCRIPTION OF THE DISCLOSURE

In one aspect, disclosed herein is a fluorescent nanoconstruct. The nanoconstruct generally comprises a plasmonic nanostructure having at least one localized surface plasmon resonance wavelength ($\lambda$LSPR), at least one spacer coating, and at least one fluorescent agent having a maximum excitation wavelength ($\lambda$EX). The fluorescent nanoconstruct has a fluorescent intensity that is at least 500 times greater than a fluorescent intensity of the at least one fluorescent agent alone.

In another aspect, disclosed herein is a method for constructing a fluorescent nanoconstruct. The method generally comprises coating a plasmonic nanostructure with at least one spacer coating; optionally coating the at least one spacer coating with a functional layer; conjugating a fluorescent agent to one of the at least one spacer coating or the functional layer; and, optionally conjugating a biorecognition element to one of the at least one spacer coating or the functional layer.

In yet another aspect, disclosed herein is a method for detecting an analyte using an assay. The method generally comprises adding a fluorescent nanoconstruct to the assay to produce a fluorescent signal; and, detecting the analyte by analyzing the fluorescent signal.

BRIEF DESCRIPTION OF THE DRAWINGS

FIG. 24 is an exemplary embodiment of enhancement of a generic, sandwich immunoassay using a streptavidin-conjugated plasmonic-fluor in accordance with the present disclosure.

FIG. 26 is an exemplary embodiment of a generic, sandwich immunoassay using a primary antibody-conjugated plasmonic-fluor where the antibody conjugated to the plasmonic-fluor recognizes the analyte in accordance with the present disclosure.

FIG. 42 left-side plot shows the stability of plasmonic-fluor suspension stored at 4° C. and reconstituted from lyophilized powder. Error bar represents s.d. (n=6 repeated tests). NS: not significant. P value>0.9999 by one-way ANOVA with Tukey's post test. FIG. 42** also shows photographs depicting the lyophilized powder of plasmonic-fluor before and after reconstitution.

FIG. 46 is an exemplary embodiment of individual data points, mean value, and standard deviation from human IL-6 FLISA, p-FLISA, and ELISA in accordance with the present disclosure.

FIG. 59(A-D) is an exemplary embodiment of images of the Luminex microbeads after being stained with plasmonic-fluor-Cy3 in accordance with the present disclosure.

FIG. 63 is an exemplary embodiment of individual data points, mean value, and standard deviation from mouse IL-6 Luminex, plasmonic-fluor-Cy3 enhanced mouse IL-6 Luminex, mouse TNF-α Luminex, and plasmonic-fluor-Cy3 enhanced mouse TNF-α Luminex assays in accordance with the present disclosure.

FIG. 73 is an exemplary embodiment of individual data points, mean value, and standard deviation with plasmonic-fluor in accordance with the present disclosure.

FIG. 74 is an exemplary embodiment of individual data points, mean value, and standard deviation without plasmonic-fluor in accordance with the present disclosure.

FIG. 79B is an exemplary embodiment of an SEM image of conventional fluor labeled SK-BR-3 cell in accordance with the present disclosure. FIG. 79C is an exemplary embodiment of an SEM image of plasmonic-fluor-800CW labeled SK-BR-3 cell, with inset showing the uniformly distributed plasmonic-fluors on the cell membrane, in accordance with the present disclosure.

FIG. 99 is an exemplary embodiment of individual data points (absorbance and concentration), mean concentration, and standard deviation of ELISA results corresponding to the secreted inflammatory cytokines after LPS stimulation in accordance with the present disclosure.

FIG. 100(A-C) is an exemplary embodiment of plots showing the IL-6 dose-dependent fluorescence intensity from p-FLISA in accordance with the present disclosure.

FIG. 102(A-B) is an exemplary embodiment of bead-based mouse IL-6 standard curves obtained after applying plasmonic-fluor-Cy3 in accordance with the present disclosure.

FIG. 108A is another exemplary embodiment of fluorescence intensity distribution corresponding to naïve (control) and LPS-stimulated BMDCs obtained using conventional fluors (680LT) in accordance with the present disclosure. FIG. 108B is another exemplary embodiment of fluorescence intensity distribution corresponding to naïve (control) and LPS-stimulated BMDCs obtained using plasmonic-fluor-680LT in accordance with the present disclosure.

FIG. 109A is yet another exemplary embodiment of fluorescence intensity distribution corresponding to naïve (control) and LPS-stimulated BMDCs obtained using conventional fluors (680LT) in accordance with the present disclosure. FIG. 109B is yet another exemplary embodiment of fluorescence intensity distribution corresponding to naïve (control) and LPS-stimulated BMDCs obtained using plasmonic-fluor-680LT in accordance with the present disclosure.

DETAILED DESCRIPTION OF THE DISCLOSURE

The present disclosure is based, at least in part, on the discovery that fluorescent plasmonic nanostructures can be tuned to match the wavelength of the conjugated fluorophore to result in at least a 500-fold enhancement in fluorescence intensity.

The present disclosure is directed to ultrabright fluorescent nanoconstructs specifically designed to be used in biological detection and quantitation of target analytes. As an example of the immense power, the plasmonic-fluor conjugated to a standard targeting agent (e.g. streptavidin) is at least 500-fold brighter than the same standard targeting agent coupled to commonly used fluorescent molecule in a microplate-based fluorescence-linked immunosorbent assay. This leads to extreme improvements in the performance of the assays both from the sensitivity (lower limit of detection improvements of more than an order of magnitude) and the dynamic range.

Design Advantages of the Present Disclosure

Advantages of the design disclosed herein over previous versions include, but are not limited to: (1) plasmonic-fluors are solution phase which are much more useful than substrates decorated with plasmonic species; (2) straightforward, wet chemistry synthesis—compared to things like alloyed Cu—Ag NPs, lithography created structures, or vapor deposition, or layer-by-layer synthesis; (3) particle uniformity/stability/synthesis control is high which is crucial for immunoassays: (a) aggregation is a huge issue with nanoparticles in general and can cause serious artifacts; (b) additionally, high non-specific background is a recognized issue; (4) the spacer between the fluorophore and the plasmonic nanostructure core using MTPMS/APTMS/TMPS can be tightly controlled to achieve precise thicknesses on the nanometer scale and can be applied in solution; (5) the silane-based spacer layer is easily functionalized; (6) improvement of assay performance is higher than previous methodologies; (7) enhancement of fluorescence per dye molecule (on average) is higher than previously reported for arrangements which are suitable for immunoassay applications; and, (8) the larger particles used in the present disclosure can be loaded with more dye molecules than other designs—more dyes plus enhancement of all conjugated dyes equals super-bright construct.

In accordance with the present disclosure, the plasmonic enhancement improves the conjugated dye's quantum yield (which is a key factor in a dye's resulting "brightness") and decreases its fluorescence lifetime. Thus, it is possible to achieve higher enhancement factors (relative brightness increase) with a dye that has a low quantum yield and/or a long fluorescence lifetime than with a dye that already has a high quantum yield and short fluorescence lifetime.

Figure 1:
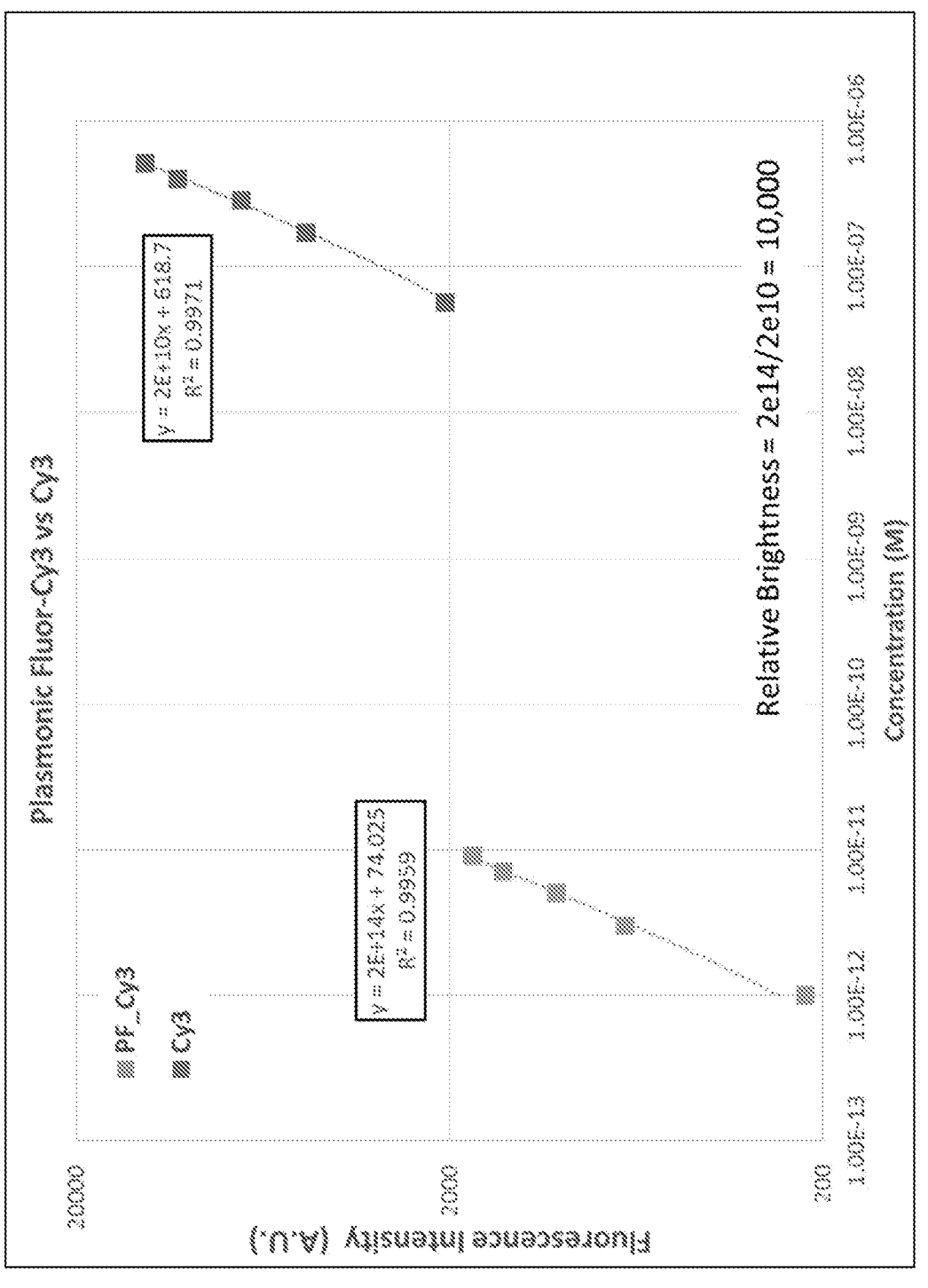
FIG. 1 is an exemplary embodiment of fluorescence intensity of conventional Cy3 and plasmonic-fluor-Cy3 at their different molar concentrations in accordance with the present disclosure.
Figure 2:
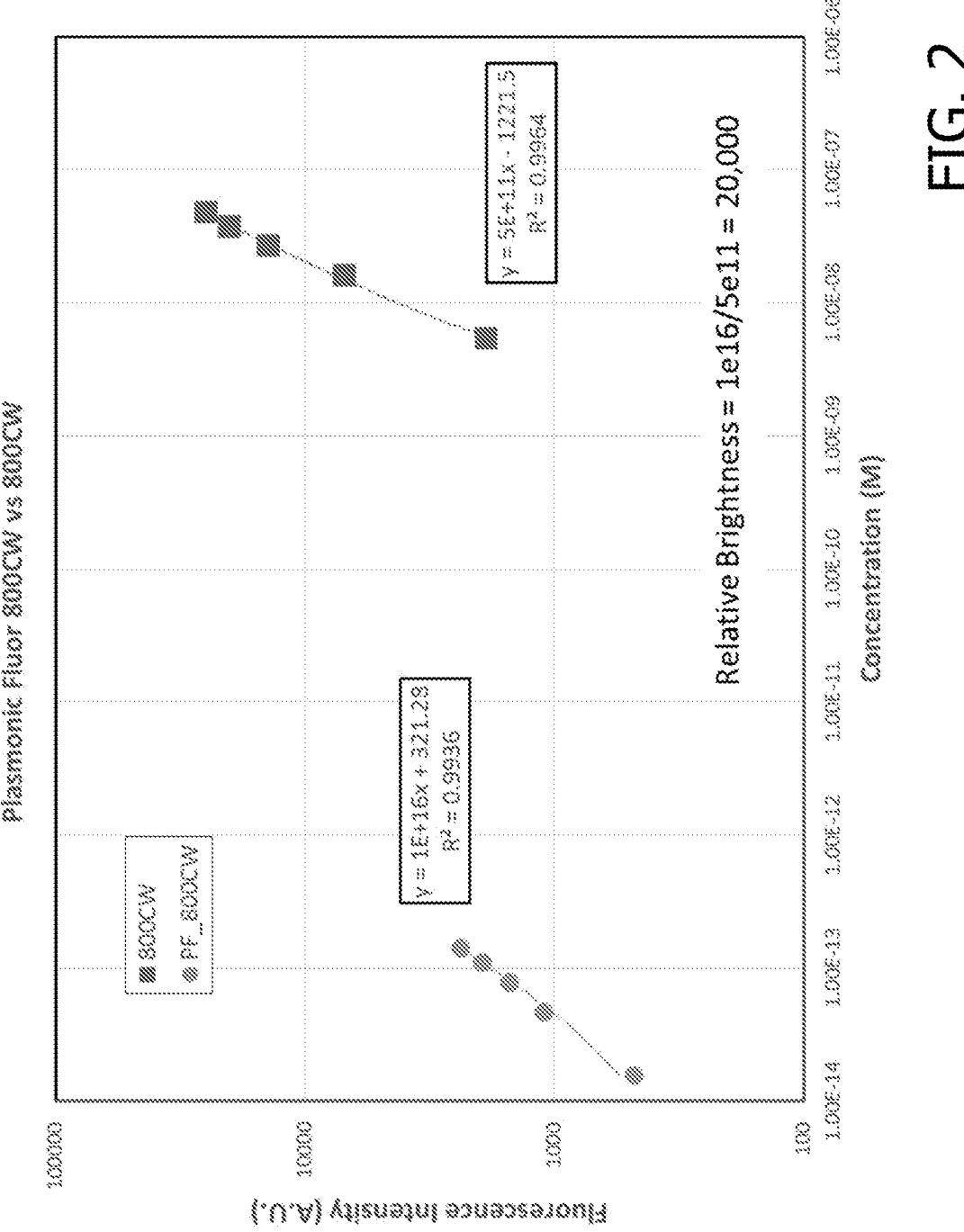
FIG. 2 is an exemplary embodiment of fluorescence intensity of conventional fluor-800CW and plasmonic-fluor-800CW at their different molar concentrations in accordance with the present disclosure.
Figure 3:
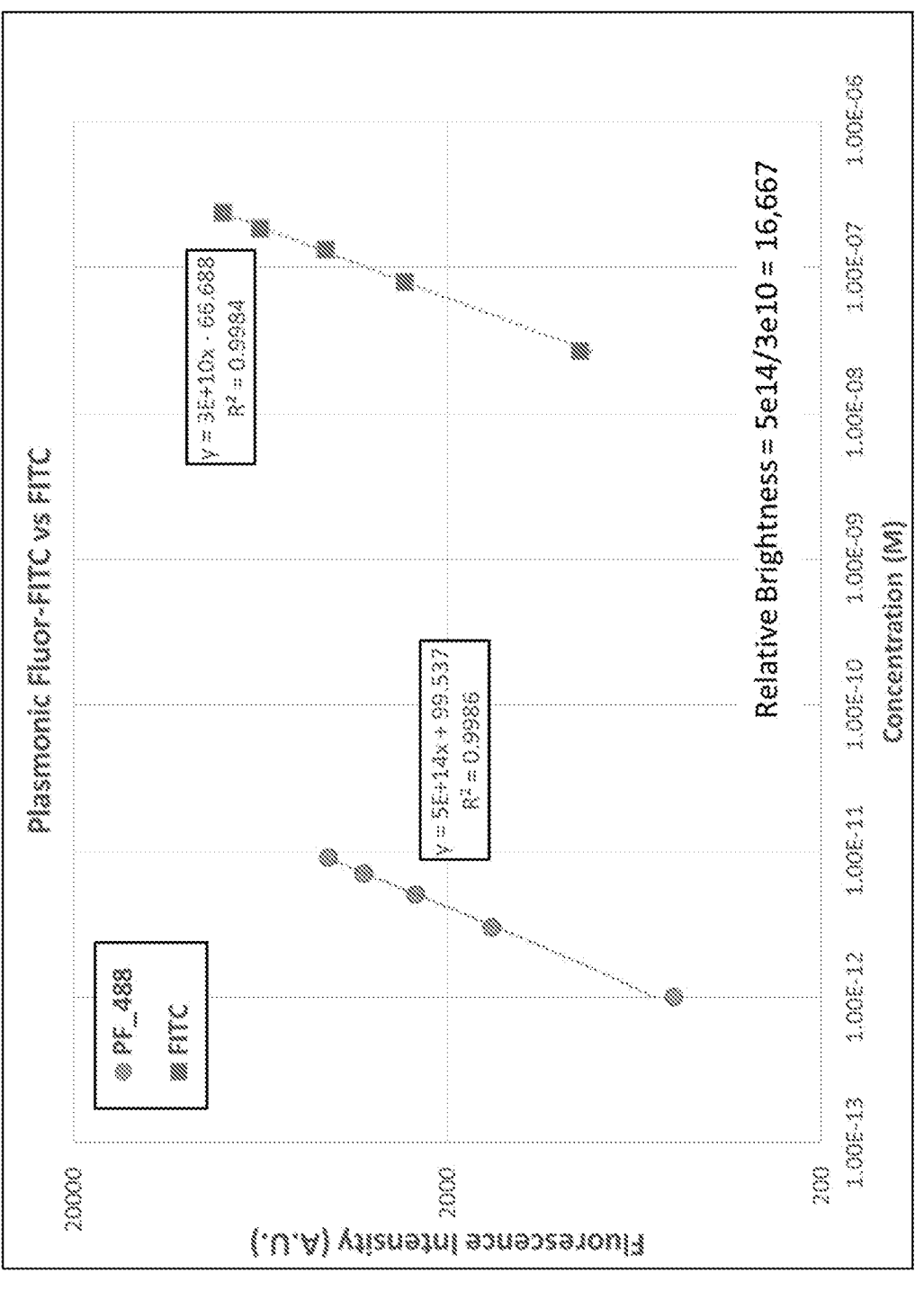
FIG. 3 is an exemplary embodiment of fluorescence intensity of conventional FITC and plasmonic-fluor-FITC at their different molar concentrations in accordance with the present disclosure.

The fluorescent nanoconstruct particles disclosed herein are at least 500-fold brighter than the fluorescent species to which they are attached, when these fluorescent species are measured in free solution, not plasmonically enhanced. A brightness metric or test is used which simply compares fluorescence intensity of the plasmonic-fluor to the fluorescent species/agent alone. This brightness metric is independent of the functional layer and/or the biorecognition element used in the nanoconstruct. This test for "relative brightness" is illustrated in FIG. 1, FIG. 2, and FIG. 3, for example. In this test, the fluorescence intensity is plotted as a function of concentration of the fluorescent species, for identical excitation and detection conditions. The ratio of the slopes indicates the relative brightness of the fluorescent species. As disclosed herein below, data collected for multiple PF's at different wavelengths compares the relative brightness to its conjugated fluorophore.

In some embodiments, the nanoconstruct comprises a fluorescent agent that has a brightness that is at least about 5 times, at least about 10 times, at least about 50 times, at least about 100 times, at least about 500 times, at least about 1,000 times, at least about 2,000 times, at least about 3,000 times, at least about 4,000 times, at least about 5,000 times, at least about 6,000 times, or at least about 7,000 times brighter than a free fluorescent species of the fluorescent agent.

Features of the Present Disclosure Include:

(1) A plasmonic nanostructure that acts as a nanostructure over a wavelength range of light, with the maxima being defined by a particle's localized surface plasmon resonance (LSPR) wavelength. A plasmonic particle can have one or more LSPR wavelengths. The plasmonic particle "pulls" in light of the wavelengths corresponding to the LSPR wavelengths, effectively concentrating the light and enhancing the electromagnetic field in the near vicinity of the particle surface.

Figure 4:
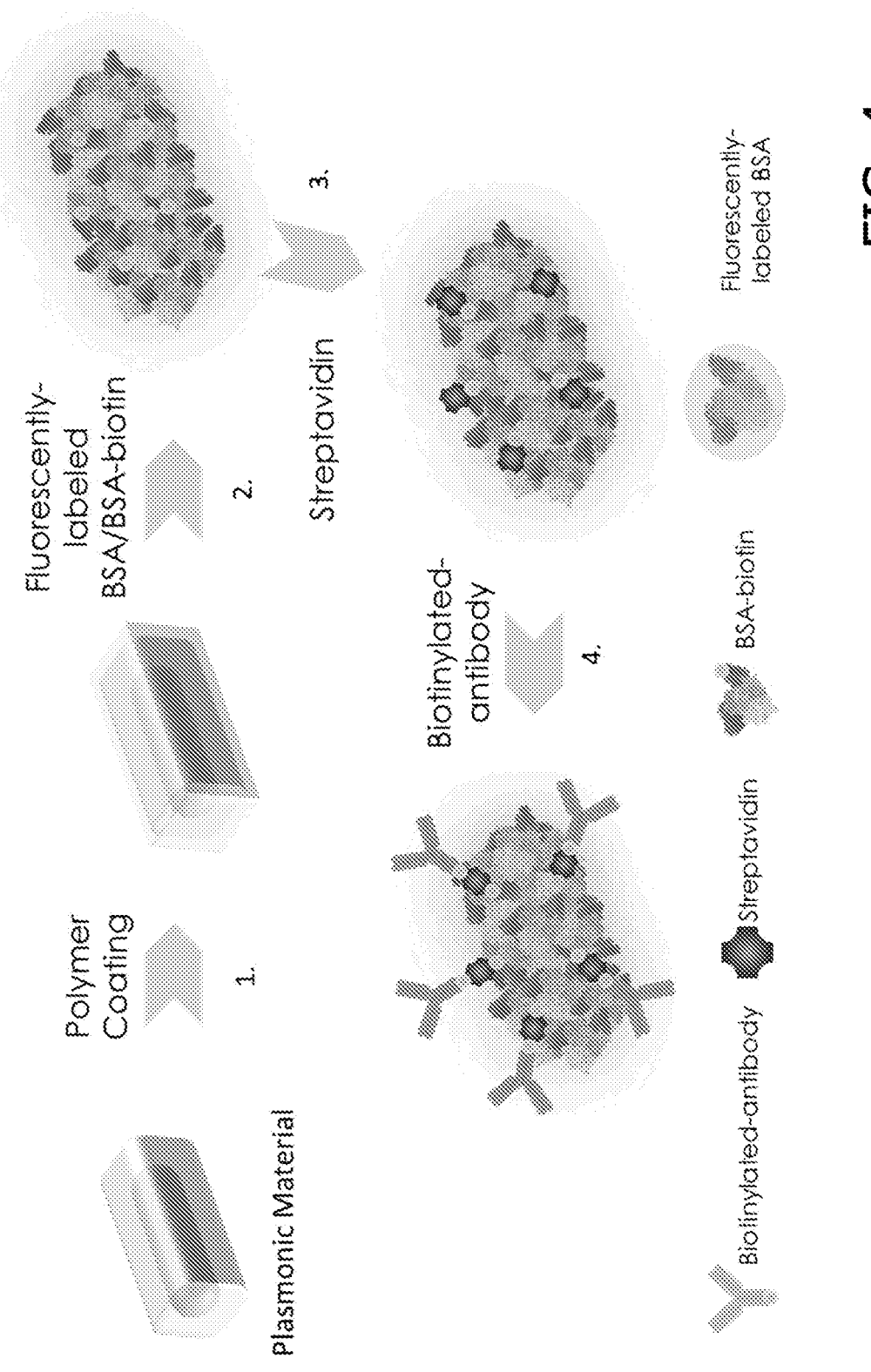
FIG. 4 is an exemplary embodiment of a design of the plasmonic-fluor in accordance with the present disclosure.

(2) A fluorescent species (such as an organic fluorophore) that is excited by a wavelength of light near at least one of the particle's LSPR wavelengths and that is maintained near the surface of the plasmonic particle such that it is in the enhanced EM field while not being close enough to undergo what is known as 'metal-induced quenching'. Optimally, the separation between the plasmonic nanostructures and fluorescent species ranges from about 2 nm to about 10 nm. In some embodiments, this separation distance is the spacer thickness. In other embodiments wherein the fluorescent species is conjugated to a functional layer, as in FIG. 4, this separation distance is the spacer thickness plus the average spacing provided by the functional layer between the fluorophore and the spacer surface.

(3) A spacer layer which provides a barrier to prevent metal-induced quenching and to which the fluorophore can be anchored (either directly or via attachment to a carrier molecule) to remain at an optimal distance from the plasmonic particle surface. The spacer material ideally contains functional groups that allow covalent conjugation of the fluorophore and/or a biorecognition element at the surface distal to the plasmonic particle surface.

(4) A functional layer which can serve several purposes: stabilization of the nanoconstruct from aggregation and non-specific binding; an attachment point for a biorecognition element; and even as a carrier for the fluorophores.

(5) A biorecognition element which allows the plasmonic-fluor to be used in specifically detecting the target of the biorecognition element (e.g. a target antigen if the biorecognition element is an antibody and aptamer; biotin if the biorecognition element is streptavidin; or an oligonucleotide if the biorecognition element is a complementary oligonucleotide).

It is presently believed that there has never been a particle with the composition and performance characteristics of the fluorescent nanoconstruct described herein. Many previous attempts at creating solution-phase, plasmonically-enhanced fluorescent nanoconstructs have achieved "brightness enhancements" on the order of approximately 10-fold.

Fluorescent Nanoconstruct

The fluorescent nanoconstruct disclosed herein overcomes the above-mentioned challenges and provides a path forward for broad application of these fluorescent nanoconstructs to immunoassays and other bioassays. As used herein, the term "fluorescent nanoconstruct" also refers to a plasmonic-fluor (PF). In one example, with respect to the detection of biomarkers related to kidney function, the results illustrate that the fluorescent nanoconstruct significantly enhances the ability to elucidate low-level kidney function parameters (biomarkers) to provide holistic kidney disease information. Notably, the better performance of the multiplexed microarray emanates from the extremely simple addition of the nanostructures to the assay prior to detection using standard techniques. Additionally, this technique represents an inexpensive and easily implemented approach for the enhancement of fluorescence. This easily-deployable technique is seamlessly applied to a broad range of platforms in diagnostics, proteomics, and genetics to address the unmet need for brighter signal intensity.

In one aspect disclosed herein is a fluorescent nanoconstruct, the nanoconstruct generally comprises: a plasmonic nanostructure, a polymer, a biorecognition element, and a fluorescent agent. In some embodiments, the fluorescent nanoconstruct comprises a plasmonic nanostructure having at least one localized surface plasmonic resonance wavelength ($\lambda$LSPR); at least one spacer coating; at least one fluorescent agent having a maximum excitation wavelength ($\lambda$EX); and at least one biorecognition element.

The fluorescent nanoconstruct disclosed herein is useful for enhancing the bioanalytical parameters (sensitivity, LOD, and dynamic range) of fluoroimmunoassays implemented in a microplate format, membrane format, an antibody microarray format, and bead-based formats in addition to many other formats. In some embodiments, the microplate is in the form of a standard 6-well, 12-well, 24-well, 48-well, 96-well, 384-well, or 1536-well plate. In other embodiments, the format of the immunoassay is on a glass slide, nitrocellulose or PVDF membrane, latex microbead, or other formats as are known in the art. In some aspects, the format of the assay or analysis is solution phase. In other embodiments, the assay is applied to cells or tissues. In some embodiments the fluorescent nanoconstruct results in more than a 10-fold, 50-fold, 100-fold, 200-fold, 250-fold, 500-fold, 1000-fold, or even 10,000 fold fluorescence intensity enhancement compared to a biorecognition element labeled with a fluorescent agent without plasmonic enhancement.

Most of the existing plasmon-enhanced fluorescence techniques require the fluorescence-based bioassay to be implemented on pre-fabricated plasmonic substrates, typically glass slides coated with metal nanostructures, instead of standard or sometimes irreplaceable bioanalytical platforms (e.g., 96-well plates, nitrocellulose membranes, or microbeads), which significantly limits the broad applicability of the technique. More importantly, the requirement of special substrates limits cross-platform and cross-laboratory consistency and seamless integration with widely employed bioanalytical procedures, which represents a major bottleneck of conventional plasmon-enhanced fluorescence techniques. The present disclosure developed a "non-invasive" (no change of current assays protocols) ultrabright fluorescence technology based on the plasmonic-fluors, which will be simply added to the microtiter well (or microarray, microbead, cell surface) instead of conventional fluors.

Customizable Plasmonic-Fluors (PFs) to Maximize Fluorescence Enhancement

In accordance with the present disclosure, the optical properties (e.g., LSPR wavelength of the metal nanostructure, which plays a critical role in final enhancement efficiency) of the plasmonic-fluor, are easily tailored and optimized for a given fluorescence emitter (organic dyes, quantum dots, or upconversion nanoparticles) through rational choice of the size, shape and composition of the nanostructures. This is in stark contrast to the conventional plasmonic substrates (e.g., metal nanoislands), which offer poor control of LSPR wavelength and are typically limited to sub-optimal "one-size fits all" approach.

TABLE 1

| Plasmonic-Fluor PF Architecture | | | | | |
| --- | --- | --- | --- | --- | --- |
| Core (center component) | Purpose | Key Physical/ Functional Features | First layer (covering the Core) | Purpose | Key Physical/ Functional Features |
| Plasmonically active material | To couple incident light and fluorophore. Effect is most powerful when LSPR, | Absorbs light of a specific wavelength range. Plasmon generating. | Spacer | To maintain fluorophore far enough from plasmonically active surface so as to not get quenched but | Does not allow quenching (must be non-metallic). Rigid enough to maintain |

TABLE 1-continued

| Plasmonic-Fluor PF Architecture | | | | |
|---|---|---|---|---|
| fluorophore's fluorescence excitation maximum, and incident light share a common wavelength | | | near enough to strongly couple to the plasmonically active material | fluorophore at an appropriate distance (>1 nm) |

| Species | Purpose | Structural Arrangement | Important Points | Other considerations |
|---|---|---|---|---|
| Fluorophores | Light emitter after excitation | Attached to spacer or functional layer | Overlap of excitation wavelength and LSPR | Coating density is 20-2000 fluorophores per nanoconstruct |
| Biorecognition Element | To specifically attach the plasmonic-fluor to a target of interest | Attached to spacer or functional layer | | |

| Core (center component) | Purpose | Key Physical/ Functional Features | First layer (covering the Core) | Purpose | Key Physical/ Functional Features |
|---|---|---|---|---|---|
| Functional Layer | Can be used to reduce non-specific binding, can be used to attach targeting agent, and can be used to attach fluorophores or combinations thereof | Covering the fluorophore and spacer layer or covering the spacer layer and attached to the fluorophore | The functional layer is not absolutely required | The functional layer also acts to protect fluorophores from photobleaching by excluding reactive oxygen species | |

Variable** components (structural arrangement)
**These components can have a variable arrangement High Stability and Performance and Affordability The techniques disclosed herein for enhancing biological assays are a cost-effective solution for improving bioassay performance with estimated cost of plasmonic-fluors for one processing a 96-well microtiter plate to be comparable to current industry standards, and substantially less expensive than aforementioned special substrates (e.g. glass slides coated with metal island films). High stability of metal nanostructures further ensures the integrity and functionality of plasmonic-fluors under typical storage/transport/handling conditions used in bioassays. In general, the plasmonic fluors can be stored and handled as one would handle fluorescently-labeled biorecognition elements. In summary, enhanced signal-to-noise ratio achieved by the techniques described herein significantly improve the assay sensitivity, relax the stringent instrumentation requirements (such as low background noise and high sensitivity), decrease the required sample volume, and/or significantly shorten the overall assay time, thereby enabling these assays to be implemented in a broad range of research and clinical diagnostic settings with minimal effort or cost and substantial assay performance improvements.

In an assay in which fluorescence detection is already used as a readout, an increase in the fluorescence intensity by using the plasmonic fluor in lieu of the current gold-standard fluorophore leads to an improvement in the lower limit of detection (LLOD) of the bioassay. In some embodiments, the LLOD decreases by at least 2-fold, 5-fold, 10-fold, 20-fold, 40-fold, 50-fold, 100-fold, 500-fold, or even 1,000 fold. Additionally, this increases the dynamic range of detection. In some embodiments, the increase in the dynamic range is greater than 2-fold, 5-fold, 10-fold, 20-fold, 40-fold, 50-fold, 100-fold, 500-fold, or even 1,000 fold. In an assay in which fluorescence detection is not already used as a readout, but the readout method is chemiluminescence or colorimetric, in, for example, chemiluminescent/colorimetric ELISA or Western blot, switching to fluorescence detection and using a plasmonic fluor with appropriate detection instrumentation will lead to at least comparable performance in the LLOD and dynamic range of the bioassay vis-à-vis the gold standard reporter method of said assay. The improvement in the bioanalytical parameters was found to be consistent across different assay formats, target biomarkers, and fluorophores. Significantly, this method is implemented with existing bioassays with minimal modification of the standard operating procedures, and no additional operational training. In some aspects, the only modification from existing assay protocols is the addition of the fluorescent nanoconstruct in lieu of the existing fluorescent reporter molecule. In some aspects, the only modification from existing assay protocols is the addition of the fluorescent nanoconstruct in lieu of the existing reporter molecule and detecting fluorescence with appropriate detection instrumentation.

As a part of rigorous validation of the technology, urine samples from patients with kidney disease and healthy volunteers have been analyzed. As opposed to unenhanced fluoroimmunoassay and ELISA, the plasmon-enhanced fluoroimmunoassay enabled the detection and quantification of low concentration biomarkers, and from all patients and healthy volunteers. The added sensitivity of the plasmon-enhanced assay enables the facile quantification of biomarkers of low abundance and provides physiological and pathological information that are often missed by the conventional immunoassays.

Plasmonic Nanostructures

The nanoconstructs as described herein comprise a plasmonic nanostructure core. The plasmonic nanostructures used herein provide the plasmonic enhancement to the fluorescent signal and is selected based on numerous criteria (see e.g., Table 2). The plasmonic nanostructures can comprise any material which has surface plasmons that can resonate at suitable wavelengths of light, such as gold (Au), silver (Ag), copper (Cu), or combinations thereof. Suitable examples of plasmonic nanostructures include, but are not limited to, nanorods, nanocubes, nanospheres, bimetallic nanostructures (e.g. Au@Ag core-shell nanocube), nanostructures with sharp tips (e.g. nanostars), hollow nanostructures such as nanocages and nanorattles, nanobipyramids, nanoplates, self-assembled nanostructures, and nanoraspberries. In some aspects, the nanostructure is selected from the group consisting of gold core silver shell nanocuboids, nanotubes, gold nanorods, silver nanocubes, silver nanospheres, bimetallic nanostructures, gold nanorod core, silver shell (AuNR@Ag) canocuboids, nanostructures with sharp tips, nanostars, hollow nanostructures, nanocages, nanorattles, nanobipyramids, nanoplates, self-assembled nanostructures, nanoraspberries, and combinations thereof.

Figure 5:
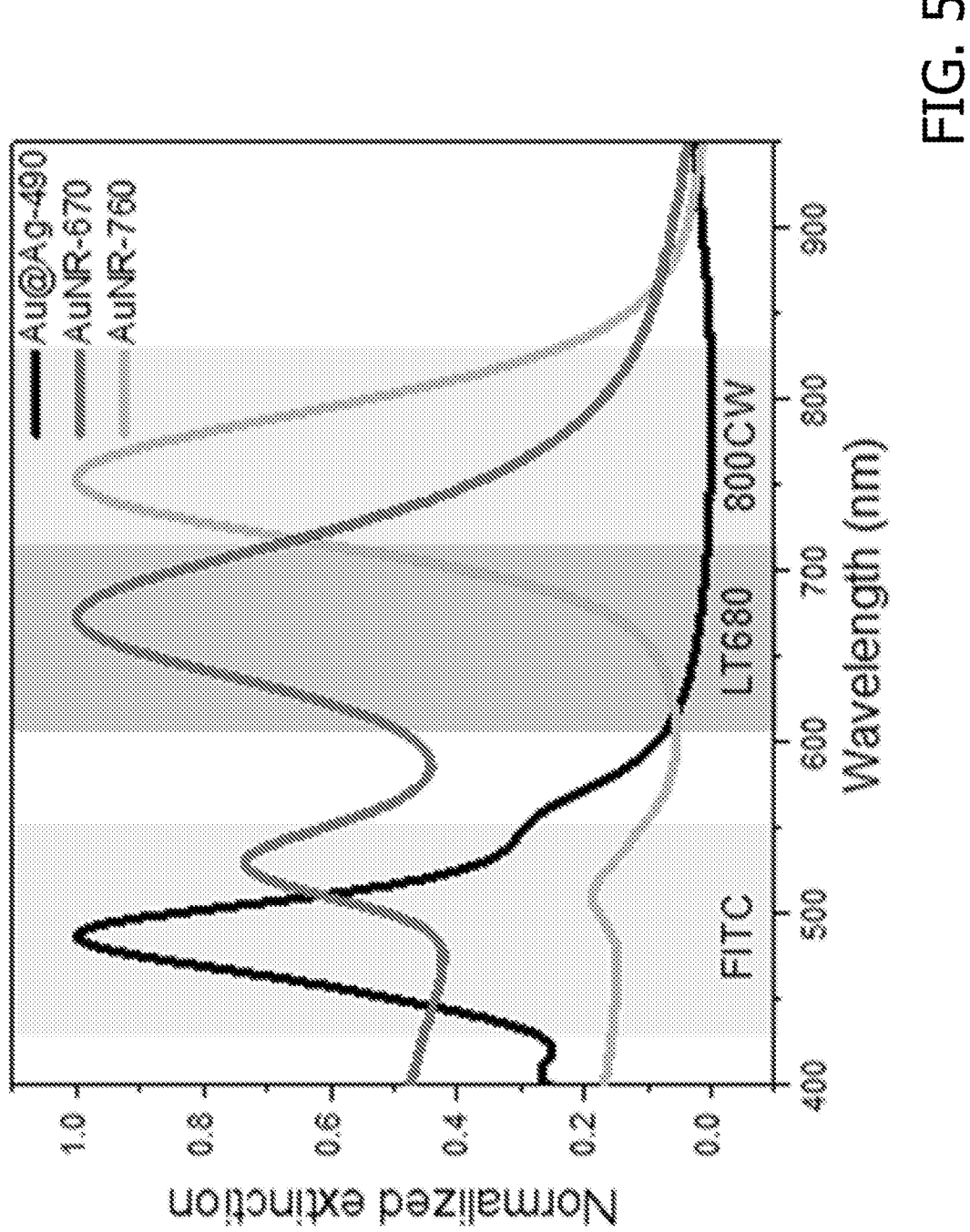
FIG. 5 is an exemplary embodiment of the normalized extinction spectra of the aqueous solutions of the three representative plasmonic nanostructures (from left to right: Au@Ag-490, AuNR-670, and AuNR-760) in accordance with the present disclosure. The extinction spectra of Au@Ag-490, AuNR-670, and AuNR-760 exhibit significant overlap with the absorption spectra (excitation spectra) and the appropriate excitation wavelengths of FITC, 680LT, and 800CW, respectively.

One criterion in selecting the plasmonic nanostructure to use in the fluorescent nanoconstruct is the LSPR wavelength (s). Different plasmonic nanostructures have different LSPR wavelengths as illustrated in FIG. 5. Even the same plasmonic nanostructure can have multiple LSPR wavelengths corresponding to different resonance modes of the surface plasmons. The specific LSPR wavelength that is optimal for fluorescence enhancement of a fluorophore is based upon the excitation spectrum of that fluorophore. Specifically, it is important that there is overlap of the LSPR wavelength and the excitation spectrum of the fluorophore. Generally, more overlap leads to better enhancement. The ideal situation for fluorescence enhancement occurs when the LSPR wavelength, the fluorophore excitation maximum, and the wavelength of light used for excitation are the same. This allows for the fluorescent nanoconstruct to be selectively tuned to match the fluorophore that it will be used to enhance. In some embodiments, the LSPR wavelength is between about 200 and about 1200 nm, between about 250 and about 950 nm, between about 300 and about 850 nm, between about 350 and about 800 nm, between about 400 and about 750 nm. In yet another embodiment, the LSPR wavelength is approximately (meaning ±25 nm) 300 nm, 350 nm, 400 nm, 450 nm, 500 nm, 550 nm, 600 nm, 650 nm, 700 nm, 750 nm, 800 nm, 850 nm, 900 nm, 950 nm, 1000, 1050, 1100, 1150, or 1200 nm.

In some embodiments, gold nanorod (AuNR)-based fluorescent nanoconstructs can have LSPR wavelengths between about 600-1200 nm. As another example, plasmonic fluors with a core of either silver-nanocube, AuNR@Ag cuboids, or —Au@Ag cubes, can have LSPR wavelengths between about 400 nm and about 600 nm.

In some embodiments, the plasmonic nanostructure has an LSPR wavelength between about 400 to about 1,000 nm. In some embodiments, the plasmonic nanostructure that serves as the plasmonic core of the fluorescent nanoconstruct) is an Au@Ag cuboid. In some embodiments, the plasmonic nanostructure is an Au nanorod (AuNR). In some embodiments, the plasmonic nanostructure is a silver-coated gold nanorod (AuNR@Ag). In some embodiments, the plasmonic nanostructure is one of any other number of plasmonic structures.

In some embodiments of the fluorescent nanoconstruct, the plasmonic nanostructure comprises a gold nanorod (AuNR) or a silver-coated gold nanorod (AuNR@Ag); the spacer coating comprises a stable silane network containing a reactive group capable of being functionalized; and the biorecognition element comprises biotin, streptavidin, an antibody or any combination of these.

TABLE 2

| Plasmonic nanostructures (plasmonic-fluor core) | |
| --- | --- |
| Nanostructures | Plasmonically Active Materials |
| Gold Core Silver Shell Nanocuboids (Au@Ag) | Gold |
| Nanorods (all plasmonic nanostructures) | Silver |
| Nanospheres | Platinum |
| Nanostars | Copper |
| Hollow nanostructures | Aluminum |
| Nanorattles | Magnesium |
| Nanoraspberries | Palladium |
| Nanobipyramids | Doped Semiconducting nanoparticles |
| Nanoplates | Semiconducting nanoparticles |
| Self-assembled nanostructures | Metal Alloys |
| bowtie antenna | Bimetallic particles |
| Nanooctahedra, rhombic dodecahedra, nanourchins | |
| nanostructures with sharp tips | |
| Nanocubes | |
| nanocages | |
| Nanoshells, Nanoboxes and nanoframes | |
| Concave nanostructures | |
| Magnetic-plasmonic nanostructures | |
| Coupled plasmonic nanostructures, including lightly aggregated or intentionally assembled particles | |

Plasmonic Nanostructure Size

The size of the plasmonic nanostructure forming the core of the plasmonic-fluor can be any size suitable to enhance or amplify fluorescence intensity of a conjugated fluorophore. In some embodiments, at least one dimension of the plasmonic nanostructure is at least 20 nm, 30 nm, 40 nm, 50 nm, 60 nm, 70 nm, 80 nm, 90 nm, 100 nm, 110 nm, 120 nm, 130 nm, 140 nm, 150 nm, 160 nm, 170 nm, 180 nm, 190 nm, or 200 nm. In some embodiments, the plasmonic nanostructure's size and its LSPR wavelength(s) are coupled such that the nanostructure's size is tuned to have the LSPR wavelength(s) overlapping the excitation maximum wavelength maximum of the fluorophore.

Wavelength Matching

Figure 6A:
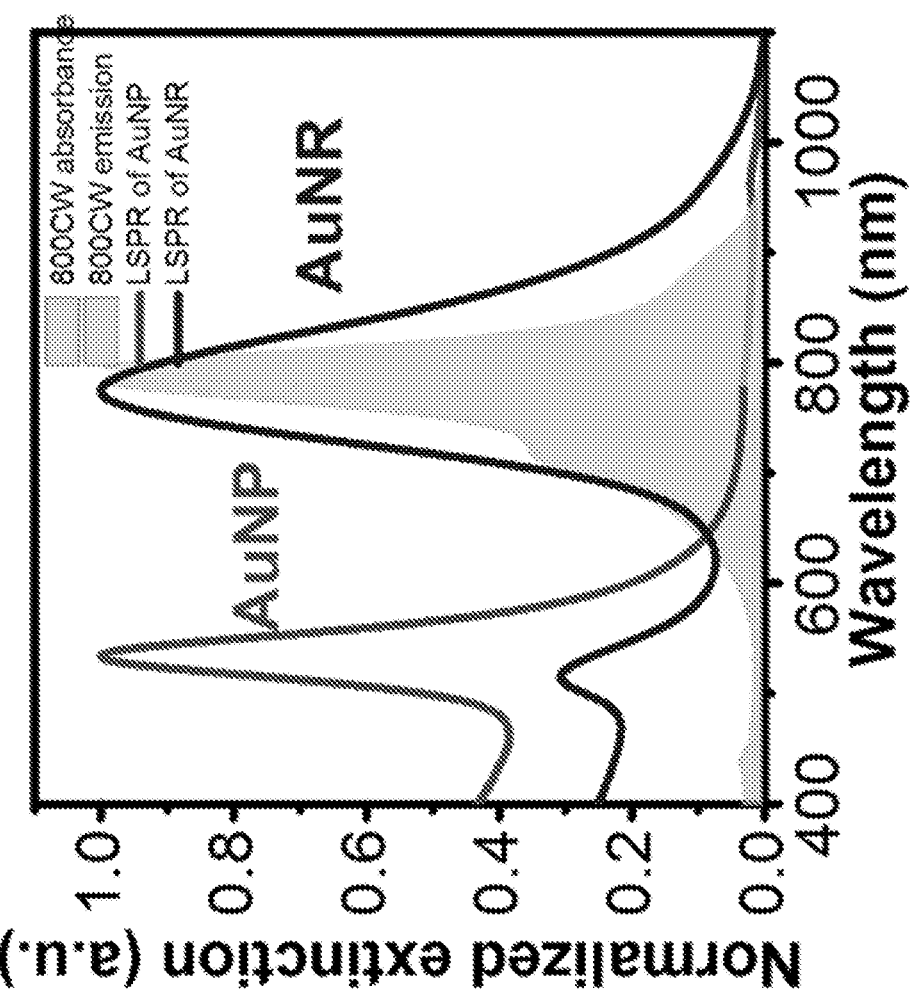
FIG. 6A and FIG. 6B are exemplary embodiments of the importance of overlap of the absorbance of the plasmonic particle and the absorbance/excitation spectrum of the conjugated dye in accordance with the present disclosure.
Figure 6B:
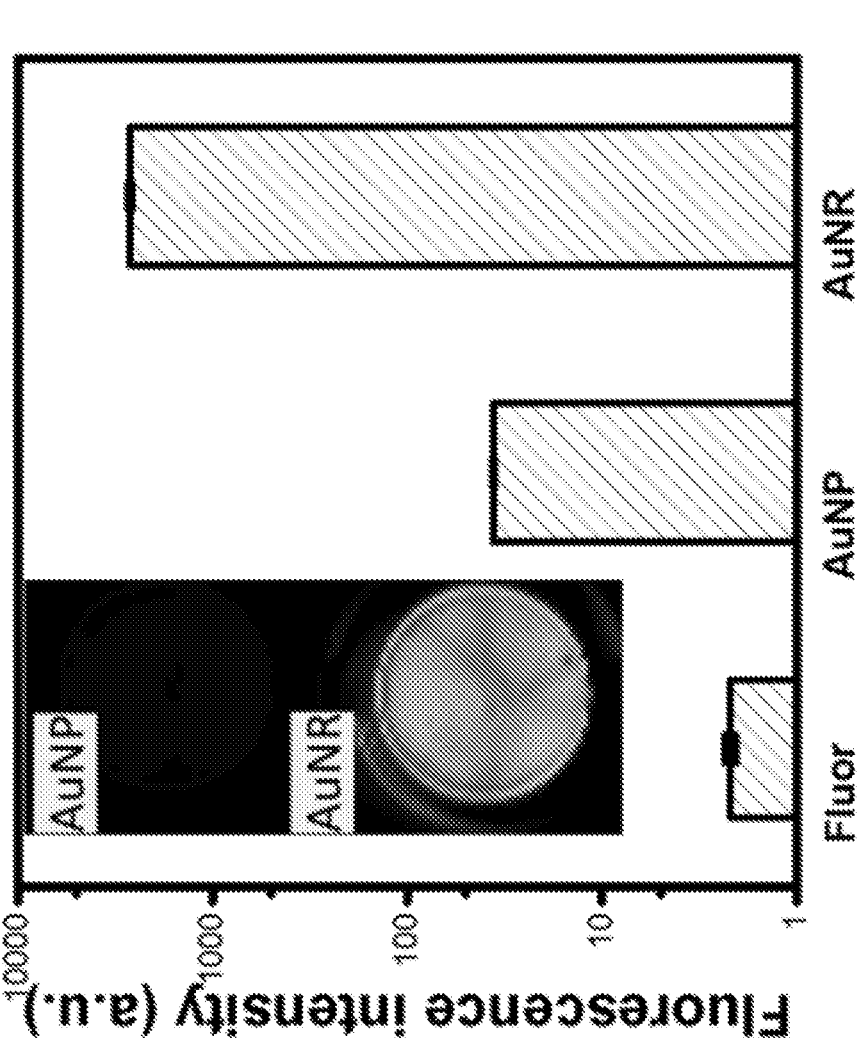

As described herein, the plasmonic nanostructure's size, shape, and composition can be tuned to have LSPR wavelength(s) matching the excitation maximum wavelength maximum of the fluorophore. Additionally, the LSPR maximum/maxima will shift after coating with the spacer layer and/or functional layer, and the overlap/matching described below needs to be with reference to the spacer- and/or functional layer-coated plasmonic nanostructure core. Wavelength matching can be a significant overlap of the LSPR wavelength(s) and the excitation spectrum of the fluorophore; a significant matching of an LSPR wavelength to a maximum excitation maximum wavelength of the fluorophore (see e.g., FIG. 5 and FIG. 6(A-B)) showing LSPR/fluorophore excitation maximum match and overlap); or the extinction spectrum of the nanostructure in solution shows significant overlap with the extinction spectrum and/ or the absorption maximum of the fluorophore in solution. excitation maximum wavelength The overlap of the LSPR wavelength(s) and the conjugated fluorophore excitation maximum wavelength can be 100% overlap or a 100% maximum LSPR wavelength to maximum excitation maximum wavelength of the fluorophore matching or overlap. In some embodiments, the result of the LSPR wavelength and the conjugated fluorophores excitation maximum wavelength matching is an at least 500-fold greater fluorescence intensity of the fluorescent nanoconstruct, conjugated with 20-2000 fluorescent agents, compared to the free fluorescent agent in solution when interrogated under similar excitation and detection conditions.

The maximum LSPR wavelength of gold nanorods (AuNRs) can be easily tuned to match a fluorophore's excitation maximum wavelength between 600 nm and >1200 nm. The maximum LSPR wavelength of silver cubes, AuNR@Ag cuboids, and Au@Ag cuboids can be easily tuned to match a fluorophore excitation maximum wavelength between 400 nm and 600 nm. As such, these were used as exemplary materials, but any plasmonic nanostructure that can be tuned to have an LSPR wavelength matching a specific fluorophore's excitation maximum wavelength (e.g., any visible or IR fluorescent dyes) can be used according to the methods described herein.

The plasmonic nanostructure's size, shape, and materials are tuned to match LSPR wavelength to maximum excitation maximum wavelength of a fluorophore. As another example, a cuboid with at least one dimension between about 60 nm and about 130 nm was discovered to be sufficient for tunably matching wavelengths <600 nm. As another example, a gold nanorod with a length between about 30 nm and about 130 nm was discovered to be sufficient for tunably matching wavelengths >600 nm. As an example, wavelengths can be considered matched if the fluorophore's excitation maximum wavelength ($\lambda$EX) is within about 100 nm of an LSPR wavelength ($\lambda$LSPR) of the plasmonic-fluor (PF).

In some embodiments, the absolute value of $\Delta$, the difference between the at least one $\lambda$LSPR and the $\lambda$EX, is 100 nm (i.e., $\pm$100 nm). In some embodiments, the absolute value of $\Delta$ is less than about 75 nm. In some embodiments, the absolute value of $\Delta$ is 50 nm (i.e., $\pm$50 nm). A smaller absolute value of $\Delta$ is preferable (i.e., values closer to zero), but the LSPR absorption peak is generally quite broad (full width at half-maximum of >50 nm or even >100 nm), meaning that there can be sufficient overlap of the extinction spectra of the plasmonic fluor and the fluophore, resulting in significant fluorescence enhancement, even if the maxima of the spectra ($\lambda$LSPR and $\lambda$EX, respectively) are mismatched. Windows for the plasmonic nanostructure and dye pairs are also disclosed (e.g. there are a number of fluorescent dyes (fluorophores) that can absorb and emit in a similar region to fluorescein, Cy3, Cy5, 680LT, and 800CW).

Spacer Coating

As described herein, a spacer coating is used to coat the plasmonic nanostructure to reduce or prevent quenching by maintaining the fluorophore a sufficient distance, on average, from the surface of the plasmonic nanostructure (e.g., at least about 0.5 nm to 4 nm away from the plasmonic nanostructure). The spacer coating is any material that can coat the plasmonic nanostructure and which can be controlled to have a thickness of 0.5-100 nm. In some embodiments, the spacer can be functionalized with a fluorophore.

In some aspects, the fluorescent nanoconstruct further comprises a spacer in the form of a coating on the plasmonic nanostructure. In some embodiments, the spacer is a dielectric material. In some embodiments, the thickness of the coating can be tuned to achieve differing amounts of fluorescent enhancement of the fluorescent signal. In some embodiments, the thickness (d) of the coating is from about 0.5 nm to about 100 nm. In yet other embodiments, the thickness of the coating is approximately, 2 nm, 3 nm, 4 nm, 5 nm, 8 nm, 10 nm, 15 nm, 20 nm, 25 nm, 30 nm, 35 nm, 40 nm, 45 nm, 50 nm, 55 nm, 60 nm, 65 nm, 70 nm, 75 nm, 80 nm, 85 nm, 90 nm, 95 nm or 100 nm. Approximately as used here means $\pm$25%. In some embodiments, the thickness of the coating is controlled by increasing the concentration of the monomers during preparation. In some embodiments, the spacer coating has a thickness of at least 0.5 nm, at least 1 nm, at least 2 nm, at least 3 nm, at least 4 nm, or at least 5 nm. In some embodiments, the variation of thickness of the spacer coating on a single fluorescent nanoconstruct is less than about 2 nm, 3 nm, 4 nm, or 5 nm.

In some embodiments, the coating comprises any polymer or mixtures of polymers that can be deposited uniformly across the plasmonic nanostructures and controlled to have a thickness stated above can be used. Examples of polymers for use as the spacer include, but are not limited to, proteins (e.g. BSA), silanes, and polyethylene glycol. Preferably the coating is MPTMS, APTMS, TMPS or a combination thereof. In some embodiments, the spacer is a siloxane network. Preferably the coating can be applied in solution. In some embodiments, the spacer coating is covalently attached to the plasmonic nanostructure. Additionally, in some embodiments, inorganic coatings such as silica, alumina and/or zinc oxide are used. In some embodiments, the spacer is a rigid polymer network. In some embodiments, the spacer coating contains functional groups for covalently attaching other molecules such as amines, aldehydes, carboxylic acids, sulfhydryls, ketones, and moieties compatible with click chemistry. In some embodiments, the spacer coating is a polymer coating comprising a dielectric, rigid polymer network, capable of being functionalized.

In some embodiments, the spacer is functionally active and contains any number of reactive groups and mixtures thereof. In some embodiments, the spacer is initiated with a mercapto-containing moiety to form a reactive layer on the gold/silver surface, and a siloxane network is built from this initiation layer using a mixture of functional silanes. Advantage of silanes are that they are: 1) wet chemistry compatible, 2) a variety of functional groups are available for further modification and tailoring of particle characteristics [e.g. PEG, amino, epoxy, mercapto, vinyl, Click-chemistry moieties (TCO, azide), PEG-biotin, aldehydes, fluorophores, and amino acids]; and there is 3) tight control over spacer thickness from 0.5 nm-100 nm.

TABLE 3

Suitable spacer coatings (defined generally as any material which can adhere to the plasmonic nanostructure and which can maintain a fluorescent agent an average distance of at least 0.5 nm from the surface of the plasmonic nanostructure)

| Spacer Coating Materials | |
| --- | --- |
| APTMS/APTES | Titanium oxide |
| TMPS | Polydopamine |
| MPTMS | Polyoctopamine |

23

TABLE 3-continued

Suitable spacer coatings (defined generally as any material
which can adhere to the plasmonic nanostructure and which can
maintain a fluorescent agent an average distance of at least
0.5 nm from the surface of the plasmonic nanostructure)

Spacer Coating Materials

| | |
|---|---|
| Silanes and mixtures of silanes | PEG |
| Metal oxides | Polyelectrolyte bilayers, layer-by-layer assembled multilayers |
| Zinc oxide | Alumina |
| Polysaccharides | |
| Silica | |
| Proteins | |
| Peptides | |
| Polyproline | |
| DNA/RNA | |
| PSS/PAH | |
| Chitosan, Alginate | |

TABLE 4

Suitable spacer coatings and/or functional layers (defined
generally as a material that can be stably attached
to the spacer layer and or plasmonic nanostructure)
Materials for Spacer and/or Functional Layers bovine serum albumin
human serum albumin
Hemoglobin
Ovalbumin
Lysozyme and homologs, albumin and
homologs
Stable protein layer
Polymers (including homo, di-block, triblock,
random, alternating, and statistical
copolymers)
Also, amphoteric and zwitterionic polymers
carboxybetaines and sulfobetaines
polymers containing carboxybetaines and/or
sulfobetaines
polymers containing both PEG and betaines
Polynucleotides
Polysaccharides
Polypeptides
Mixtures of the above In some embodiments, the spacer coating or functional layer serve as the scaffold for the light emitter (fluorophore) and biorecognition element (e.g., biotin, streptavidin, antibody, nucleic acids). In some embodiments, the fluorophore is attached to the functional layer, in which case, the functional layer also acts as an additional spacer between the fluorophore and the plasmonic nanostructure surface, even in the presence of a separate spacer coating layer. In some embodiments, the spacer coating or functional layer serves as a stabilizing agent preventing aggregation of the fluorescent nanoconstruct. The functional layer also helps to minimize non-specific binding of the fluorescent nanoconstruct to bioassay surfaces. In some aspects, the spacer coating or functional layer is a protein. Specific examples include, but are not limited to, albumin, lysozyme, Protein A, and hemoglobin. In some aspects, the protein on the fluorescent nanoconstruct is bovine serum albumin (BSA), human serum albumin (HSA) or a combination thereof. In some aspects, the protein is BSA.

Functional Layer

In some aspects, the spacer coating is the functional layer or the fluorescent nanoconstruct can further comprise a functional layer coating a spacer layer. In some aspects the functional layer is a polymer. Any polymer or combination of polymers that can adhere to or be attached to the surface of the spacer coating on the surface of the nanostructure can be used as a functional layer. In some aspects the polymer contains functional groups for covalently attaching other molecules such as amines, aldehydes, carboxylic acids, sulfhydryls, ketones, and moieties compatible with click chemistry. In some embodiments, the functional layer comprises a polypeptide. In some embodiments, the functional layer is an albumin protein or homolog thereof. In some embodiments, the functional layer is adsorbed to the spacer layer through hydrophobic or electrostatic interactions, or a combination thereof. In some embodiments, the functional layer is covalently linked to the spacer layer. In some embodiments, the functional layer is the same material which is used to 'block' in an immunoassay. For example, in plate-based immunoassays, BSA is used to block non-specific binding on the surface and BSA is used as the functional layer material.

Biorecognition Element

As described herein, the fluorescent nanoconstruct comprises a biorecognition element (see e.g., Table 5). The biorecognition element targets a specific analyte or species. For example, the biorecognition element can be an antibody if the target is an antigen, or the biorecognition element can be streptavidin.

In some embodiments, the biorecognition element is selected from the group consisting of: biotin, streptavidin, antibodies (or functional fragments thereof), oligos (such as DNA, PNA), aptamers, "click" moeities (e.g. tetrazine), molecularly imprinted polymers ("artificial antibody"), digoxigenin, peptide tags, protein tags, and combinations thereof. In some embodiments, the target is selected from the group consisting of: streptavidin, biotin, a target antigen, complementary oligos (DNA, RNA), target analyte, complementary "click" moiety to create pair, DIG-binding protein or anti-digoxigenin antibody, and combinations thereof.

In some embodiments, biorecognition elements such as antibodies, streptavidin, aptamers, and nucleic acids are added to the spacer layer or the functional layer via many of the same chemistries by which the fluorophores are added below. Additionally, in some embodiments, a biotinylated plasmonic-fluor is conjugated to streptavidin directly, and this can be further conjugated to a biotinylated antibody. In some embodiments, the biorecognition element is attached to the PF using a flexible linker. In some embodiments, the flexible linker is PEGx, wherein x is 2-36. In some embodiments, the fluorescent nanoconstruct comprises a plasmonic nanostructure having at least one localized surface plasmon resonance (LSPR) wavelength ($\lambda$LSPR), and a spacer comprising a first material; at least five fluorescent organic dyes having an excitation maximum wavelength ($\lambda$EX); a biological recognition element; wherein the plasmonic nanostructure is substantially covered with a spacer having a thickness between 0.5 and 20 nm; wherein the fluorescent species is attached to the spacer surface distal to the surface of the plasmonic nanostructure; wherein the spacer is substantially covered with the functional layer; wherein the biological recognition element is attached to the functional layer; wherein the difference between the LSPR wavelength and the excitation maximum wavelength of the fluorescent organic dyes is less than 75 nm; wherein each fluorescent organic dye is at least ten times brighter than the unconjugated fluorescent species in aqueous solution under typical illumination and detection conditions.

TABLE 5

| Exemplary Biorecognition Elements/Targeting Agents | |
|---|---|
| Biorecognition Element | Target |
| Biotin | Streptavidin |
| Streptavidin | Biotin |
| Antibody | Target Antigen (including other antibodies) |
| Oligo (DNA, PNA) | Complementary Oligo (DNA, RNA) |
| Aptamers | Target Analyte |
| "Click" moiety (e.g. tetrazine) | Complementary "Click" moiety to create pair (e.g. TCO) |
| Molecularly imprinted polymer ("artificial antibody") | Target antigen |
| Digoxigenin | DIG-binding protein or anti-digoxigenin antibody |
| Peptide tags | |
| Protein tags | |

Fluorescent Agent

The fluorescent agent is selected based upon a variety of criteria. As discussed herein, the terms fluorescent agent, fluorescent species, fluorophore, fluorescent dye are used interchangeably. One selection criterion is the wavelength of the fluorescent excitation maximum of the fluorescent agent. Another selection criterion is the ease in which the fluorescent agent is attached to the spacer coating of functional layer in the fluorescent nanoconstruct. In some embodiments, the fluorescent agent is any, UV, visible, near infrared (NIR), or infrared (IR) organic fluorophore. In some embodiments, the fluorescent agent is selected from the group consisting of fluorescein, Cy3, Cy5, 680LT, 800CW, acridines, acridones, anthracenes, anthracylines, anthraquinones, azaazulenes, azo azulenes, benzenes, benzimidazoles, benzofurans, benzoindocarbocyanines, benzoindoles, benzothiophenes, carbazoles, coumarins, cyanines, dibenzofurans, dibenzothiophenes, dipyrrolo dyes, flavones, fluoresceins, imidazoles, indocarbocyanines, indocyanines, indoles, isoindoles, isoquinolines, naphthacenediones, naphthalenes, naphthoquinones, phenanthrenes, phenanthridines, phenanthridines, phenoselenazines, phenothiazines, phenoxazines, phenylxanthenes, polyfluorobenzenes, purines, pyrazines, pyrazoles, pyridines, pyrimidones, pyrroles, quinolines, quinolones, rhodamines, squaraines, tetracenes, thiophenes, triphenyl methane dyes, xanthenes, xanthones, and derivatives thereof.

Additionally, the fluorescent nanoconstruct disclosed herein is suitable for enhancing a fluorescent signal from a large variety of different fluorescent sources or species. In addition to the fluorescent agents and assays disclosed elsewhere herein, in some embodiments, the fluorescent nanoconstruct enhances the fluorescent signal from quantum dots and upconversion nanoparticles.

In some embodiments, fluorescent molecules are added via standard chemistries: succinimidyl ester, NHS-ester, TFP ester, or isothiocyanate to a primary amine; maleimide to mercapto group; click chemistry either directly to functionalized silane (e.g. tetrazine-linked fluorophore to TCO-PEGn-triethoxysilane) or by first functionalizing another reactive group to have a click moeity; hydrazide or hydroxylamine to aldehyde or ketone. Additionally, in some embodiments, fluorophores are conjugated first to a functional layer molecule, such as a protein, which then adheres to spacer layer.

In some embodiments, the fluorescent species is an organic dye. In some embodiments, the organic dye is present at a coating density of 5-2000 fluorophores per plasmonic-fluor. In some embodiments, the fluorescent species is covalently attached to the spacer layer. In some embodiments, the fluorescent species is covalently attached to the functional layer.

TABLE 6

| Fluorescent Species (i.e., a fluorophore) Fluorescent Species |
|---|
| Organic Dyes |
| Quantum Dots |
| Upconversion nanoparticles |
| Nanodiamonds |
| Carbon dots |
| Metal nanoclusters (e.g., Au and Ag nanoclusters) |
| Fluorophore-doped nanoparticles |
| Eu-doped nanoparticles |
| Transition metal complexes |
| Lanthanide complexes |
| Fluorescent Proteins |

Exemplary Embodiments of Plasmonic-Fluors (PFs)

Variants of the plasmonic-fluor (PF) described below differ in the arrangement of the components of the PF, but all include a plasmonic nanostructure coated in a spacer layer with a fluorophore maintained at a specific distance from the plasmonic nanostructure surface, a biological recognition element attached somewhere to the PF, and a coupling between the fluorophore and the plasmonic nanostructure as defined by the overlap of at least one of the PF LSPR wavelengths and the excitation maximum of the attached fluorophore. In some instances, there is a layer referred to as a 'functional layer'. This can serve several purposes: to attach molecules (fluorophores, biorecognition elements); to stabilize the structure against aggregation and non-specific binding.

In some embodiments, a functional layer is present on the PF. In particular, a plasmonic nanostructure with at least one localized surface plasmon resonance wavelength ($\lambda$LSPR), a spacer material of a particularly thickness (d) substantially covering the surface of the plasmonic nanostructure, a fluorophore conjugated to the spacer material, a functional layer material substantially covering the spacer material, and, a biorecognition element conjugated to the functional layer material is disclosed.

In some embodiments, the method comprises coating a plasmonic nanostructure with at least one spacer coating; optionally coating the at least one spacer coating with a functional layer; conjugating a fluorescent agent to one of the at least one spacer coating, or the functional layer; and conjugating a biorecognition element to one of the at least one spacer coating, or the functional layer.

In some embodiments, coating the plasmonic nanostructure with at least one spacer coating comprises applying an initiating layer onto the plasmonic nanostructure core and applying a polysiloxane coating onto the initiating layer. In some embodiments, the initiating layer comprises 3-mercaptopropyl)trimethoxysilane (MPTMS). In some embodiments, the polysiloxane coating comprises trimethoxypropylsilane (TMPS) and 3-aminopropyl trimethoxysilane (APTMS).

In some embodiments, a plasmonic nanostructure with a localized surface plasmon resonance wavelength ($\lambda$LSPR), a spacer material of a particularly thickness (d) substantially covering the surface of the plasmonic nanostructure, a fluorophore conjugated to the spacer material, and a biorecognition element conjugated to the spacer material is disclosed. In some embodiments, the fluorescent nanoconstruct comprises a plasmonic nanostructure having a localized surface plasmon resonance (LSPR) wavelength ($\lambda$LSPR), and a spacer comprising a first material; a fluorescent species; a biorecognition element; wherein the nanostructure is substantially covered with a spacer having a thickness (d); wherein the spacer is conjugated with a fluorescent species; wherein the biorecognition element is attached to the spacer; wherein the fluorescent species has an excitation maximum wavelength ($\lambda$EX), wherein the difference between the LSPR wavelength and the excitation maximum wavelength is |$\Delta$|.

In some embodiments, a plasmonic nanostructure with a localized surface plasmon resonance wavelength ($\lambda$LSPR), a spacer material of a particularly thickness (d) substantially covering the surface of the plasmonic nanostructure, a fluorophore conjugated to the spacer material, a biorecognition element conjugated to the spacer, and a functional layer material substantially covering the spacer is disclosed. In some embodiments, the fluorescent nanoconstruct comprises a plasmonic nanostructure having a localized surface plasmon resonance (LSPR) wavelength ($\lambda$LSPR), and a spacer comprising a first material; a fluorescent species; a biorecognition element; a functional layer comprising a second material; wherein the nanostructure is substantially covered with a spacer having a thickness (d); wherein the spacer is conjugated with a fluorescent species; wherein the biorecognition element is attached to the spacer; wherein the functional layer material is attached to the spacer; wherein the fluorescent species has an excitation maximum wavelength ($\lambda$EX), wherein the difference between the LSPR wavelength and the excitation maximum wavelength is |$\Delta$|.

In some embodiments, a plasmonic nanostructure with a localized surface plasmon resonance wavelength ($\lambda$LSPR), a spacer material of a particularly thickness (d) substantially covering the surface of the plasmonic nanostructure, a functional layer material substantially covering the spacer material, a fluorophore conjugated to the functional layer material, and a biorecognition element conjugated to the functional layer material is disclosed. In some embodiments, the fluorophore is attached to the functional layer with the biorecognition element attached directly to the spacer. In some embodiments, the fluorescent nanoconstruct comprises a plasmonic nanostructure having a localized surface plasmon resonance (LSPR) wavelength ($\lambda$LSPR), and a spacer comprising a first material; a fluorescent species; a functional layer comprising a second material; a biological recognition element; wherein the nanostructure is substantially covered with a spacer having a thickness (d); wherein the spacer is substantially covered with a functional layer; wherein the fluorescent species is attached to the functional layer; wherein the biological recognition element is attached to the functional layer; wherein the fluorescent species has an excitation maximum wavelength ($\lambda$EX), wherein the difference between the LSPR wavelength and the excitation maximum wavelength is |$\Delta$|.

In some embodiments, the fluorescent nanoconstruct has a Zeta potential in pH 7 water with an absolute value greater than about 20 mV, or about 25 mV, or about 30 mV, or about 35 mV, or about 40 mV, or about 45 mV.

In some embodiments, the brightness of the plasmonic-fluor is at least 500 times, at least 600 times, at least 700 times, at least 800 times, at least 900 times, at least 1,000 times, at least 2,000 times, at least 3,000 times, at least 4,000 times, at least 5,000 times, and even at least 10,000 times brighter than the fluorescent species alone under typical, identical illumination and detection conditions. In some embodiments, the brightness of each fluorescent species attached to a plasmonic-fluor is at least 10 times, at least 20 times, at least 30 times, at least 40 times, or at least 50 times brighter on average than the free fluorescent species under typical, identical illumination and detection conditions.

Assays Suitable for Use with the Fluorescent Nanoconstructs

The fluorescent nanoconstruct disclosed herein is suitable for use with any assay that uses or can use fluorescence for the detection and/or quantification of the analytes. Examples of assays that are suitable for use herein include, but are not limited to, antibody/protein microarrays, bead/suspension assays, biochip assays, capillary/sensor assays, cell assays, tissue assays, DNA/RNA microarrays, polymerase chain reaction (PCR)-based assays, glycan/lectin arrays, immunoassays, enzyme-linked immunosorbent assay (ELISA), microfluidic chips, and membrane-based assays.

Disclosed herein is a method for improving performance of a bioassay. The method generally comprises using a fluorescent nanoconstruct as described elsewhere herein as a reporter molecule in a bioassay wherein the fluorescent nanoconstruct is targeted to a specific analyte or species via a biorecognition element and the fluorescent signal is detected using any method known in the art for detecting a fluorophore or a fluorescent signal wherein the analyte concentration is proportional to the fluorescent signal. In some embodiments, the biorecognition element is targeted directly to a specific analyte of interest (e.g. the biorecognition element is a primary antibody to an analyte or is a complementary oligonucleotide to a specific target oligonucleotide). In some embodiments, the biorecognition element is targeted to a moiety on another molecule which specifically binds a target analyte (e.g. the biorecognition element is a secondary antibody which recognizes a primary antibody bound to the target analyte or the biorecognition element is a streptavidin which recognizes a biotinylated primary detection antibody).

Because of the large fluorescent signal that is generated by use of the fluorescent nanoconstruct relative to standard fluorophores, the lower limit of detection of a fluorescent assay is greatly improved (i.e., the LOD is lower and the detection of less concentrated samples is possible) relative to the lower limit of detection achievable using the current standard fluorescent reporter molecule. In some aspects, the lower limit of detection of an assay using the fluorescent nanoconstruct is lower than the lower limit of detection of the same assay using the current standard fluorescent reporter molecule. In some aspects, the LOD is improved by 2× (i.e., meaning the LOD is half that of the same assay using the current standard fluorescent reporter molecule—twice the detection sensitivity). In some aspects, the LOD is at least 2× better, at least 3× better, at least 4× better, at least 5× better, at least 10× better, at least 25× better, at least 50× better, at least 100× better, at least 500× better, at least 1000× better, at least 5000× better, or even at least 10,000× better than the same assay using the current standard fluorescent reporter molecule.

TABLE 7

Assays which can use the plasmonic fluor as a reporter molecule

| Immunotargeting-based Assays | Nucleic Acid-Based Assays |
|---|---|
| FLISA | Northern blot |
| FACS | Microarrays |
| Flow cytometry | Next generation sequencing |
| Western Blot | RNA-seq |
| Protein Microarrays | FISH |

TABLE 7-continued

Assays which can use the plasmonic fluor as a reporter molecule

| Immunotargeting-based Assays | Nucleic Acid-Based Assays |
| --- | --- |
| Bead-based multiplexed immunoassays (e.g. Luminex) | EMSA |
| Immunohistochemistry | |
| Immunocytochemistry | |
| Lateral flow assay | |
| Microfluidics | |
| ELISPOT | |
| Fluorescence microscopy | |
| FLIM | |
| Dot blot | |
| Single cell Western, in-cell Western | |
| Competitive immunoassay | |
| Digital immunoassay | |
| ImmunoCAP Assays | |
| Protein Simple's ELLA assay | |

Method of Manufacture

In some embodiments, the plasmonic-fluor synthesis is as follows: (1) Coat plasmonic nanostructure with spacer layer; (3) Conjugate fluorescent species to spacer layer; (4) Coat resultant nanoconstruct from (3) with functional layer; and, (5) Conjugate biorecognition element to functional layer. This synthesis also includes several variants and other embodiments.

Variant 1: Biorecognition Element Conjugated to the functional layer: (1) Start with plasmonic nanostructure; (2) Coat plasmonic nanostructure with spacer layer, wherein the spacer layer is a mixture of MPTMS, APTMS, and TMPS, or can use alternative silanes with different functional moieties (e.g. aldehyde or tetrazine) for attaching fluorescent species (e.g. via hydrazine or TCO, respectively); (3) Conjugate fluorescent species to spacer layer, wherein the fluorescent species is covalently attached to an amine (via NHS or TFP ester) or can use alternative silanes with different functional moieties (e.g. aldehyde or tetrazine) for attaching fluorescent species (e.g. via hydrazine or TCO, respectively); (4) Conjugate biorecognition element to functional layer: (a) Biorecognition element is biotin and functional layer is bovine serum albumin (BSA), wherein biotin is covalently attached to BSA (or another suitable protein) using an NHS ester, wherein biotin is on a PEGx spacer; or (b) Click Chemistry is used to attach streptavidin or antibody to BSA directly by reacting, for example, NHS-PEGx-TCO with BSA and NHS-PEGy-tetrazine with the streptavidin or antibody, coating the nanoconstruct with BSA-TCO, and then mixing in the tetrazine-biorecognition element after step (5) below; (5) Coat nanoconstruct from (3) with functional layer in (4), using a mixture of biotinylated-BSA (or other suitable protein) with native BSA (or other suitable protein) in the functional layer step.

Variant 2: Fluor-Biorecognition Element Conjugated to the functional layer: (1) Start with plasmonic nanostructure; (2) Coat plasmonic nanostructure with spacer layer; (3) Conjugate biorecognition element and fluorophore to functional layer; and, (4) Coat particle from (2) with functional layer from (3).

In some embodiments, biotinylated PF's are used as a building block to add other biorecognition elements. It is possible to use biotin as the biorecognition element, but it is also possible to use biotin to link additional biorecognition elements (e.g. streptavidin). Thus, there would be an additional step wherein streptavidin is conjugated to the biotinylated PF nanoconstruct. Similarly, it is possible to take this streptavidin-conjugated PF and attach a biotinylated antibody. In this case, there would be yet another step wherein the biotinylated antibody is conjugated to the streptavidin-conjugated PF.

In some embodiments, the PF is further modified by attaching linear or branched hydrophilic polymers to the functional layer, streptavidin, or antibodies. In some embodiments, the hydrophilic polymer is PEG.

Methods of Use

Plasmonic-fluors are designed to enhance the performance of fluorescence-based biological assays. Specifically, they are to be used as a reporter molecule wherein the fluorescence signal generated by the plasmonic-fluor upon excitation at an appropriate wavelength is correlated to the concentration of a target analyte. The PF can be used in a number of different assay types and formats. The most obvious use of the PF is as a reporter molecule in an immunoassay. In this case, a primary detection antibody is used to detect a target analyte, and the PF is used to report on the concentration of detection antibody present, which is proportional to the amount of target analyte. This can be done by attaching the detection antibody directly to the PF (biorecognition element is the detection antibody) and using the resultant construct to bind the target analyte; by binding a streptavidin-conjugated PF (biorecognition element is the streptavidin) to a biotinylated detection antibody which is already bound to the target analyte; binding a biotinylated PF (biorecognition element is a biotin) to a streptavidin which is bound to a biotinylated detection antibody which is bound to the target analyte; or binding a PF which is conjugated to a secondary antibody (biorecognition element is the secondary antibody) which is directed against the detection antibody which is bound to the target analyte.

Additionally, one can use the PF's to detect a target nucleic acid sequence by either: 1) using a complementary nucleic acid sequence as the biorecognition element; or 2) using a biotinylated nucleic acid sequence to bind the target first and detecting this with a streptavidin-linked PF (biorecognition element is a streptavidin).

In some embodiments, the method of detecting an analyte comprises: providing a plasmonic-fluor wherein the at least one biorecognition element is targeted to the analyte (either directly or through means described above); exciting the plasmonic-fluor with an appropriate excitation wavelength; and, detecting emitted light where the amount of light detected is proportional to the concentration of the analyte.

In some embodiments, the assay comprises an immuno-targeting-based assay selected from the group consisting of: FLISA, FACS, flow cytometry, Western Blot, protein microarrays, bead-based multiplexed immunoassays (e.g. Luminex), immunohistochemistry, immunocytochemistry, lateral flow assay, microfluidics, ELISPOT, fluorescence microscopy, FLIM, Dot blot, Single cell Western, in-cell Western, competitive immunoassay, digital immunoassay, ImmunoCAP Assays, Protein Simple's ELLA assay, and combinations thereof. In some embodiments, the assay comprises a nucleic acid-based assay selected from the group consisting of: Northern blot, microarrays, next generation sequencing, RNA-seq, FISH, EMSA, and combinations thereof.

Kits

Also provided are kits. Such kits can include an agent or composition described herein and, in certain embodiments, instructions for use. Such kits can facilitate performance of the methods described herein. When supplied as a kit, the different components of the composition can be packaged in separate containers and admixed immediately before use. Components include, but are not limited to assays or fluorescent nanoconstructs or components thereof, such as fluorophores, plasmonic nanostructures, coating or spacer reagents, polymers, biotin, streptavidin, antibodies, proteins, binding agents, or linkers. Such packaging of the components separately can, if desired, be presented in a pack or dispenser device which may contain one or more unit dosage forms containing the composition. The pack may, for example, comprise metal or plastic foil such as a blister pack. Such packaging of the components separately can also, in certain instances, permit long-term storage without losing activity of the components.

In some embodiments, the kits include reagents in separate containers such as, for example, sterile water or saline to be added to a component packaged separately. For example, sealed glass ampules may contain a component and in a separate ampule, sterile water, sterile saline or sterile each of which has been packaged under a neutral non-reacting gas, such as nitrogen. Ampules may consist of any suitable material, such as glass, organic polymers, such as polycarbonate, polystyrene, ceramic, metal or any other material typically employed to hold reagents. Other examples of suitable containers include bottles that may be fabricated from similar substances as ampules, and envelopes that may consist of foil-lined interiors, such as aluminum or an alloy. Other containers include test tubes, vials, flasks, bottles, syringes, and the like. Containers may have a sterile access port, such as a bottle having a stopper that can be pierced by a hypodermic injection needle. Other containers may have two compartments that are separated by a readily removable membrane that upon removal permits the components to mix. Removable membranes may be glass, plastic, rubber, and the like.

In certain embodiments, kits are supplied with instructional materials. Instructions may be printed on paper or other substrate, and/or may be supplied as an electronic-readable medium or video. Detailed instructions may not be physically associated with the kit; instead, a user may be directed to an Internet web site specified by the manufacturer or distributor of the kit.

In some embodiments, the kit comprises a fluorescent nanoconstruct; or a plasmonic nanostructure, a spacer material, a biorecognition element, and at least one fluorescent agent. In some embodiments, fluorescent nanoconstruct or a combined plasmonic nanostructure, a spacer material, a biorecognition element, and at least one fluorescent agent are capable of having an at least 500-fold greater fluorescence intensity compared to the at least one fluorescent agent alone. In some embodiments, the kit contains a liquid suspension of PF's. In some embodiments, the kit contains a frozen solution of PF's. In some embodiments, the kit contains a lyophilized solution of PF's. In some embodiments, the kit contains streptavidin-conjugated PFs and instructions for a user to conjugate the streptavidin-conjugated PF's to a biotinylated primary antibody and to purify such primary-antibody conjugated PFs.

Exemplary embodiments of the fluorescent nanoconstruct and methods for its use are described above in detail. The fluorescent nanoconstruct and methods described herein are not limited to the specific embodiments described, but rather, components of apparatus, systems, kits, and/or steps of the methods may be utilized independently and separately from other components and/or steps described herein. For example, the methods may also be used in combination with other polymers, nanostructures and bioassays, and are not limited to practice with only the apparatuses, systems, and methods described herein. Rather, the exemplary embodiments can be implemented and utilized in connection with many other systems.

Although specific features and applications of various embodiments of the disclosure may be shown in some drawings and not in others, this is for convenience only. In accordance with the principles of the disclosure, any feature illustrated herein may be referenced and/or claimed in combination with any feature.

In the following specification and the claims, reference will be made to a number of terms, which shall be defined to have the following meanings. The singular forms "a," "an," and "the" include plural references unless the context clearly dictates otherwise. The terms "comprising," "including," and "having" are intended to be inclusive and mean that there may be additional elements other than the listed elements. "Optional" or "optionally" means that the subsequently described event or circumstance may or may not occur, and that the description includes instances where the event occurs and instances where it does not.

Approximating language, as used herein throughout the specification and claims, may be applied to modify any quantitative representation that could permissibly vary without resulting in a change in the basic function to which it is related. Accordingly, a value modified by a term or terms, such as "about," "approximately," and "substantially," are not to be limited to the precise value specified. In at least some instances, the approximating language may correspond to the precision of an instrument for measuring the value. Here and throughout the specification and claims, range limitations may be combined and/or interchanged; such ranges are identified and include all the sub-ranges contained therein unless context or language indicates otherwise.

EXAMPLES

The following example describes compositions and methods of making and using plasmonic-fluor (PFs) to maximize fluorescence enhancement.

Example 1

In the design and synthesis of the fluorescent nanoconstruct, two factors require careful consideration: (i) the attached fluorophores must be far enough away from the plasmonic nanostructure surface to avoid metal-induced fluorescence quenching; and (ii) the fluorophores must be close enough to the plasmonic nanostructure surface to benefit from the enhanced electromagnetic field which decays rapidly as the distance from the surface of the plasmonic nanostructure increases. It is known that the evanescent nature of the enhanced electromagnetic field at the surface of the plasmonic nanostructures results in a highly distance-dependent enhancement of fluorescence at the surface of the plasmonic nanostructures. When fluorophores are brought in direct contact (or in extreme proximity) to plasmonic nanostructures, non-radiative energy transfer between the fluorophore and metal surface results in fluorescence quenching. On the other hand, increase in the distance between the fluorophores and metal nanostructures results in a decrease in the enhancement due to the decay in the electromagnetic field from the surface of the nanostructures. Taken together, an optimal distance between the metal surface and fluorophore is one key aspect of the nanostructures to ensure maximum enhancement. The optimal spacer thickness (d) is <10 nm. More specifically, for maximum enhancement the spacer thickness should be between 1 and 10 nm when the fluorophore is attached directly to the spacer layer and between 0.5 and 5 nm when the fluorophore is attached to the functional layer.

To achieve an optimal distance between plasmonic nanostructures and fluorophores on the surface, a polysiloxane copolymer layer was formed on the surface of the plasmonic nanostructures as a spacer layer. 3-Mercaptopropyl) trimethoxysilane (MPTMS) was used to bind the plasmonic nanostructure surface to create an initiation layer for the spacer. Trimethoxypropylsilane (TMPS) and 3-aminopropyl trimethoxysilane (APTMS), which are hydrolytically unstable, were copolymerized on the plasmonic nanostructures via the initiation layer. Formation of the spacer layer resulted in a red shift in the longitudinal LSPR wavelength of the plasmonic nanostructures owing to the increase in the refractive index of the medium surrounding the nanostructures.

Figure 7A:
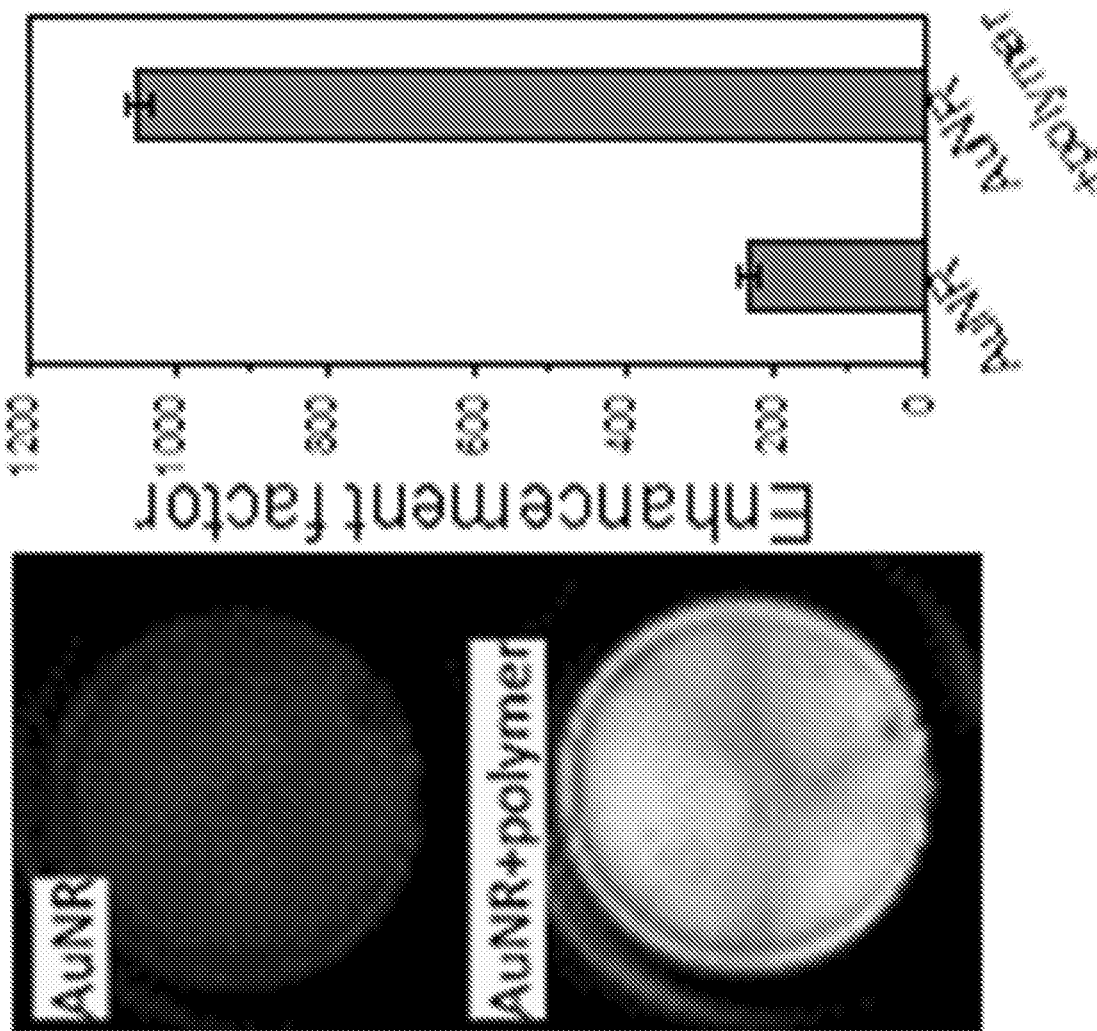
FIG. 7A is an exemplary embodiment of fluorescence intensity map (left) and enhancement factor (right) obtained AuNR and AuNR with polymer spacer layer in accordance with the present disclosure.
Figure 7B:
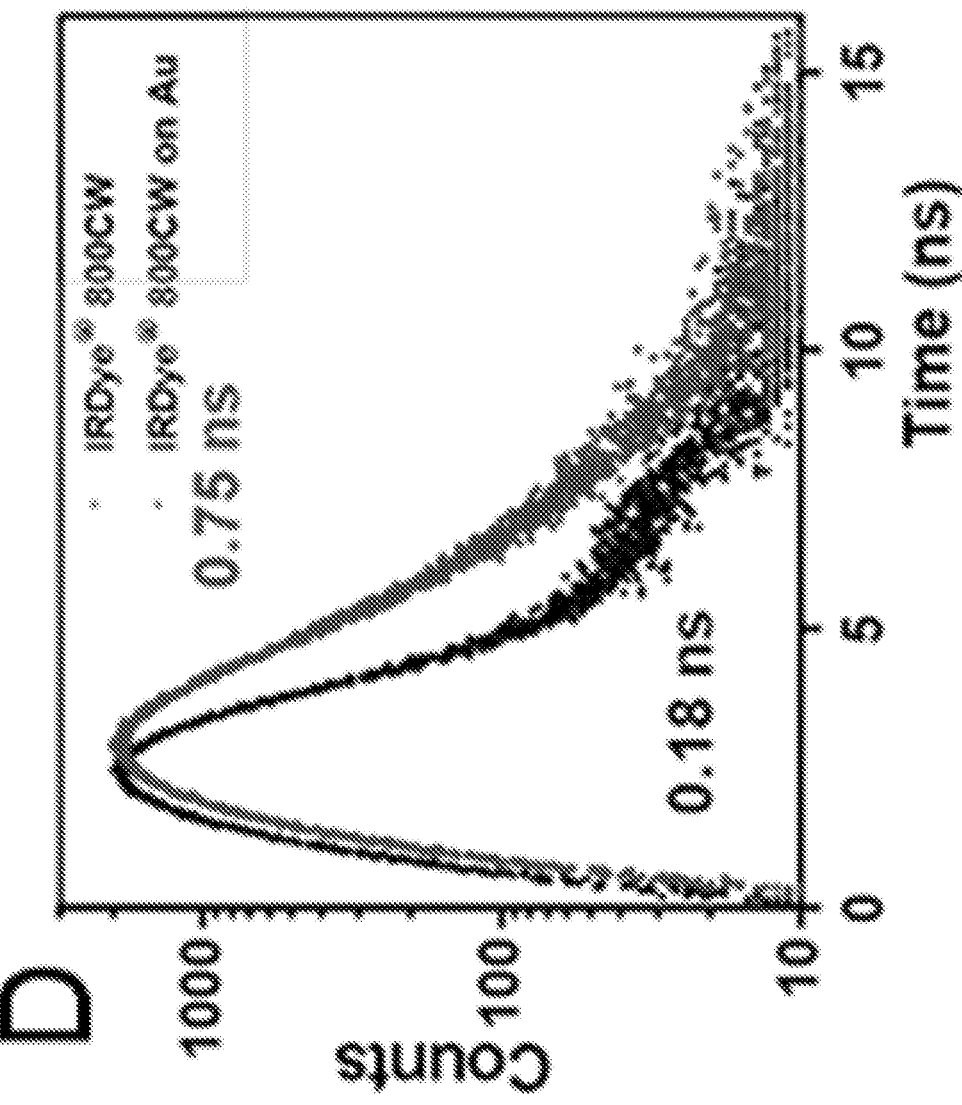
FIG. 7B is an exemplary embodiment of fluorescence lifetime of conventional fluorophore (800CW) and fluorescent nanoconstruct (AuNR-800CW) in accordance with the present disclosure.

Transmission electron microscopy and atomic force microscopy (AFM) imaging confirmed the successful formation of the spacer layer on the plasmonic nanostructures. AFM height profile of AuNR before and after polymerization revealed the thickness of the spacer layer to be ~3 nm. Fluorescence enhancement of the nanostructures with and without a dielectric spacer was investigated by binding them to a substrate coated with streptavidin-800CW. The ensemble fluorescence enhancement factors for identical densities (confirmed by scanning electron microscopy imaging) of the nanostructures with and without polymer spacer layer was found to be ~1000 and ~200, respectively, highlighting the importance of spacer layer for large fluorescence enhancement (FIG. 7A). It is noted that these particles have fluorophores attached to the BSA, which provides some spacing. If the fluorophores were attached directly to the AuNR, there would be nearly no fluorescence. The observed bright emission is caused by both enhanced excitation (enhanced EM field) and altered radiative rate. For a detailed investigation of rate enhancements, the excited state lifetimes of 800CW-BSA dispersed in solution and nanostructures comprised of 800CW-BSA were determined. The fluorescence lifetime of 800CW-BSA adsorbed on AuNR exhibited more than fourfold lower lifetime (0.18 ns) compared to that of the free 800CW-BSA (0.75 ns) (FIG. 7B). The large reduction in the fluorescence lifetime directly lends itself to enhanced emissive rate of the fluorophore.

Example 2: Assay Validation

Following the synthesis of the fluorescent nanoconstruct, the application of these novel materials and novel approach was validated in several bioanalytical techniques to enhance the feeble fluorescent signal and the associated bioanalytical parameters. For comparisons of enhancements in assay parameters of commercially available assays described below, the assays were performed according to the vendor specifications and plasmonic-fluors were added at a concentration <10× the concentration of the gold standard reporter molecule. It is possible that even higher performance can be achieved by optimizing reagent incubation times and concentrations.

The plasmonic-fluor acts as an ultra-bright fluorescent probe in the last step of bioassays to enhance the feeble fluorescence and signal-to-noise ratio (SNR) without entailing any change or modification of the existing bioassay protocols (i.e. "non-invasive" method). The ultra-brightness of the plasmonic-fluor is due to the presence of the metal core, which acts as the antenna to strongly enhance the fluorescence emission of the fluorophores on the surface. The enhancement of the emission of fluorophores in the vicinity of metal nanostructures is attributed to the enhanced electromagnetic field (local excitation field) at the surface of the plasmonic nanostructures and a decrease in the fluorescence lifetime due to the coupling between excited fluorophores and surface plasmons of the nanostructures. The plasmonic-fluor is highly versatile and universal and is seamlessly integrated with a variety of existing fluorescence-based bioanalytical techniques.

The present disclosure tested the application of plasmonic-fluors as a fluorescence enhancer in fluorophore-linked immunosorbent assays (FLISAs). A typical sandwich FLISA involves the following major steps: (i) capture of the target antigen by an immobilized antibody; (ii) binding of the biotinylated detection antibody to the captured antigen; and (iii) binding of a fluorescently-labeled streptavidin. As shown herein, the addition of a biotinylated plasmonic-fluor after the last step (i.e. binding the fluorescently-labeled streptavidin) resulted in a large enhancement of fluorescence intensity and significantly improved the limit-of-detection (LOD). The addition of the biotinylated plasmonic-fluor allowed direct comparison of assay improvement vis-à-vis the current fluorescently labeled reporter standard (fluorescently labeled streptavidin). This method, adding biotinylated PF's to a sample which has already been interrogated with streptavidin also allows users to interrogate samples over an extremely high dynamic range of target analyte concentrations in the cases where the readout device cannot sufficiently attenuate the signal (i.e. high concentrations of analyte result in fluorescence that saturates the detector when using the PF, but are readable using the standard fluorophore-labeled streptavidin, wherein the streptavidin can be conjugated to one or more fluorophores). To achieve the high dynamic range, a user would first add fluorescently labeled streptavidin and measure the resultant fluorescence from the assay, and would then add the biotinylated PF's and re-read the resultant fluorescence from the assay. This is particularly attractive for plate-based and bead-based assays. In practice, the end-user may prefer to use streptavidin-conjugated or detection-antibody PF's directly instead of first adding a fluorescently-labeled streptavidin, reading, and then re-probing with biotinylated PF's. In accordance with the present disclosure, FLISA was implemented in a heterogeneous, solid phase format by using a 96-well microtiter plate as a sampling platform, a standard assay format extensively employed in biomedical research and clinical diagnostics.

The first application investigated was the fluoroimmunoassay implemented in a 96-well plate where human IL-6 was employed as the model target. The preliminary results showed that the fluorescence intensity was increased by up to 2000-fold by simply adding the fluorescent nanoconstruct as the last step of the assay. Owing to the significant improvement of the fluorescence intensity, in some embodiments, the assay sensitivity is lowered by five orders of magnitude, down to 3 fg/ml, which is three-orders lower than that achievable using the current gold standard ELISA assay even using the same antibodies and standard analyte.

800CW-streptavidin, the conventional fluorescence tag, was followed by the addition of the nanostructures as the last-step signal enhancer. To probe the enhancement in sensitivity and LOD, serial dilutions of IL-6 of known concentrations (6 fg/mL to 6 ng/mL) in phosphate buffered saline (PBS) with 1% bovine serum albumin (BSA) were employed as standards. Fluorescence images obtained after applying the nanostructures revealed a 2,000-fold enhancement in fluorescence intensity compared to the conventional FLISA. Specifically, fluorescence signal with conventional fluors (800CW) was detectable only for the two highest concentrations (6 and 0.6 ng/mL). On the other hand, fluorescence signal with the fluorescent nanoconstruct could be detected down to 6 fg/mL. The lower limit of detection (LLOD=mean+3σ of the blank) of the unenhanced and plasmon-enhanced IL-6 assays were determined to be 600 pg/mL and 6 fg/mL, respectively, which represents a 105-fold improvement in the LOD after the addition of the fluorescent nanoconstructs. Remarkably, the LOD of the plasmonic-enhanced assay was found to be 1000-fold lower than the vendor-specified enzyme-linked immunosorbent assay (ELISA), which involves enzymatic amplification of the colorimetric signal. More surprisingly, the plasmon-enhanced assay exhibited seven-order-magnitude dynamic range, which is more than four orders higher compared to ELISA. In essence, the nanostructures offer the possibility to greatly improve the bioanalytical parameters (LLOD, lower limit of quantification (LLOQ=mean+10σ of the blank), dynamic range) of commercially available immunoassay kits without requiring tedious and repeated steps or any specialized or expensive instruments.

The second application investigated was the enhancement of signal in a protein microarray. For this purpose, human kidney biomarker microarrays were utilized in a 3D microporous nitrocellulose membrane. By simply adding the fluorescent nanoconstruct, all 38 protein biomarkers in a human patient urine sample were visualized through one simple test, compared with the 15 biomarkers revealed in an assay using fluorescently-labeled streptavidin.

In yet another aspect, the applicability of fluorescent nanoconstructs in enhancing the sensitivity of immuno-microarrays was investigated. A microarray of antibodies to biomarkers of human kidney disease (R&D systems ARY019)27) was utilized as a representative example to test the performance of the fluorescent nanoconstruct in spatially multiplexed and high throughput biosensing platform. This microarray is comprised of 38 capture antibodies corresponding to human kidney protein biomarkers, printed in duplicates on a three-dimensional nitrocellulose membrane. Biotinylated IgGs were printed in duplicates as reference (positive controls). Duplicate spots of PBS were printed as a negative control. Human urine samples from kidney disease patients were diluted 2-fold using blocking buffer and added to the array. Subsequently, the captured biomarker proteins were exposed to a biotinylated detection antibody cocktail followed by exposure to 800CW-streptavidin. Conventional microarray procedure ends at this step, at which point the biomarker concentration is (semi-) quantified by analyzing the fluorescence intensity corresponding to each analyte. In the plasmon-enhanced assay, a biotinylated fluorescent nanoconstruct solution was added onto the microarray, incubated for 30 minutes and thoroughly rinsed to remove the weakly bound nanostructures. This allowed direct comparison of the gold-standard reporter method and the nanoconstruct, but, in practice, a user may prefer to used streptavidin-conjugated PF's instead of first adding fluorescently-labeled streptavidin and then labeling this with biotinylated PF's.

The fluorescence map obtained with conventional fluor and fluorescent nanoconstruct using human urine sample illustrates the improvement of the fluorescent signal. First, the brightness and SNR of the positive controls was found to be 80 times enhanced after the addition of the nanostructure. Concurrently, no signal was detected from the negative control, indicating minimal non-specific binding of the nanostructure to the nitrocellulose membrane, which critical to ensure low background. With conventional fluors, out of the 38 protein biomarkers targeted, only 14 were detectable, most of them exhibiting weak intensity. After addition of the nanostructure, the fluorescence signal intensity from each spot of the microarray increased significantly. SEM image of the nitrocellulose after the addition of fluorescent nanoconstructs revealed uniform distribution of AuNRs on the porous membrane with no sign of aggregation. The fluorescence signal corresponding to cystatin C, β2 microglobulin (Beta 2M), serpin A3, and neutrophil gelatinase-associated lipocalin (NGAL) was found to be enhanced by up to 500-fold compared to that obtained with fluorescently-labeled streptavidin. Furthermore, the nanostructure enabled the detection and quantification of all other targets that could not be detected by the fluorescently-labeled streptavidin. For example, kidney injury molecule-1 (KIM1), which is a specific biomarker for early detection of acute kidney injury, could only be detected after fluorescent nanoconstruct addition.

Example 3

Figure 8A:
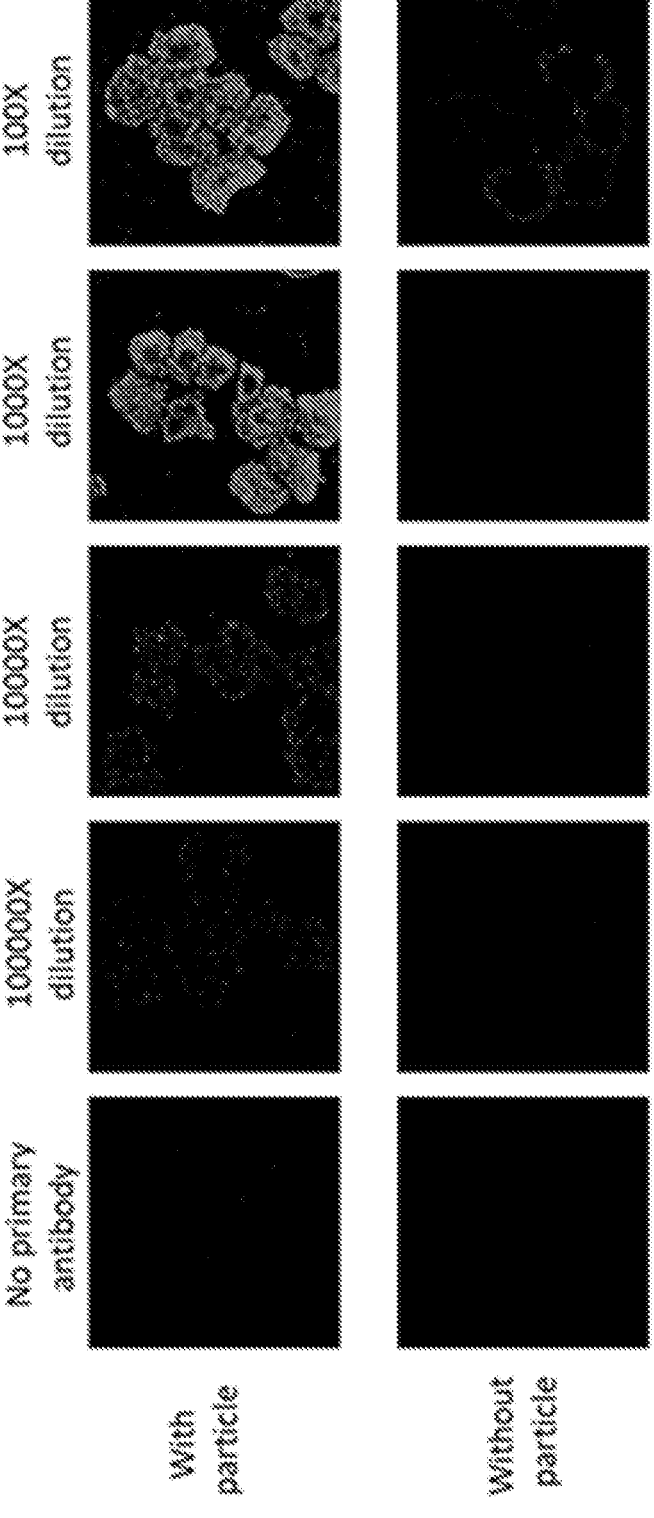
FIG. 8A is an exemplary embodiment of a plurality of confocal laser scanning microscopy images showing the fluorescence signals corresponding to the over expressed protein biomarker (ErbB2) on breast cancer cell by probing them with different dilutions of ErbB2 primary antibody (top: with particle enhancement; bottom: without particle enhancement) in accordance with the present disclosure. The fluorescence signal is revealed even after 100000-fold dilution of ErbB2 primary antibody with the nanostructure enhancement.
Figure 8B:
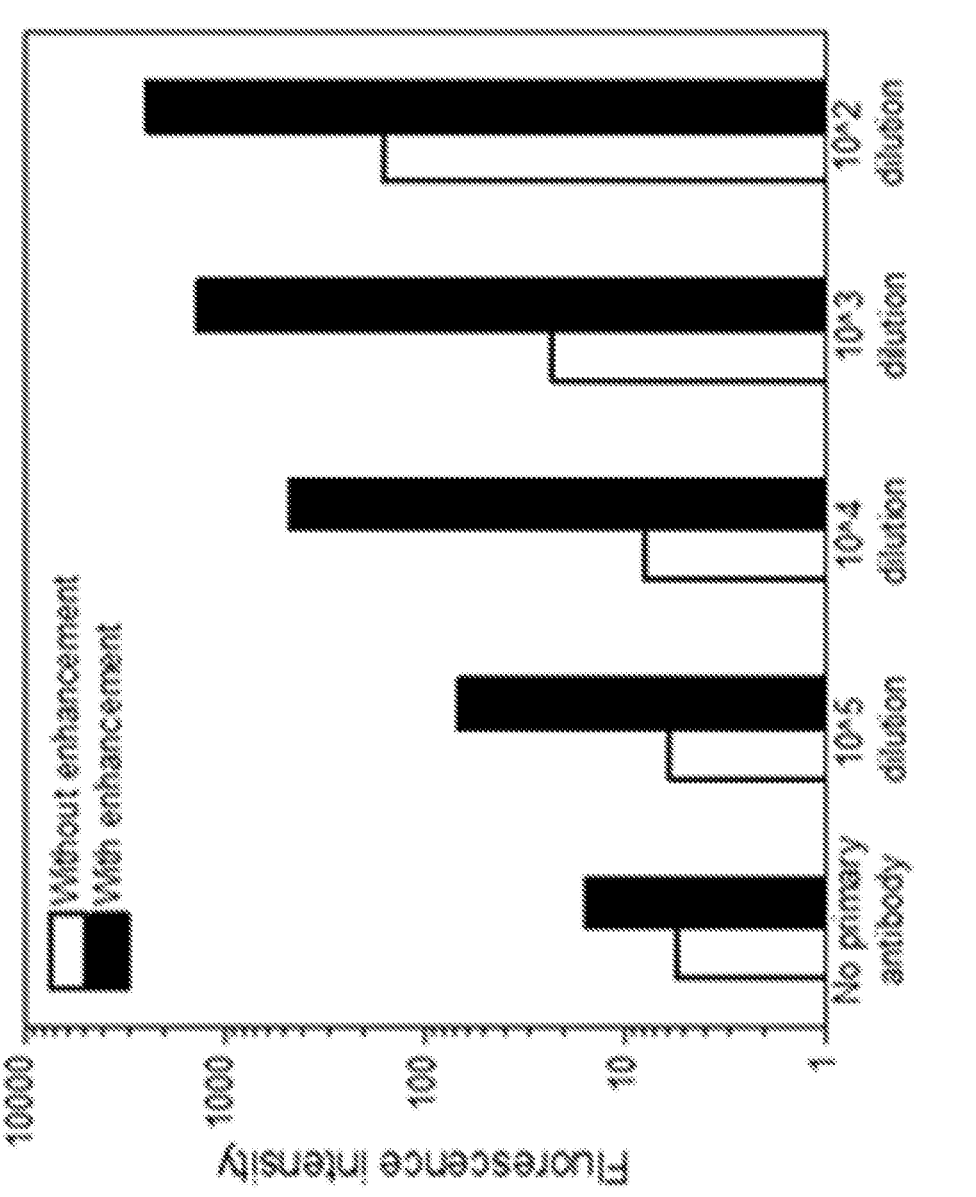
FIG. 8B is an exemplary embodiment of an average fluorescence intensity of the labeled breast cancer cells with and without particle enhancement in accordance with the present disclosure.

The ultrabright fluorescent nanoconstructs were also applied to cell imaging to probe and reveal cell surface biomarkers. A breast cancer cell line was selected as the model and probed for the over expressed biomarker ErbB2 using different dilutions of ErbB2 primary antibody, followed by 800CW labeled streptavidin. The experiment illustrates that after the addition of the biotinylated fluorescent nanoconstruct, the fluorescence intensity corresponding to the ErbB2 increased by up to 100-fold (FIG. 8A and FIG. 8B). The fluorescence microscopic image still reveals the overexpressed ErbB2 even at a primary antibody dilution of 105 fold (FIG. 8A). In practice, most users would use a PF attached to a secondary antibody or primary antibody for cell- or tissue-based experiments including flow cytometry, immunocytochemistry, and immunohistochemistry. By attaching the PF to antibodies, a user can more easily multiplex (i.e. detect multiple markers simultaneously by using specific antibody/PF pairs wherein the antibody/PF pair has a unique fluorescent spectral signature, a technique which is commonly employed in these types of experiments using antibodies labeled with conventional fluorophores).

Example 4

In still yet another aspect, the capacity of fluorescent nanoconstruct to enhance the SNR in flow cytometry-based cell analysis (FIG. 8(A-B) and FIG. 9(A-B)). ErbB2 (human epidermal growth factor receptor 2)-positive epithelial breast cancer cells (SKBR3) were tested as a model cell line. The cell surface receptor ErbB2 was immuno-stained using standard fluorescence probe followed by the addition of the nanostructures. The conventional two-step staining procedure was carried out by incubating formaldehyde-fixed SKBR3 single cell suspension with the biotinylated anti-ErbB2 and streptavidin-fluorophore (streptavidin-680LT) sequentially. The nanostructures were optimized for 680LT by changing the aspect ratio to tune the longitudinal LSPR wavelength to 660 nm. After labeling with streptavidin-fluorophore, the cells were further incubated in nanostructure suspension for an hour. Before proceeding to flow cytometry, the fluorescence signal enhancement was tested and visually confirmed. Confocal laser scanning microscopy (CLSM) images of the cells were obtained with conventional fluors and nanostructures. As noted above, anti-ErbB2 was diluted to different concentrations before incubation with cell suspensions. Compared with conventional staining (i.e. streptavidin-fluorophore), significantly brighter fluorescence signal was observed after the addition of nanostructure, which is detectable even at 100,000-fold dilution of the primary antibody (FIG. 8(A-B) and FIG. 9(A-B)).

Figure 9A:
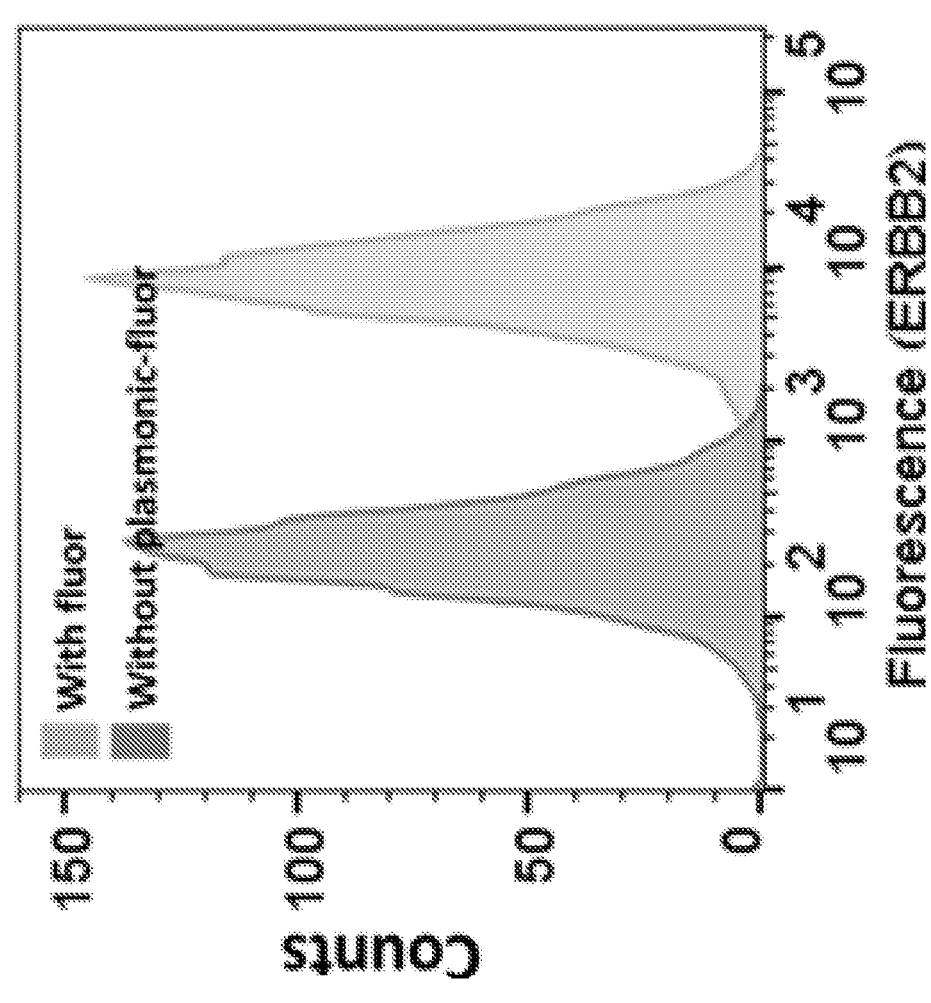
FIG. 9A is an exemplary embodiment of a fluorescence intensity histograms corresponding to ErbB2 receptors obtained with fluors and fluorescent nanoconstruct in accordance with the present disclosure.
Figure 9B:
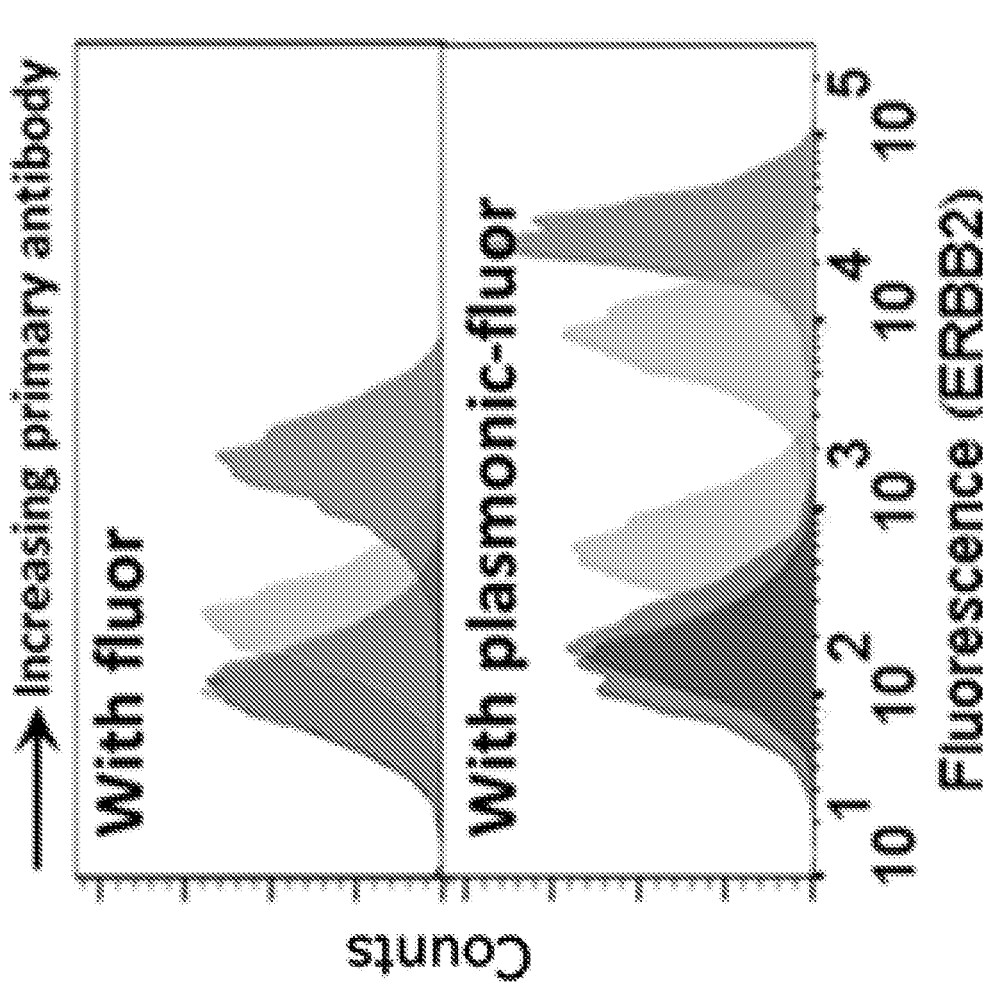
FIG. 9B is an exemplary embodiment of the fluorescence intensity histograms in accordance with the present disclosure.

In flow cytometry experiment, 5000 cells were analyzed by Guava InCyte to acquire the fluorescence signal (RED-R channel (excitation laser: 642 nm; filter: 662/15 nm)) in combination with forward scatter (FSC) and side scatter (SSC). Owing to their nanoscale size (~75 nm), the binding of the nanostructures to the cell surface did not change the forward scatter or side scatter intensity (data not shown). Histograms of fluorescence signals demonstrate a 60-fold higher intensity with nanostructures compared to cells with streptavidin-fluor (FIG. 9A). Fluorescence histograms also show that the expression of ErbB2 on the cell surface is detected even at 100,000-fold dilution of primary antibody after the addition of the nanostructures (FIG. 9B and FIG. 8B). On the other hand, with streptavidin-fluor alone, the fluorescence signal could not be detected at dilutions higher than 1000-fold. Fluorescence mean value obtained at different dilutions of the primary antibody with fluors and nanostructures demonstrate the promise of the novel nanoconstruct in detecting low-abundance targets on cell surface (FIG. 8B).

Example 5—Alternative Designs of PF

Figure 10:
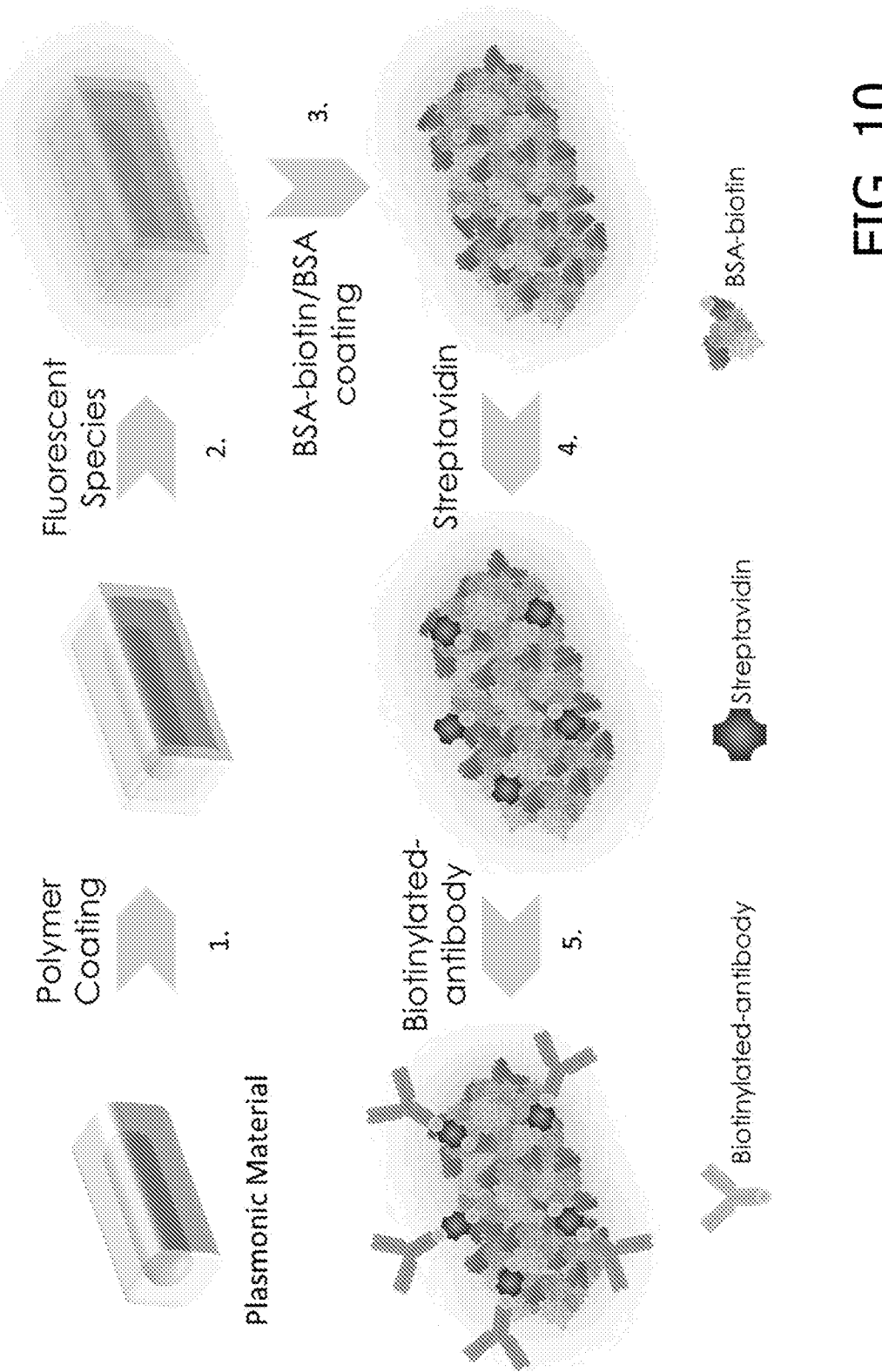
FIG. 10 is an exemplary embodiment of a plasmonic-fluor design in accordance with the present disclosure.

FIG. 10 shows an exemplary embodiment wherein a plasmonic nanostructure is first coated with a polymer (step 1) which serves as a spacer between the fluorescent species and the surface of the plasmonic nanostructure. At least one fluorescent species is then conjugated (step 2) to the polymer-coating such that the fluorescent species is maintained, on average, a distance of >0.5 nm from the surface of the plasmonic nanostructure. The plasmonic nanostructure and the fluorescent species are chosen such that there is significant overlap between the absorption spectrum of the plasmonic nanostructure and the excitation spectrum/absorption spectrum of the fluorescent species. The fluorescent nanocomposite resulting from step 2 is at least 500-fold brighter than an unattached, individual fluorescent species with which it is coated under suitable excitation and detection conditions. The fluorescent nanocomposite/nanoconstruct resulting from step 2 is then coated with a functional polymer layer (step 3), in this, example, bovine-serum albumin and biotinylated bovine serum albumin. The nanocomposite resulting from step 3 is a biotinylated plasmonic-fluor. The biotinylated plasmonic-fluor can be conjugated to at least one Streptavidin (step 4), yielding a streptavidin-plasmonic-fluor. Finally, this streptavidin-plasmonic-fluor can be further modified with at least one biotinylated antibody (step 5), to yield an antibody-conjugated-plasmonic-fluor.

Figure 11:
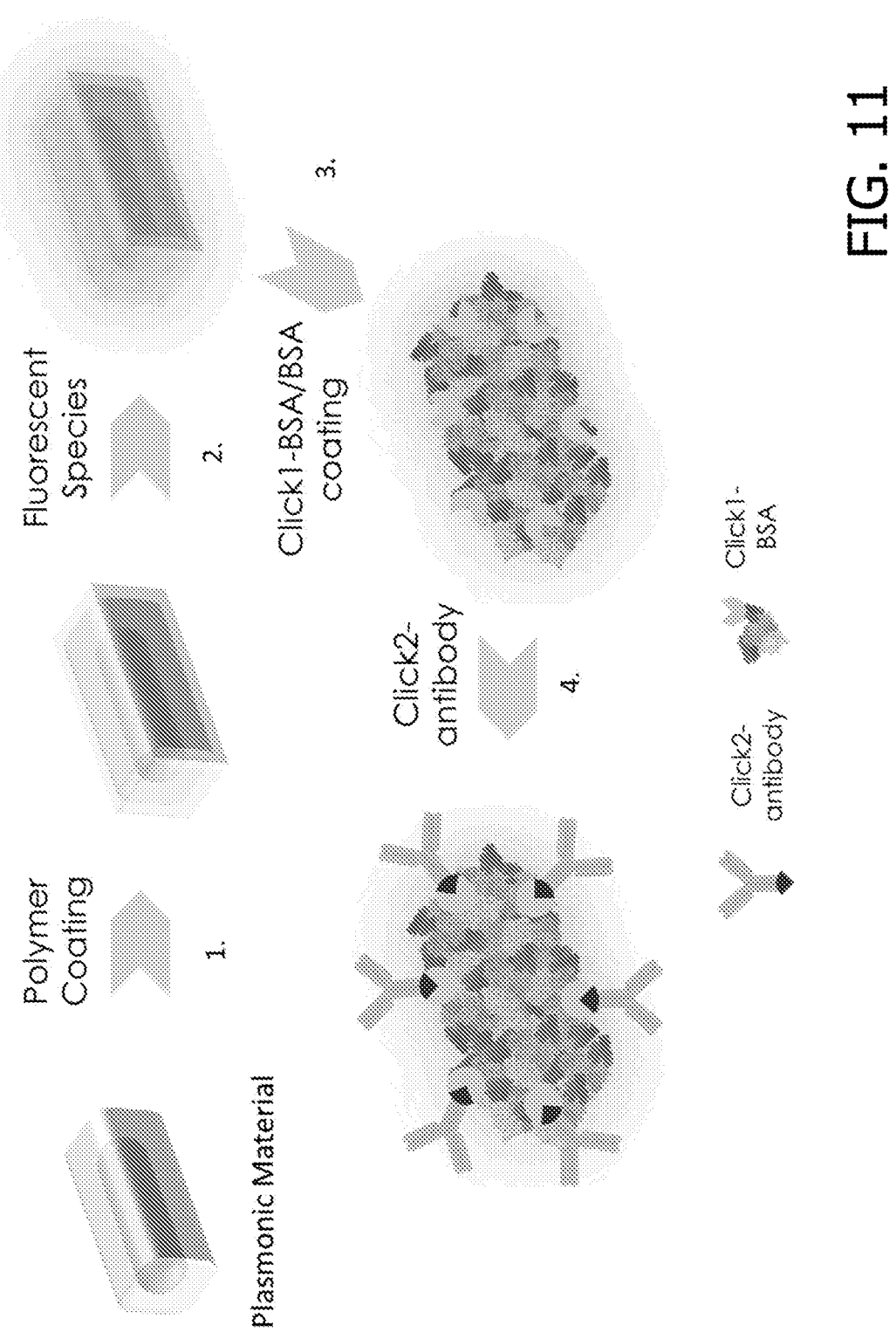
FIG. 11 is an exemplary embodiment of an alternative design of the plasmonic-fluor in accordance with the present disclosure.

FIG. 11 shows an exemplary embodiment wherein a plasmonic nanostructure is first coated with a polymer (step 1) which serves as a spacer between the fluorescent species and the surface of the plasmonic nanostructure. At least one fluorescent species is then conjugated (step 2) to the polymer-coating such that the fluorescent species is maintained, on average, a distance of >0.5 nm from the surface of the plasmonic nanostructure. The plasmonic nanostructure and the fluorescent species are chosen such that there is significant overlap between the absorption spectrum of the plasmonic nanostructure and the excitation spectrum of the fluorescent species. The fluorescent nanocomposite/nanoconstruct resulting from step 2 is at least 500-fold brighter than an unattached, individual fluorescent species with which it is coated under suitable and identical excitation and detection conditions. The fluorescent nanocomposite resulting from step 2 is then coated with a functional polymer layer (step 3), in this, example, bovine-serum albumin and bovine serum albumin conjugated with a reactive moiety suitable for use in a click-chemistry reaction, for example, trans-cyclooctene (TCO). The nanocomposite resulting from step 3 can be conjugated to at least one antibody by reacting an antibody which has been labeled with a click-chemistry compatible moiety complementary to that used in step 3, for example, a tetrazine, resulting in an antibody-plasmonic-fluor.

Figure 12:
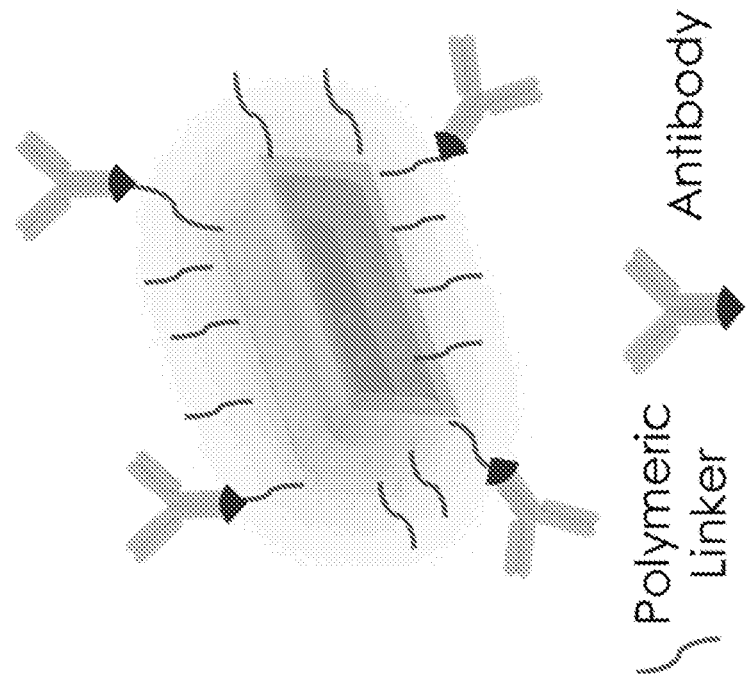
FIG. 12 is an exemplary embodiment of an additional alternative design of the plasmonic-fluor in accordance with the present disclosure.

FIG. 12 shows an additional alternative design wherein the biorecognition element, depicted herein as an antibody, is attached to the polymeric spacer layer through a linker moiety, for example polyethylene glycol. Other non-limiting examples of the biorecognition element are streptavidin, oligonucleotide, or aptamer. It should be noted that elements from FIGS. 9-12 can be mixed and matched. For example, it's possible that there is a polymeric linker like that depicted here which is also used with BSA as in FIGS. 9-11.

Silane-aldehydes can be used to link hydrazine-conjugated materials (PEG or fluorophores) to the spacer layer. In this case, silane aldehydes would be added during the spacer layer formation with TMPS/APTMS.

Figure 13:
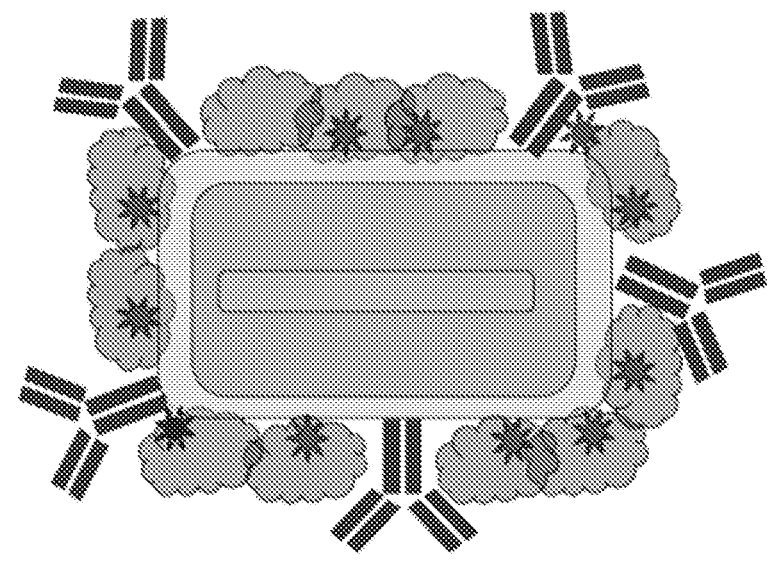
FIG. 13 is another exemplary embodiment of a plasmonic nanostructure in accordance with the present disclosure. The plasmonic nanostructure (gold nanorod coated with silver) is embedded in a dielectric material matrix. The dielectric material matrix is coated with a functional layer (blue clouds). Targeting agents (pink 'y'-shapes, e.g., antibodies) are conjugated to the functional layer.

FIG. 13 shows an example plasmonic nanostructure in a dielectric material matrix serving as a spacer layer/coating. The dielectric material matrix is coated with a functional layer (blue clouds). Targeting agents (pink 'y'-shapes, e.g., antibodies) are conjugated to the functional layer.

Figure 14:
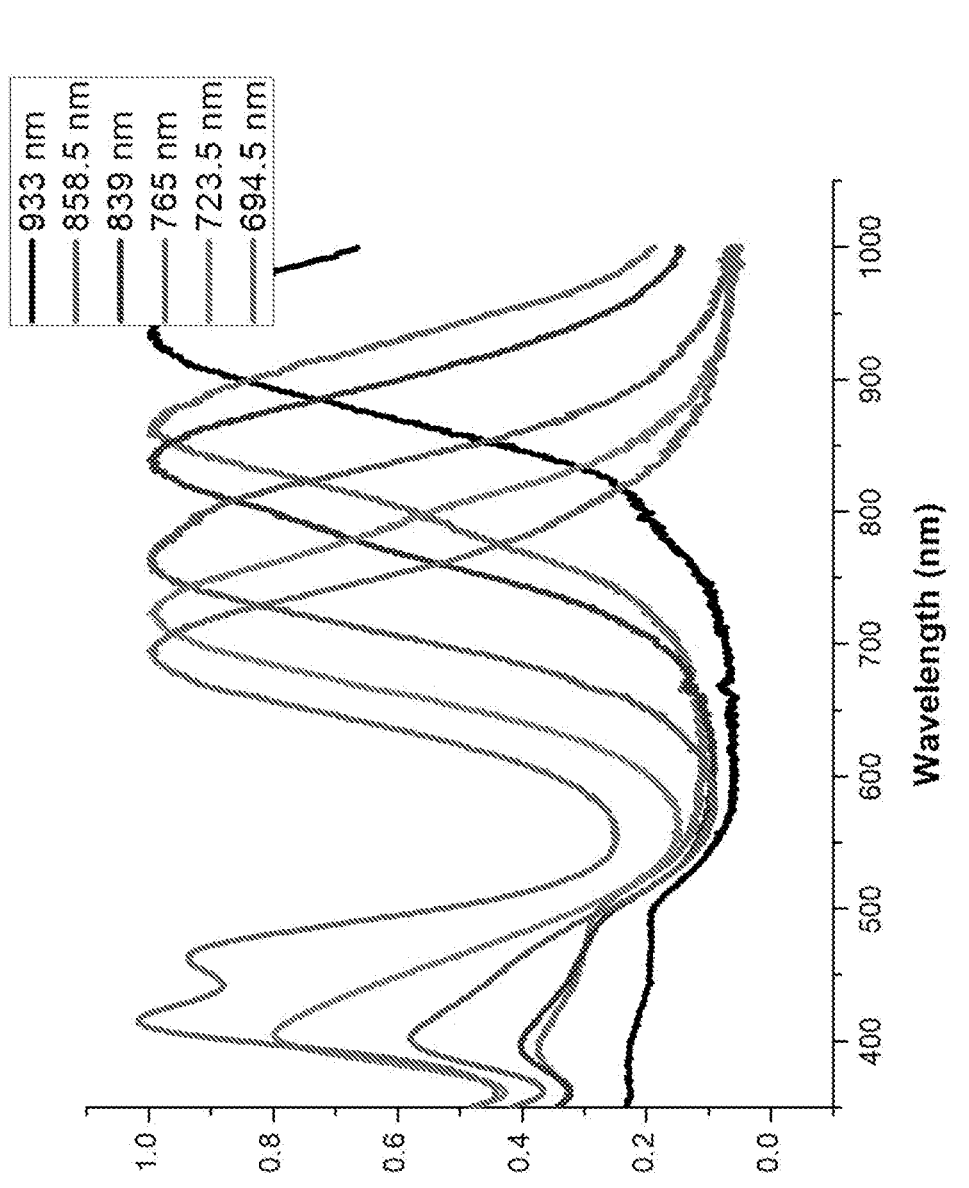
FIG. 14 is an exemplary embodiment of extinction spectra of plasmonic-fluors conjugated to IRDye 800CW (excitation maximum=784 nm) in accordance with the present disclosure.

FIG. 14 shows extinction spectra of plasmonic-fluors (AuNR coated with Ag plasmonic nanostructure) conjugated to IRDye 800CW (excitation maximum=784). The inset shows the LSPR maximum.

Figure 15:
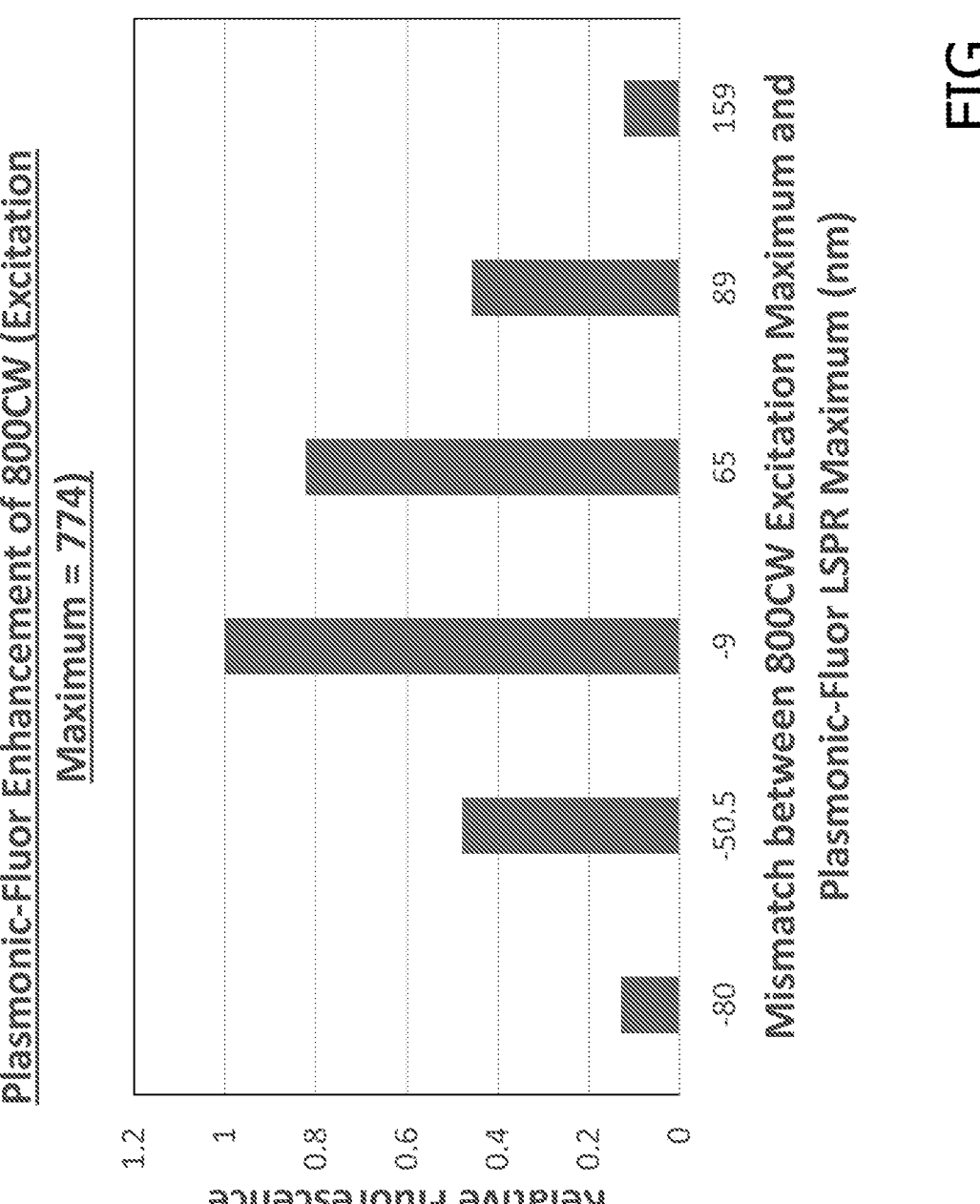
FIG. 15 is an exemplary embodiment of mismatch between the LSPR maximum of the plasmonic-fluor and the excitation maximum of IRDye 800CW in accordance with the present disclosure.

FIG. 15 shows the mismatch between the LSPR maximum of the plasmonic-fluor (AuNR coated with Ag plasmonic nanostructure) and the excitation maximum of IRDye 800CW shows significant influence of the resulting overall plasmonic-fluor brightness on the overlap between the plasmonic-fluor's LSPR maximum and the dye's excitation maximum.

Figure 16:
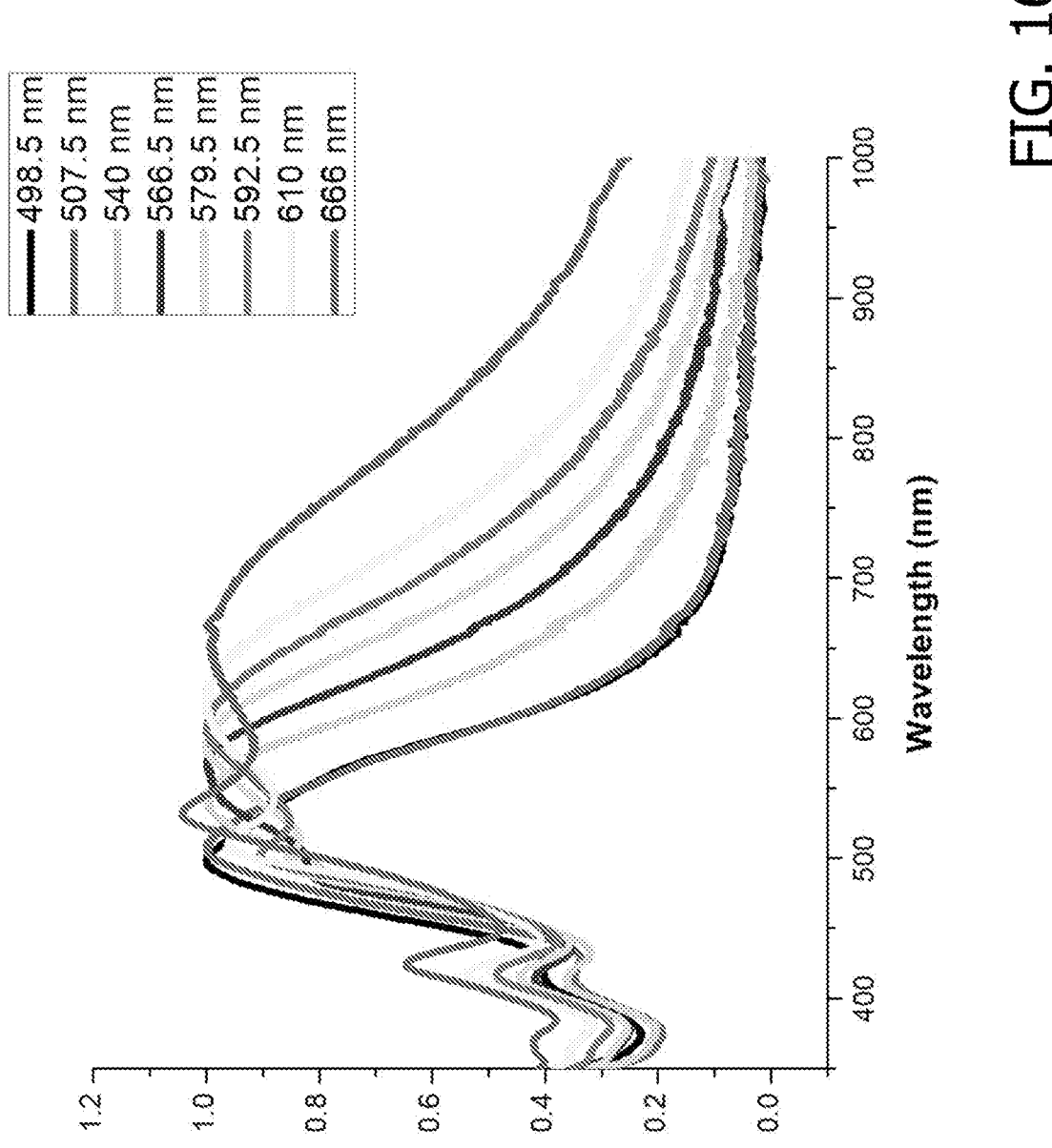
FIG. 16 is an exemplary embodiment of extinction spectra of plasmonic-fluors (AuNR@Ag cuboid plasmonic nanostructures) conjugated to Cy3 (excitation maximum=550 nm) in accordance with the present disclosure.

FIG. 16 shows extinction spectra of plasmonic-fluors (AuNR@Ag cuboid plasmonic nanostructure) conjugated to Cy3 (excitation maximum=550 nm). The inset shows the maximum LSPR wavelength.

Figure 17:
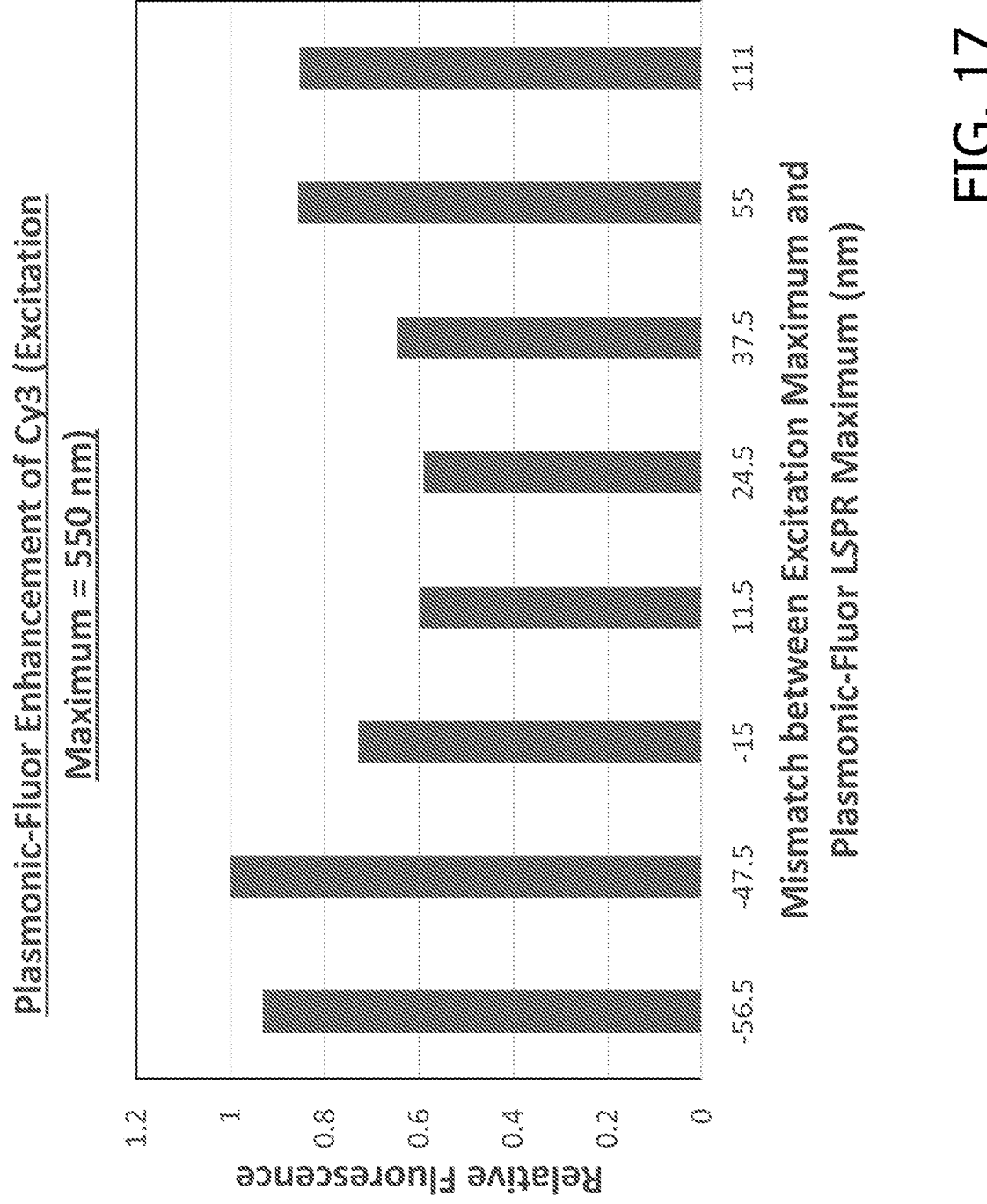
FIG. 17 is an exemplary embodiment of mismatch between the LSPR maximum of the plasmonic-fluor (AuNR@Ag cuboid plasmonic nanostructures) and the excitation maximum of Cy3 in accordance with the present disclosure.

FIG. 17 shows the mismatch between the LSPR maximum of the plasmonic-fluor (AuNR@Ag cuboid plasmonic nanostructure) and the excitation maximum of Cy3 shows much less significant influence of the resulting overall plasmonic-fluor brightness on the overlap between the plasmonic-fluor's LSPR maximum and the dye's excitation maximum. The reason for this is that all of the plasmonic-fluors with AuNR@Ag cuboid plasmonic nanostructure have significant absorption in the region of Cy3's excitation maximum (i.e. all of these structures show significant overlap with Cy3's excitation spectrum). Additionally, there exist multiple LSPR peaks for these nanostructures and some are in the region of Cy3's excitation maximum even if the LSPR peak with the highest amplitude is significantly different from Cy3's excitation maximum wavelength. Compared to the extinction spectra in FIG. 14 and to FIG. 15, for the plasmonic-fluors (AuNR coated with Ag plasmonic nanostructure) conjugated to IRDye 800CW, it is clear that an important parameter for significant enhancement is that the plasmonic-fluor has substantial absorption in the vicinity of the fluorescent dye's excitation maximum and the absorption spectrum of the plasmonic-fluor shows substantial overlap with the excitation spectrum of the dye.

Figure 18:
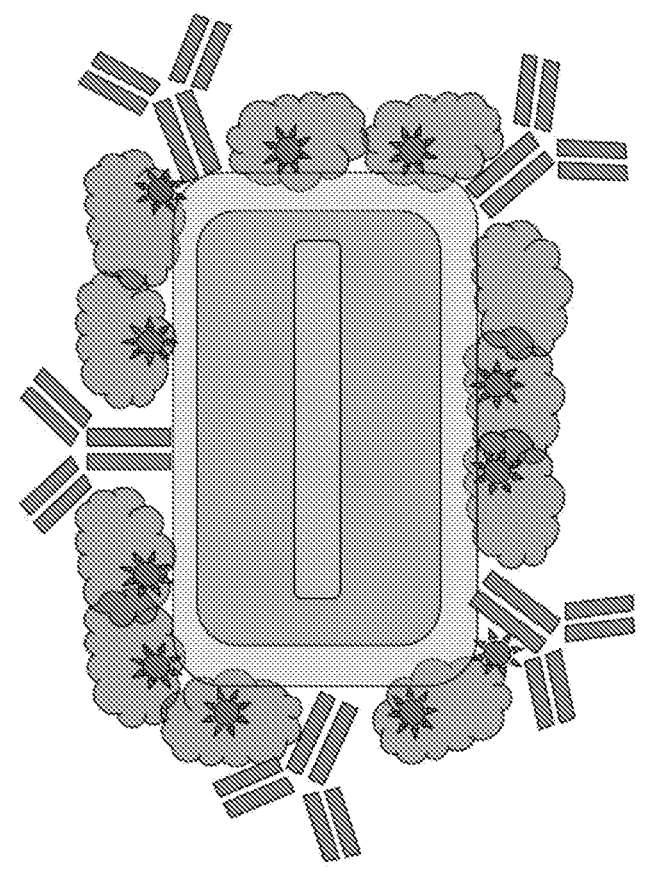
FIG. 18 is an exemplary embodiment of a plasmonic nanostructure in accordance with the present disclosure. The plasmonic nanostructure is covered in a dielectric matrix of a particular thickness (green shell). A fluorophore (red starburst) is attached directly to the outer surface of the dielectric matrix. Biorecognition elements (pink 'y'-shapes, e.g., antibodies) can be conjugated directly to the spacer, and the spacer can be covered with a functional layer material (blue clouds).

FIG. 18 shows a plasmonic nanostructure (gold nanorod coated with silver) covered in a dielectric matrix of a particular thickness (green shell). A fluorophore (red starburst) is attached directly to the outer surface of the dielectric matrix. Biorecognition elements (pink 'y'-shapes, e.g., antibodies) can be conjugated directly to the spacer, and the spacer can be covered with a functional layer material (blue clouds).

Example 6—Plasmonic-Fluor Preparation Procedure

In some embodiments, the plasmonic-fluor is prepared with Streptavidin and/or antibody-conjugated plasmonic-fluors. To have only BSA-biotin fluors, one can stop after Step 7. The steps are as follows:

Step 1: Calibration. Based on the extinction of the core plasmonic nanostructures, make a 40 mL solution with extinction 2 at the LSPR maximum.

Step 2: Interfacial layer. In a fume hood, add 40 µL of MPTMS to the plasmonic nanostructure solution and put it on orbital shaker for 1 hour at 125 RPM.

Step 3: Spacer layer. In a fume hood, add 160 µL of APTMS and invert the tube 10 times and add 160 µL of TMPS and invert it 10 times and put it on the orbital shaker for 4 hours. (So that the M:A:T ratio is 1:4:4 for this volume).

Step 4: Free monomer/polymer purification. Centrifuge solution from step 3. Spacer coated plasmonic nanostructures collects in pellet. Remove supernatant and replace with 1 mM CTAC to remove free silane.

Step 5: Dye labeling. To the above NP solution at a volume of 4 mL, extinction 20 at the LSPR maximum, add 250 µL of 10×PBS buffer, pH 7.4. Add 0.1-20 µL of NHS-ester conjugated dye molecule, and react for 1 hour at room temperature.

Step 6: Free dye purification. Centrifuge the dye labelled nanoparticle solution and remove supernatant.

Step 7: BSA/BSA-biotin coating. Resuspend nanoparticles from Step 6 in a solution of 5 mg/mL BSA-biotin (or a mixture of BSA-biotin and free BSA to alter biotin density) at a pH >6, mix well and incubate in 4° C. overnight under dark. Purify the coated nanoparticles from free BSA-biotin with centrifugation.

Step 8: Streptavidin coating. Resuspend particles from Step 7 in a solution of 10 mg/mL Streptavidin at pH >6 and shake for 2 hrs. Remove free Streptavidin via centrifugation.

Step 9: Antibody conjugation. Resuspend particles from Step 7 in a solution of 10 mg/mL biotinylated-Antibody at pH >6 and shake for 2 hrs. Remove free antibody via centrifugation.

For storage, resuspend in 1×PBS, pH 7.4 and store at 4 C.

Example 7—Nanostructures and Dye Combinations for Use in Plasmonic-Fluors

The following are sorted according to commonly used laser excitation wavelengths. One skilled in the art would appreciate that any excitation source that can be used to excite the conjugated fluorescent species could also be used to excite the plasmonic-fluor containing that species. It is important to note that the LSPR wavelength(s) of the optimal plasmonic nanostructure is/are generally blue-shifted (i.e. of a lower wavelength) relative to the optimal LSPR wavelength because the LSPR red-shifts after coating with spacer and functional layer. The resultant plasmonic-fluor has an absorption maximum close to the absorption maximum of the dye, and significant overlap in the plasmonic-fluor extinction spectrum and the excitation/absorption spectrum of the dye.

In some embodiments, with a laser excitation wavelength of 488 nm, suitable dyes include: Fluorescein/FITC/FAM, AlexaFluor 488, Atto 488, Bodipy, Cy2, and Oregon Green. In some embodiments, suitable plasmonic nanostructures include AuNR@Ag nanocuboids (built from a gold nanorod coated with silver) characterized by: length=92 nm (variable depending on LSPR, but size and LSPR are tightly linked in these particular plasmonic nanostructures, unlike AuNR where the LSPR is a function of the aspect ratio), width=63 nm (see above), and LSPR=460-510 nm.

In some embodiments, with a laser excitation wavelength of 532 nm or 543 nm, suitable dyes include: Cy3, AlexaFluor 532, AlexaFluor 543, AlexaFluor 555, Atto 532, Atto 550, Rhodamine/Tetramethylrhodamine/ Rhodamine6G/TAMRA/TRITC, Cy3.5. In some embodiments, suitable plasmonic nanostructures include: AuNR@Ag nanocuboids characterized by length=86 nm (variable depending on LSPR, but size and LSPR are tightly linked in these particular particles, unlike AuNR where the LSPR is a function of the aspect ratio), width=73 nm (see above), and LSPR=500-570 nm.

In some embodiments, with a laser excitation wavelength of 633 nm, suitable dyes include: Cy 5, Cy 5.5, Alexa fluor 633, Alexa fluor 647, Alexa fluor 660, and Atto 633. In some embodiments, suitable plasmonic nanostructures include: AuNR with LSPR=600-670 nm.

In some embodiments, with a laser excitation wavelength of 784 nm, suitable dyes yes include: IRDye 800CW (LI-COR), Cy 7.5, CF 770, CF 790, CF 800, CF 820, Alexa 790, and DyLight 800. In some embodiments, suitable plasmonic nanostructures include: and AuNR with LSPR of 720-800 nm.

Example 8

Figure 19:
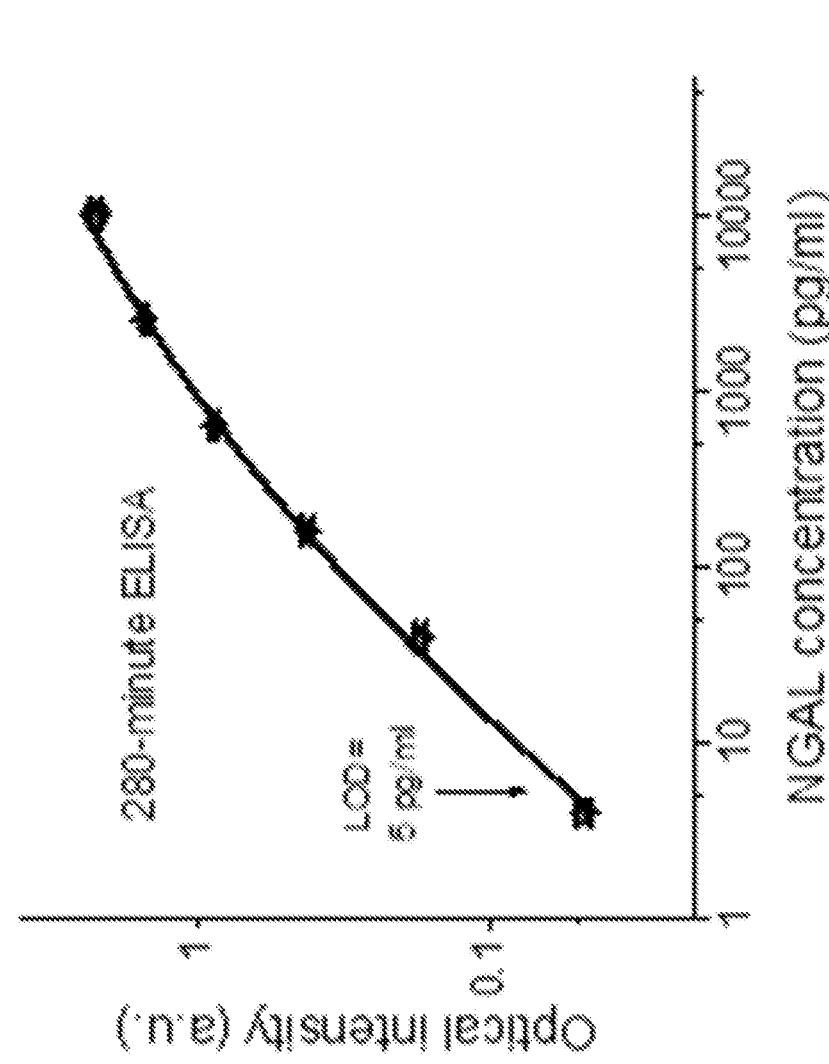
FIG. 19 is an exemplary embodiment of a plot showing the standard curve (dose-dependent colorimetric signal) of human NGAL ELISA taking 280 minutes for completion in accordance with the present disclosure.
Figure 20:
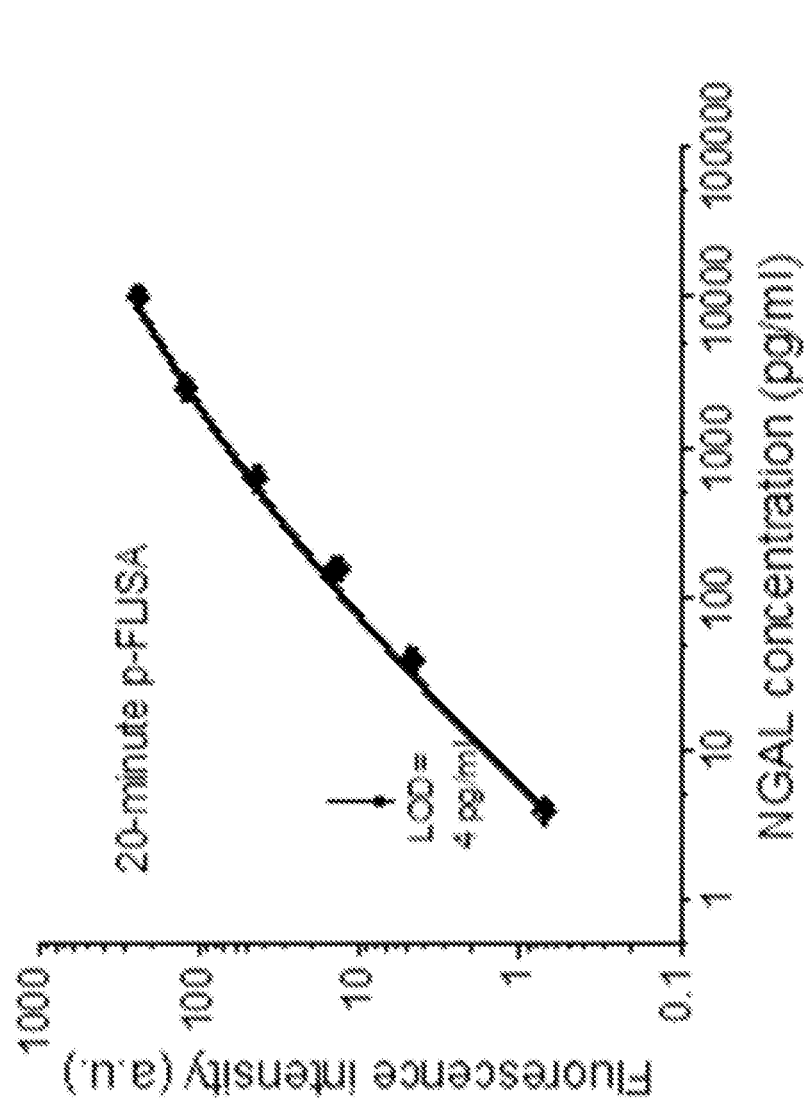
FIG. 20 is an exemplary embodiment of plots showing human NGAL dose-dependent fluorescence intensity from p-FLISA performed within 20 min in accordance with the present disclosure.
Figure 21:
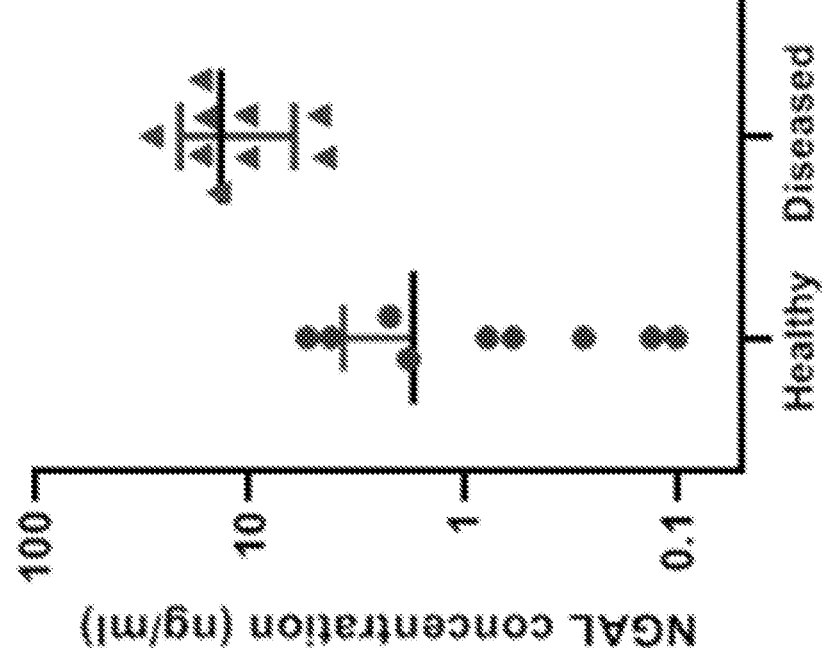
FIG. 21 is an exemplary embodiment of NGAL concentrations in urine samples from kidney patients and healthy volunteers as determined using p-FLISA completed within 20 min in accordance with the present disclosure.
Figure 22:
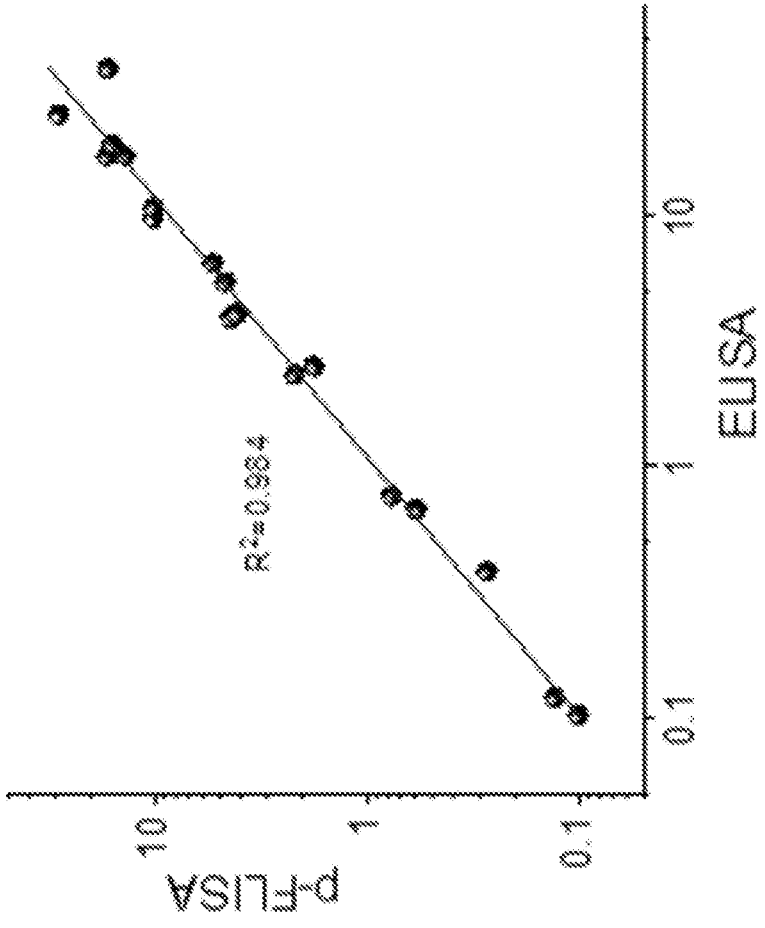
FIG. 22 is an exemplary embodiment of a plot showing the correlation between the concentrations of human NGAL determined using ELISA (280 min assay) and p-FLISA (20 min) in accordance with the present disclosure.

Using plasmonic-fluors, the time required to complete a sandwich immunoassay (compared to standard ELISA) can be significantly shortened while maintaining detection sensitivity similar to or even better than ELISA, as shown in FIGS. 19-22. FIGS. 19-22 show a comparison between conventional ELISA and p-ELISA for human NGAL detection and measurement. FIG. 19 shows a plot showing the standard curve (dose-dependent colorimetric signal) of human NGAL ELISA taking 280 minutes for completion. FIG. 20 is a plot showing human NGAL dose-dependent fluorescence intensity from p-FLISA performed within 20 min. Compared to conventional ELISA, the p-FLISA involving an ultrabright fluorescent nanoconstruct (plasmonic-fluor-800CW) could be completed within 10-fold shorter duration while achieving similar limit-of-detection. FIG. 21 shows NGAL concentrations in urine samples from kidney patients and healthy volunteers as determined using p-FLISA completed within 20 min. FIG. 22 is a plot showing the correlation between the concentration of human NGAL determined using ELISA (280 min assay) and p-FLISA (20 min) showing the excellent quantitative correlation ($R^2=0.984$) between the two methods. Summarized, a human NGAL detection assay can be completed in 20 min using plasmonic-fluor as opposed to the 280 min required for conventional ELISA (recommended by the vendor and validated by the experiments described herein). The 20-min assay based on plasmonic-fluor exhibited the same limit-of-detection as the 280-min ELISA.

Example 9—Ultrabright Plasmonic-Fluor as a Cross-Platform Nanolabel for Femtomolar Detection of Bioanalytes As noted throughout this disclosure, detection, imaging, and quantification of low abundant biomolecules within biological fluids, cells, and tissues is of fundamental importance but remains extremely challenging in biomedical research as well as clinical diagnostics. Harnessing plasmon-enhanced fluorescence, plasmonic-fluor-800CW exhibited nearly 6700-fold brighter signal compared to the streptavidin labeled with the corresponding near infrared (NIR) fluorophore (800CW). It should be noted that the fluorescently-labeled streptavidin can be labeled with one or more fluorescent dyes.

Figure 23:
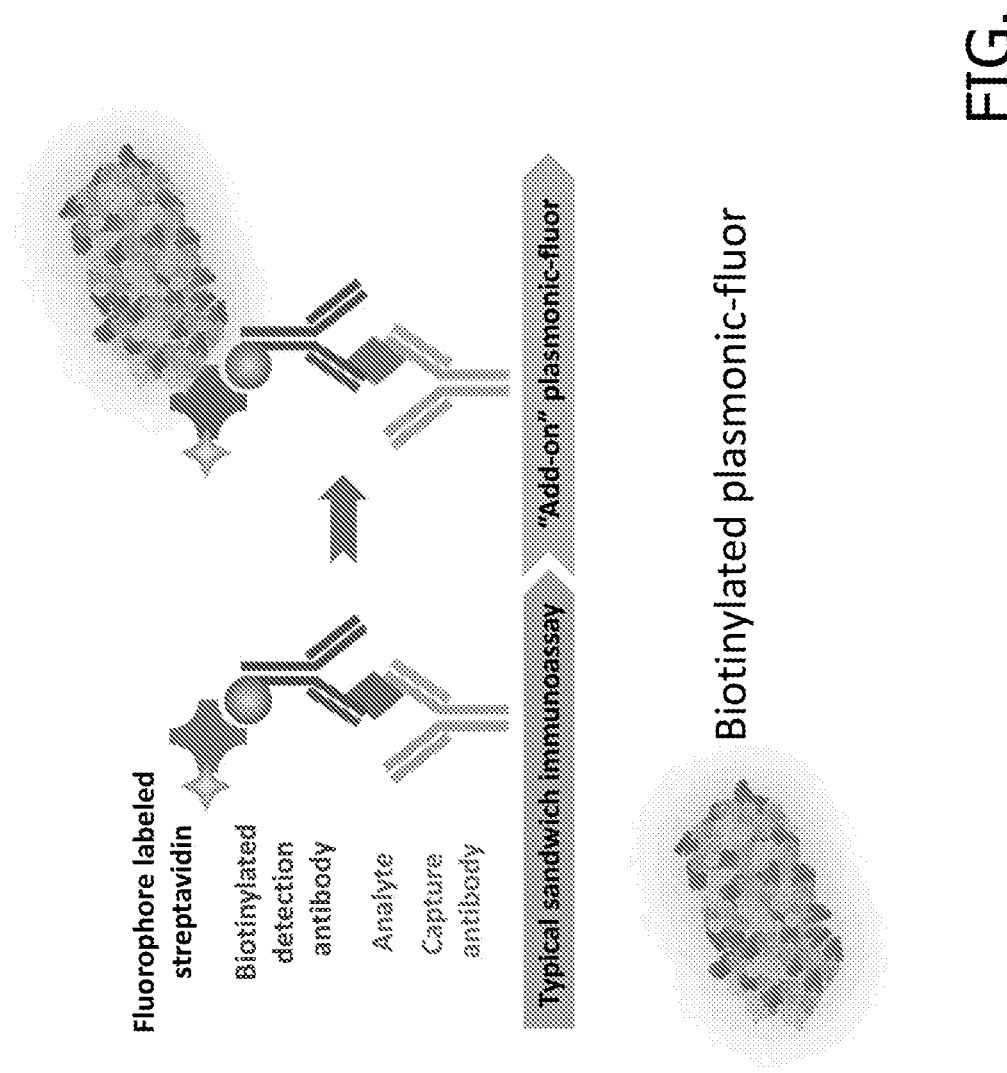
FIG. 23 is an exemplary embodiment of a generic, sandwich immunoassay using a biotinylated plasmonic-fluor in accordance with the present disclosure.
Figure 24:
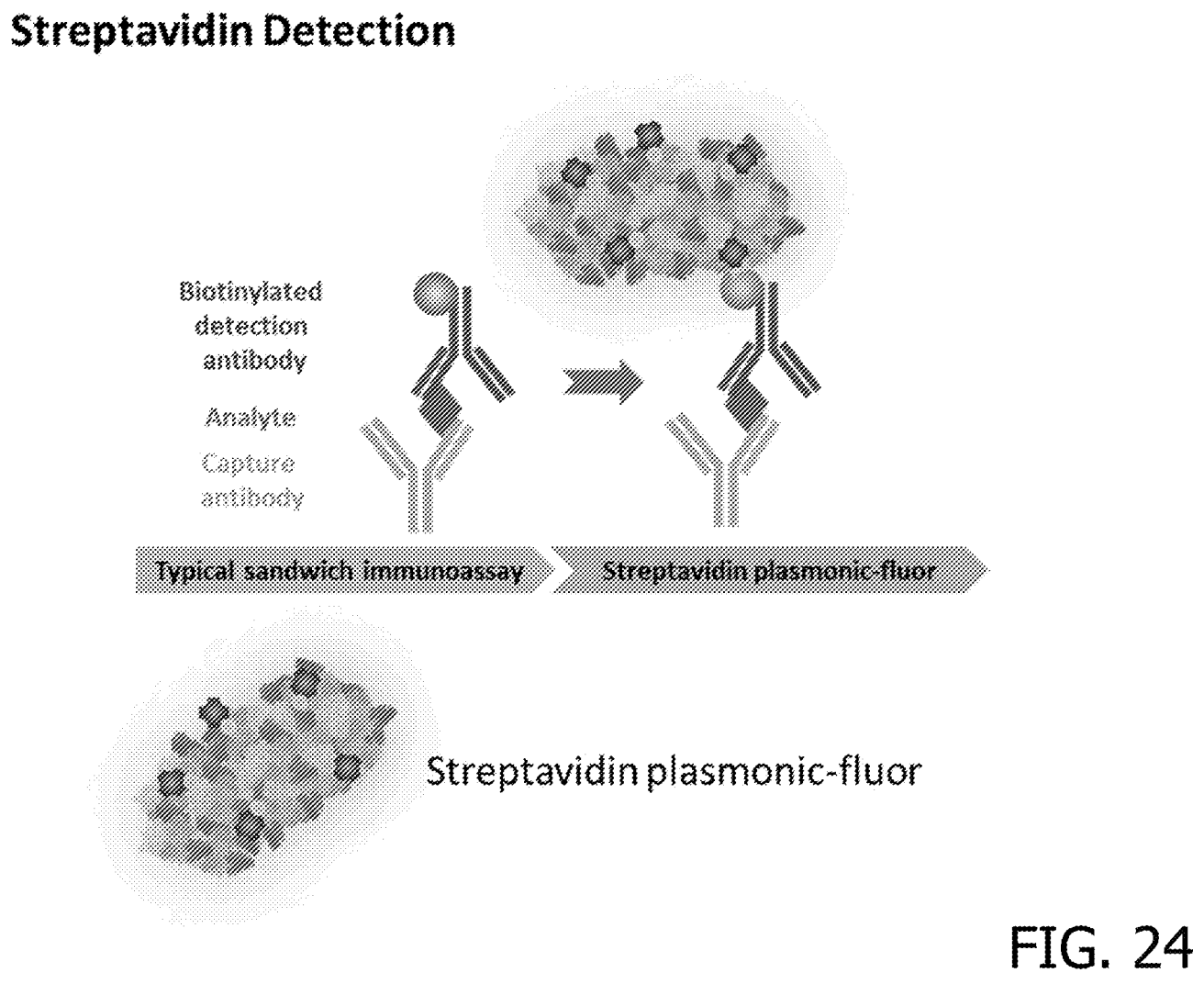
Figure 25:
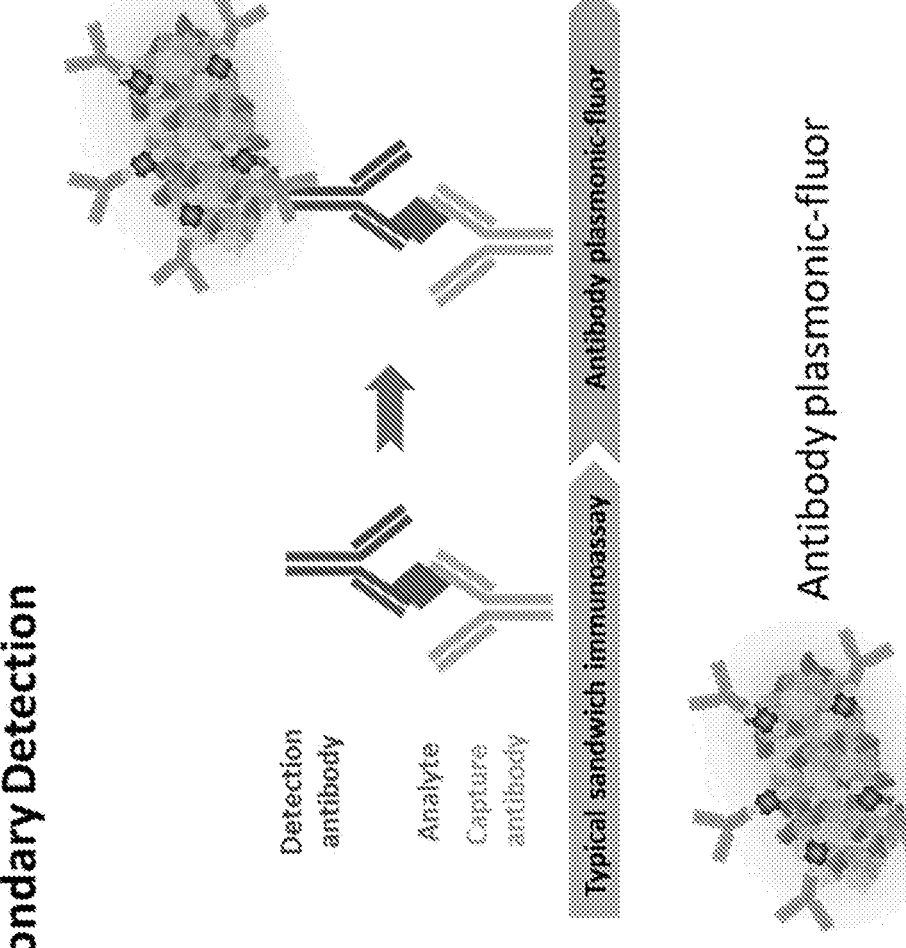
FIG. 25 is an exemplary embodiment of a generic, sandwich immunoassay using a secondary-antibody-conjugated plasmonic-fluor where the antibody conjugated to the plasmonic-fluor recognizes the detection antibody in accordance with the present disclosure.

FIG. 23 illustrates the working principle of plasmonic-fluor as an "add-on" biolabel to enhance the fluorescence intensity and consequent signal-to-noise ratio of fluorescence-based assays, without changing existing assay workflows. FIG. 24 is an exemplary embodiment of enhancement of a generic, sandwich immunoassay using a streptavidin-conjugated plasmonic-fluor in accordance with the present disclosure. FIG. 25 is an exemplary embodiment of a generic, sandwich immunoassay using a secondary-antibody-conjugated plasmonic-fluor where the antibody conjugated to the plasmonic-fluor recognizes the detection antibody in accordance with the present disclosure. FIG. 26 is an exemplary embodiment of a generic, sandwich immunoassay using a primary antibody-conjugated plasmonic-fluor where the antibody conjugated to the plasmonic-fluor recognizes the analyte in accordance with the present disclosure. It should be noted that the above examples of detection and readout are compatible with other assay types besides just sandwich immunoassay. If the antigen is bound to a surface (e.g. cell surface, membrane, substrate), the same generic detection schemes can be used

Example 10

Figure 27B:
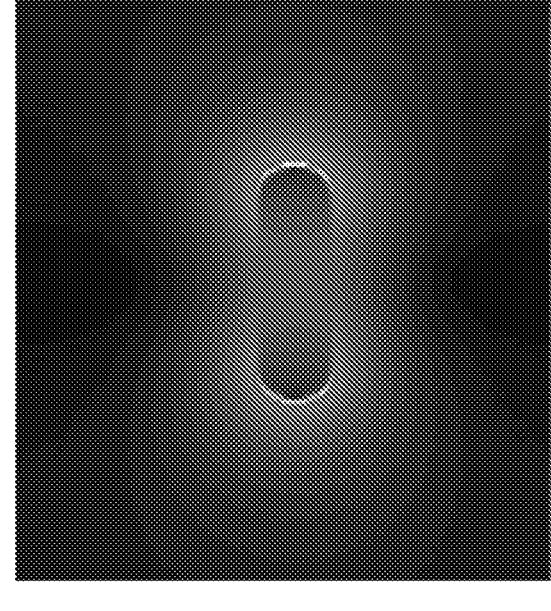
FIG. 27B is an exemplary embodiment of a finite-difference time-domain (FDTD) simulation showing the distribution of electric field intensity around the AuNR in accordance with the present disclosure.
Figure 27A:
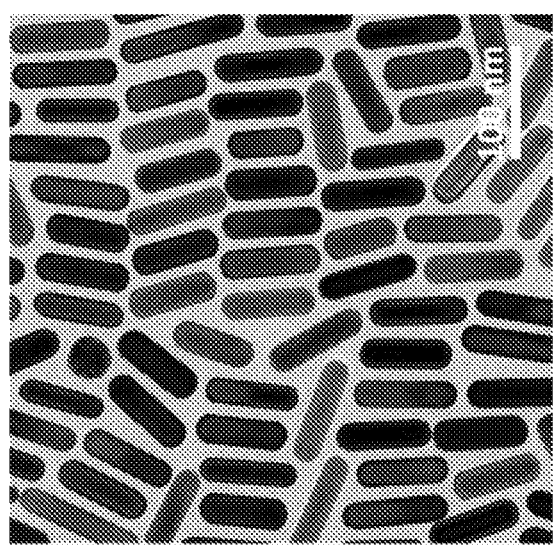
FIG. 27A is an exemplary embodiment of a TEM image of gold nanorod (AuNR) employed as the nanostructure in plasmonic-fluor-800CW in accordance with the present disclosure.
Figure 28:
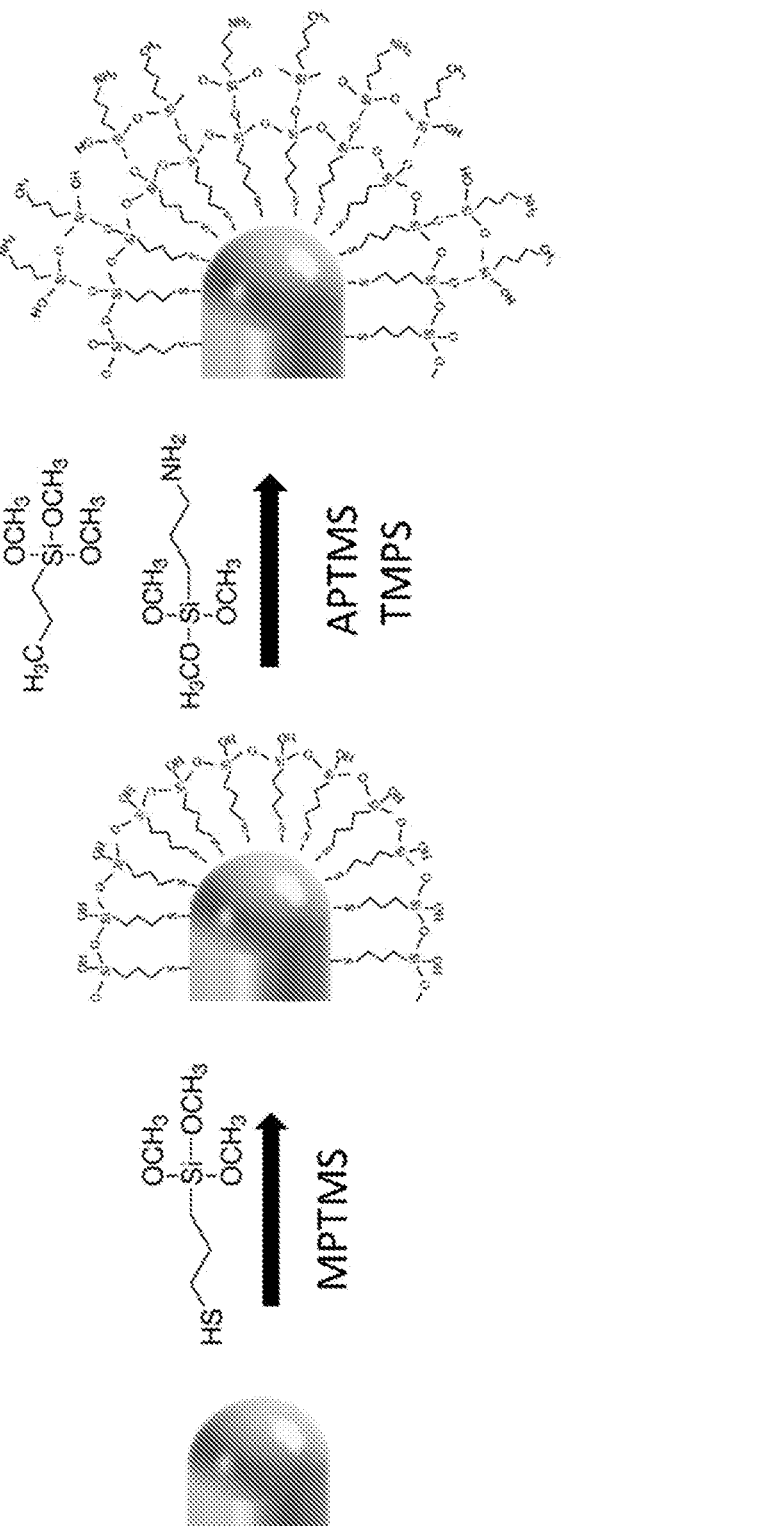
FIG. 28 is an exemplary embodiment of a schematic illustration showing the steps involved in the formation of polymer spacer on the plasmonic nanostructure AuNR in accordance with the present disclosure.
Figure 29:
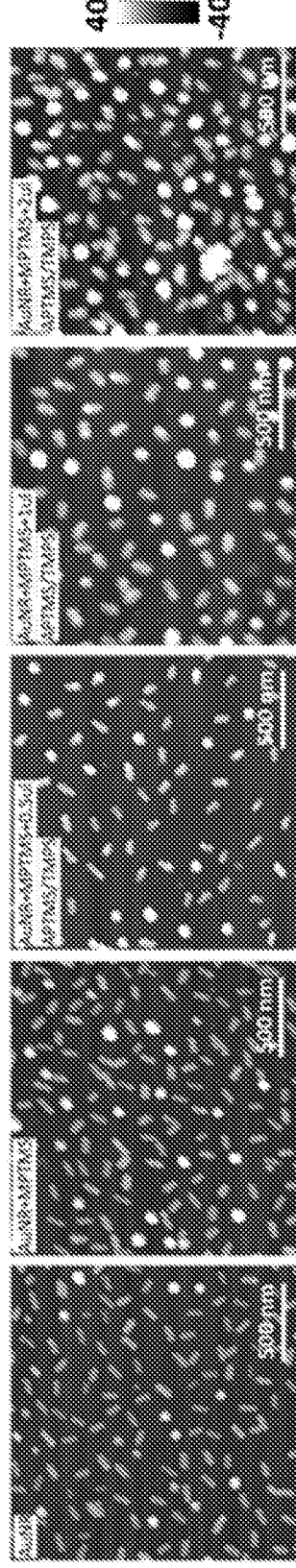
FIG. 29 is an exemplary embodiment of an AFM image depicting an increase in the diameter of AuNR/polymer under increasing amount of monomer (MPTMS, TMPS, and APTMS) in accordance with the present disclosure.
Figure 30:
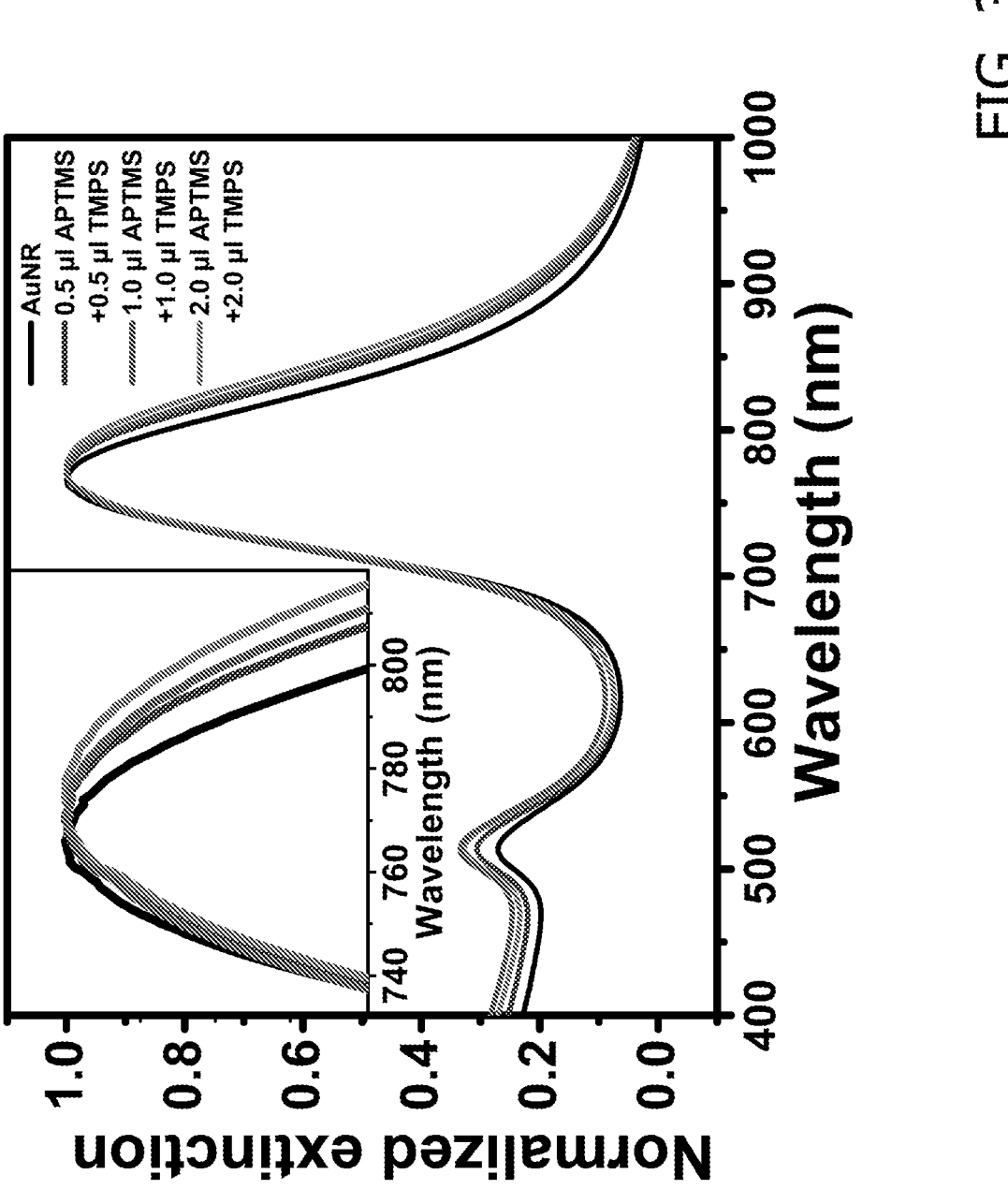
FIG. 30 is an exemplary embodiment of UV-vis spectra of AuNR under different polymerization conditions in accordance with the present disclosure.
Figure 31:
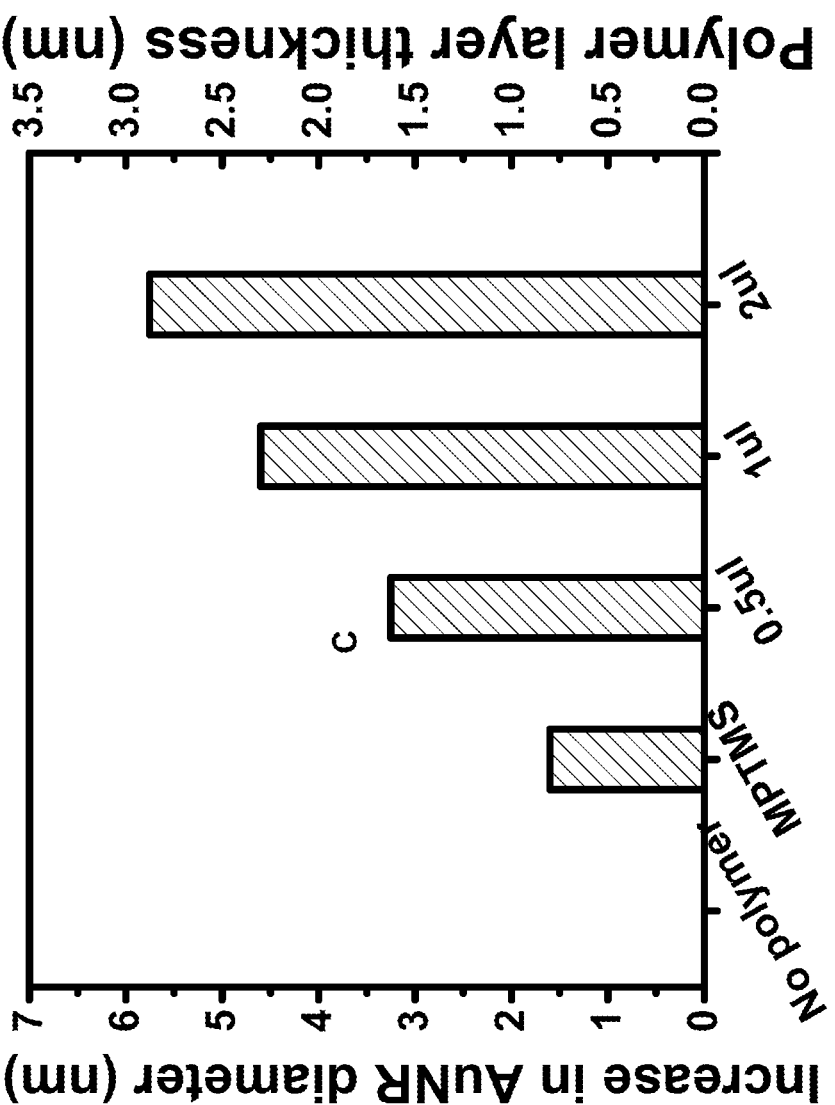
FIG. 31 is an exemplary embodiment of a plot showing an increase in the diameter of AuNR (two-fold higher than polymer layer thickness) under each polymerization condition measured from AFM images in accordance with the present disclosure.
Figure 32:
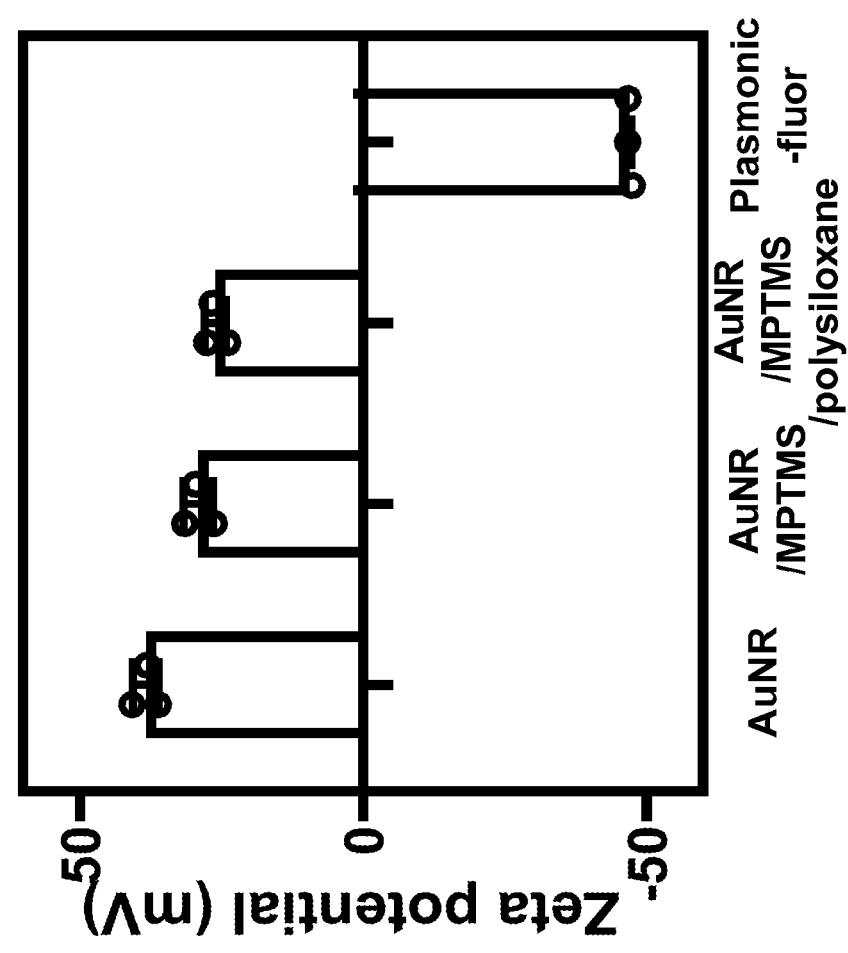
FIG. 32 is an exemplary embodiment of Zeta potential of AuNR, AuNR/MPTMS, AuNR/MPTMS/polysiloxane (AuNR/polymer), and the plasmonic-fluor-800CW (AuNR/polymer/BSA-biotin-800CW) in accordance with the present disclosure.

Gold nanorods (AuNRs) are employed as representative plasmonic nanostructure owing to the facile tunability of their longitudinal localized surface plasmon resonance (LSPR) wavelength with aspect ratio and large electromagnetic field enhancement at their ends (see FIG. 27(A-B)). FIG. 27A shows a TEM image of gold nanorod (AuNR) employed as the nanostructure in plasmonic-fluor-800CW. FIG. 27B is a finite-difference time-domain (FDTD) simulation showing the distribution of electric field intensity around the AuNR (polarization of the incident beam is along the long-axis of the AuNR). AuNRs (length 83.0±8.0 nm; diameter 24.3±1.8 nm) were modified with (3-mercaptopropyl)trimethoxysilane (MPTMS), which served as an interfacial layer for the copolymerization of two organosilane monomers, namely (3-aminopropyl)trimethoxysilane (APTMS) and trimethoxypropylsilane (TMPS) (FIG. 28). FIG. 28 is a schematic illustration showing the steps involved in the formation of polymer spacer on AuNR. In aqueous media, APTMS and TMPS undergo rapid hydrolysis and subsequent condensation around the MPTMS-modified AuNRs, yielding an amorphous copolymer network (FIG. 28). The siloxane copolymer serves as a spacer layer between metal surface and the fluorophore to prevent fluorescence quenching. This sol-gel approach enables facile control over the thickness of the spacer layer down to 1 nm, as evidenced by atomic force microscopy (AFM) (FIGS. 29-31). FIG. 29 is an AFM image depicting an increase in the diameter of AuNR/polymer under increasing amount of monomer (MPTMS, TMPS, and APTMS). FIG. 30 shows UV-vis spectra of AuNR under different polymerization conditions. FIG. 31 is a plot showing an increase in the diameter of AuNR (two-fold higher than polymer layer thickness) under each polymerization condition measured from AFM images. Modification of AuNRs with MPTMS and subsequent polymerization of APTMS/TMPS reduced the Zeta potential of cetyl trimethylammonium bromide (CTAB)-capped AuNR from +38.4±2.3 mV to +29±2.6 mV and +25.8±1.9 mV, respectively, due to the partial replacement of the positively charged capping agent (CTAB) with less charged siloxane copolymer (FIG. 32). FIG. 32 shows Zeta potential of AuNR, AuNR/MPTMS, AuNR/MPTMS/polysiloxane (AuNR/polymer), and the plasmonic-fluor-800CW (AuNR/polymer/BSA-biotin-800CW). Error bar represents s.d. (n=3 repeated tests).

Example 11

Figures 33A, 33B:
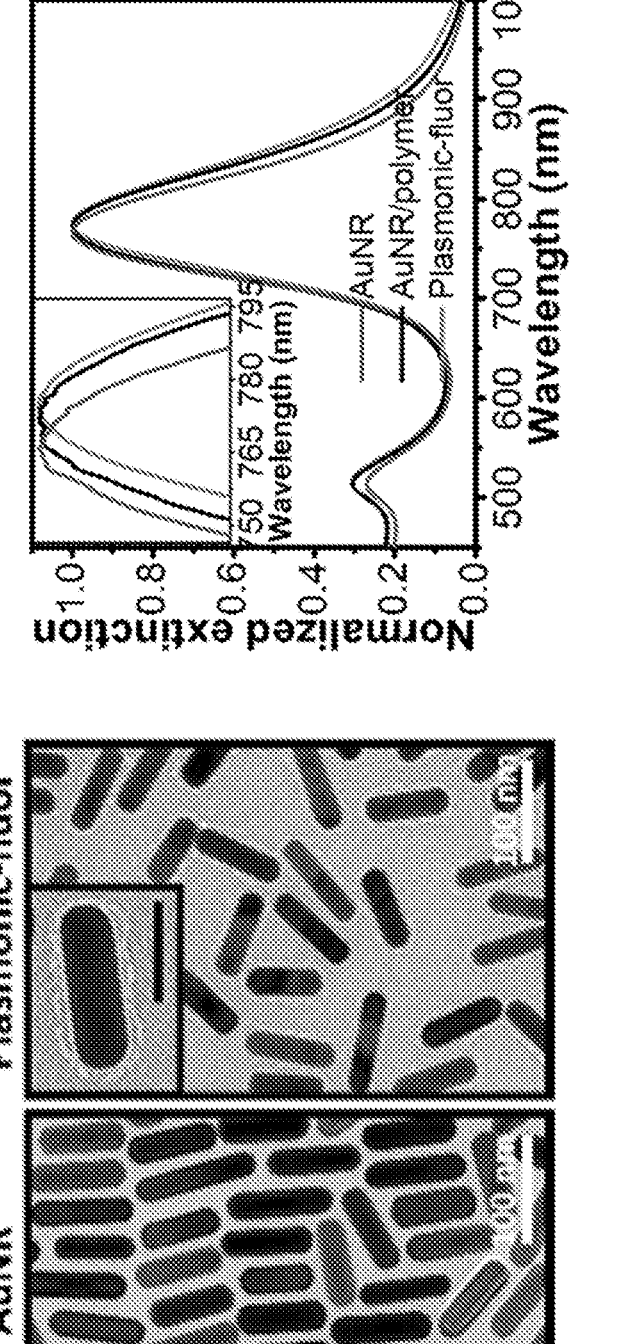
FIG. 33A and FIG. 33B are exemplary embodiments of PF-800CW TEM and extinction spectra in accordance with the present disclosure.

Near infrared (NIR) fluorophore 800CW and biotin were conjugated to BSA through carbodiimide coupling chemistry to realize conjugates with protein/biotin/fluorophore ratio of 1:8.7:1.2. Due to the stronger affinity to avidin, biotin replaces the HABA bound to avidin and causes a decrease in the absorbance intensity. The absorbance values at 780 nm and 280 nm were employed to quantify the dye to BSA ratio. Subsequently, the BSA-biotin-800CW conjugates are adsorbed on polysiloxane-coated AuNR through electrostatic, hydrophobic and hydrogen bonding interactions between BSA and the functional groups ($—NH3+$, $—CH3$, $—OH$) of the polysiloxane layer to realize plasmonic-fluor-800CW. As formed plasmonic-fluor-800CW exhibited a negative charge (Zeta potential −46.9±0.5 mV at pH=10) due to abundant carboxylic acid groups in BSA with an isoelectric point of 4.7 (FIG. 32). LSPR wavelength of AuNR exhibited a progressive red shift of 2.6 nm and 2.7 nm with the formation of polymer spacer layer and BSA-biotin-800CW adsorption, respectively (FIG. 33(A-B)). FIG. 33(A-B) shows a PF-800CW TEM image and extinction spectra.

Following the structural characterization of plasmonic-fluor-800CW, the brightness of the fluorescent nanoconstruct was determined. The excited state fluorescence lifetimes of free 800CW (conjugated to BSA) and plasmonic-fluor-800CW were measured to be 0.74±0.01 ns and 0.179±0.001 ns, respectively, accounting to a 7-fold increase in the quantum yield (from ~11% to ~79%, as calculated herein). To further understand the brightness of plasmonic-fluor-800CW, the number of fluorophores conjugated to a single AuNR was estimated. Plasmonic-fluor-800CW at concentration of 76.2 pM (extinction of ~0.63) is comprised of ~16 nM 800CW (as calculated herein). Therefore, it is estimated that approximately 210 fluorophores are conjugated to a single AuNR. Notably, fluorescence intensity from 76.2 pM plasmonic-fluor-800CW (containing 16 nM 800CW) was found to be equivalent to the fluorescence intensity from 544 nM 800CW (measured based on FIG. 2). The difference in the slopes of two curves indicates that a single plasmonic-fluor-800CW is as bright as 6700 (±900) fluorophores. Therefore, it can be concluded that each 800CW is enhanced by nearly 30-fold due to the presence of plasmonic nanostructure. Error bar represents s.d. (n=3 repeated tests). This represents an enhancement of about 30-fold per attached fluorophore. This result was obtained for a plasmonic-fluor wherein the 800CW is conjugated to the functional layer, BSA. FIG. 2 shows fluorescence intensity of conventional fluor-800CW and plasmonic-fluor-800CW at their different molar concentrations, wherein this plasmonic-fluor 800CW has the 800CW attached directly to the spacer layer which was ~2-4 nm thick. The difference in the slopes on a plot of the fluorescence intensity of an AuNR-based plasmonic-fluor conjugated with 800CW versus the unconjugated 800CW, free in solution, as a function of the fluorescent species concentration indicates that plasmonic-fluor 800CW is ~20,000× brighter than free 800CW. These data were collected on an Azure Sapphire scanner with the same excitation and emission conditions for the plasmonic fluor and the free 800CW (excitation at 784 nm and detection through a bandpass filter centered at 832 nm with a width of 37 nm). The observed intense emission can be attributed to the enhanced electromagnetic field (local excitation field) at the surface of the plasmonic nanostructures (FIG. 27(A-B)) and decrease in the fluorescence lifetime due to the coupling between excited fluorophores and surface plasmons of the nanostructures.

Figure 34:
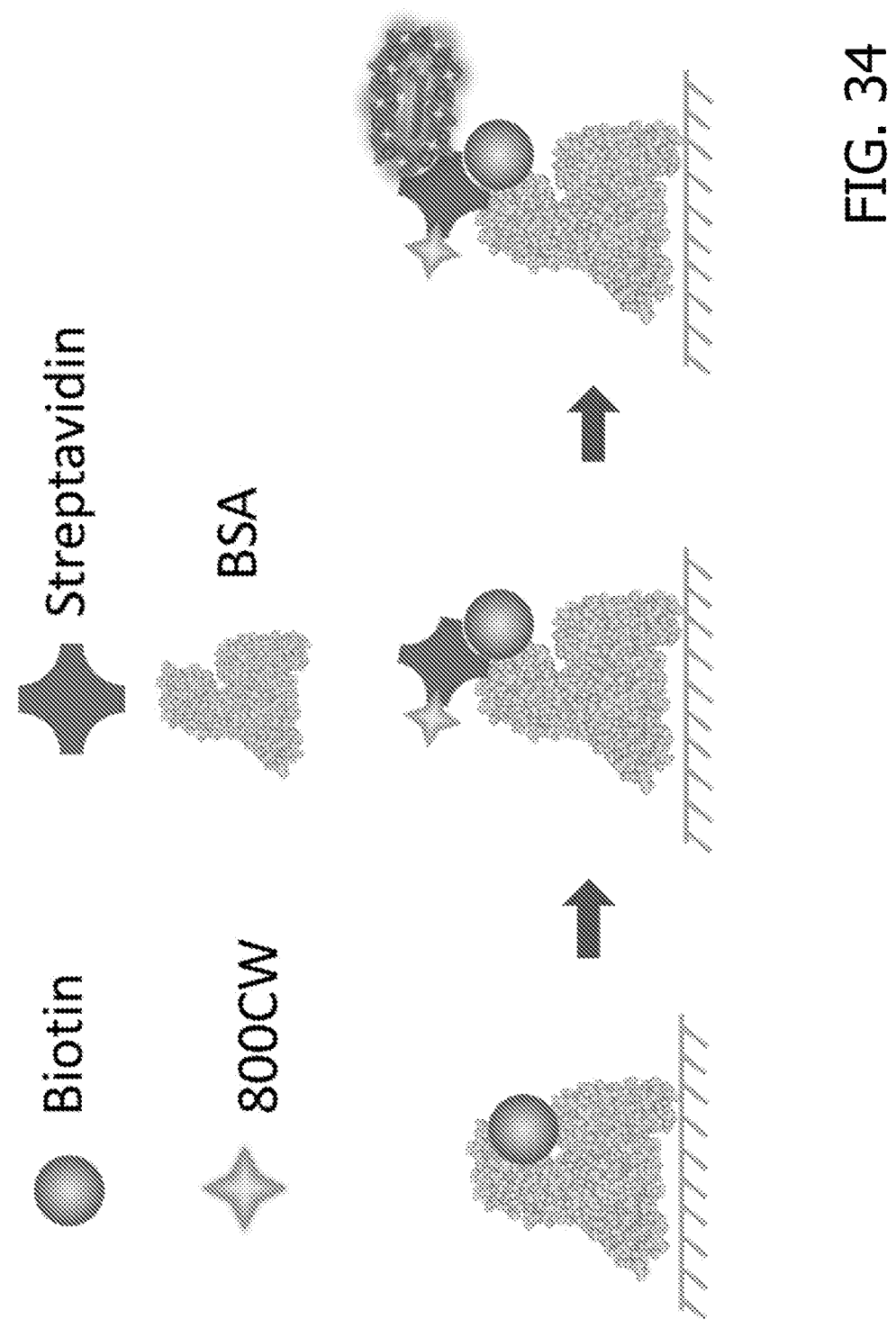
FIG. 34 is an exemplary embodiment of a schematic illustration (not to scale) showing the model system based on the binding events that occur in fluorophore-labeled immunosorbent assay in accordance with the present disclosure.

The feasibility was tested of using plasmonic-fluor-800CW as ultrabright fluorescent reporters by binding them to a substrate coated with streptavidin-800CW as shown in FIG. 34, which is a schematic illustration (not to scale) showing the model system based on the binding events that occur in this test. Binding of plasmonic-fluor-800CW resulted in an average of 1200 (±40)-fold increase in the ensemble fluorescence intensity compared to streptavidin-800CW shows fluorescence intensity of 800CW-streptavidin followed by the specific binding of plasmonic-fluor-800CW through biotin-streptavidin interaction, showing an average of 1200 (±40)-fold increase in fluorescence intensity. Significant signal enhancement was achieved by using a relatively low concentration of the plasmonic-fluors (76 pM). It should be noted that in all of the immunoassays, to further validate the plasmonic enhancement of fluorescence, "off-resonant" gold nanoparticle (AuNP) with similar surface area as the "on resonant" AuNR (7850 nm2/AuNP; 8064 nm2/AuNR) was employed (see FIG. 5(A-B)). To illustrate the importance of overlap of the absorbance of the plasmonic nanostructure and the absorbance/excitation spectrum of the conjugated dye, plasmonic-fluors were created using either a gold sphere, AuNP, and a gold nanorod, AuNR as the plasmonic nanostructure core, 800CW as the conjugated fluorescent species bound to BSA and then adsorbed to the spacer layer, and biotin as the biorecognition element. Their respective extinction spectra and the absorption/excitation and emission spectra of 800CW are shown in the plot to the left. The resultant fluorescence of the same concentration of material excited at 784 nm is shown in the plot to the right. The AuNP shows some increased fluorescence relative to the fluor, 800CW, alone, but is nearly 100-fold less bright than the plasmonic-fluor with AuNR as the core plasmonic nanostructure. Not surprisingly, AuNP-plasmonic-fluor-800CW resulted in only 18-fold enhancement in the fluorescence intensity, which is ~70-fold lower than that obtained with AuNR-plasmonic-fluor-800CW, confirming the plasmon enhanced fluorescence (FIG. 5(A-B)).

FIG. 1 shows the difference in the slopes on a plot of the fluorescence intensity of an AuNR@Ag nanocuboid-based, plasmonic-fluor conjugated with Cy3 versus the unconjugated Cy3, free in solution, as a function of the concentration indicates that plasmonic-fluor Cy3 is ~10,000× brighter than free Cy3. These plasmonic-fluors had the dye directly conjugated to the polymer spacer layer, which was ~2-nm thick. These data were collected on a BioTek Synergy H1 with the same excitation and emission conditions for the plasmonic-fluor and the free Cy3 (excitation at 530 nm and detection at 570 nm).

Figure 35:
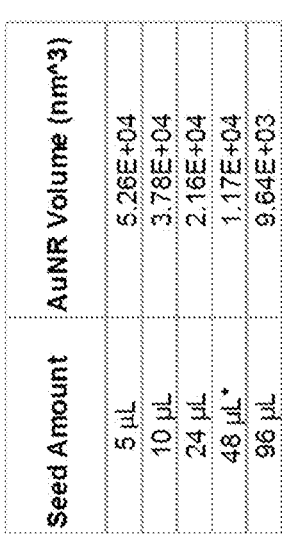
FIG. 35 is an exemplary embodiment of various volumes of core AuNR plasmonic nanostructures for enhancing 800CW in accordance with the present disclosure.
Figure 35:
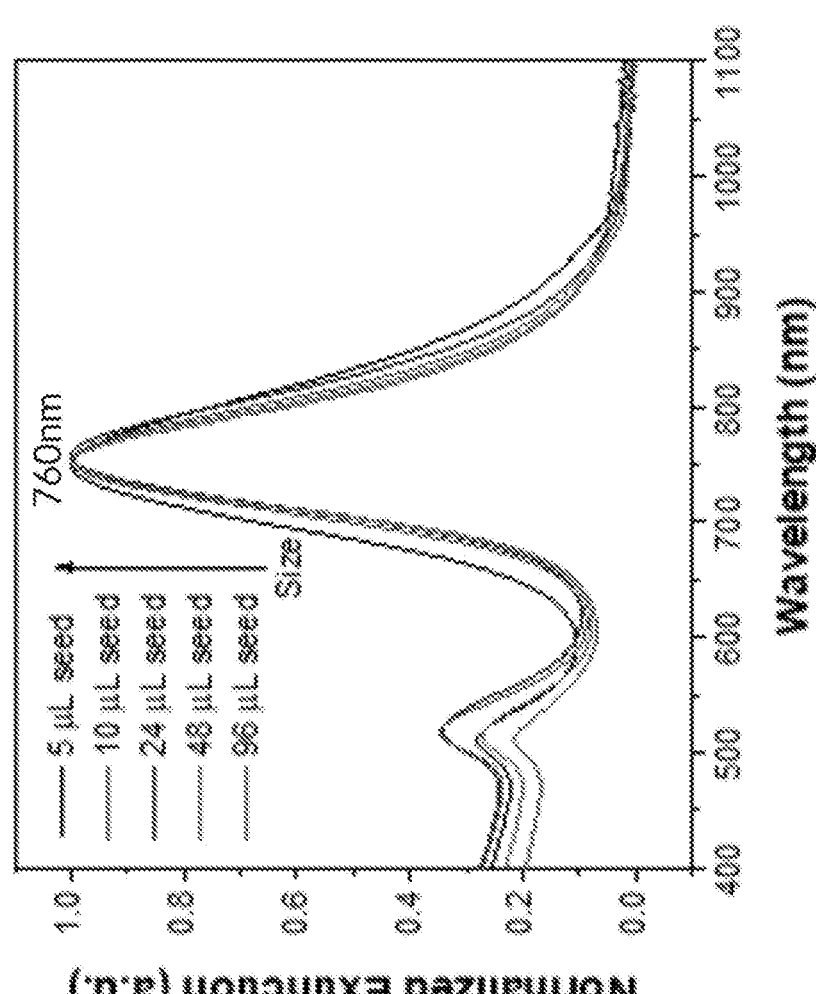
Figure 36:
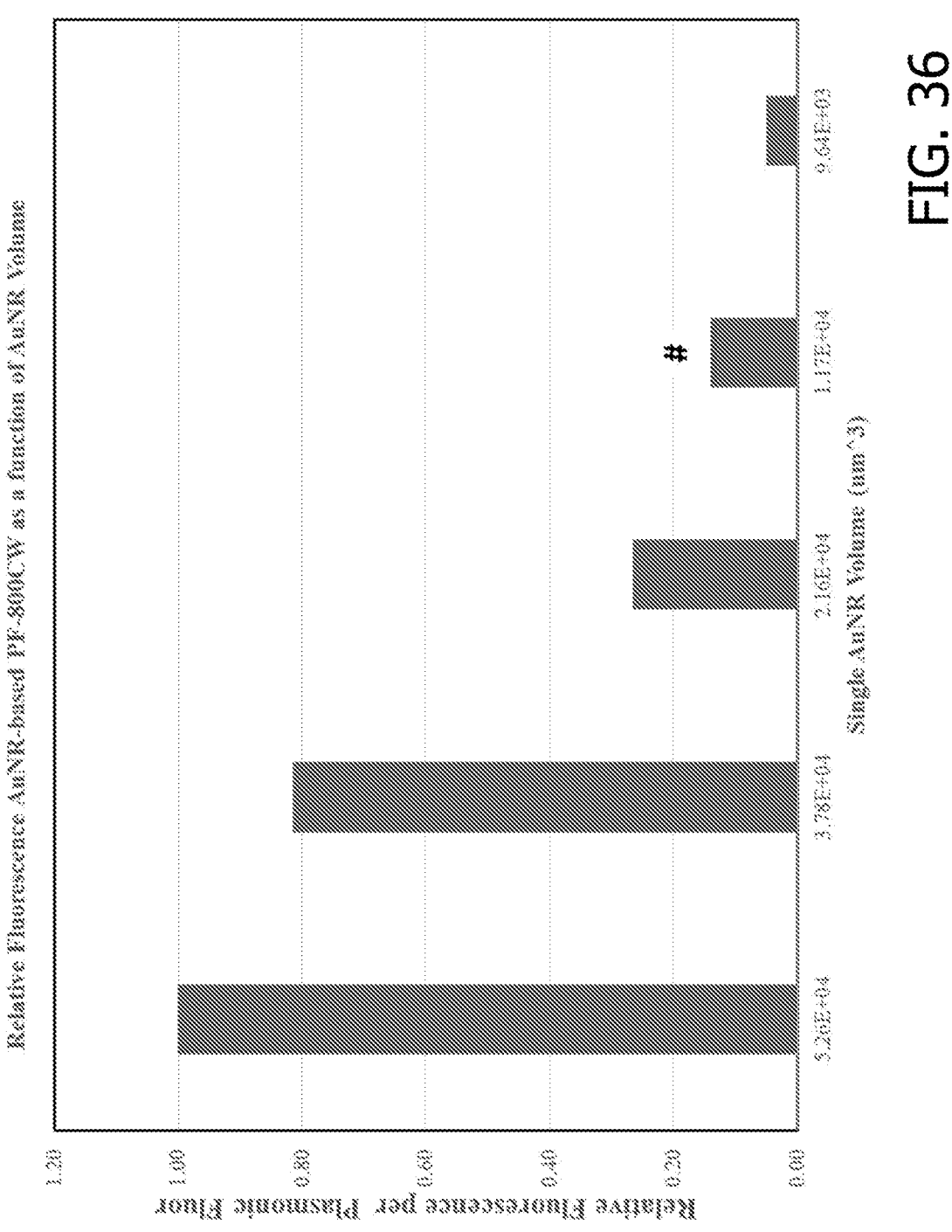
FIG. 36 is an exemplary embodiment of various volumes of core AuNR plasmonic nanostructures for enhancing 800CW in accordance with the present disclosure.

FIG. 35 and FIG. 36 show various volumes of core AuNR particles for enhancing 800CW, created by adjusting the seed amount added. The most commonly used seed amount in the plasmonic nanoparticle literature is 48 μL. Plasmonic-fluors were created from the various AuNR core particles and 800CW, and after normalizing to the same molar concentration, the fluorescence intensity was measured using an Azure Sapphire scanner with an excitation wavelength of 784 nm and detection through a bandpass filter centered at 832 nm with a width of 37 nm. The larger AuNR has a significantly higher brightness than the most commonly used AuNR for the same LSPR wavelength (indicated by #).

Figure 37:
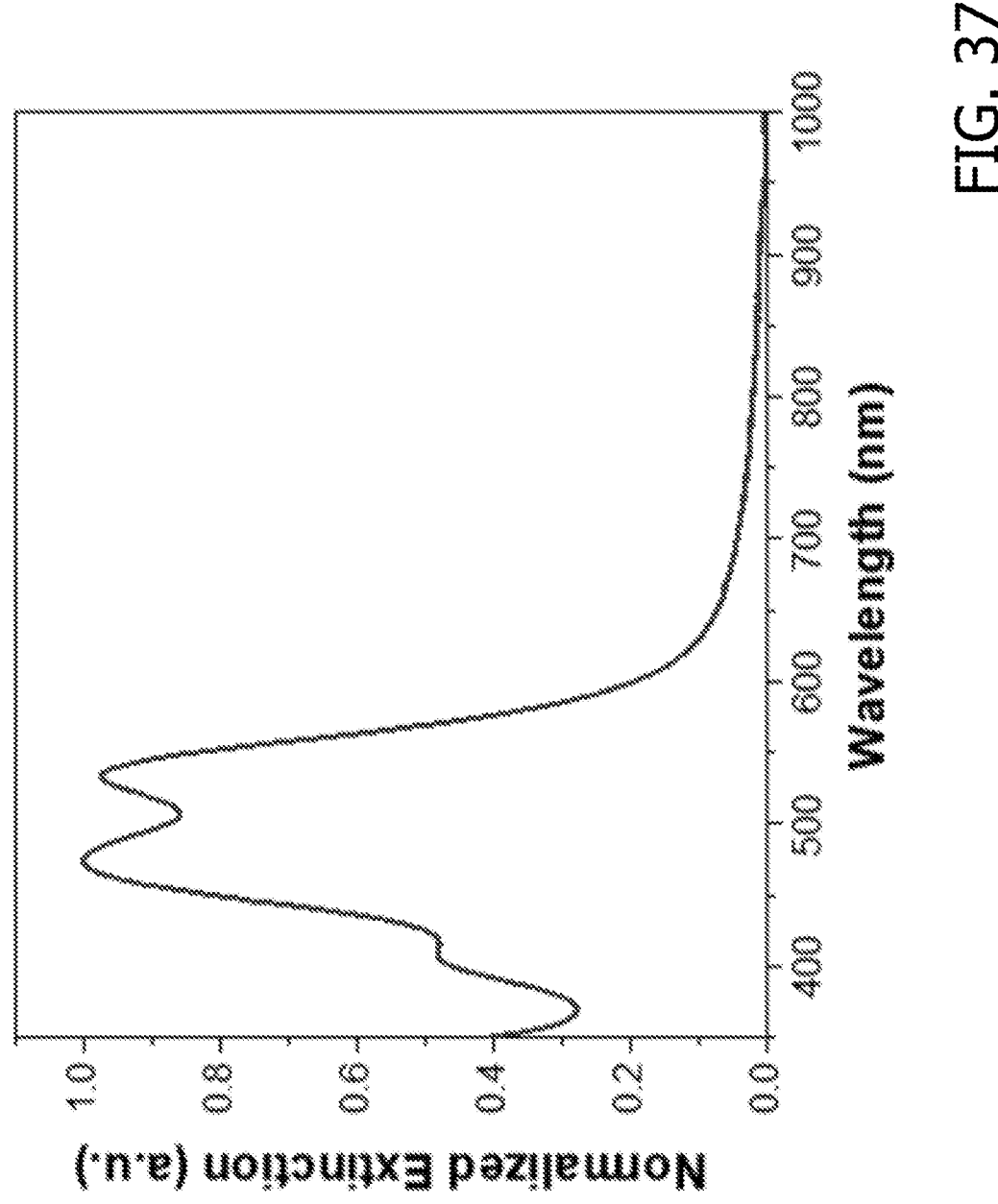
FIG. 37 is an exemplary embodiment of extinction spectrum for AuNR@Ag cuboids in accordance with the present disclosure.

FIG. 37 shows an extinction spectrum for AuNR@Ag cuboids which form the core particle for plasmonic-fluors designed to enhance a dye with an excitation maximum near 488 nm, such as FITC and AlexaFluor 488.

FIG. 3 shows the difference in the slopes on a plot of the fluorescence intensity of an AuNR@Ag nanocuboid-based, plasmonic-fluor (see FIG. 35) conjugated with FITC versus the unconjugated FITC, free in solution, as a function of the concentration indicates that plasmonic-fluor FITC is ~16,667× brighter than free FITC. These plasmonic fluors had the dye directly conjugated to the polymer spacer layer, which was ~2-4 nm thick. These data were collected on a BioTek Synergy H1 with the same excitation and emission conditions for the plasmonic fluor and the free FITC (excitation at 490 nm and detection at 530 nm).

Example 12

Figure 38:
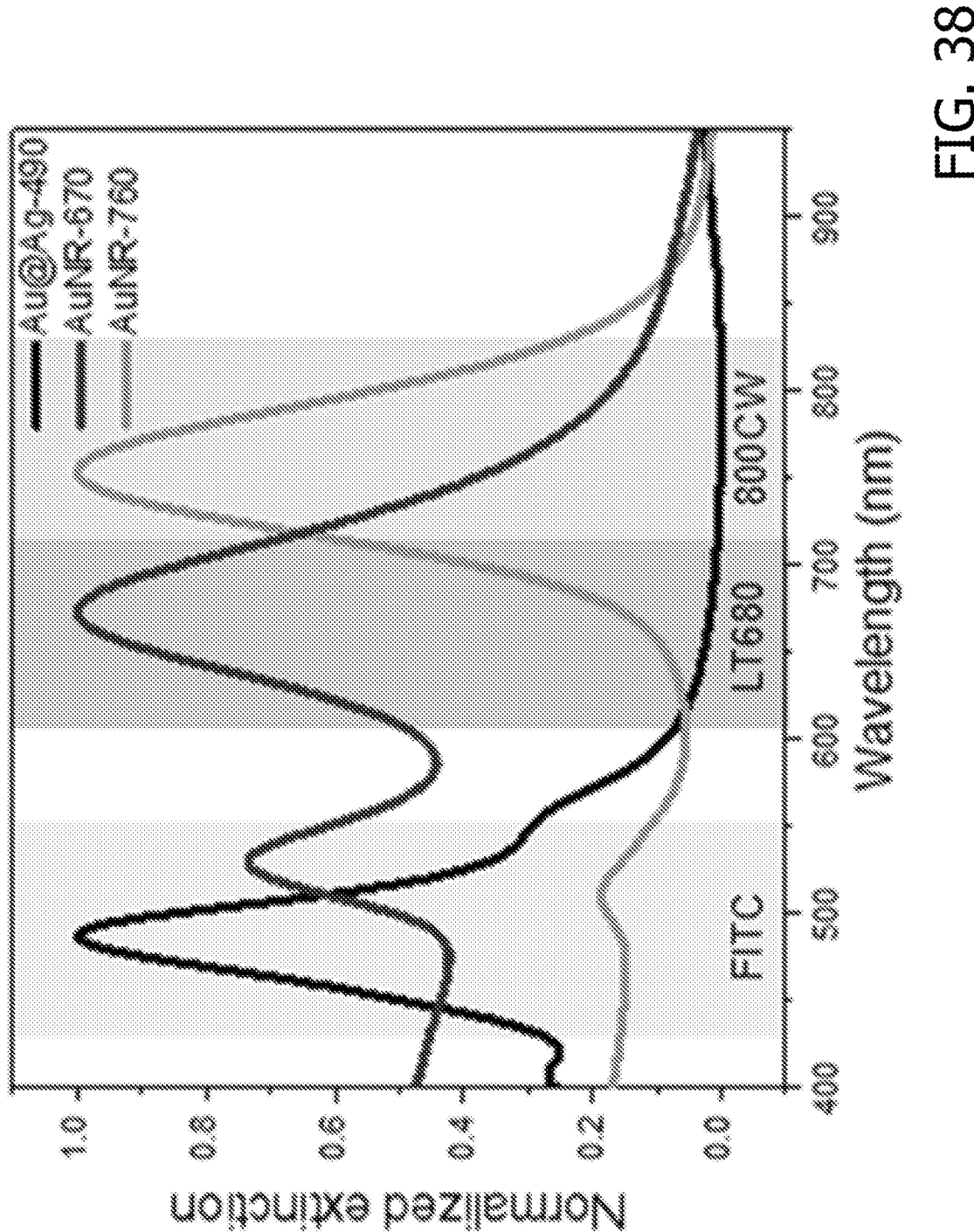
FIG. 38 is an exemplary embodiment of plasmonic nano-structures suitable for enhancing fluorophores which can be excited at 488 nm (Au@Ag-490), 658 nm (AuNR-670), and 784 nm (AuNR-760) in accordance with the present disclosure.

FIG. 38 shows plasmonic nanostructures suitable for enhancing fluorophores which can be excited at 488 nm (Au@Ag-490), 658 nm (AuNR-670), and 784 nm (AuNR-760). Common standard fluorophore excitation regimes corresponding to the corresponding plasmonic particle are highlighted.

Example 13

Figure 39B:
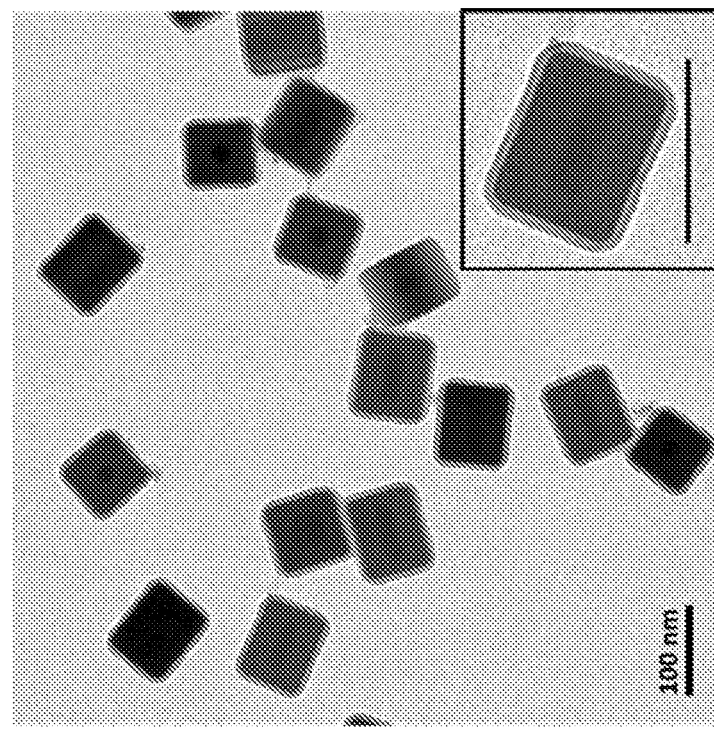
FIG. 39A and FIG. 39B are exemplary embodiments of TEM for PF-532 (Cy3) in accordance with the present disclosure.
Figure 39A:
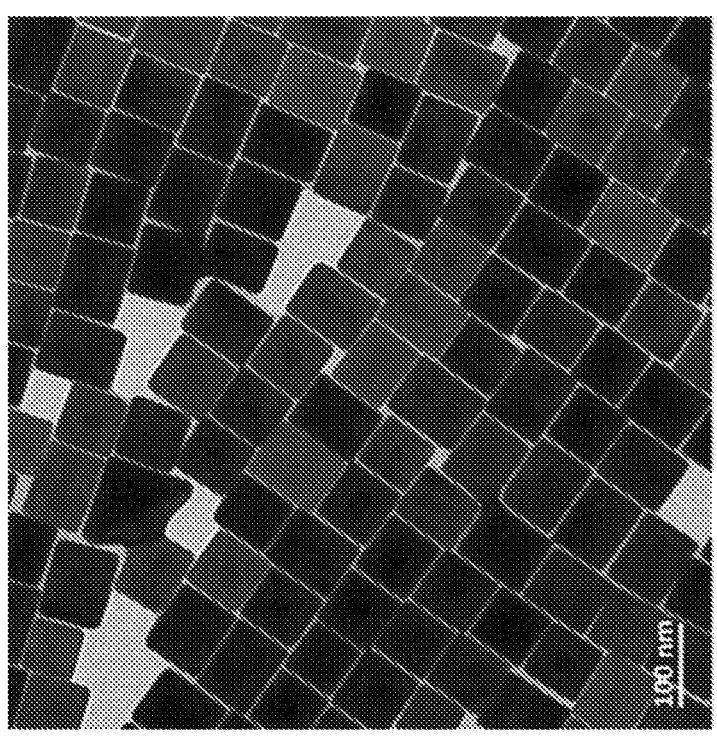
Figure 40:
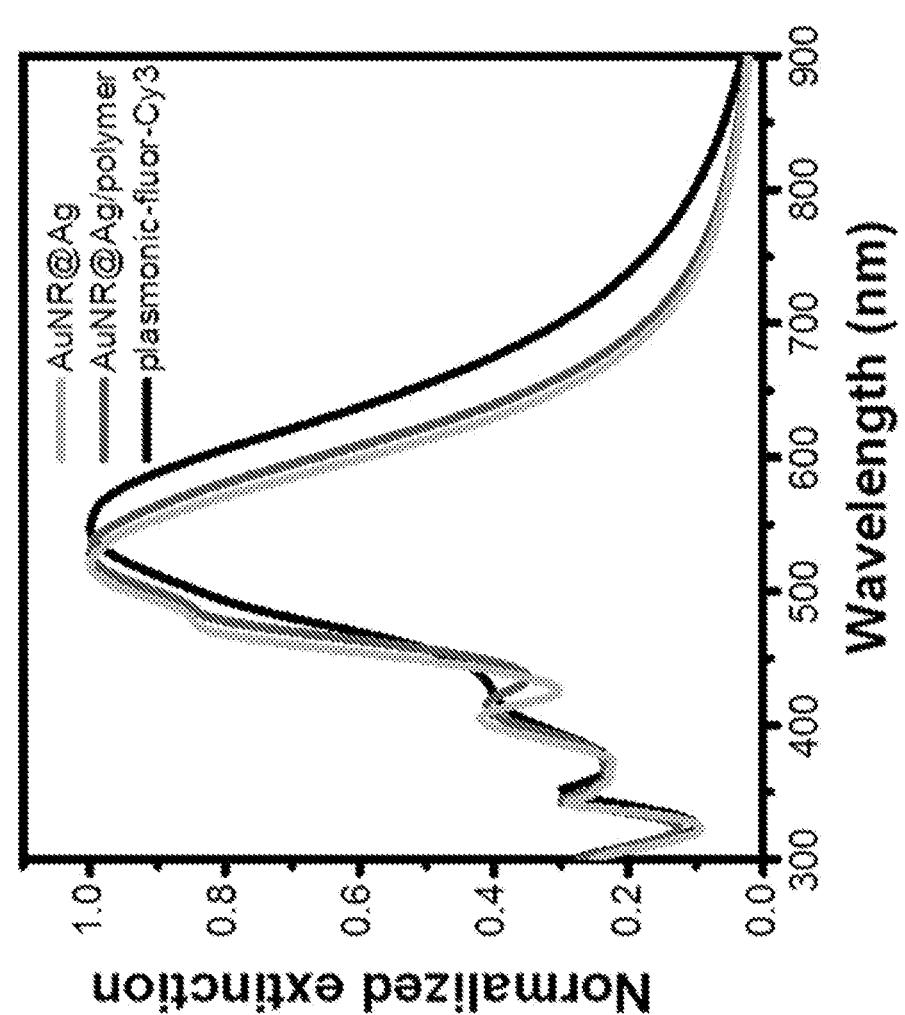
FIG. 40 is an exemplary embodiment of extinction spectra PF-532 (Cy3) in accordance with the present disclosure.

FIG. 39(A-B) shows TEM images of (left) AuNR@Ag nanocuboids and (right) plasmonic-fluor-Cy3, which consists of AuNR@Ag nanocuboids, polymer shell, and a coating of BSA-biotin-Cy3. Coating (functional layer plus spacer layer) is ~6 nm thick. FIG. 40 shows Extinction spectra of AuNR@Ag nanocuboids, AuNR@Ag nanocuboids coated with polymer spacer, and plasmonic-fluor-Cy3, revealing a continuous red shift after each coating step.

Example 14

An optimal distance between the metal surface and fluorophore is critical to maximize fluorescence enhancement by balancing the two opposing factors, namely, enhanced electromagnetic field and non-radiative energy transfer. Fluorescence enhancement of plasmonic-fluor-800CW with different thicknesses of the dielectric spacer (MPTMS, APTMS, and TMPS) was investigated by binding them to a substrate coated with streptavidin-800CW. The ensemble fluorescence enhancement factor (defined as the ratio of fluorescence intensities obtained after and before the addition of plasmonic-fluors on a surface coated with fluorophore-conjugated streptavidin) of the plasmonic-fluors without polymer spacer layer was found to be ~146±81. Enhancement efficiency progressively increased to ~1200

Figure 41:
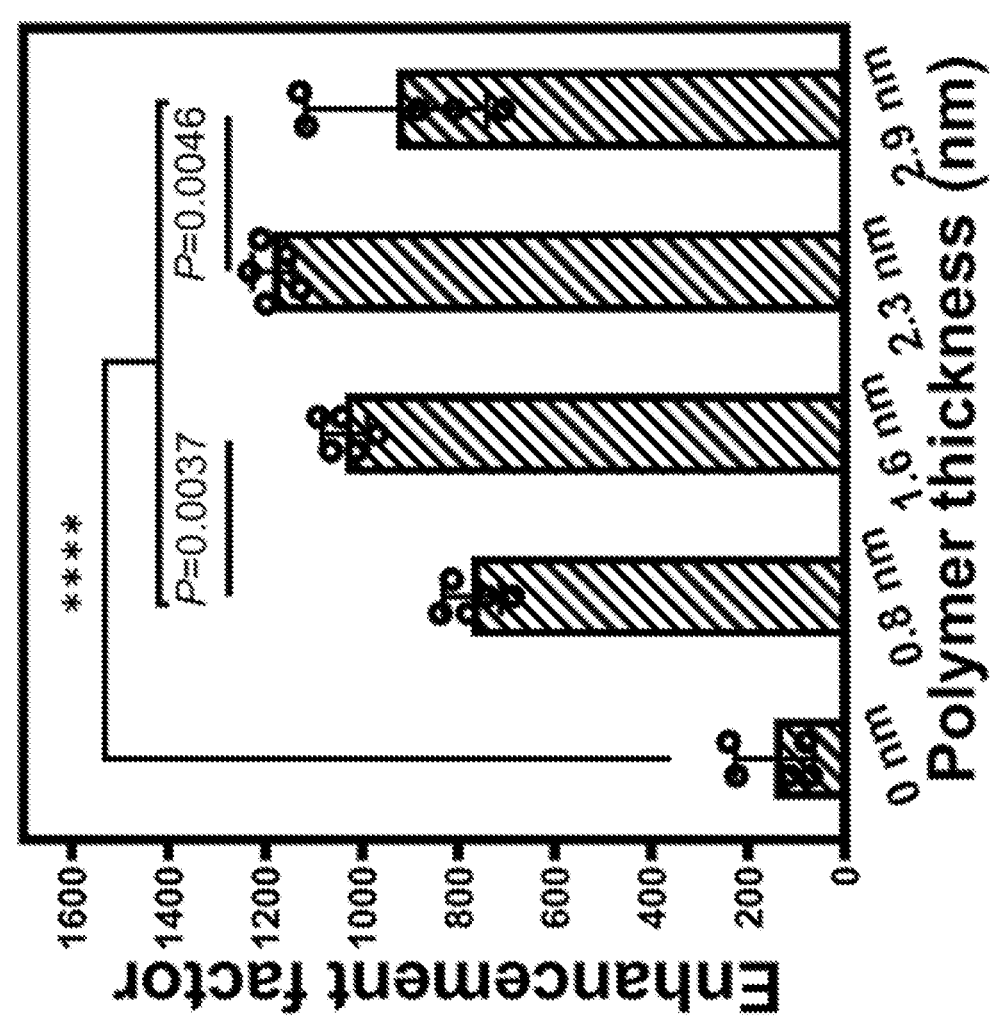
FIG. 41 is an exemplary embodiment of fluorescence enhancement factor obtained using plasmonic-fluor-800CW with different polymer spacer thickness in accordance with the present disclosure.
Figure 42:
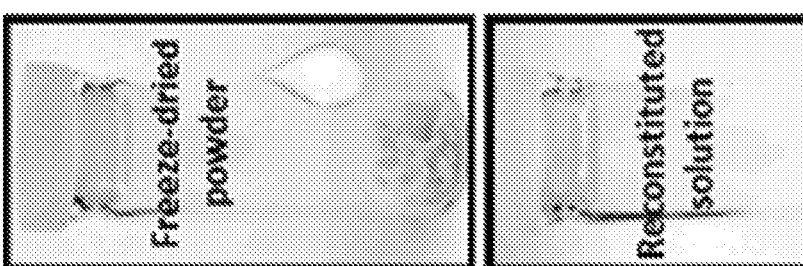
FIG. 42 is an exemplary embodiment of plasmon-enhanced fluorescence and colloidal stability of plasmonic-fluors in accordance with the present disclosure. Error bar represents s.d. (n≥3 independent tests). Data statistically significant P value=0.0013, P<0.01 by two-tailed unpaired t-test with Welch's correction.
Figure 42:
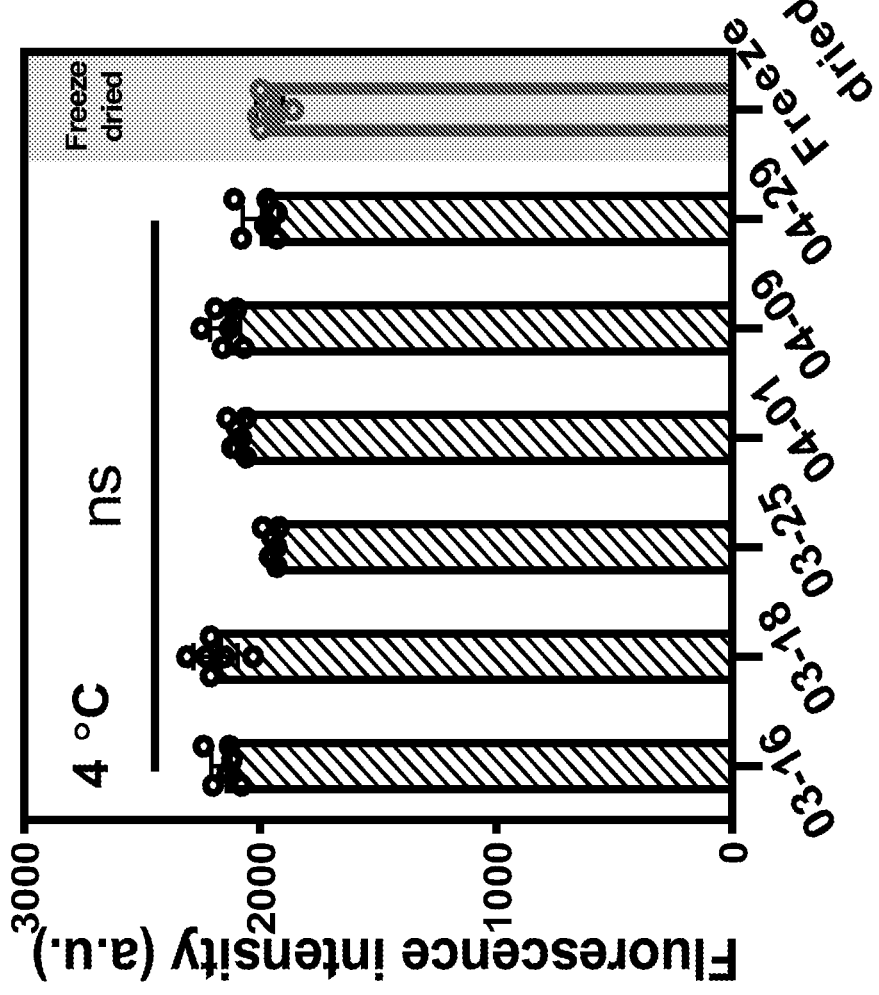

(±40)-fold with the increase of the spacer thickness (FIG. 41. Note that the polymer thickness plotted here is actually not the distance between the attached fluor and the metal surface. This figure represents plasmonic fluors in which the BSA was fluorescently labeled. While this figure would seem to indicate that, generally, the optimal spacer thickness is between 0.8 and 2.9 nm, that is not necessarily the case for plasmonic fluors in which the fluorophore is attached directly to the spacer coating. In cases where the fluorophores are attached to the BSA, which serves as the functional layer, In other words, the polymer thickness is actually not the distance between the attached fluor and the surface of the plasmonic nanostructure because the BSA itself acts as a spacer between the fluorophore and the plasmonic nanostructure. With fluorophore-conjugated BSA, some fluorophores are immediately adjacent to the spacer layer and some are ~4 nm distal from the spacer layer. Therefore, one can assume the average distance of the fluorophore from the surface of plasmonic nanostructure is ~2 nm greater than the thickness of the spacer layer. From the work in U.S. Provisional Application 62/590,877 titled "Plasmonic Film as a Universal Fluorescent Enhancer" filed on Nov. 27, 2017, which is herein incorporated by reference in its entirety, it was found that the optimal spacing between a fluorophore and the plasmonic nanostructure surface was between 2 and 5 nm, consistent with the results shown here. Notably, the colloidal solution of plasmonic-fluor exhibited stable fluorescence signal after storage in the dark at 4° C. for one month (FIG. 42). For further ease of storage, transportation, and handling, the plasmonic-fluors can be lyophilized and reconstituted as needed without noticeable degradation in the fluorescence signal (FIG. 42).

Figure 43:
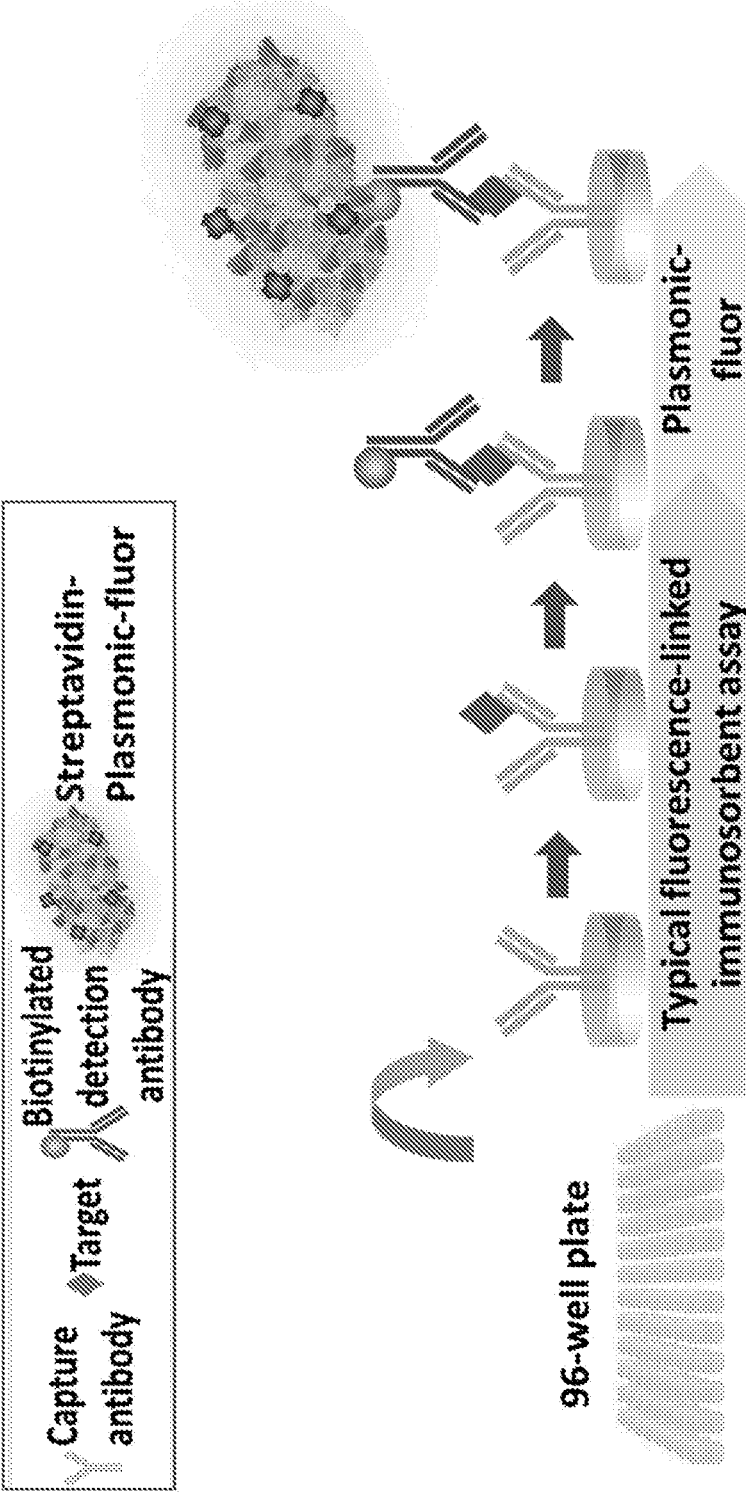
FIG. 43 is an exemplary embodiment of a schematic showing the concept of conventional FLISA (800CW) and plasmonic-fluor-800CW enhanced FLISA (p-FLISA), implemented in a standard 96-well plate in accordance with the present disclosure.
Figure 44:
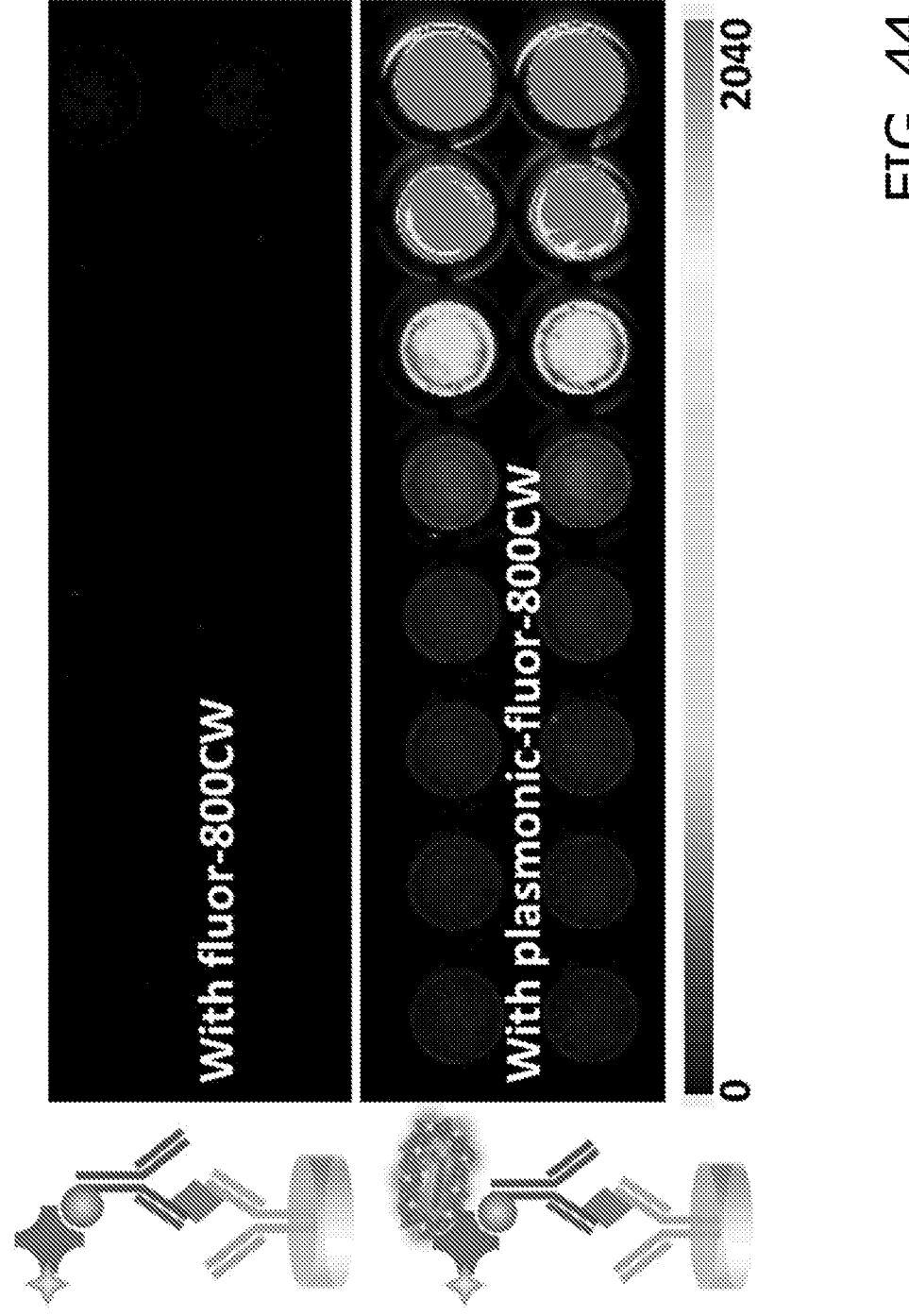
FIG. 44 is an exemplary embodiment of fluorescence intensity maps of human IL-6 FLISA and p-FLISA at various analyte concentrations in accordance with the present disclosure.
Figure 45:
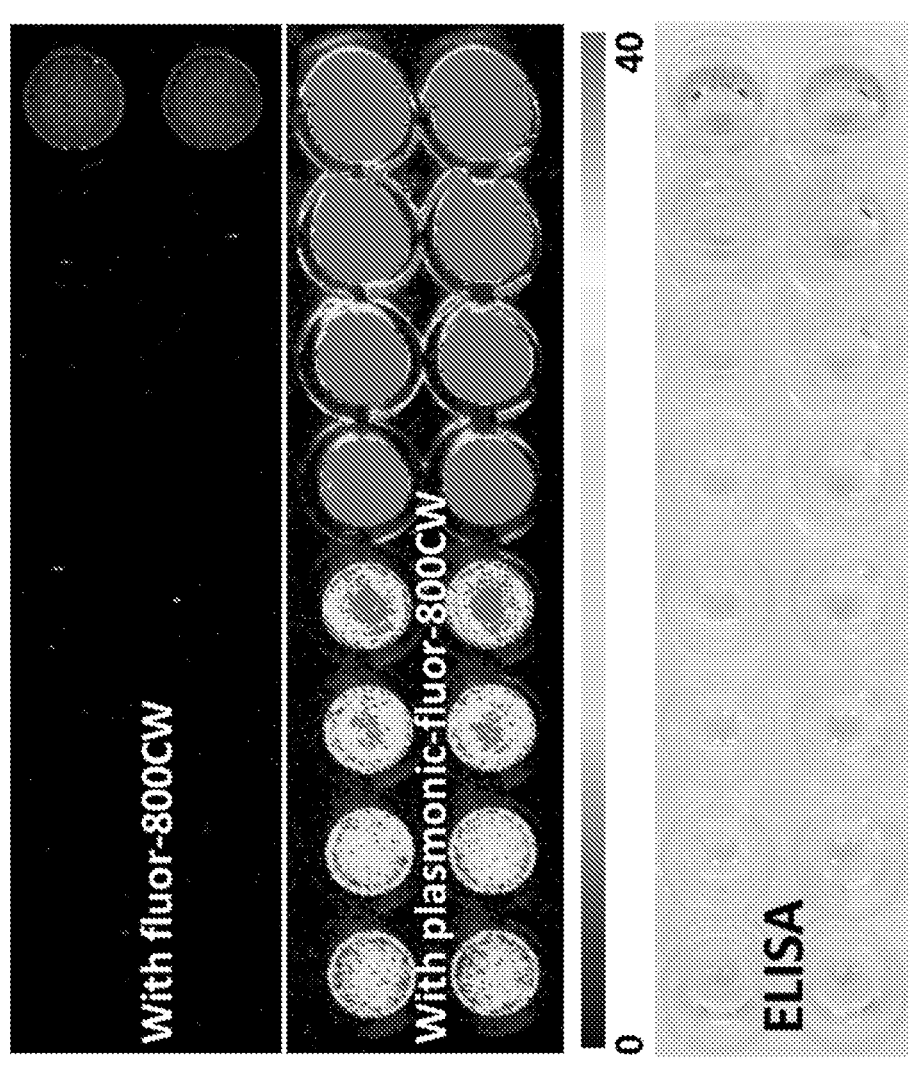
FIG. 45 is an exemplary embodiment of fluorescence intensity maps (with zoomed-in scale bar) of human IL-6 FLISA and p-FLISA and photograph of colorimetric signal of "gold standard" human IL-6 ELISA in accordance with the present disclosure.

Example 15—Plasmonic-Fluor Enhanced Fluorescence-Linked Immunosorbent Assay (p-FLISA) and Multiplexed Bead-Based Assay Of the numerous applications of plasmonic-fluors, plasmon-enhanced fluorophore-linked immunosorbent assay (p-FLISA) was implemented on a standard microtiter plate. Human interleukin 6 (IL-6), a pro-inflammatory cytokine, was employed as a representative protein biomarker. Conventional FLISA involves a standard sandwich format of capture antibody, analyte (IL-6), biotinylated detection antibody, followed by exposure to streptavidin-fluorophore (800CW in this study) (FIG. 43). FIG. 43 is a schematic showing the concept of conventional FLISA (800CW) and plasmonic-fluor-800CW enhanced FLISA (p-FLISA), implemented in a standard 96-well plate. P-FLISA assay does not require any change in the routine workflow except adding the plasmonic-fluor as the new, last step. In p-FLISA, plasmonic-fluor-800CW is introduced after the last step as the signal enhancer (FIG. 43). To determine the improvement in sensitivity and limit-of-detection ((LOD), defined as mean+3σ of the blank), serial dilutions of IL-6 of known concentration (6 ng/ml to 6 fg/ml, in 1% BSA buffered with phosphate buffered saline (PBS)) were employed as standards. Fluorescence signal obtained after applying the plasmonic-fluor-800CW revealed nearly 1440-fold enhancement in the ensemble fluorescence intensity compared to the conventional FLISA at the highest analyte concentration tested here (6 ng/ml) (FIG. 44, FIG. 45, and FIG. 46). FIG. 44 shows fluorescence intensity maps of human IL-6 FLISA and p-FLISA at various analyte concentrations. FIG. 45 shows fluorescence intensity maps (with zoomed-in scale bar) of human IL-6 FLISA and p-FLISA and photograph of colorimetric signal of "gold standard" human IL-6 ELISA.

Figure 47:
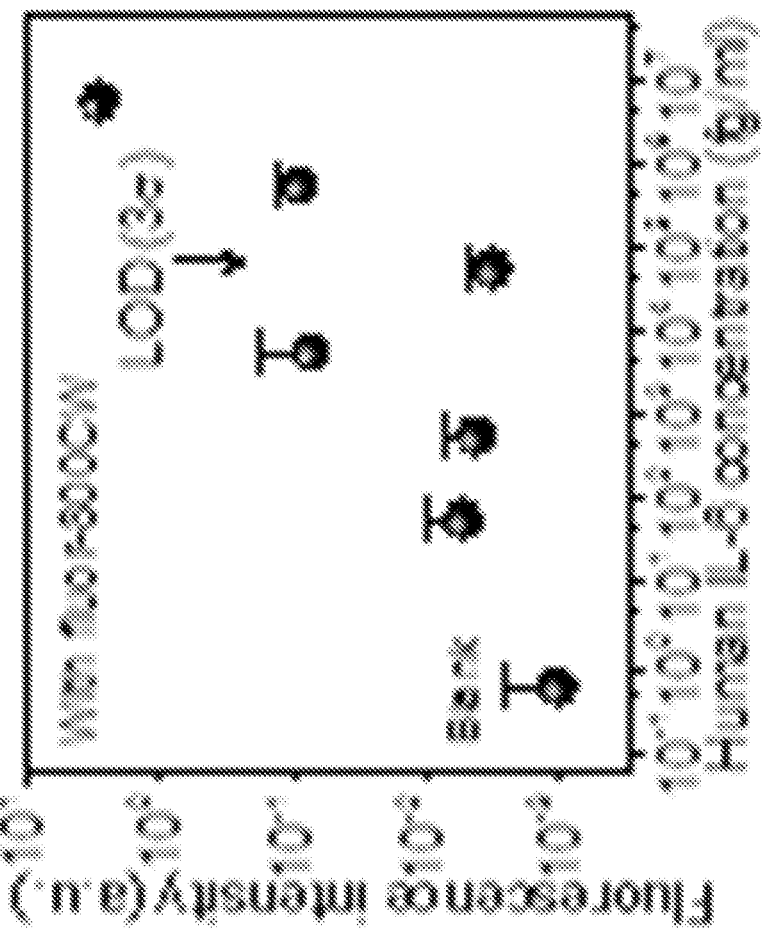
FIG. 47 is an exemplary embodiment of a plot of human IL-6 dose-dependent fluorescence intensity from conventional FLISA in accordance with the present disclosure.
Figure 48:
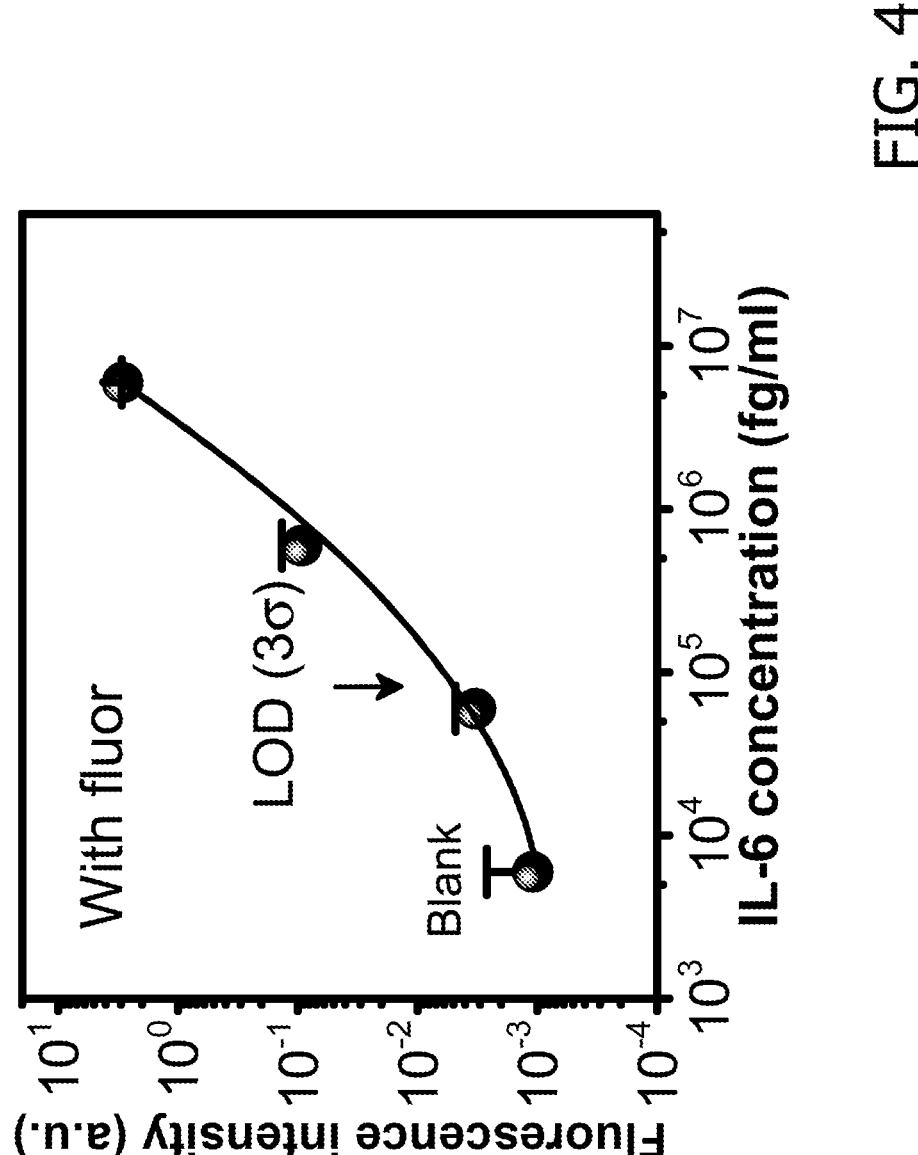
FIG. 48 is an exemplary embodiment of LOD of conventional IL-6 FLISA in accordance with the present disclosure.
Figure 49:
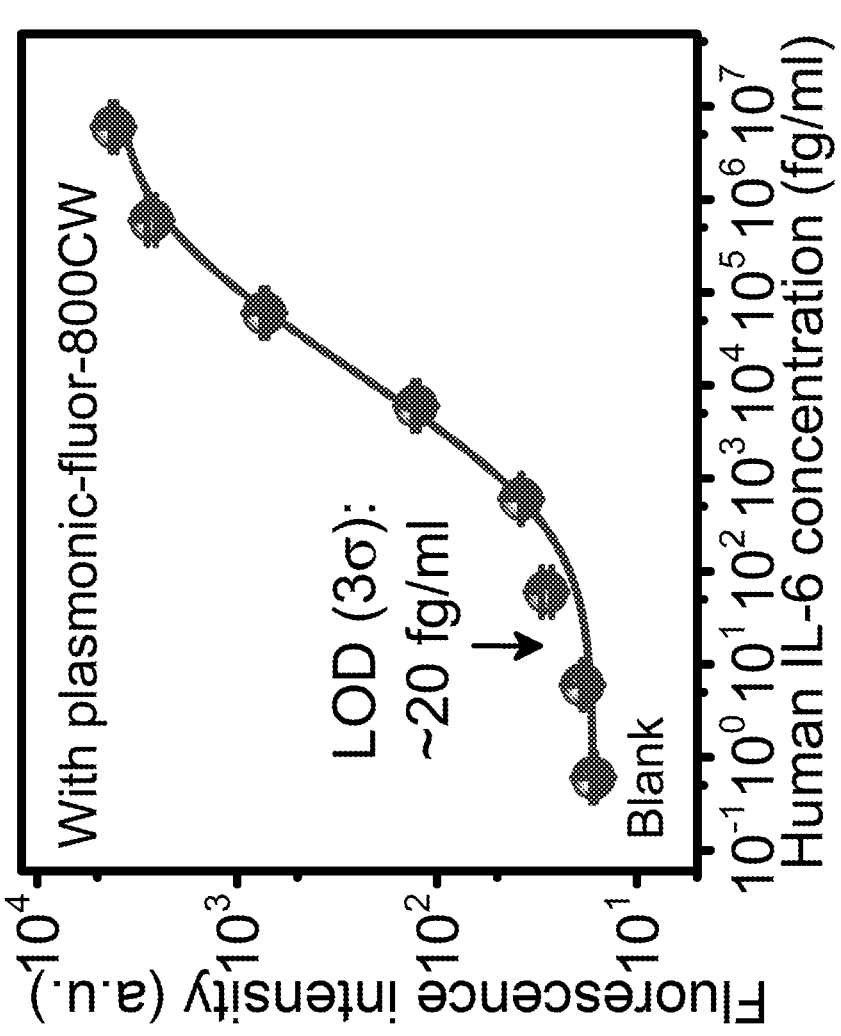
FIG. 49 is an exemplary embodiment of a plot of human IL-6 dose-dependent fluorescence intensity from p-FLISA in accordance with the present disclosure.
Figures 50A, 50B:
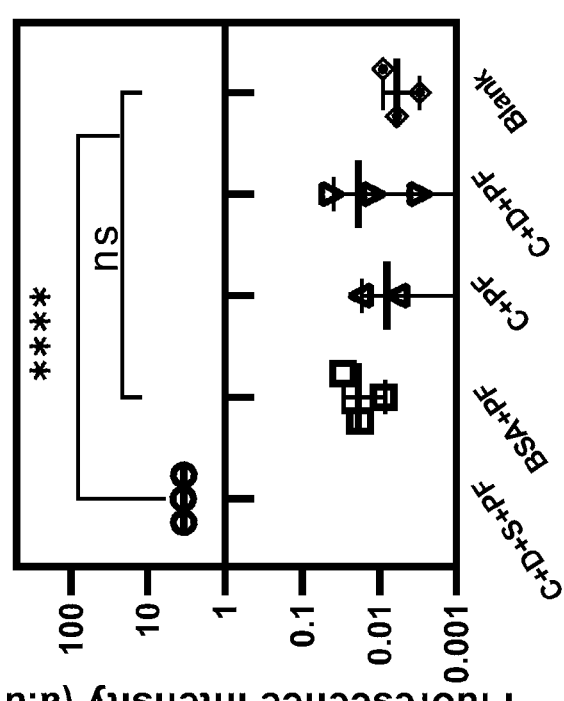
FIG. 50A is an exemplary embodiment of IL-6 dose-dependent fluorescence intensity from p-FLISA in accordance with the present disclosure.
FIG. 50B is an exemplary embodiment of non-specific binding of plasmonic-fluor-800CW in accordance with the present disclosure.
Figure 51:
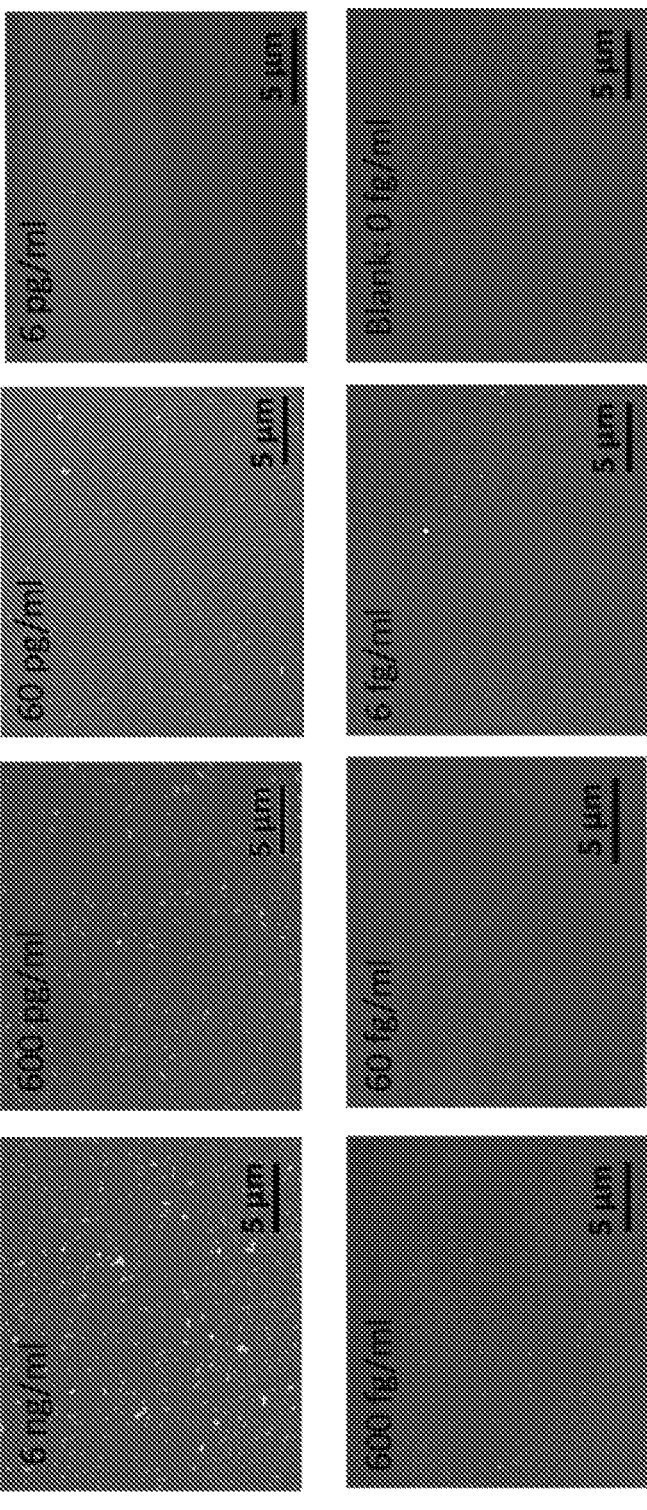
FIG. 51 is an exemplary embodiment of SEM images of the bottom surface of 96-well plate following IL-6 p-FLISA in accordance with the present disclosure.

The LOD of conventional FLISA was calculated to be ~95 pg/ml (FIG. 47, FIG. 48, and FIG. 46, polynomial fit). FIG. 47 shows a plot of human IL-6 dose-dependent fluorescence intensity from conventional FLISA. FIG. 48 shows LOD of conventional IL-6 FLISA. The standard curve was generated using polynomial fitting. Error bar represents s.d. (n=2 repeated tests). FIG. 46 shows individual data points, mean value, and standard deviation from human IL-6 FLISA, p-FLISA, and ELISA. On the other hand, fluorescence signal with p-FLISA could be detected down to 20 fg/ml (~1 fM) (FIG. 49 and FIG. 46, four-parameter logistic (4PL) fit), which represents a 4750-fold improvement in the LOD compared to conventional FLISA. FIG. 49 shows a plot of human IL-6 dose-dependent fluorescence intensity from p-FLISA. Compared to conventional FLISA, p-FLISA exhibits 4750-fold improvement in the limit-of-detection (LOD) and more than three-order-magnitude larger dynamic range. Notably, plasmonic-fluor exhibited extremely high specificity (to streptavidin) and low non-specific binding to the interference biomolecules in the bioassays (FIG. 50(A-B)). FIG. 50A shows IL-6 dose-dependent fluorescence intensity from p-FLISA. Error bar represents s.d. (n=2 repeated tests). FIG. 50B shows non-specific binding of plasmonic-fluor-800CW. C: capture antibody; D: detection antibody; S: streptavidin; PF: plasmonic-fluor; Blank: no plasmonic-fluor. Compared to blank, no signal was observed after applying plasmonic-fluor-800CW to BSA, capture antibody, or capture and detection antibody. **P<0.0001 by one-way ANOVA with Tukey's post test. NS: not significant. Non-specific signal at zero concentration of IL-6 was present only when streptavidin was introduced, implying excellent specificity of plasmonic-fluor. Error bar represents s.d. (n=3 repeated tests). This "BSA blocking" strategy of plasmonic-fluor is critical in enhancing the signal-to-background ratio. Scanning electron microscopy (SEM) images revealed an increase in the density of plasmonic-fluor-800CW at the bottom of the microtiter wells with increasing IL-6 concentration (FIG. 51). FIG. 51 shows SEM images of the bottom surface of 96-well plate following IL-6 p-FLISA, revealing an increasing density of plasmonic-fluor-800CW with increasing concentration of IL-6. Extremely low density of plasmonic-fluors was observed in the blank well, which was incubated with 1% BSA, again indicating the low non-specific binding of the plasmonic-fluors (FIG. 51**).

Figure 52:
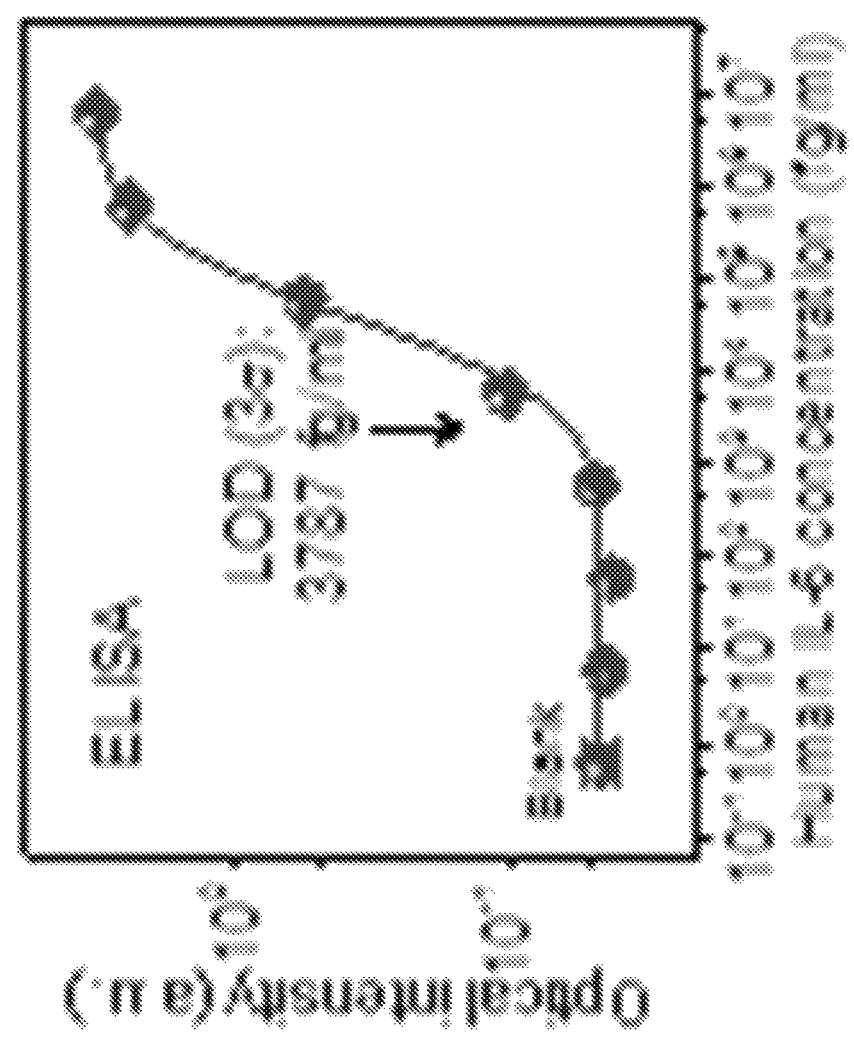
FIG. 52 is an exemplary embodiment of a plot showing the standard curve of human IL-6 ELISA in accordance with the present disclosure.
Figure 53:
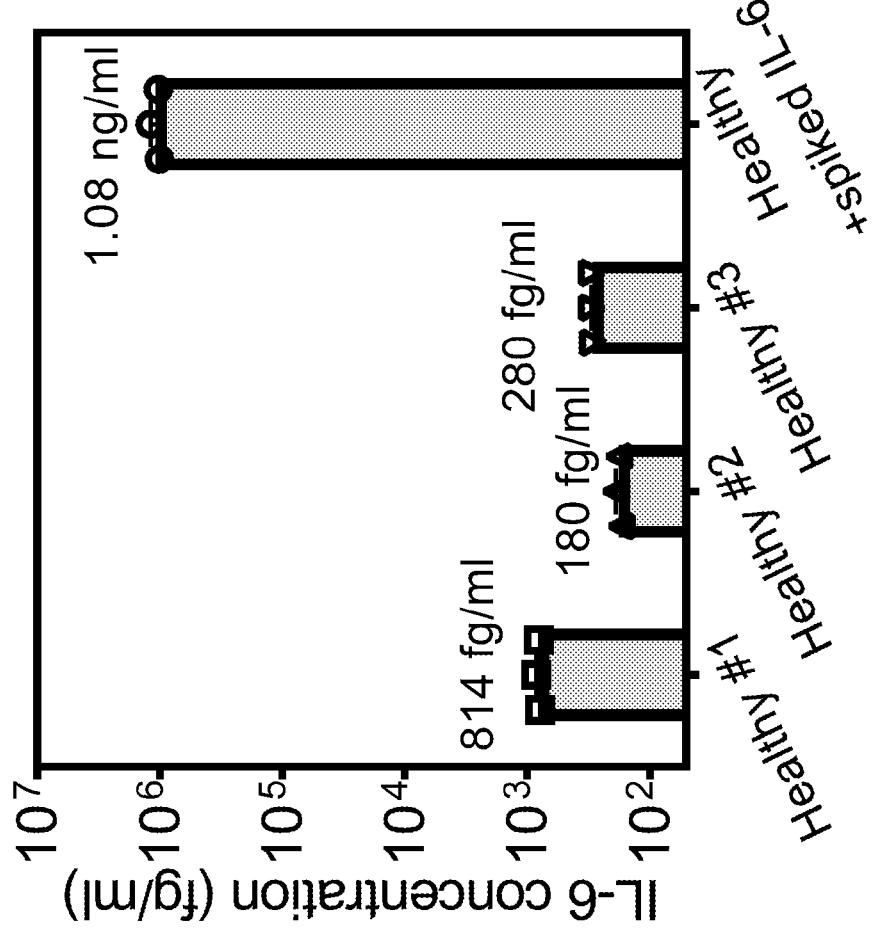
FIG. 53 is an exemplary embodiment of IL-6 concentrations in human serum samples (diluted by 10-fold) measured using p-FLISA in accordance with the present disclosure.

Remarkably, the LOD and lower limit of quantification ((LLOQ), defined as mean+10σ of the blank, ~82 fg/ml) of p-FLISA were found to be 189-fold and 120-fold lower than the "gold standard" enzyme-linked immunosorbent assay (ELISA), which involves enzymatic amplification of the colorimetric signal (FIG. 45, FIG. 52, and FIG. 46). FIG. 52 is a plot showing the standard curve of human IL-6 ELISA. Compared to ELISA, p-FLISA exhibited 189-fold lower LOD and more than two-order-magnitude larger dynamic range. More importantly, p-FLISA exhibited a dynamic range (ratio between higher and lower limit of quantification) of five orders of magnitude, which is more than two-order-magnitude higher than that of ELISA. As a validation of the assay performance, healthy human serum samples and IL-6 spiked serum using p-FLISA were tested. Serum samples were diluted by 10-fold so that only 10 μl of original sample was required for individual subjects. Concentrations of IL-6 in healthy individuals are normally in the range of 0.2-7.8 pg/ml. Increased level of IL-6 in serum can be indicative of systemic inflammatory, metabolic, and physiological stimuli. Notably, among ELISA, FLISA and p-FLISA, only the latter technique was able to determine the IL-6 concentration in healthy individuals, which was measured to be 8.1 pg/ml, 1.8 pg/ml, and 2.8 pg/ml after dilution-fold correction (FIG. 53). FIG. 53 shows IL-6 concentrations in human serum samples (diluted by 10-fold) measured using p-FLISA. Error bars represent s.d. (n=3 repeated tests).

Figure 54:
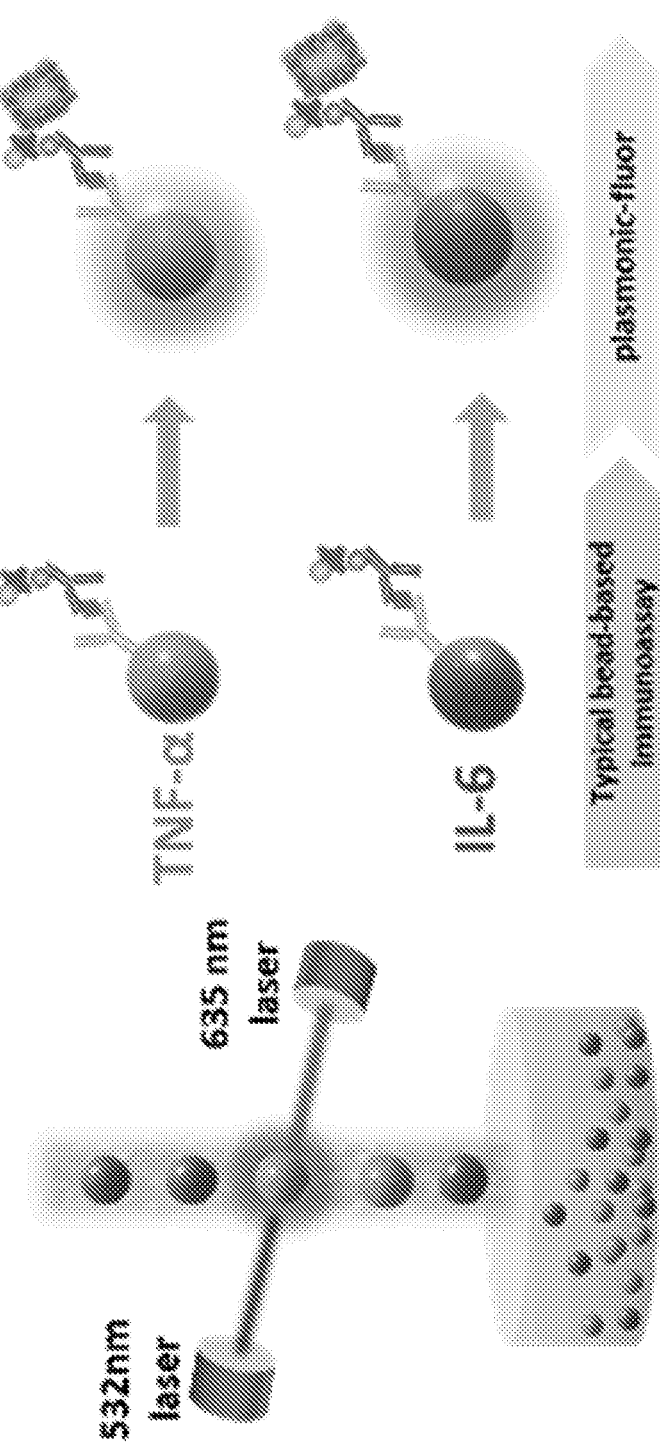
FIG. 54 is an exemplary embodiment of a schematic illustration showing the concept of using plasmonic-fluor-Cy3 to enhance the sensitivity of bead-based immunoassay (e.g., Luminex assay) in accordance with the present disclosure.
Figure 55B:
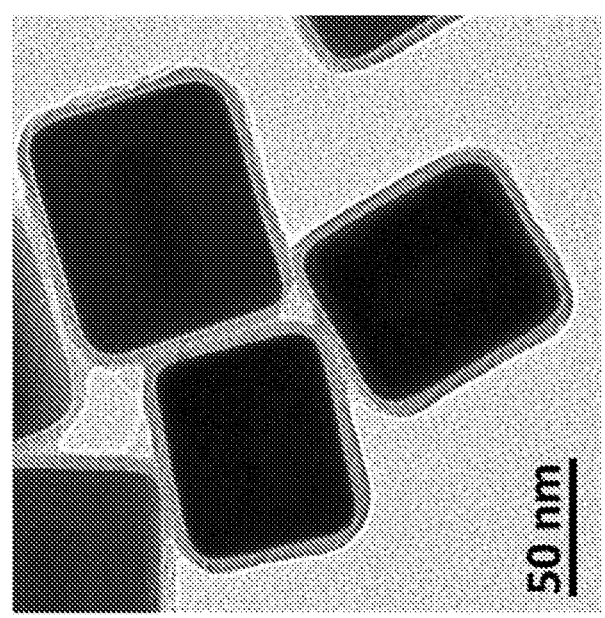
FIG. 55A and FIG. 55B are exemplary embodiments of TEM images of plasmonic-fluor-Cy3 utilizing AuNR@Ag as the plasmonic nanostructure in accordance with the present disclosure.
Figure 55A:
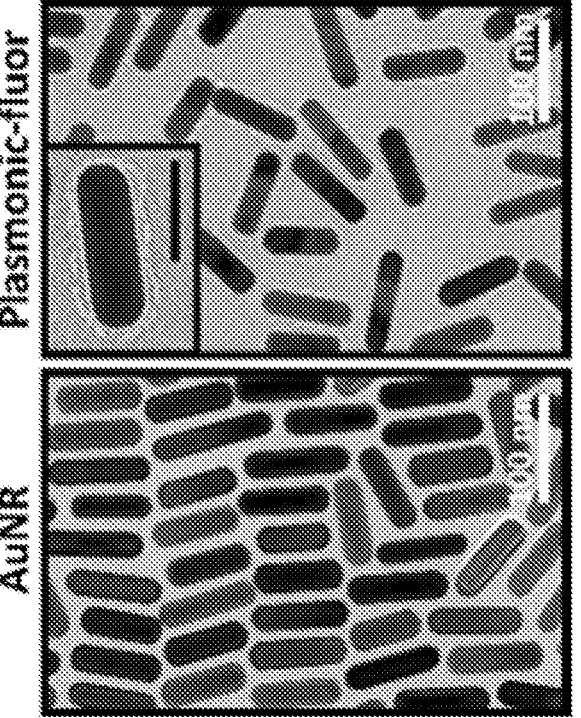
Figures 56A, 56B, 56C:
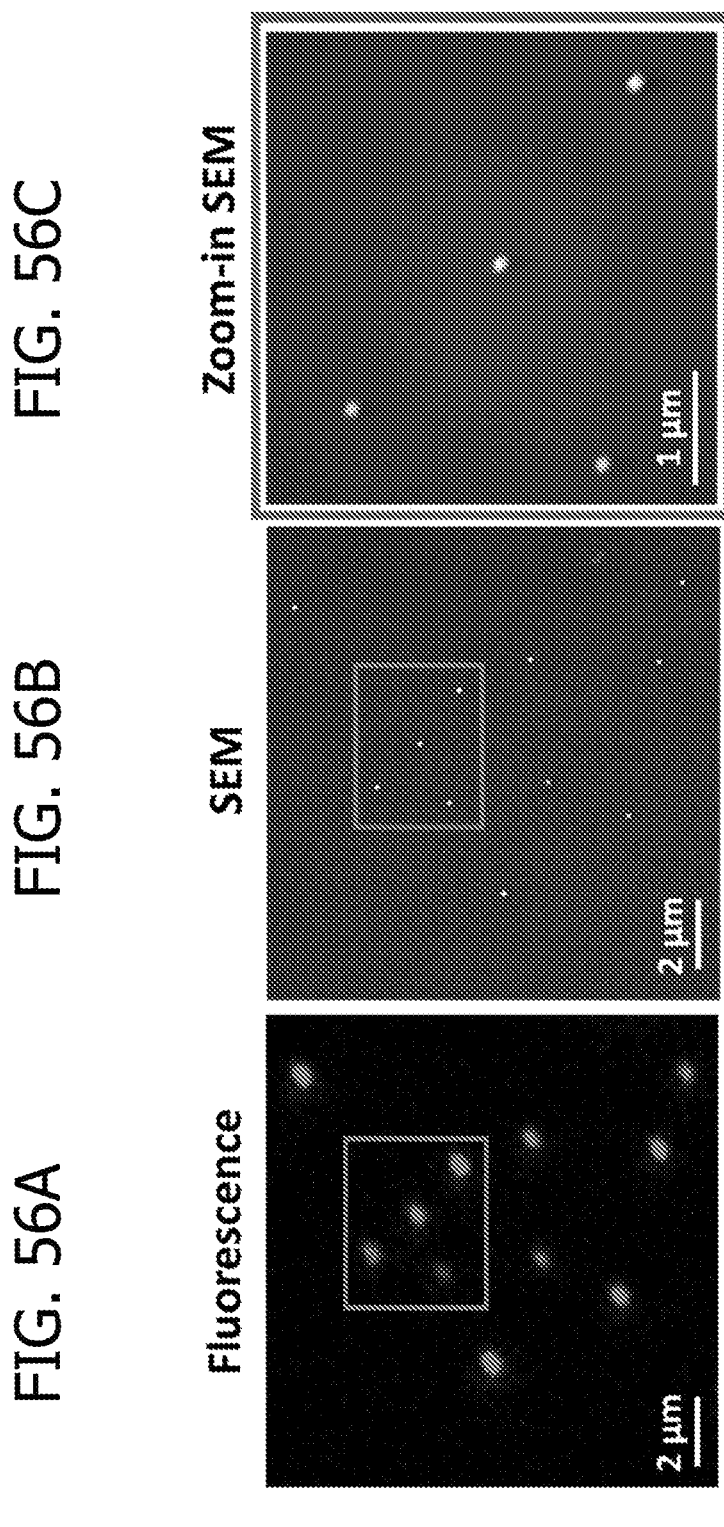
FIG. 56A is an exemplary embodiment of a fluorescence microscopic image of individual plasmonic-fluor-Cy3 in accordance with the present disclosure.
FIG. 56B is an exemplary embodiment of an SEM image of the individual plasmonic-fluor-Cy3 shown in FIG. 56A in accordance with the present disclosure.
FIG. 56C is an exemplary embodiment of a zoomed-in SEM image, corresponding to the box shown in FIGS. 56A and 56B, showing single plasmonic-fluor-Cy3 (single nanocuboids) in accordance with the present disclosure.

In addition to the microtiter plate format, the application of plasmonic-fluors as ultrabright reporters in micro bead-based multiplexed fluoroimmunoassays was also investigated, which utilizes a non-planar sampling surface. Luminex assay was employed as an example, which utilizes magnetic microbeads embedded with ratio-set fluorophores as barcode for each unique analyte (FIG. 54). FIG. 54 is a schematic illustration showing the concept of using plasmonic-fluor-Cy3 to enhance the sensitivity of bead-based immunoassay (e.g., Luminex assay). The antibody conjugated microbead captures and facilitates the detection of the analyte in a typical sandwich format and is subsequently probed by streptavidin conjugated with phycoerythrin (PE), a bright fluorescent protein isolated from red algae or cyanobacteria. However, PE employed in Luminex assays is structurally unstable and prone to photobleaching. Here, Cy3, a highly stable fluorophore with absorption and emission at 554 nm and 568 nm respectively, similar to PE, was employed as a substitute. As discussed above, it is extremely important to choose plasmonic nanostructure with LSPR wavelength matching the excitation maximum wavelength of the fluorophore. To this end, AuNR@Ag nanocuboids with LSPR wavelength of 520 nm were employed to fabricate plasmonic-fluor-Cy3 (FIG. 55(A-B), FIG. 39(A-B) and FIG. 40). FIG. 55(A-B) is a TEM image of plasmonic-fluor-Cy3 utilizing AuNR@Ag as the plasmonic nanostructure, and spacer coating thickness is approximately 6 nm. FIG. 39(A-B) shows TEM images of (left) AuNR@Ag nanocuboids and (right) plasmonic-fluor-Cy3, which consists of AuNR@Ag nanocuboids, polymer shell, and a coating of BSA-biotin-Cy3. Coating is ~6 nm thick. FIG. 40 shows extinction spectra of AuNR@Ag nanocuboids, AuNR@Ag nanocuboids coated with polymer spacer, and plasmonic-fluor-Cy3, revealing a continuous red shift after each coating step. Notably, as synthesized plasmonic-fluor-Cy3 exhibited extremely high brightness and individual nanoconstructs can be easily identified under a common epifluorescence microscope (FIG. 56(A-C)). FIG. 56A shows a fluorescence microscopic image of individual plasmonic-fluor-Cy3. FIG. 56B shows a corresponding SEM image of the individual plasmonic-fluor-Cy3 shown in FIG. 56A. FIG. 56C is a zoomed-in SEM image, corresponding to the box shown in FIG. 56A and FIG. 56B, showing single plasmonic-fluor-Cy3 (single nanocuboids). The fluorescence image was acquired by a non-laser epifluorescence microscope, which is widely available in common research labs.

Figure 57:
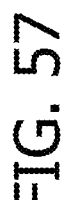
FIG. 57 is an exemplary embodiment of SEM images of microbead(s) before and after being probed with plasmonic-fluor-Cy3 in accordance with the present disclosure.
Figure 57:
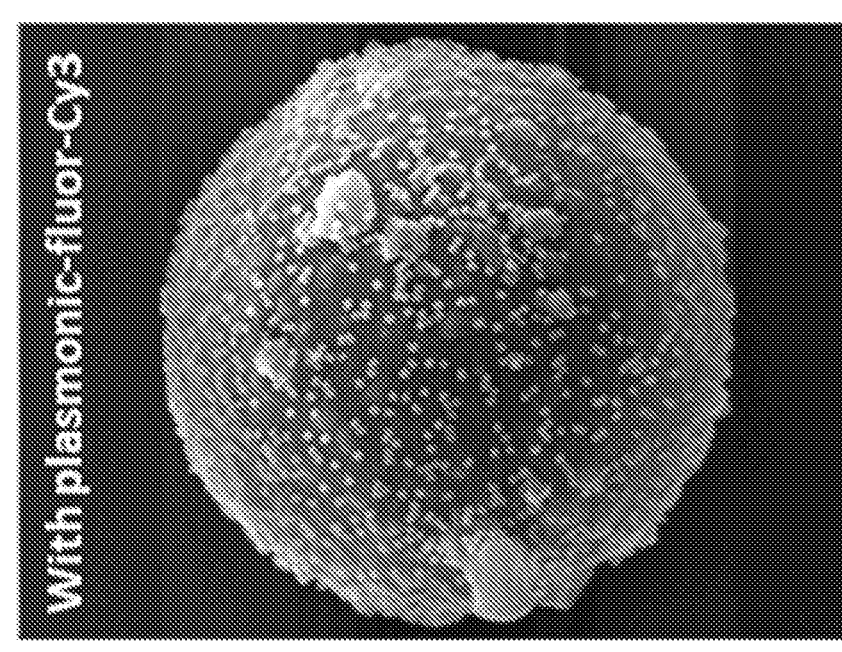
Figure 57:
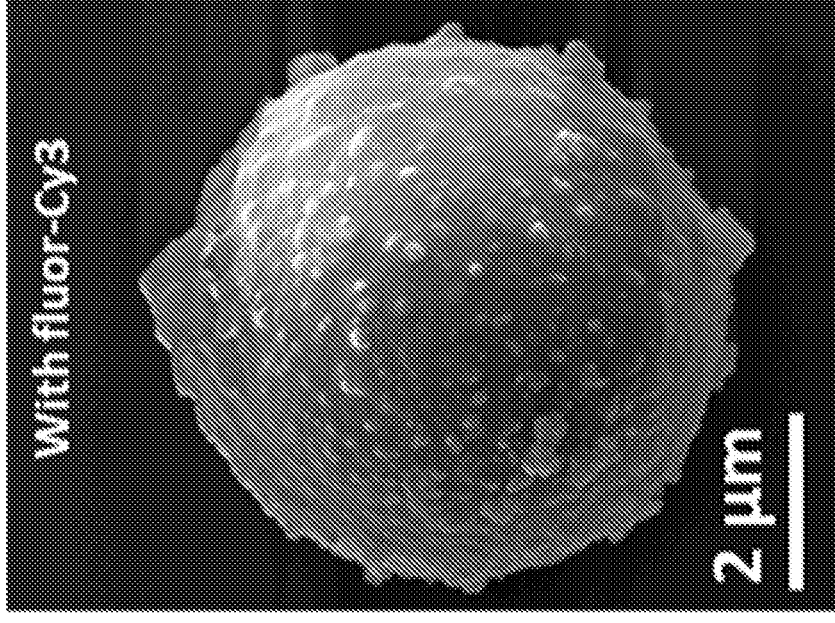
Figures 58A, 58B:
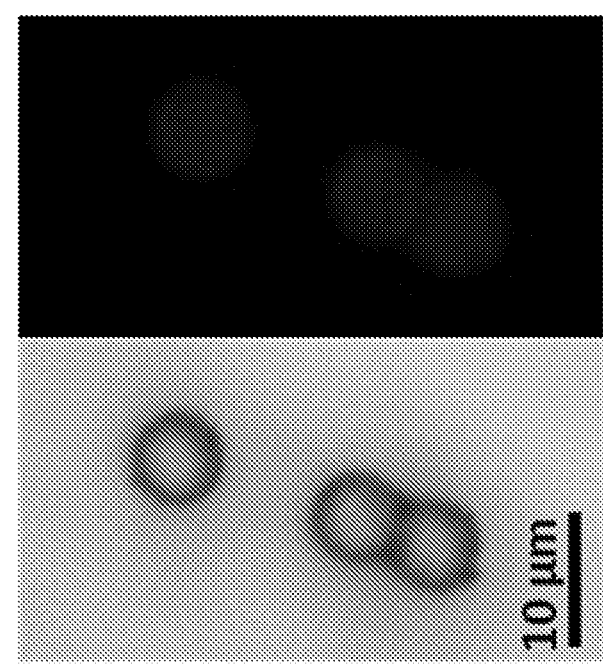
FIG. 58A is an exemplary embodiment of a microscopic bright field image and fluorescence image of Luminex microbeads before being probed by plasmonic-fluor-Cy3 in accordance with the present disclosure.
FIG. 58B is an exemplary embodiment of a microscopic bright field image and fluorescence image of Luminex microbeads after being probed by plasmonic-fluor-Cy3 in accordance with the present disclosure.
Figures 59A, 59B, 59C, 59D:
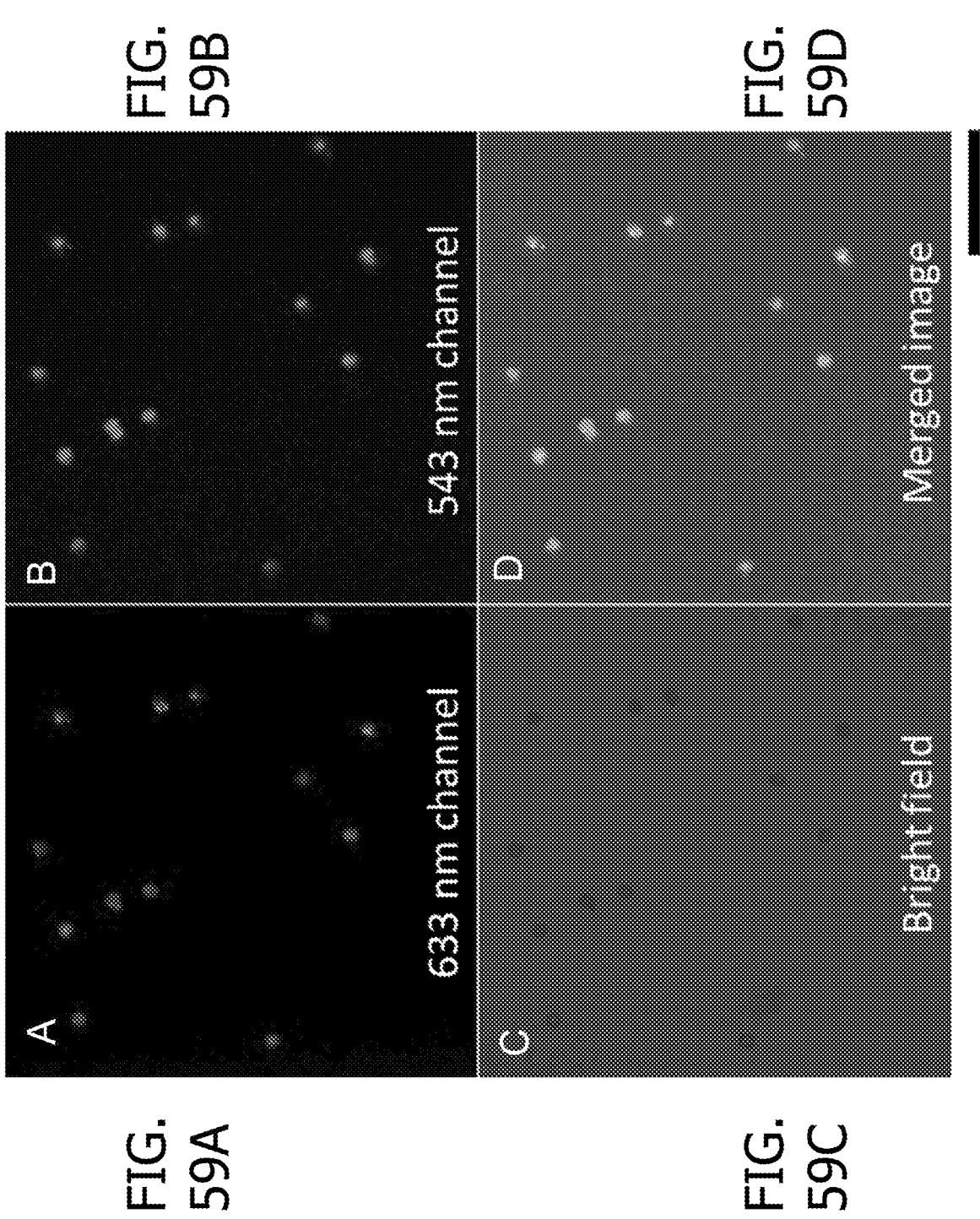
FIG. 59A is a fluorescence image of the Luminex microbeads after being stained with plasmonic-fluor-Cy3, showing the barcode of the microbeads (excited by 633 nm laser) of different emission intensities.
FIG. 59B is a fluorescence image of the Luminex microbeads after being stained with plasmonic-fluor-Cy3 showing the fluorescence of bound Cy3 (excited by 543 nm laser).
FIG. 59C is a bright field image of the microbeads.
FIG. 59D is a merged image of bright field and fluorescence shown in FIG. 59(A-C).
Figure 60:
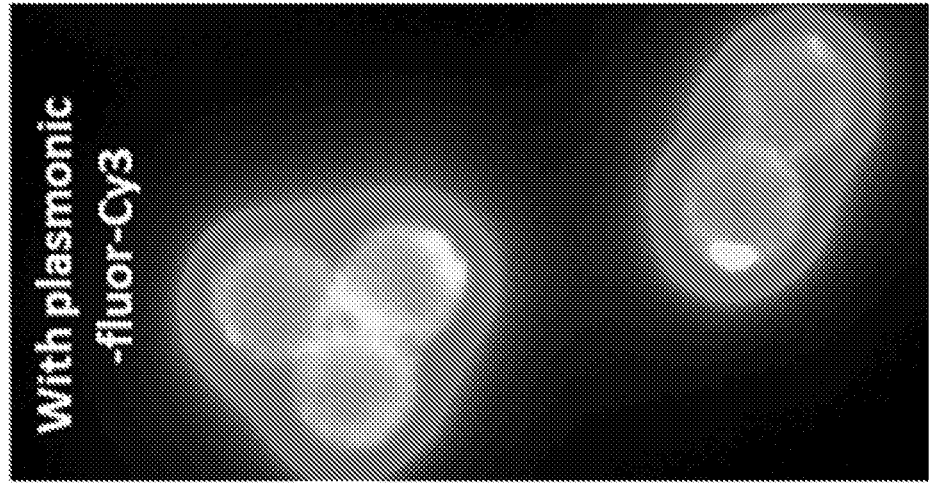
FIG. 60 is an exemplary embodiment of fluorescence images of microbead(s) before and after being probed with plasmonic-fluor-Cy3 in accordance with the present disclosure.
Figure 60:
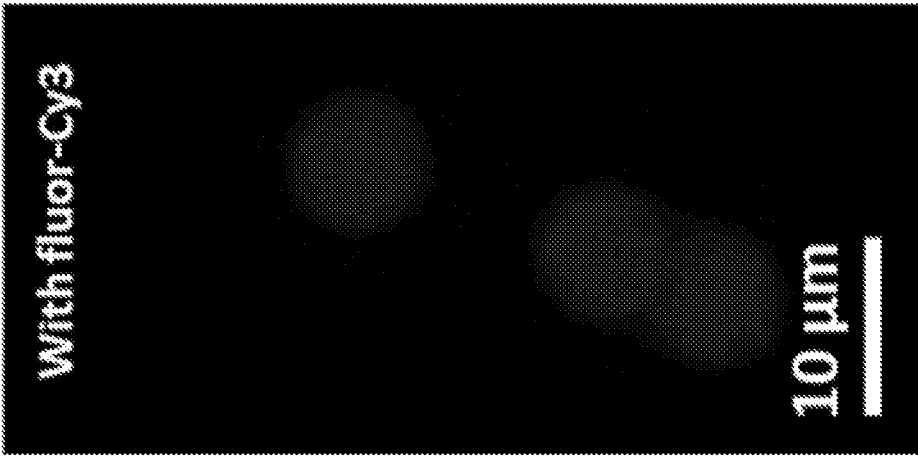
Figure 61:
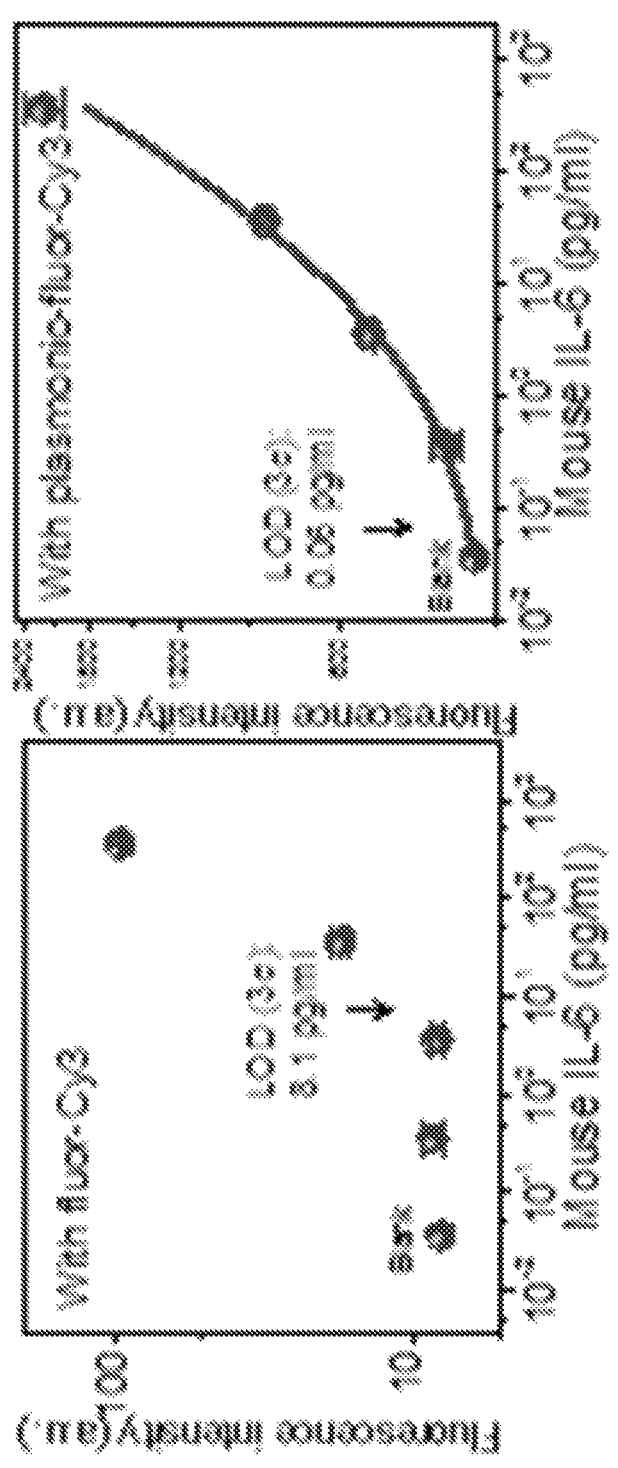
FIG. 61 is an exemplary embodiment of mouse IL-6 standard curves obtained before (left) and after (right) applying plasmonic-fluor-Cy3 in accordance with the present disclosure.
Figure 62:
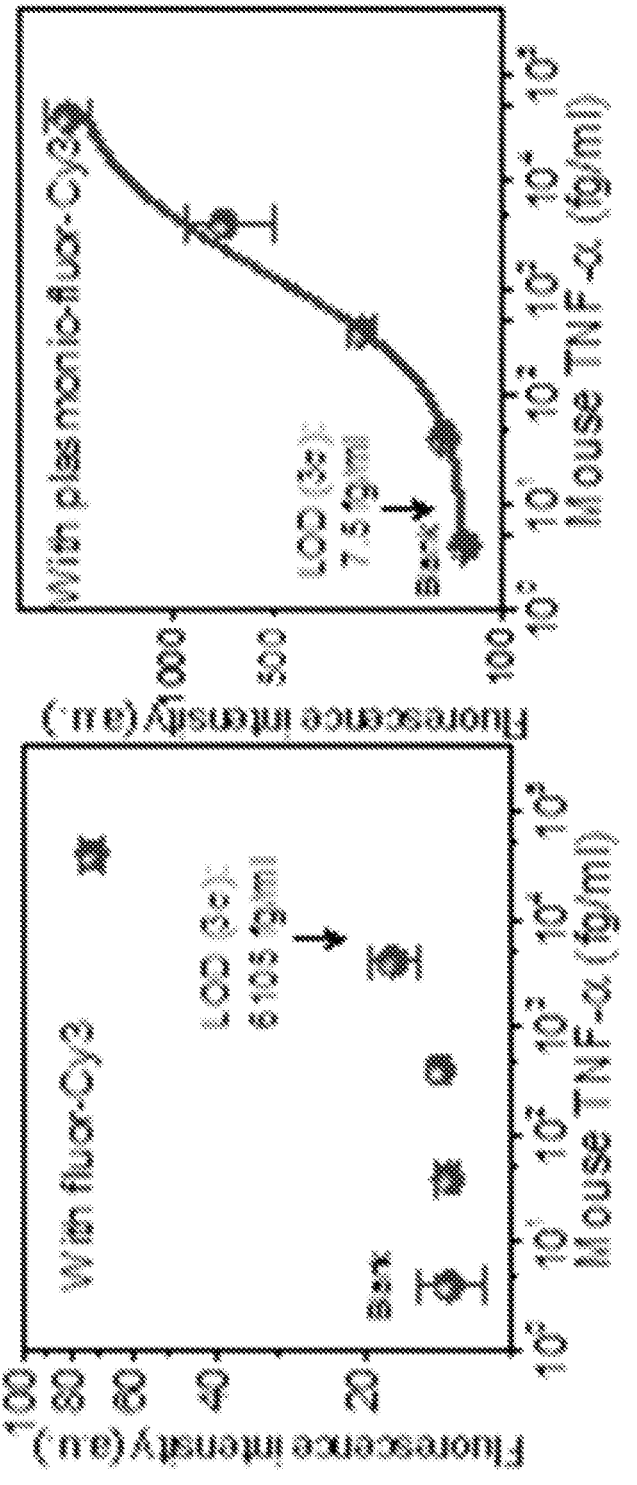
FIG. 62 is an exemplary embodiment of mouse TNF-α standard curves obtained before (left) and after (right) applying plasmonic-fluor-Cy3 in accordance with the present disclosure.
Figure 64B:
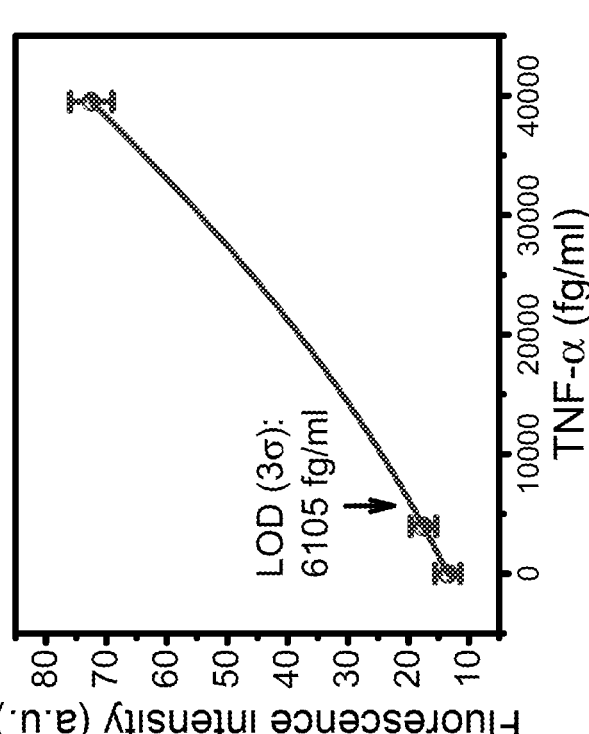
FIG. 64B is an exemplary embodiment of a plot showing the LODs of unenhanced bead-based fluoroimmunoassays (Luminex) for TNF-alpha in accordance with the present disclosure.
Figure 64A:
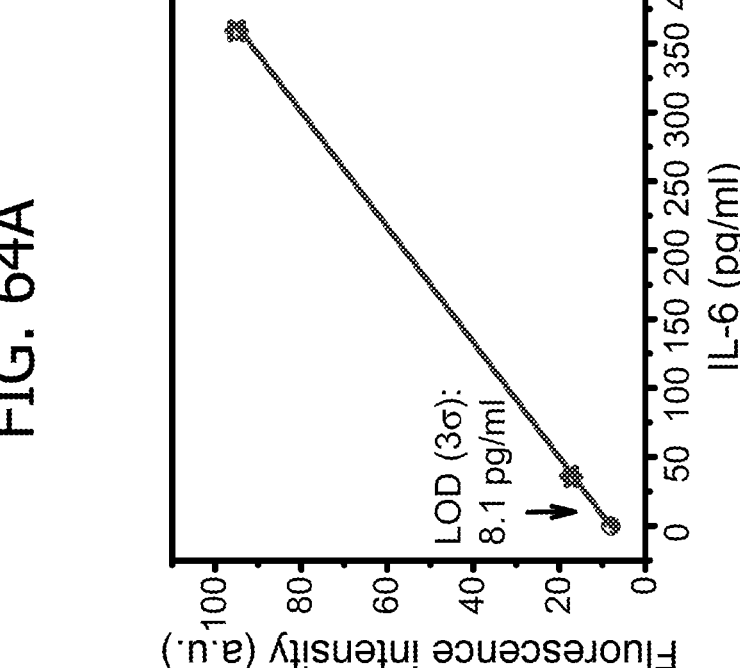
FIG. 64A is an exemplary embodiment of a plot showing the LODs of unenhanced bead-based fluoroimmunoassays (Luminex) for mouse IL-6 in accordance with the present disclosure.

The Luminex assay was customized to simultaneously detect mouse IL-6 and mouse tumor necrosis factor-α (TNF-α), which are important pro-inflammatory cytokines involved in cell signaling and immune modulation. The microbeads were incubated with a mixture of serial dilutions of TNF-α and IL-6, followed by the detection antibody cocktail, streptavidin-Cy3, and biotinylated plasmonic-fluor-Cy3 (FIG. 54). The beads are subsequently read using a dual laser flow-based instrument (Luminex 200), with the classification laser (635 nm) deciphering the barcode of each bead and the reporter laser (532 nm) determining the intensity of the Cy3 fluorescence, which is in direct proportion to the amount of analyte bound (FIG. 54). SEM image of the microbead shows uniform binding of plasmonic-fluor-Cy3 with no sign of aggregation (FIG. 57). FIG. 57 shows SEM images of microbead(s) before and after being probed with plasmonic-fluor-Cy3. The binding of plasmonic-fluor-Cy3 did not alter the size and shape of the bead (FIG. 58(A-B)) or the optical barcode signal (FIG. 59(A-D)). FIG. 58(A-B) show microscopic bright field images and fluorescence images of Luminex microbeads before (FIG. 58A) and after (FIG. 58B) being probed by plasmonic-fluor-Cy3. FIG. 59(A-D) shows fluorescence images of the Luminex microbeads after being stained with plasmonic-fluor-Cy3, revealing (FIG. 59A) the barcode of the microbeads (excited by 633 nm laser) of different emission intensities and (FIG. 59B) the fluorescence of bound Cy3 (excited by 543 nm laser). (FIG. 59C) Bright field image of the microbeads. (FIG. 59D) Merged image of bright field and fluorescence. Scale bar represents 50 μm. A significant increase in the microbead fluorescence intensity was observed after the binding of plasmonic-fluor-Cy3 (FIG. 60). FIG. 60 shows fluorescence images of microbead(s) before and after being probed with plasmonic-fluor-Cy3. The LODs of plasmon-enhanced mouse IL-6 and TNF-α assays were determined to be 56.6 fg/ml (2.7 fM) and 7.5 fg/ml (0.3 fM), respectively (FIG. 61, FIG. 62, and FIG. 63). FIG. 61 shows mouse IL-6 standard curves obtained before (left) and after (right) applying plasmonic-fluor-Cy3. FIG. 62 shows mouse TNF-α standard curves obtained before (left) and after (right) applying plasmonic-fluor-Cy3. All standard curves are performed independently on different days with different batches of plasmonic-fluors at least three times. Compared to unenhanced counterpart (FIG. 61, FIG. 62, FIG. 63, and FIG. 64(A-B)), the plasmon-enhanced assay exhibited 143-fold and 814-fold lower LOD for mouse IL-6 and mouse TNF-α, respectively. FIG. 63 shows individual data points, mean value, and standard deviation from mouse IL-6 Luminex, plasmonic-fluor-Cy3 enhanced mouse IL-6 Luminex, mouse TNF-α Luminex, and plasmonic-fluor-Cy3 enhanced mouse TNF-α Luminex assays. FIG. 64A is a plot showing the LODs of unenhanced bead-based fluoroimmunoassays (Luminex) for mouse IL-6. FIG. 64B is a plot showing the LODs of unenhanced bead-based fluoroimmunoassays (Luminex) for TNF-alpha. The curves were generated using polynomial fitting. Error bar represents s.d. (n=2 repeated tests). Notably, the vendor-specified LOD (using PE-streptavidin) for mouse IL-6 (2.3 pg/ml) and mouse TNF-α (1.47 pg/ml) were noted to be 41-fold and 196-fold inferior to the plasmon-enhanced Luminex assay. In essence, plasmonic-fluors serve as a powerful platform technology to enhance the bioanalytical parameters (LOD, LLOQ, dynamic range) of various existing immunoassays without requiring tedious steps or any specialized instruments.

Example 16—Plasmonic-Fluor Enhanced High
Throughput Multiplexed Proteomic Array

Biomolecular (micro-)arrays based on fluorescence read-out is an important clinical and research tool, especially for simple, high-throughput and rapid proteomic and genetic analysis, allowing miniaturization of thousands of assays on one small piece of analytical substrate. Despite advantages such as high multiplexity, rapid screening, and low sample volume, this methodology suffers from low sensitivity (even inferior to ELISA), which hinders its widespread application.

Figure 65:
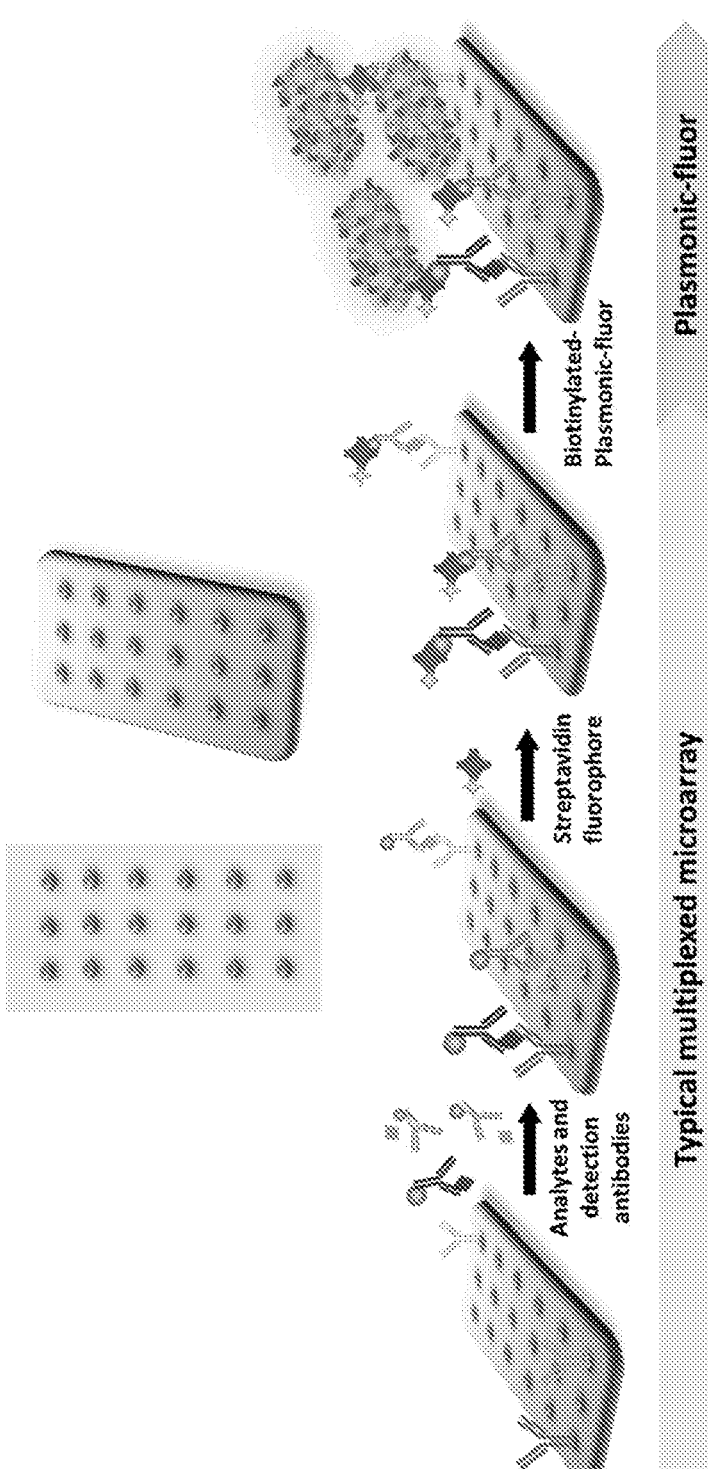
FIG. 65 is an exemplary embodiment of an illustration showing how to use a biotinylated plasmonic-fluor to enhance a typical multiplexed microarray in accordance with the present disclosure.
Figure 66:
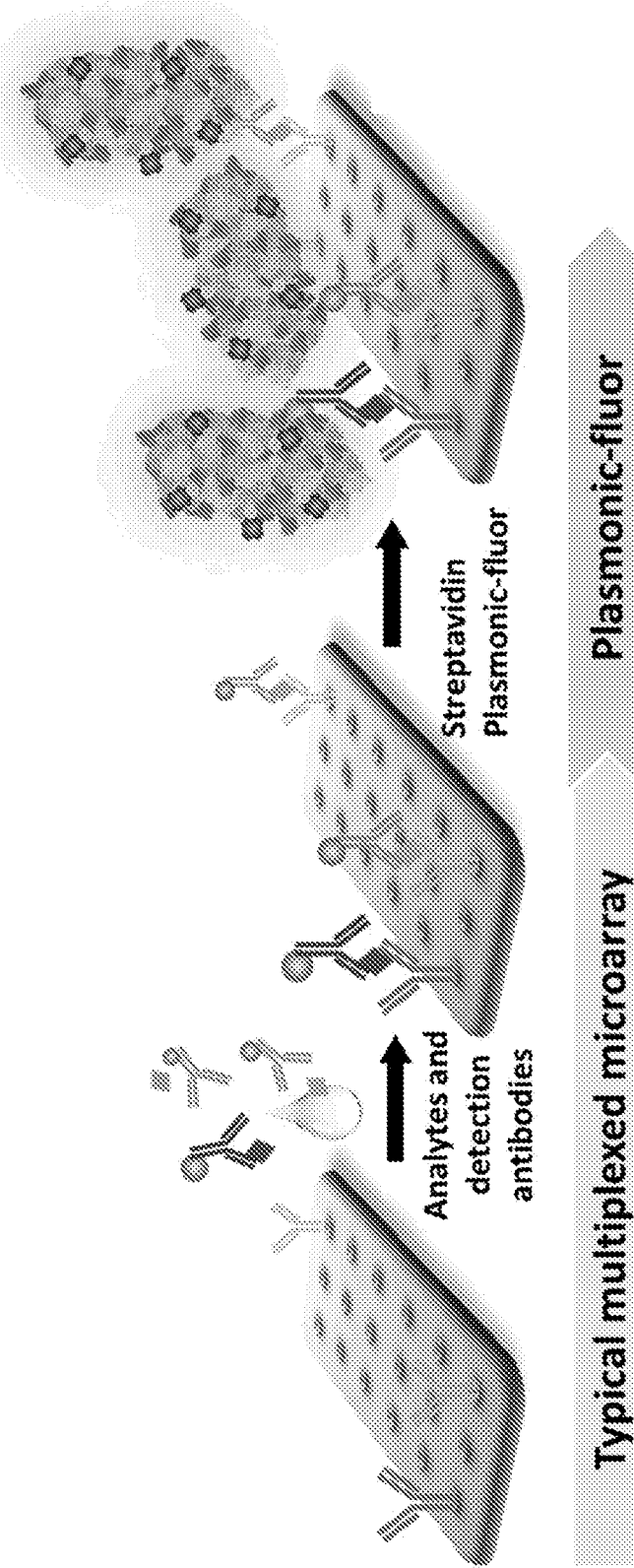
FIG. 66 is an exemplary embodiment of how to use a streptavidin-conjugated plasmonic-fluor to enhance a typical multiplexed microarray in accordance with the present disclosure.
Figure 67A:
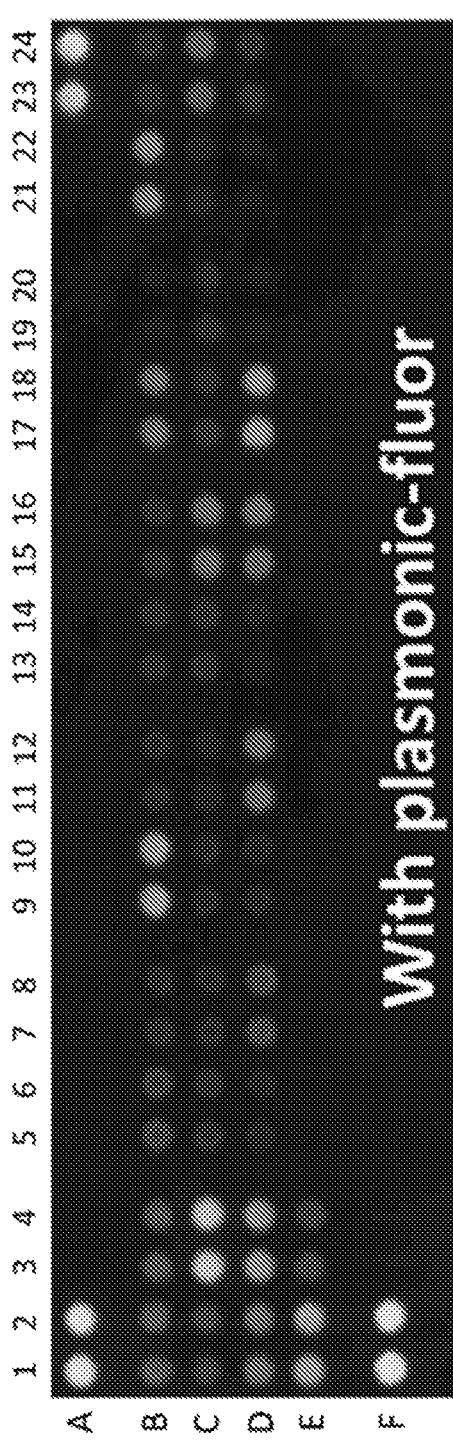
FIG. 67(A-B) is an exemplary embodiment of identification of specific analytes (or control) of each pair of fluorescence spots on the kidney biomarker array in accordance with the present disclosure. Fluorescent spots shown in FIG. 67A are identified by coordinates in FIG. 67B.

The applicability of plasmonic-fluors for enhancing the sensitivity of immuno-arrays was investigated. All error bars represent s.d. (n=2 repeated tests). An array of antibodies to biomarkers of human kidney disease was employed as a representative example (FIG. 65). FIG. 65 is an illustration showing the application of plasmonic-fluor-800CW to enhance the bioanalytical parameters of multiplexed proteome profiler for human kidney disease biomarkers implemented on a nitrocellulose membrane. This example illustrates how to use a biotinylated plasmonic-fluor to enhance a typical multiplexed microarray, wherein capture antibodies to specific analytes are printed in spatially distinct spots on either a membrane, glass slide, or polystyrene substrate. In this method, a user can first label the array with a standard fluorescently-labeled streptavidin and then label with a biotinylated plasmonic-fluor. In some embodiments, a streptavidin-conjugated plasmonic-fluor is used to enhance a typical multiplexed microarray, wherein capture antibodies to specific analytes are printed in spatially distinct spots on either a membrane, glass slide, or polystyrene substrate (FIG. 66). This array is comprised of 38 capture antibodies corresponding to human kidney disease protein biomarkers, printed in duplicates on a microporous nitrocellulose membrane (FIG. 67(A-B)). FIG. 67(A-B) shows identification of specific analytes (or control) of each pair of fluorescence spots on the kidney biomarker array. Fluorescent spots shown in FIG. 67A are identified by coordinate in FIG. 67B. Biotinylated IgGs and PBS were printed as reference positive control and negative control, respectively (FIG. 67(A-B)). A human urine sample from a patient with kidney disease was diluted 10-fold using blocking buffer, mixed with biotinylated detection antibody cocktail, and added onto the nitrocellulose membrane. After incubation, the membrane was exposed to streptavidin-800CW. Finally, plasmonic-fluor-800CW suspension is added on the array, incubated, and thoroughly rinsed to remove the unbound nanoconstructs (FIG. 65).

Figure 68:
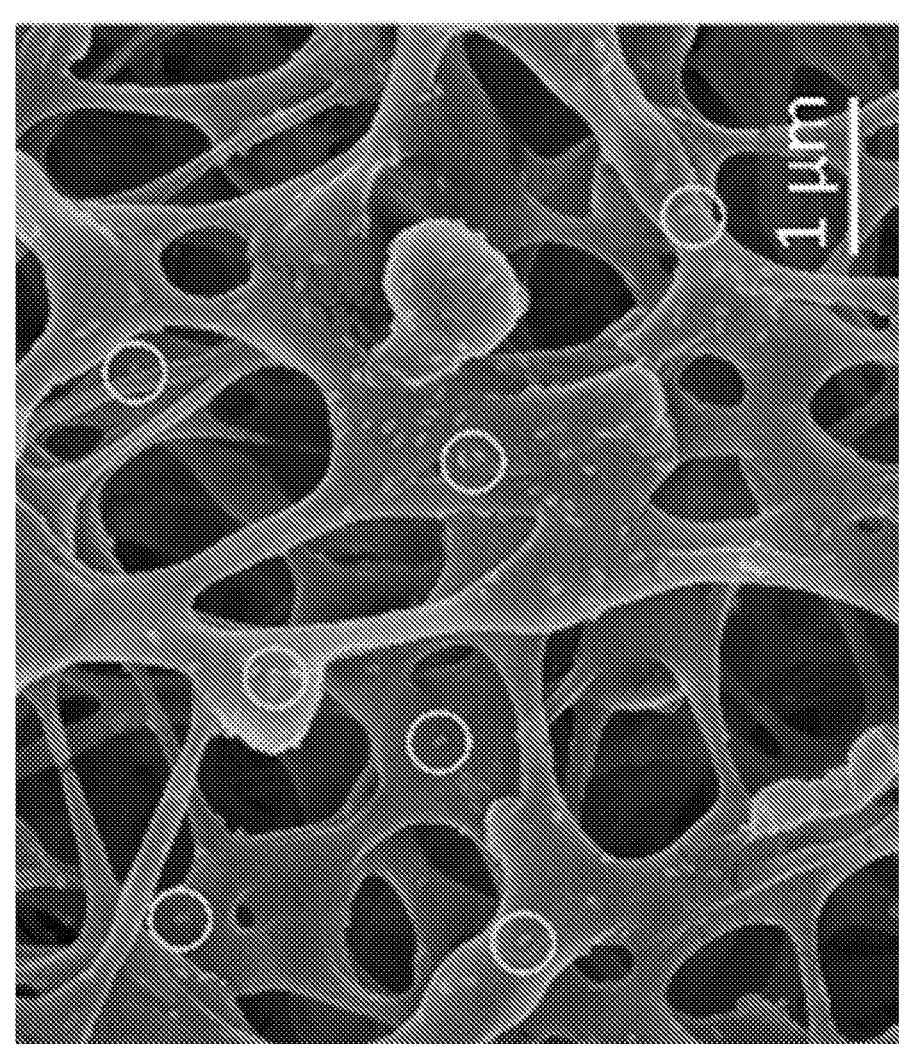
FIG. 68 is an exemplary embodiment of an SEM image showing the uniform distribution of plasmonic-fluor-800CW (a few highlighted by the yellow circles) on and in subsurface regions of the nitrocellulose membrane in accordance with the present disclosure.
Figures 69, 70, 71:
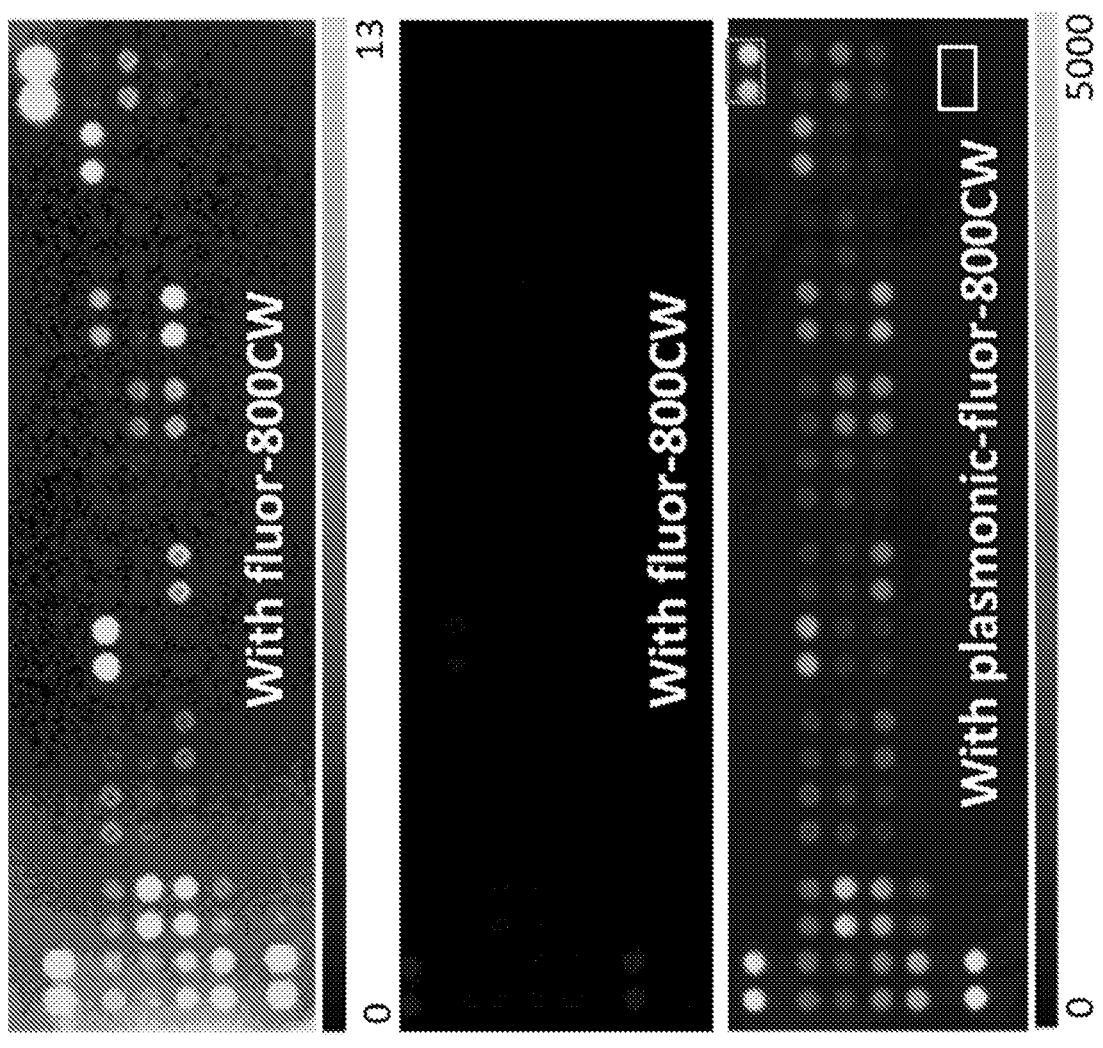
FIG. 69 is an exemplary embodiment of a fluorescence intensity map representing kidney disease protein biomarker profile of a kidney disease patient obtained using conventional fluorophores (streptavidin-800CW) with a fluorescence intensity scale bar from 0 to 13 in accordance with the present disclosure.
FIG. 70 is an exemplary embodiment of a fluorescence intensity map representing the kidney disease protein biomarker profile of FIG. 45 with a fluorescence intensity scale bar from 0 to 5000 in accordance with the present disclosure.
FIG. 71 is an exemplary embodiment of a fluorescence intensity map representing the kidney disease protein biomarker profile of the kidney disease patient shown in FIG. 69 and FIG. 70 after the addition of plasmonic-fluor-800CW and with a fluorescence intensity scale bar from 0 to 5000 in accordance with the present disclosure.
Figures 72A, 72B:
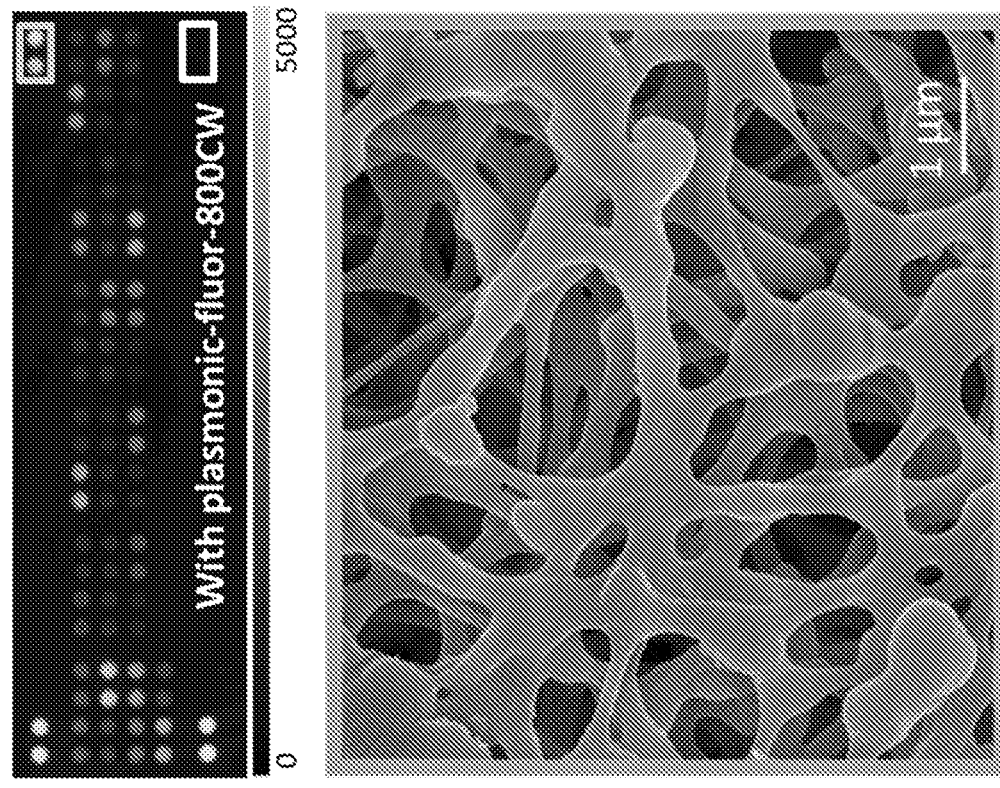
FIG. 72A is an exemplary embodiment of pairs of fluorescence spots on the kidney biomarker array shown in FIG. 67A in accordance with the present disclosure.
FIG. 72B is an exemplary embodiment of an SEM image of the nitrocellulose membrane in the negative control region (blue box shown in lower right corner of FIG. 72A, corresponding to coordinates F23 and F24 shown in FIG. 67A) in accordance with the present disclosure.
Figure 75:
FIG. 75 is an exemplary embodiment of a photographic depiction obtained from a mobile phone showing the color change of the nitrocellulose membrane with urine sample from kidney disease patient after the addition of plasmonic-fluor-800CW in accordance with the present disclosure.
Figure 75:
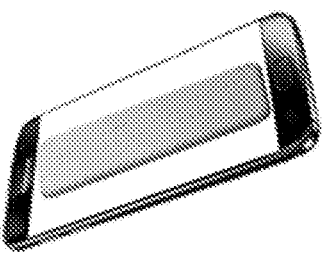
Figure 75:
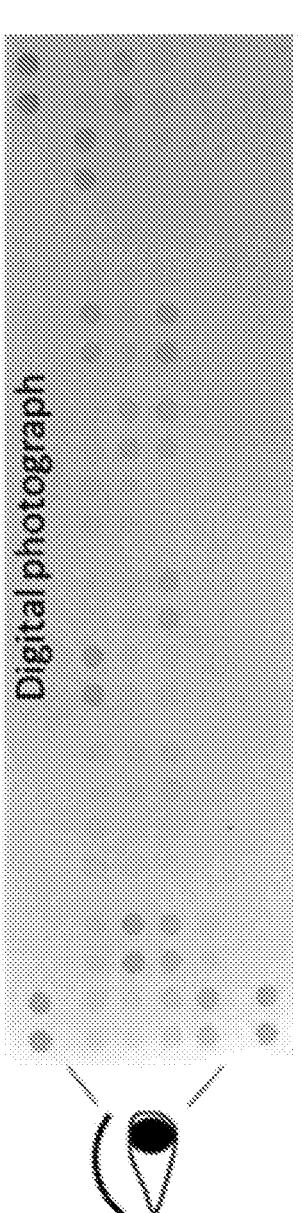
Figures 76A, 76B, 76C:
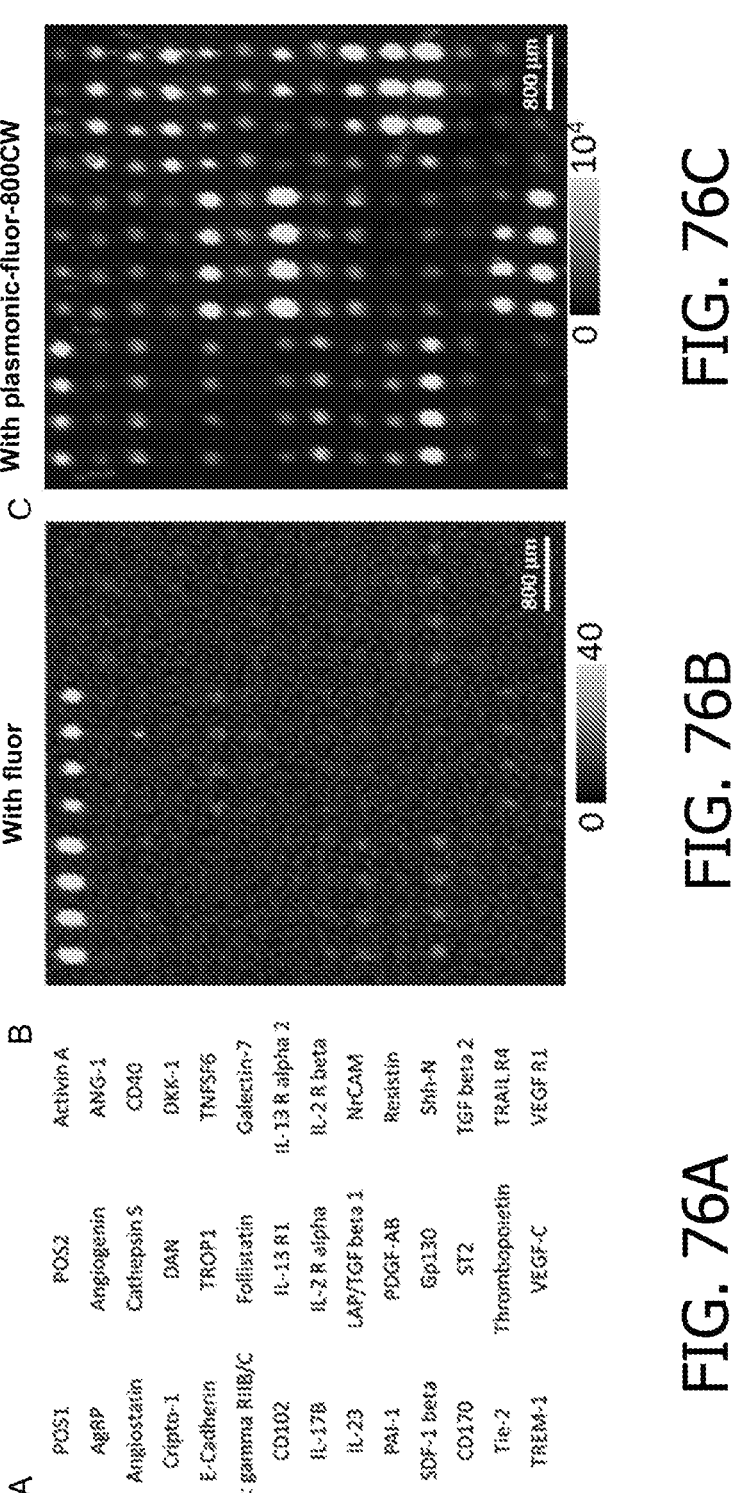
FIG. 76A is an exemplary embodiment of a layout of 40-plex cytokine microarray in accordance with the present disclosure.
FIG. 76B is an exemplary embodiment of a fluorescence map of cytokine microarray obtained using conventional fluorophore (streptavidin-800CW) in accordance with the present disclosure.
FIG. 76C is an exemplary embodiment of a fluorescence map of cytokine microarray obtained after addition of plasmonic-fluor-800CW in accordance with the present disclosure.
Figure 76D:
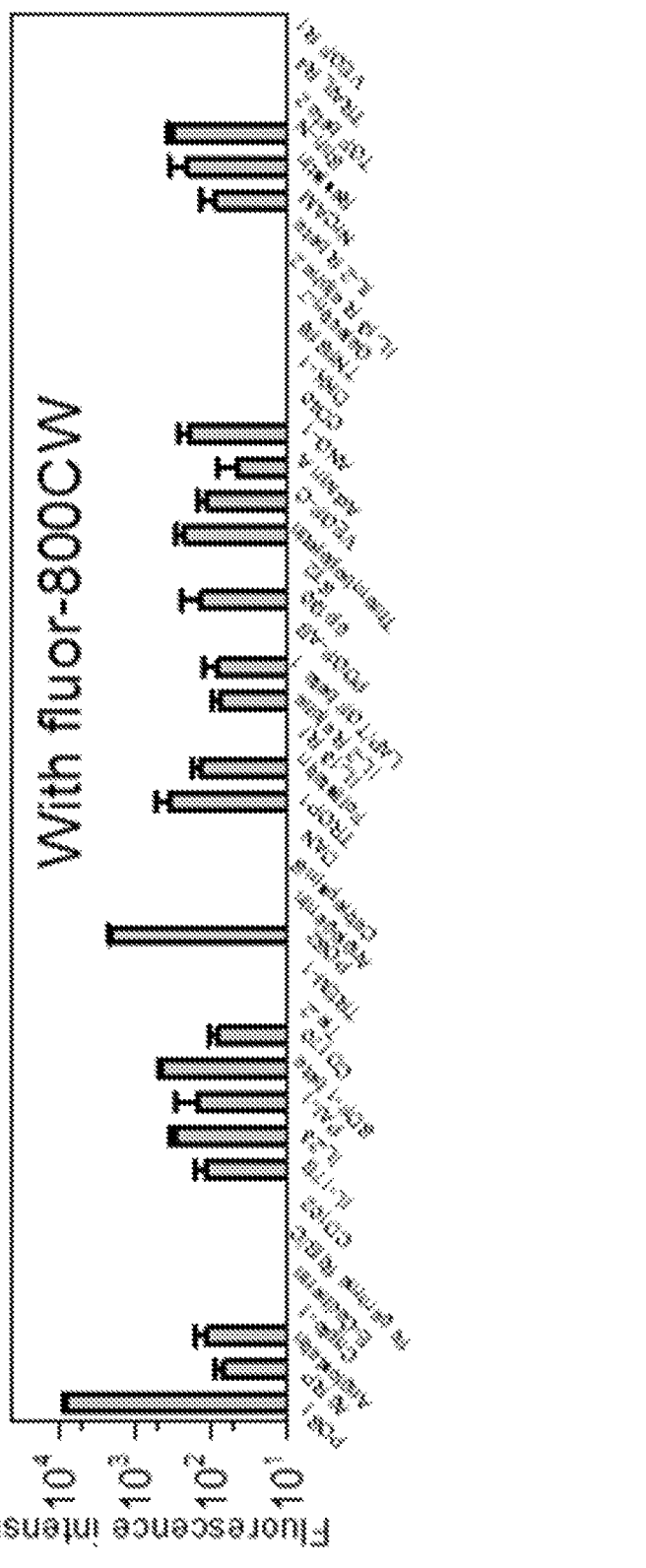
FIG. 76D is an exemplary embodiment of a plot showing the fluorescence intensity corresponding to each cytokine obtained using conventional fluorophore (streptavidin-800CW) in accordance with the present disclosure.
Figure 76E:
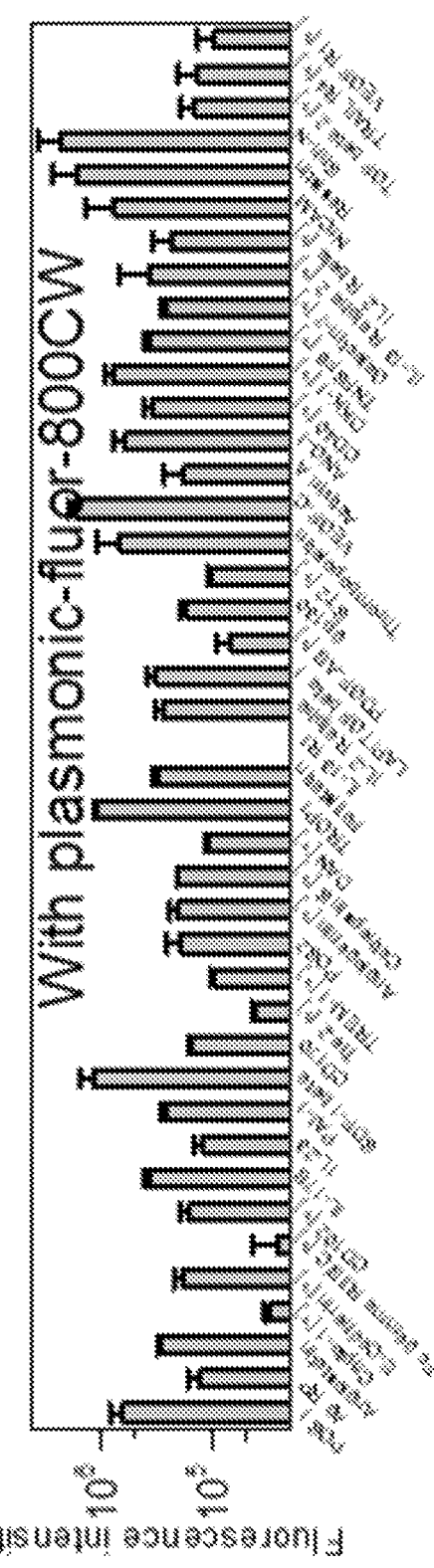
FIG. 76E is an exemplary embodiment of a plot showing the fluorescence intensity corresponding to each cytokine obtained after the addition of plasmonic-fluor-800CW in accordance with the present disclosure.
Figure 76F:
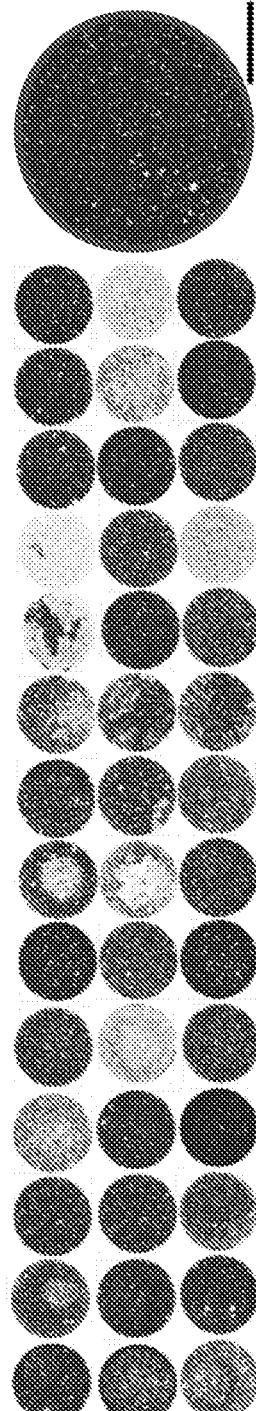
FIG. 76F is an exemplary embodiment of dark field scattering of plasmonic-fluor-800CW (AuNR) absorbed on cytokine microarray in accordance with the present disclosure.

SEM images from the positive control region revealed a uniform distribution of plasmonic-fluors on membrane (including porous subsurface regions) (FIG. 68). FIG. 68 is an SEM image showing the uniform distribution of plasmonic-fluor-800CW (a few highlighted by the yellow circles) on and in subsurface regions of the nitrocellulose membrane. FIG. 71 shows a fluorescence intensity map representing the kidney disease protein biomarker profile of the kidney disease patient shown in FIG. 69 and FIG. 70 after the addition of plasmonic-fluor-800CW (note the difference in fluorescence intensity scale bar). Concurrently, no signal was detected from the negative control (FIG. 71: blue box) and plasmonic-fluors were not observed in the SEM images from these locations, indicating their minimal non-specific binding (FIG. 72(A-B)). FIG. 72A shows the kidney biomarker array of FIG. 67A. FIG. 72B is an SEM image showing the nitrocellulose membrane in the negative control region (blue box in lower right corner of FIG. 72A (corresponding to pair at coordinates F23 and F24 shown in FIG. 67A); note the absence of fluorescence signal and plasmonic-fluors-800CW) after the addition of plasmonic-fluors-800CW, indicating the low non-specific binding of the plasmonic-fluor-800CW. Using conventional fluorophores, out of the 38 target protein biomarkers, only 26 were detectable, most of them exhibiting weak intensity (FIG. 69, FIG. 70, FIG. 73, and FIG. 74). FIG. 69 and FIG. 70 show fluorescence intensity maps representing kidney disease protein biomarker profile of a kidney disease patient obtained using conventional fluorophores (streptavidin-800CW). FIG. 73 and FIG. 74 show individual data points, mean value, and standard deviation with and without plasmonic-fluor, respectively. FIG. 75 is a digital photograph taken with a mobile phone showing the color change of the nitrocellulose membrane with urine sample from kidney disease patient after the addition of plasmonic-fluor-800CW. After addition of the plasmonic-fluor-800CW, the fluorescence signal intensity from each spot of the protein array increased significantly (FIG. 71, FIG. 73, and FIG. 74), enabling the detection and relative quantification of all of the other targets that could not be detected by the conventional fluors. Additionally, a commercially available 40-plex cytokine microarray was employed as another validation for plasmonic-fluor, where significant improvement in the microarray sensitivity was observed as well (FIG. 76(A-F)). FIG. 76A shows a layout of 40-plex cytokine microarray. Each antibody is printed in quadruplicate horizontally with each spot diameter around 140 μm. Fluorescence map of cytokine microarray obtained (FIG. 76B) using conventional fluorophore (streptavidin-800CW) and (FIG. 76C) after addition of plasmonic-fluor-800CW. Plot showing the fluorescence intensity corresponding to each cytokine obtained (FIG. 76D) using conventional fluorophore (streptavidin-800CW) and (FIG. 76E) after the addition of plasmonic-fluor-800CW. Error bar represents s.d. (n=4 repeated tests). (FIG. 76F) Dark field scattering of plasmonic-fluor-800CW (AuNR) absorbed on cytokine microarray. Each circle corresponds to one micro-spot area of each analyte. Scale bar represent 50 μm. The distribution of AuNR (plasmonic-fluor-800CW) on each micro-spot can be revealed clearly and counted digitally.

Figure 77:
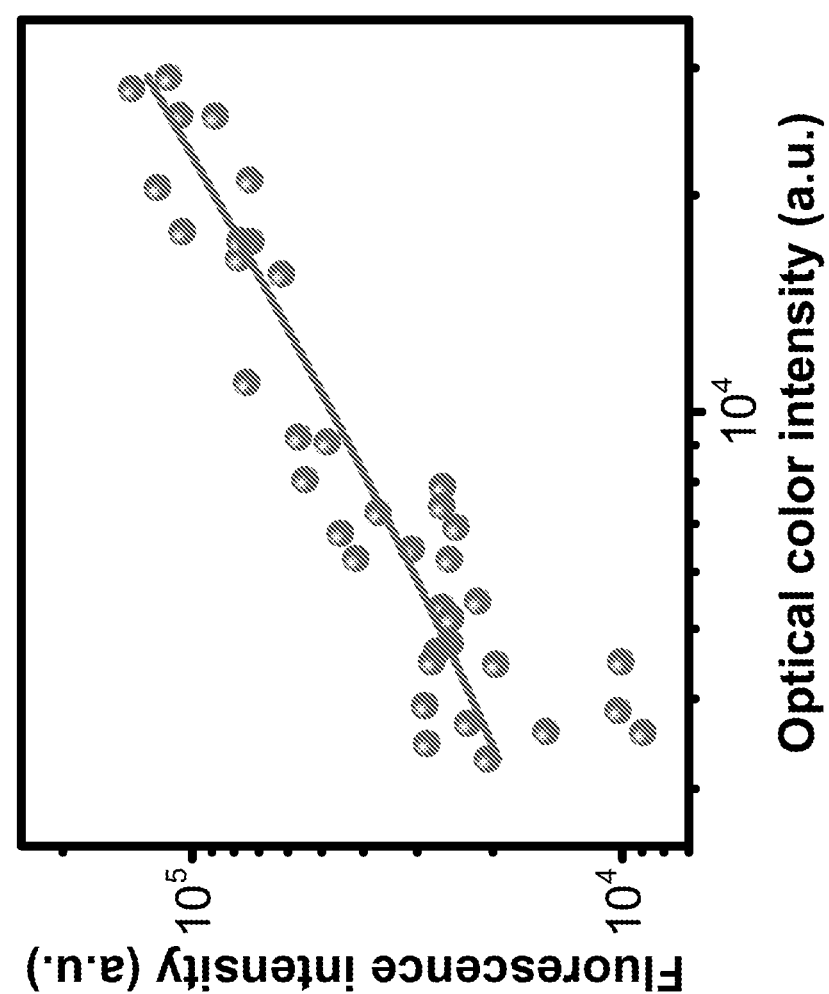
FIG. 77 is an exemplary embodiment of a plot showing the correlation between two readout modes (fluorescence vs. colorimetric readout) of the kidney biomarker array in accordance with the present disclosure.

It is known that the plasmonic nanostructures at the LSPR wavelength exhibit large extinction cross-section, which can be up to 5-6 orders of magnitude larger than light absorption of most organic dyes. This unique property of plasmonic nanostructures renders the possibility of utilizing plasmonic-fluors as multimodal bio-label. Indeed, the binding of plasmonic-fluor to the sensing domains resulted in analyte concentration-dependent color spots, which can be directly visualized by the naked eye (FIG. 75). The color intensity of each spot in a digital photograph, acquired using a smartphone camera under ambient light condition, was analyzed and compared to the corresponding fluorescence intensity. Good correlation was observed between the two acquisition modes (R2=0.88, FIG. 77), which indicates the potential applicability of this nanoconstruct as a "visible label" in resource-limited settings to alleviate the reliance on a dedicated and expensive readout instrument. FIG. 77 is a plot showing the correlation between two readout modes of the kidney biomarker array (fluorescence vs. colorimetric readout).

Example 17—Plasmonic-Fluor Enhanced
Immunocytochemistry/Immunofluorescence
(ICC/IF)

Immunocytochemistry based on immunofluorescence is a well-developed semi-quantitative method for analyzing the relative abundance, conformation, and subcellular localization of target antigens in cells. Again, this method lacks the sensitivity to distinguish low abundant biomolecules from the noise level due to the feeble fluorescence signal of conventional fluorophores. Autofluorescence, the natural emission of light by biological structures, further contributes to the overall low signal-to-noise ratio.

Figure 78:
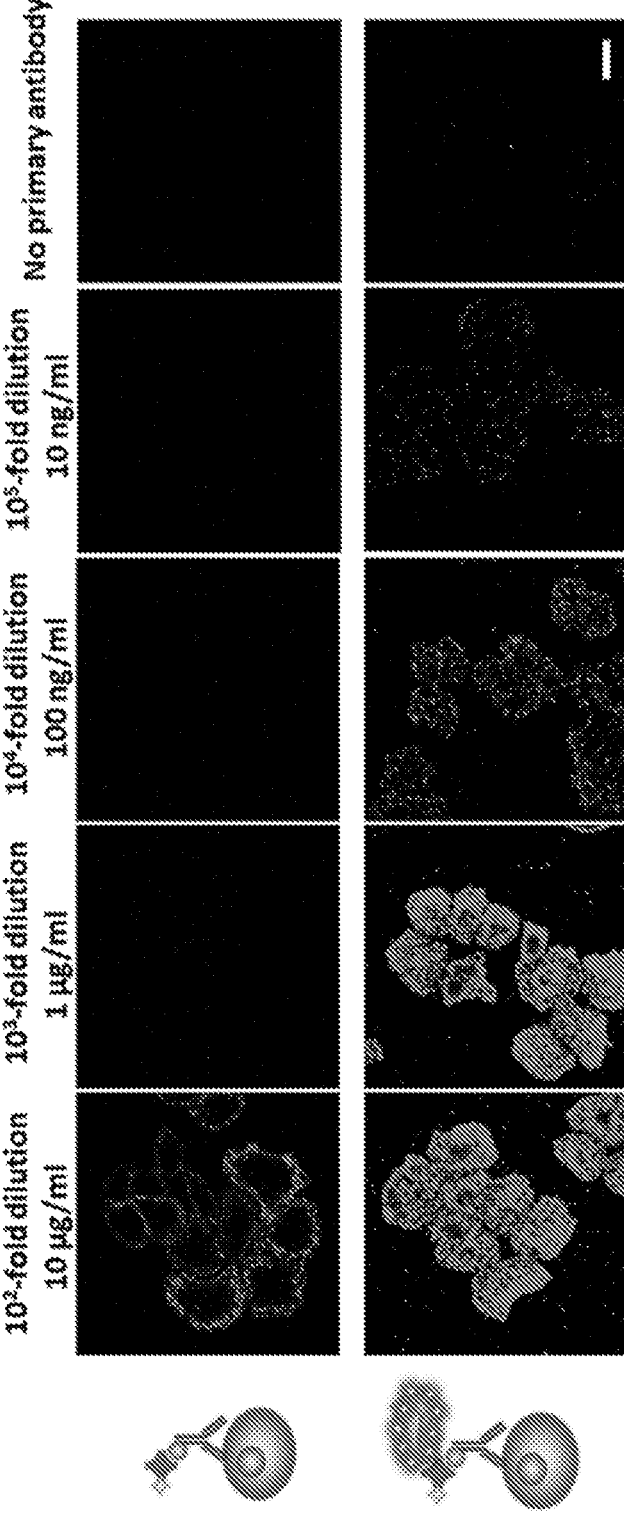
FIG. 78 is an exemplary embodiment of confocal laser scanning microscopy (CLSM) images of breast cancer cells (SK-BR-3) probed with conventional fluor (800CW, top row) and plasmonic-fluor-800CW (bottom row) at different concentrations of ErbB2 primary antibody in accordance with the present disclosure.
Figure 79A:
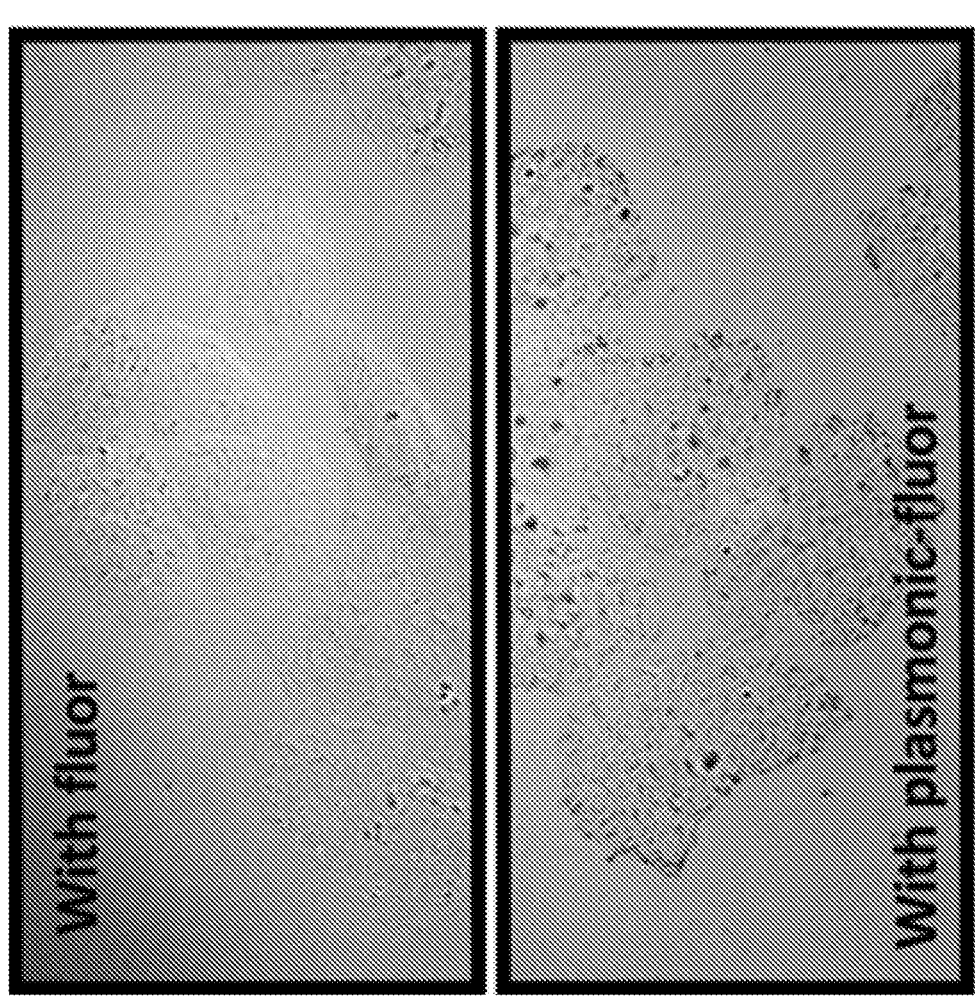
FIG. 79A is an exemplary embodiment of microscopic bright-field images of SK-BR-3 cells before (top) and after (bottom) being labeled with plasmonic-fluor-800CW in accordance with the present disclosure.
Figures 79B, 79C:
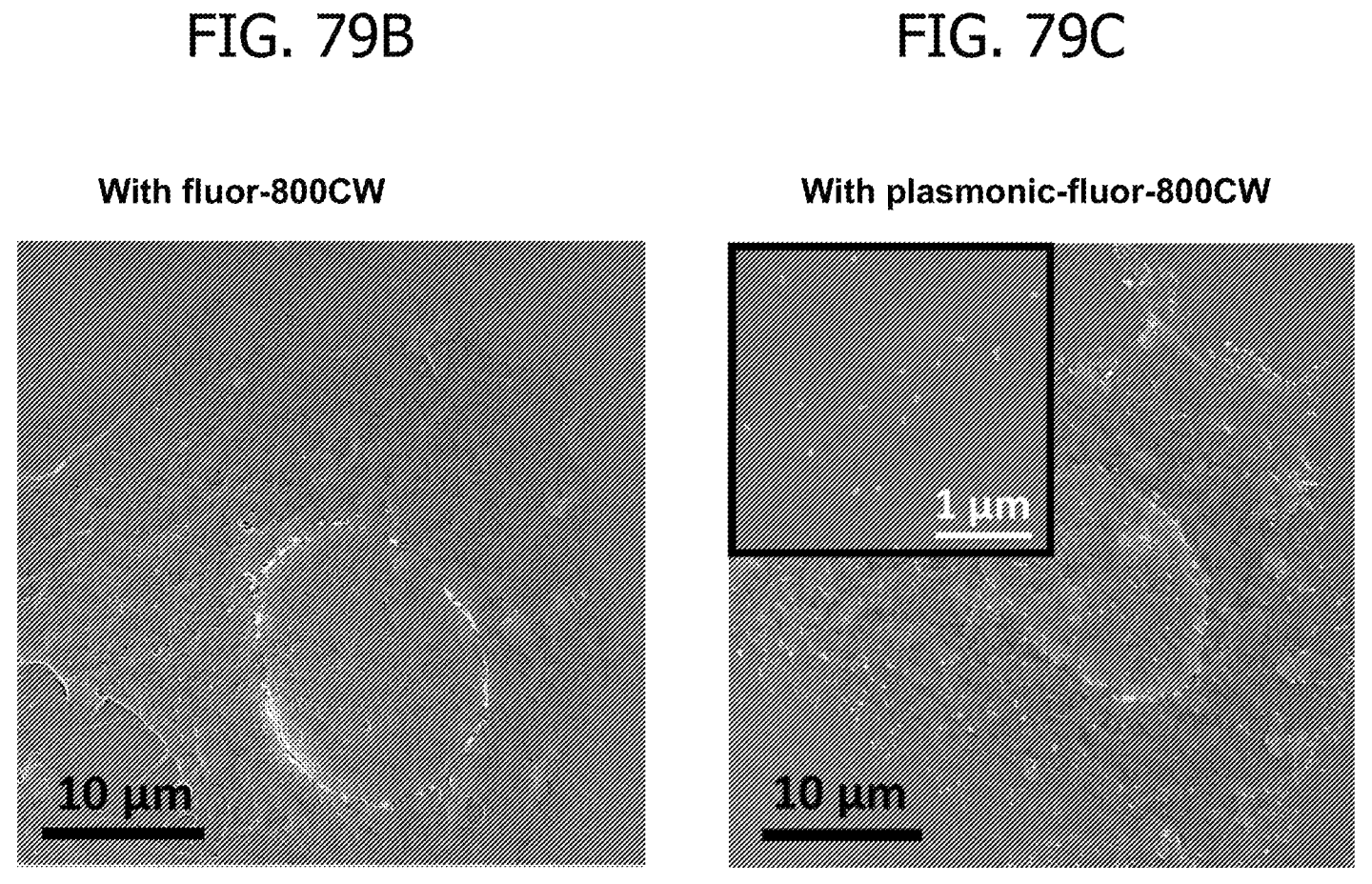
Figure 80:
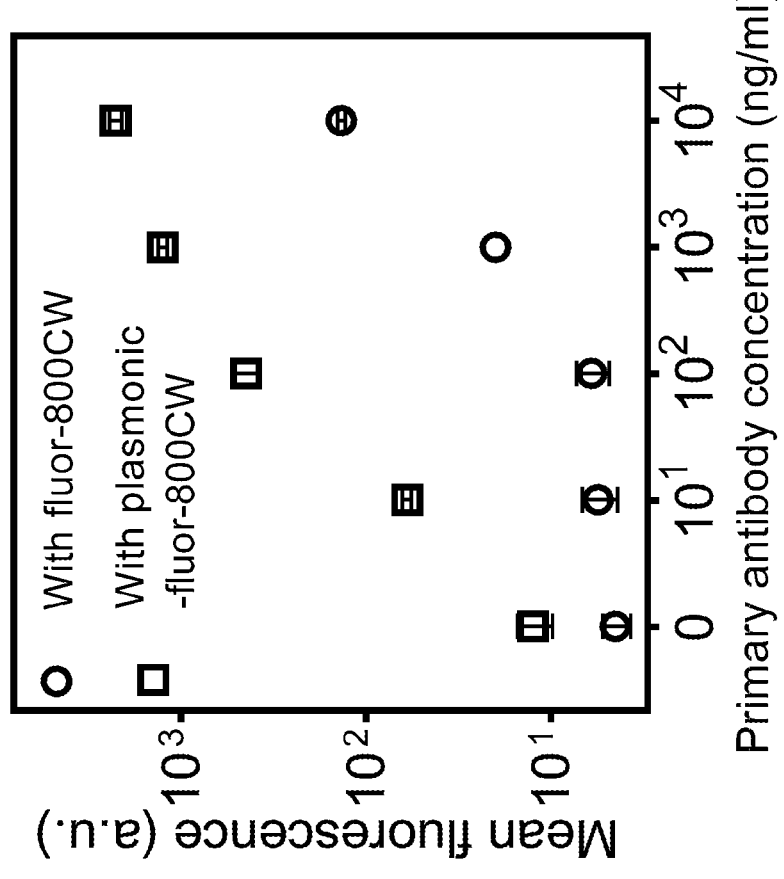
FIG. 80 is an exemplary embodiment of a plot showing the fluorescence intensity of SK-BR-3 cells stained with conventional fluor and plasmonic-fluor-800CW in accordance with the present disclosure.
Figure 81A:
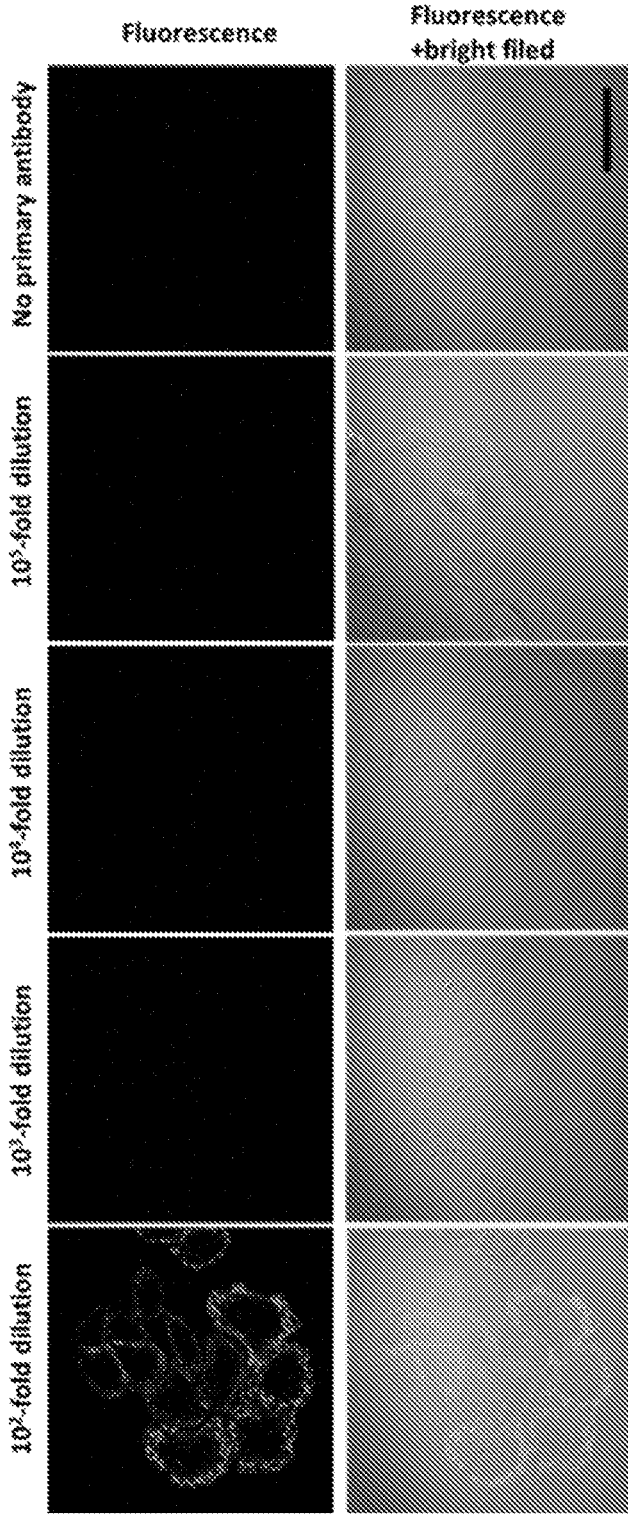
FIG. 81A is an exemplary embodiment of confocal laser scanning microscopy (CLSM) images of ErbB2 stained breast cancer cells (SK-BR-3) obtained using conventional immunocytochemistry procedure (cells are labelled with biotinylated primary antibody and streptavidin-fluor (800CW) sequentially) at different dilutions of ERbB2 primary antibody in accordance with the present disclosure.
Figure 81B:
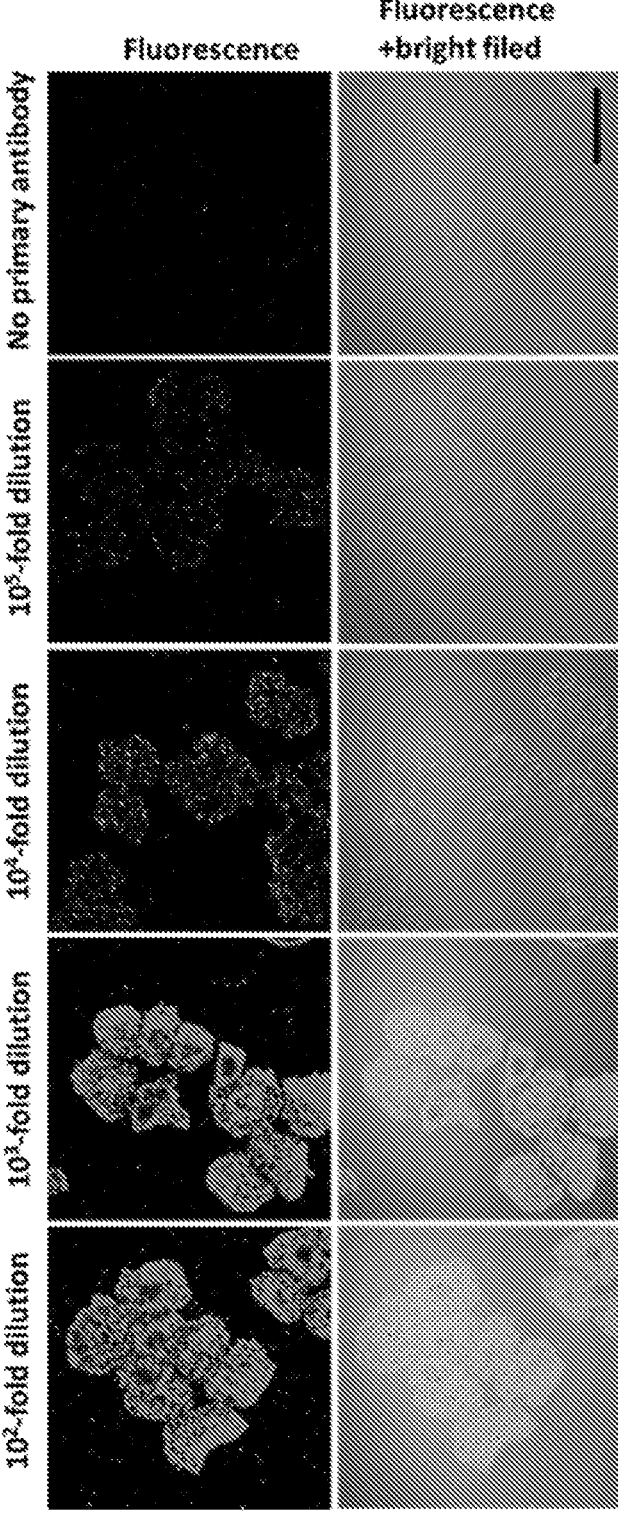
FIG. 81B is an exemplary embodiment of confocal laser scanning microscopy (CLSM) images of ErbB2 stained breast cancer cells (SK-BR-3) after the addition of plasmonic-fluor-800CW at different dilutions of ERbB2 primary antibody in accordance with the present disclosure.
Figure 82:
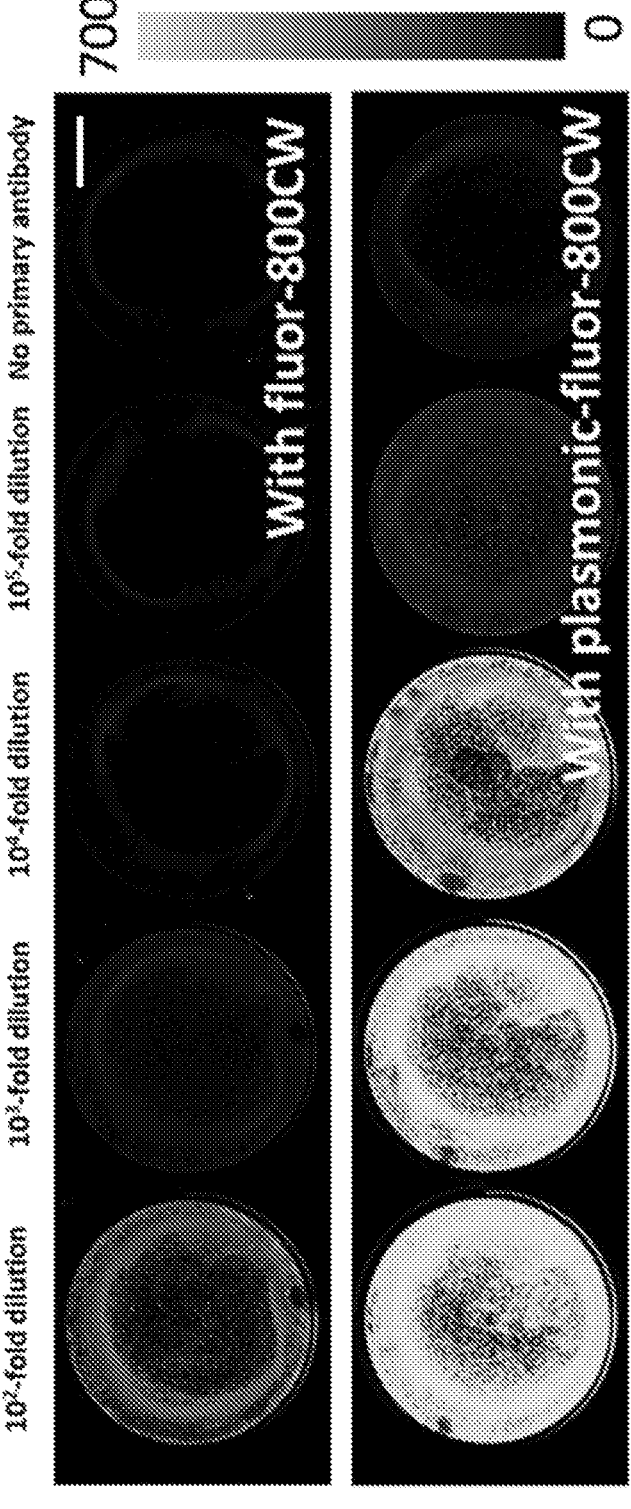
FIG. 82 is an exemplary embodiment of fluorescence mapping of SK-BR-3 cells cultured on a 6-well plate in accordance with the present disclosure.

To test the applicability of plasmonic-fluor in ICC/IF, ErbB2 (human epidermal growth factor receptor 2)-positive epithelial breast cancer cells (SK-BR-3) was employed as a model cell line. The surface receptor ErbB2 was immunostained using standard approach (biotinylated ErbB2 primary antibody and streptavidin-800CW), followed by the addition of plasmonic-fluor-800CW (FIG. 78). FIG. 78 shows confocal laser scanning microscopy (CLSM) images of breast cancer cells (SK-BR-3) probed with conventional fluor (800CW, top row) and plasmonic-fluor-800CW (bottom row) at different concentrations of ErbB2 primary antibody. Scale bar represents 10 μm. ErbB2 primary antibody (1 mg/ml) was diluted to different concentrations before incubation with cells. SEM images revealed the uniform distribution of plasmonic-fluors on the cell membrane (FIG. 79(A-C)). FIG. 79A shows microscopic brightfield images of SK-BR-3 cells before (top) and after (bottom) being labeled with plasmonic-fluor-800CW. SEM images of conventional fluor (FIG. 79B) labeled SK-BR-3 cell and plasmonic-fluor-800CW (FIG. 79C) labeled SK-BR-3 cell, inset showing the uniformly distributed plasmonic-fluors on the cell membrane. Confocal laser scanning microscopy (CLSM) images of the cells revealed up-to 100-fold higher fluorescence signal (background subtracted) after the addition of plasmonic-fluors (20 pM) (FIG. 78, FIG. 80, FIG. 81(A-B), and FIG. 82), and the expression of ErBb2 receptors could be imaged even at 100,000-fold dilution of the primary antibody (10 ng/ml) (FIG. 78, FIG. 81(A-B)). FIG. 80 is a plot showing the fluorescence intensity of SK-BR-3 cells stained with conventional fluor and plasmonic-fluor-800CW. Error bars represent s.d. (over three different locations). Confocal laser scanning microscopy (CLSM) images of ErbB2 stained breast cancer cells (SK-BR-3) obtained using conventional immunocytochemistry procedure (cells are labelled with biotinylated primary antibody and streptavidin-fluor (800CW) sequentially, see FIG. 81A), followed by the addition of plasmonic-fluor-800CW (FIG. 81B), at different dilutions of ERbB2 primary antibody. Scale bar represents 15 μm. FIG. 82 shows fluorescence mapping of SK-BR-3 cells cultured on a 6-well plate. The cells are probed with conventional fluorophores (top) followed with plasmonic-fluor-800CW (bottom). Scale bar represents 1 cm. In stark contrast, the fluorescence signal could only be imaged at a 100-fold (typical dilution; 10 μg/ml) dilution of primary antibody using conventional fluorophores (FIG. 78). These results demonstrate not only the applicability of plasmonic-fluor in significantly reducing the amount of antibody (and consequent cost) required in ICC/IF but also the ability to image low-abundance biomarkers on the cell surface using plasmonic-fluors.

Example 18—Plasmonic-Fluor Enhanced Flow Cytometry Measurement

Figure 83:
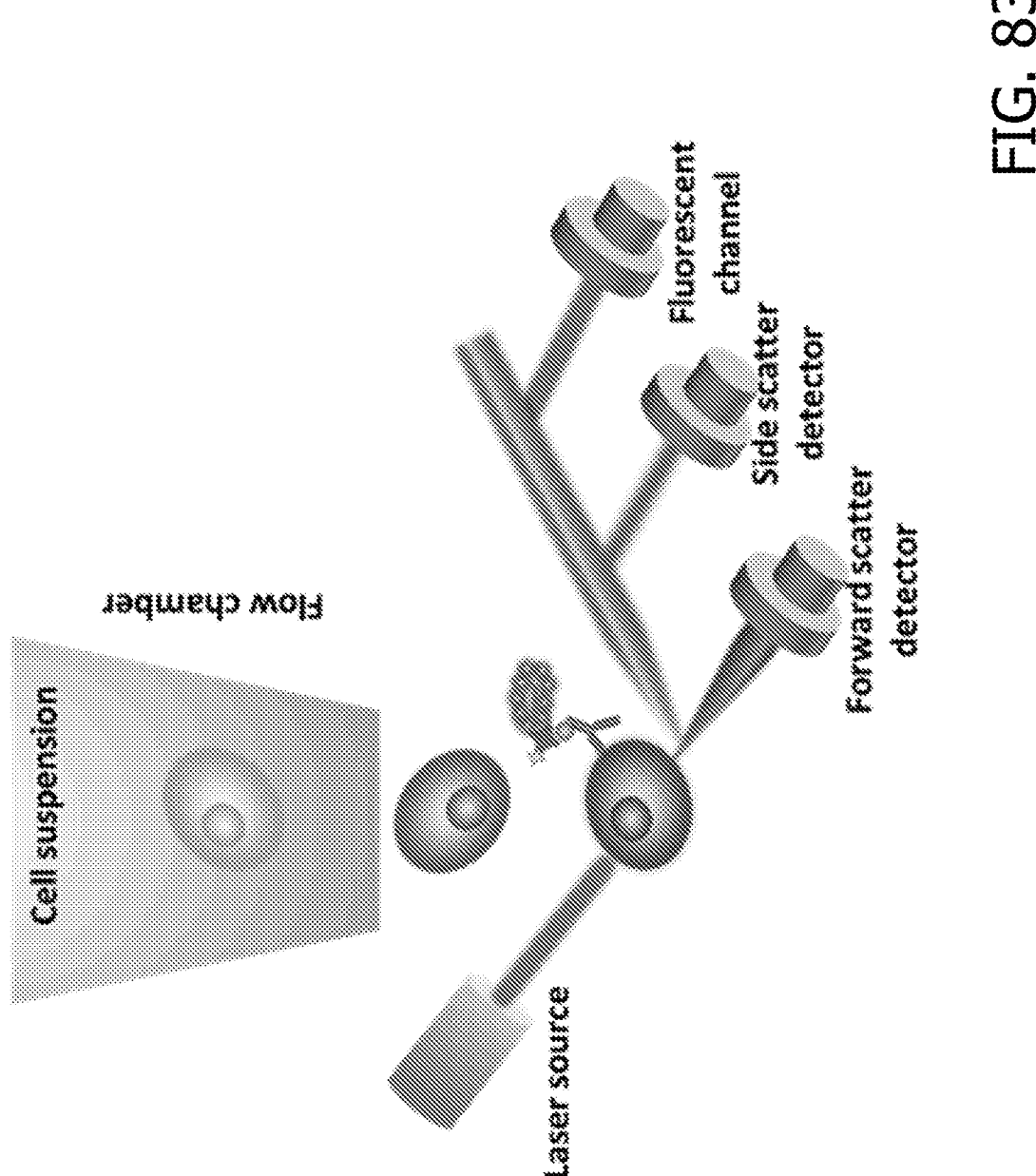
FIG. 83 is an exemplary embodiment of a schematic showing flow cytometry of ErbB2-stained SK-BR-3 cells probed by conventional fluor (680LT) followed with plasmonic-fluor-680LT in accordance with the present disclosure.

Flow cytometry is extensively employed in cell analysis to measure the expression and relative abundance of specific analytes on or within the cells at rates of thousand or more cells per second (FIG. 83). FIG. 83 is a schematic showing flow cytometry of ErbB2-stained SK-BR-3 cells probed by conventional fluor (680LT) followed with plasmonic-fluor-680LT. However, flow cytometry also suffers from significant challenges in terms of fluorescence signal-to-noise ratio due to the high speed of the target species as they cross the laser focus, limiting the time for fluorescence readout. Again, background fluorescence (autofluorescence) from cells poses difficulty in delineating small changes in the expression levels of intra- and extracellular targets.

Figure 84B:
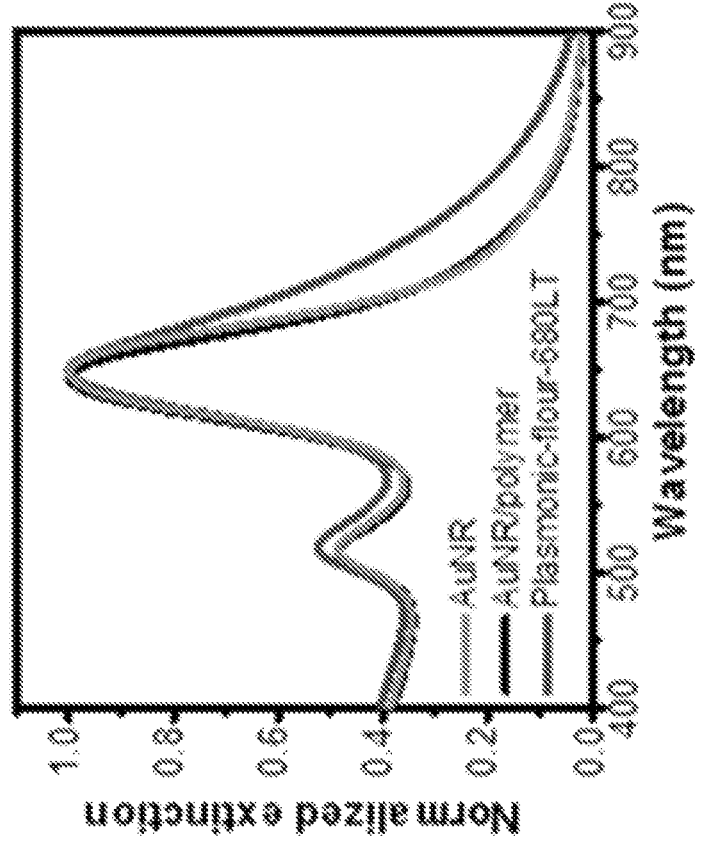
FIG. 84A and FIG. 84B are exemplary embodiments of a 680LT TEM image and extinction spectra in accordance with the present disclosure.
Figure 84A:
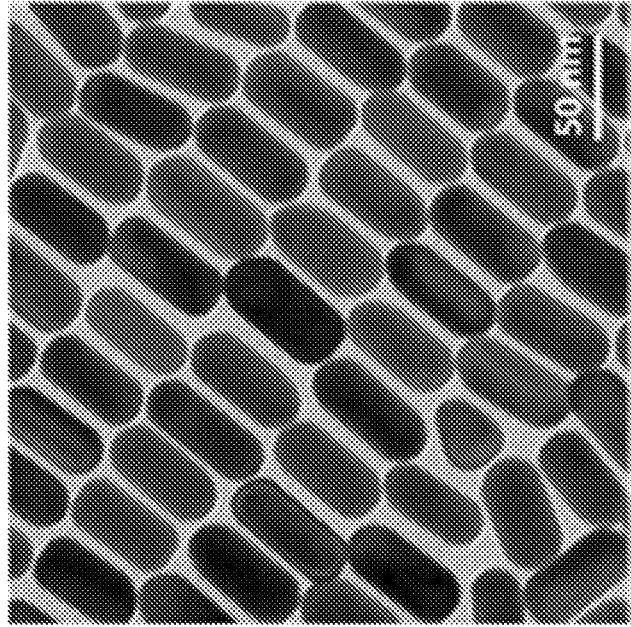
Figure 85A:
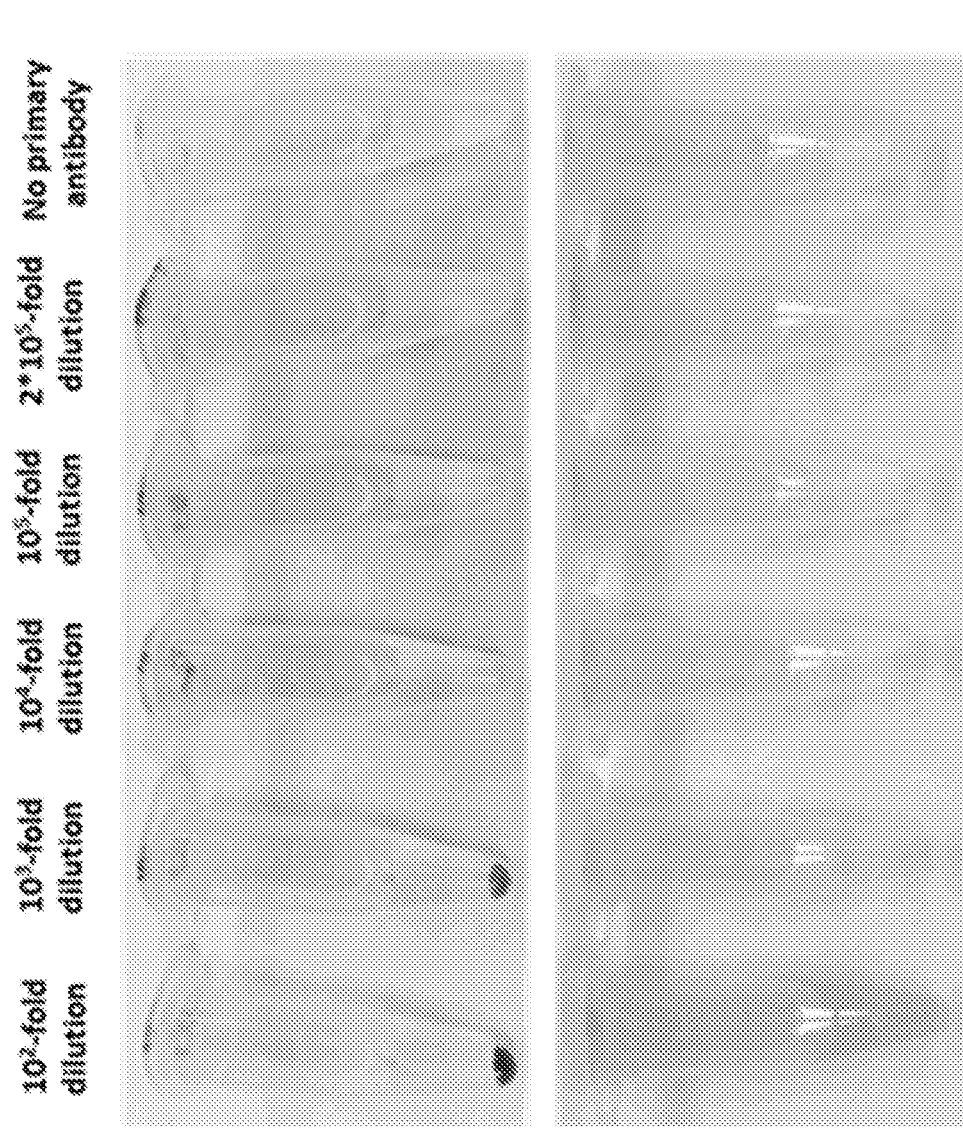
FIG. 85A is an exemplary embodiment of photographs showing the color change of SK-BR-3 cell (top: pellet; bottom: suspension) after being labeled with plasmonic-fluor-680LT in accordance with the present disclosure.
Figure 85B:
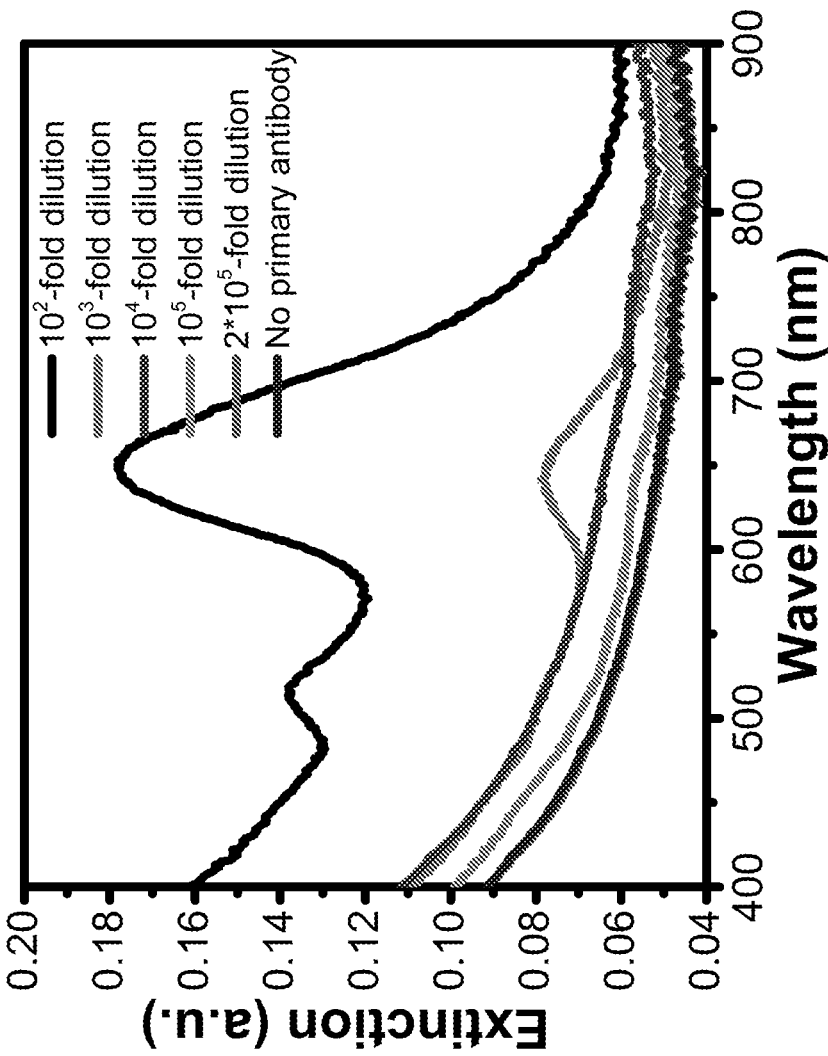
FIG. 85B is an exemplary embodiment of vis-NIR extinction spectra of plasmonic-fluor-680LT labeled SK-BR-3 cell suspensions under different dilutions of ErbB2 primary antibody in accordance with the present disclosure.
Figure 86:
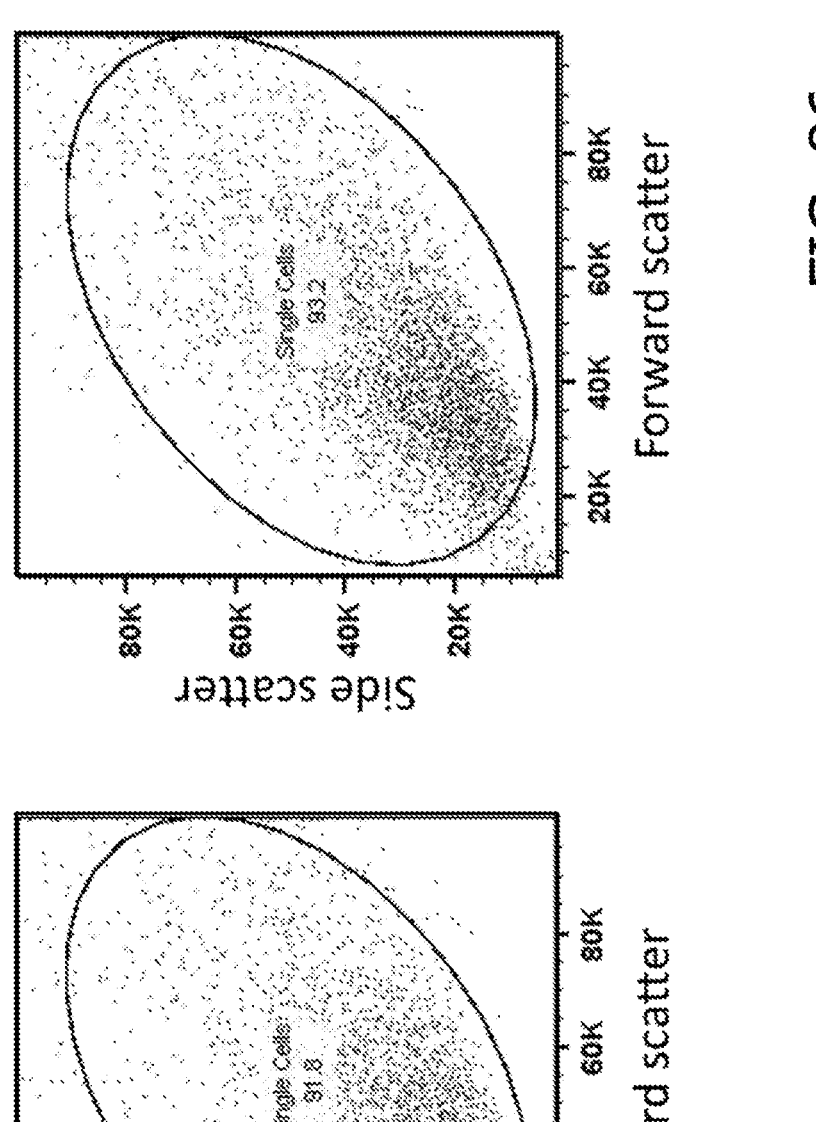
FIG. 86 is an exemplary embodiment of pseudocolor plots (with example of gating strategy to include single cell) of side scatter and forward scatter of SK-BR-3 cells before (left) and after (right) being labeled with plasmonic-fluor-680LT in accordance with the present disclosure.
Figure 87:
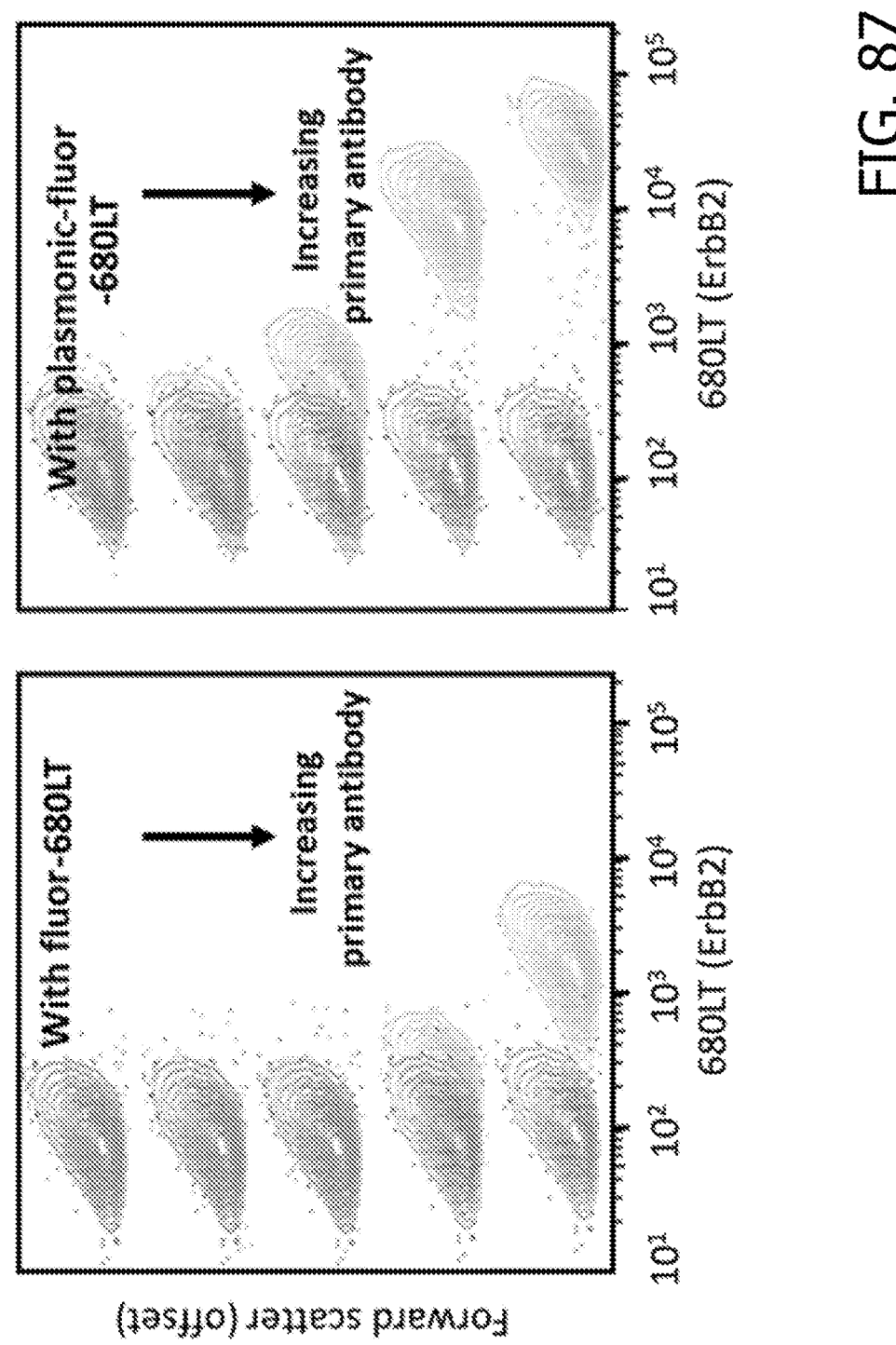
FIG. 87 is an exemplary embodiment of a flow contour plot (with outliers) of fluorescence vs. forward scatter (vertically offset for clarity) of SK-BR-3 cells probed using different concentrations of ErbB2 primary antibody in accordance with the present disclosure.
Figure 88:
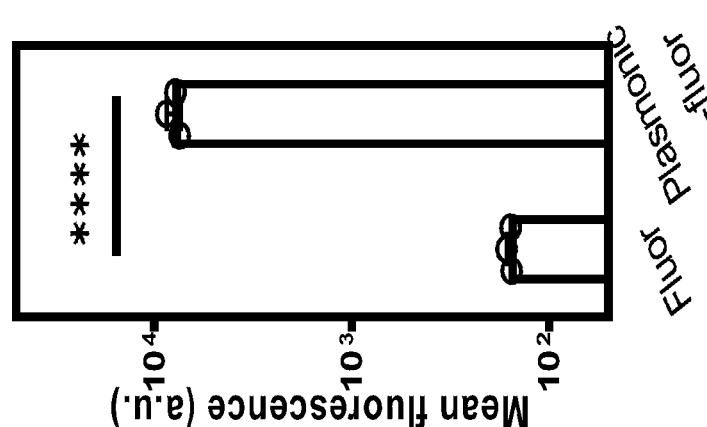
FIG. 88 is an exemplary embodiment of a fluorescence histogram of SK-BR-3 cells probed using conventional fluor (680LT) followed by the addition of plasmonic-fluor-680LT (at $10^3$-fold dilution of primary antibody) in accordance with the present disclosure.
Figure 88:
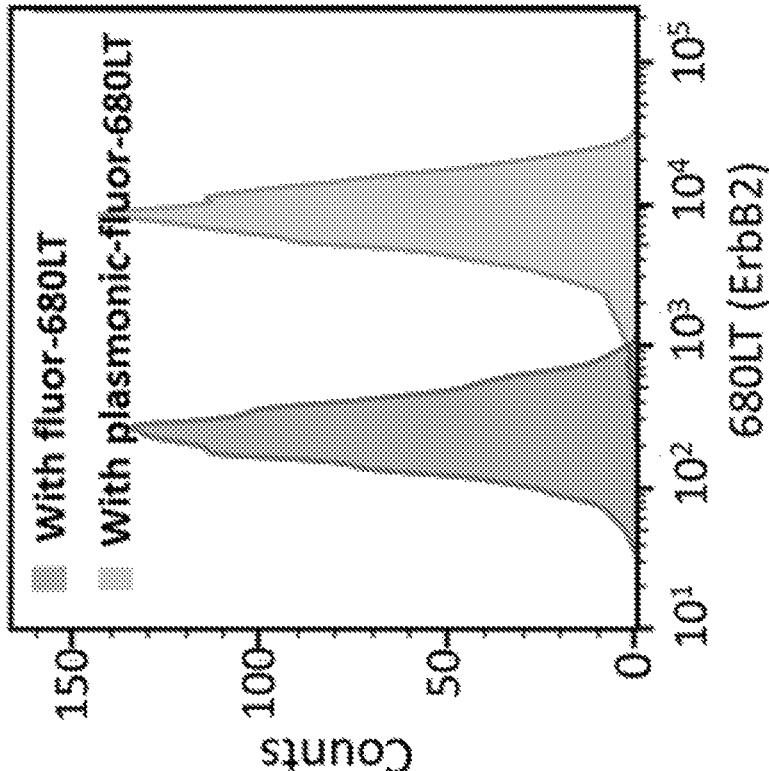
Figure 89:
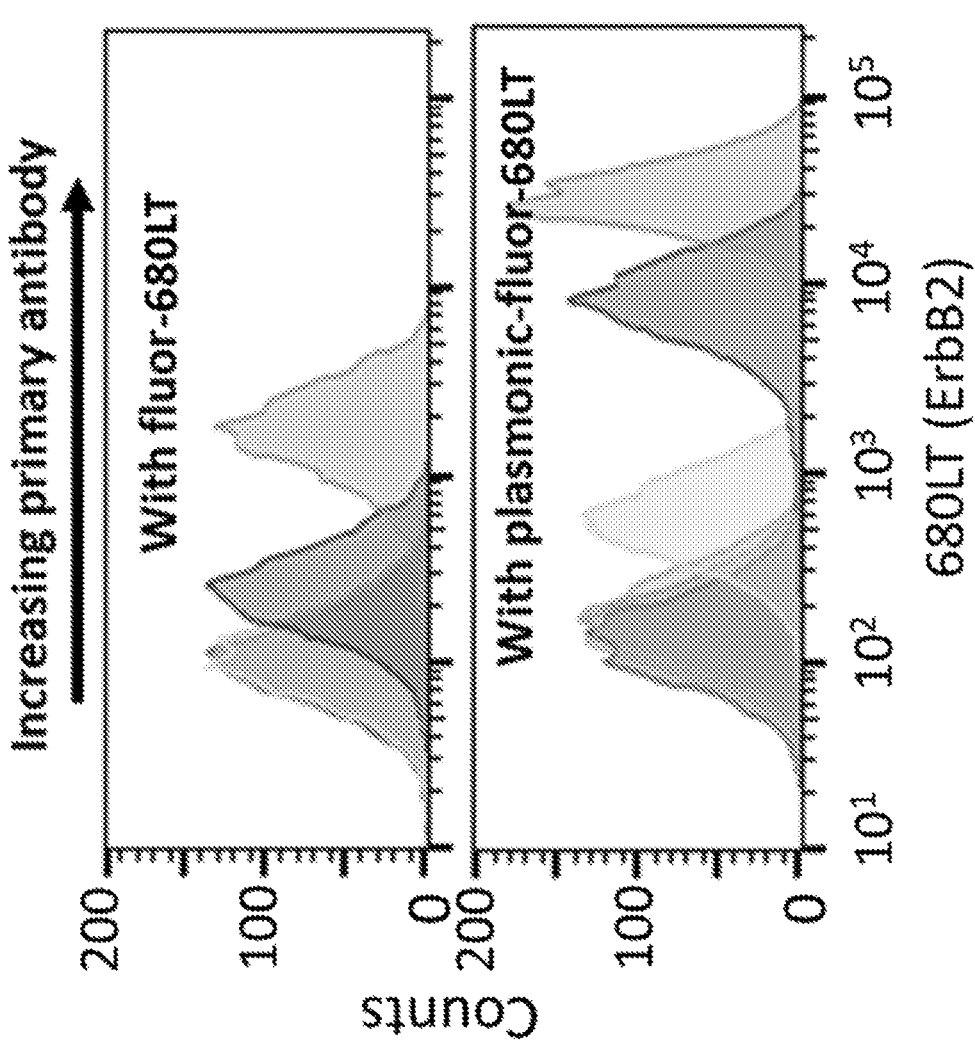
FIG. 89 is an exemplary embodiment of a histogram showing fluorescence for SK-BR-3 cells before (top) and after (bottom) the addition of plasmonic-fluor-680LT in accordance with the present disclosure.
Figure 90:
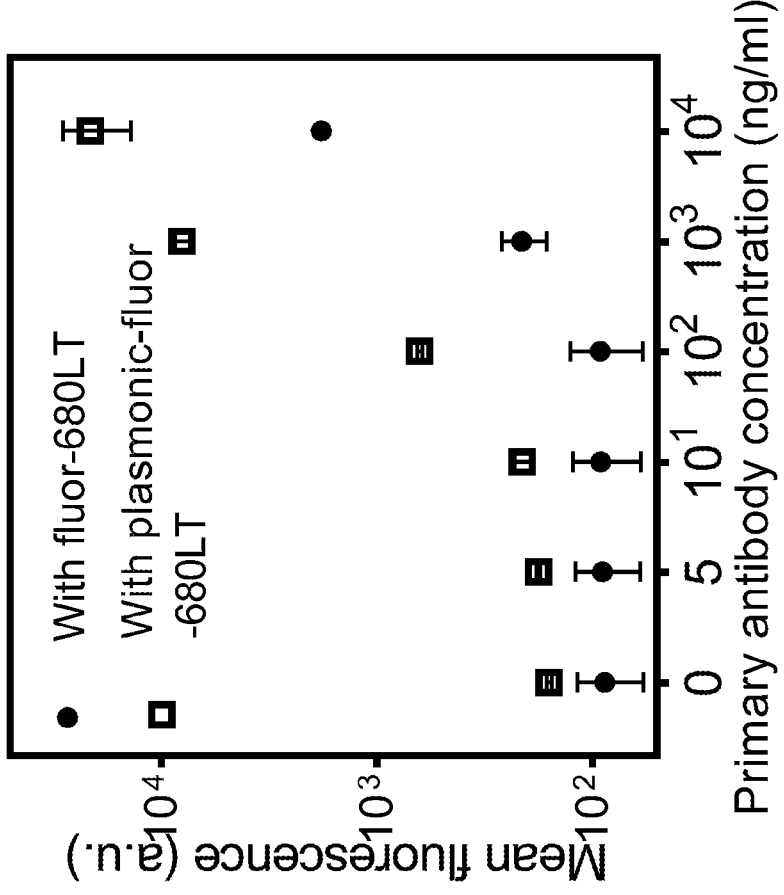
FIG. 90 is an exemplary embodiment of a plot showing the mean fluorescence intensity obtained from flow cytometry at different primary antibody concentrations in accordance with the present disclosure.

To test the ability of plasmonic-fluors to enhance the signal-to-noise ratio in flow cytometry-based cell analysis (FIG. 83), SK-BR-3 cell suspensions were incubated with ErbB2 primary antibody, streptavidin-680LT, followed by the addition of plasmonic-fluor-680LT. Subsequently, the labeled cells were collected by mild centrifugation (1000 rpm) with concomitant removal of unbound plasmonic-fluors. To match the excitation laser and fluorophore emission, AuNRs with LSPR wavelength around 647 nm as the nanostructures were employed to create plasmonic-fluor-680LT (FIG. 84(A-B)). FIG. 84(A-B) shows a 680LT TEM image and Extinction Spectra. Specific binding of the plasmonic-fluor-680LT caused a significant change in the color of the cell pellet (FIG. 85(A-B)). FIG. 85A depicts photographs showing the color change of SK-BR-3 cell (top: pellet; bottom: suspension) after being labeled with plasmonic-fluor-680LT. FIG. 85B shows vis-NIR extinction spectra of plasmonic-fluor-680LT labeled SK-BR-3 cell suspensions under different dilutions of ErbB2 primary antibody. The presence of plasmonic-fluors-680LT on the cell surface did not change the forward scatter or side scatter intensity (FIG. 86), indicating that the cell size and granularity/complexity remained virtually unaltered after binding of the plasmonic-fluor-680LT. FIG. 86 shows pseudocolor plots (with example of gating strategy to include single cell) of side scatter and forward scatter of SK-BR-3 cells before (left) and after (right) being labeled with plasmonic-fluor-680LT, showing no obvious change in their size profiles. Flow cytogram of fluorescence vs. forward scatter (vertically offset for clarity) of SK-BR-3 cells revealed a more obvious separation of cell populations stained with plasmonic-fluor-680LT compared to that obtained with conventional fluorophores (FIG. 87). FIG. 87 shows a flow contour plot (with outliers) of fluorescence vs. forward scatter (vertically offset for clarity) of SK-BR-3 cells probed using different concentrations of ErbB2 primary antibody (Red: control group without adding primary antibody. Blue: cells treated with different dilutions of primary antibody). Cells are stained with conventional fluor (680LT, left plot) followed by the addition of plasmonic-fluor-680LT (right plot). Histograms of cell fluorescence signals revealed up-to 60-fold higher intensity (background subtracted) using plasmonic-fluor-680LT compared to its conventional counterpart (FIG. 88). FIG. 88 shows a fluorescence histogram of SK-BR-3 cells probed using conventional fluor (680LT) followed by the addition of plasmonic-fluor-680LT (at $10^3$-fold dilution of primary antibody). Error bars represent s.d. (n=3 independent tests). ****$p<0.0001$ by two-tailed unpaired t-test with Welch's correction. Fluorescence histogram revealed that the expression of ErbB2 on the cell surface can be detected even at 200,000-fold dilution of primary antibody (5 ng/ml) using plasmonic-fluor-680LT labeling (FIG. 89, FIG. 90). FIG. 89 is a histogram showing fluorescence for SK-BR-3 cells before (top) and after (bottom) the addition of plasmonic-fluor-680LT. Red: no primary antibody; blue: $2\times10^5$-fold dilution; orange: $10^5$-fold dilution; light green: $10^4$-fold dilution; green: $10^3$-fold dilution; rose: $10^2$-fold dilution of the stock solution provided by the vendor. FIG. 90 is a plot showing the mean fluorescence intensity obtained from flow cytometry at different primary antibody concentrations. On the other hand, conventional labeling required the antibody to be diluted less than 1000-fold (i.e. concentration >0.5 μg/ml) to ensure a detectable increase in fluorescence signal compared to the background (blank) (FIG. 89, FIG. 90).

Figure 91:
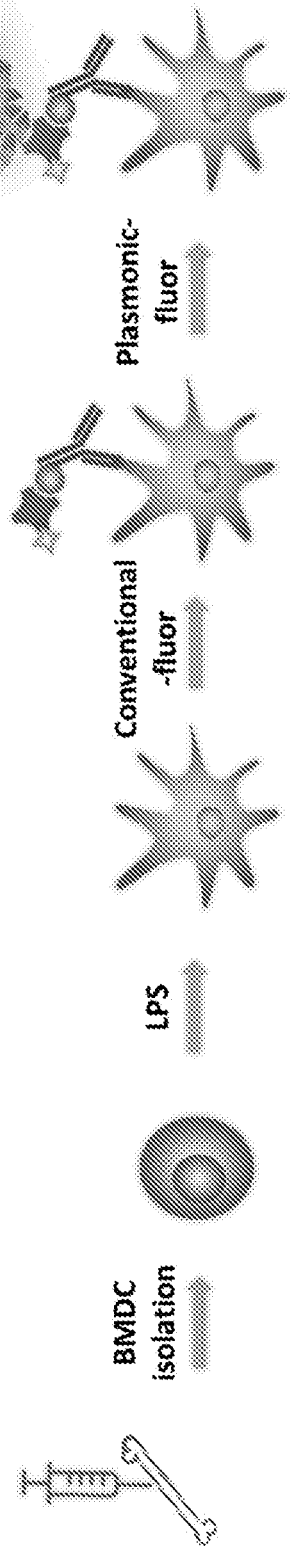
FIG. 91 is an exemplary embodiment of a schematic illustration showing bone marrow derived dendritic cells (BMDCs) treated with the immuno-stimulant (lipopolysaccharide (LPS)) in accordance with the present disclosure.
Figure 92:
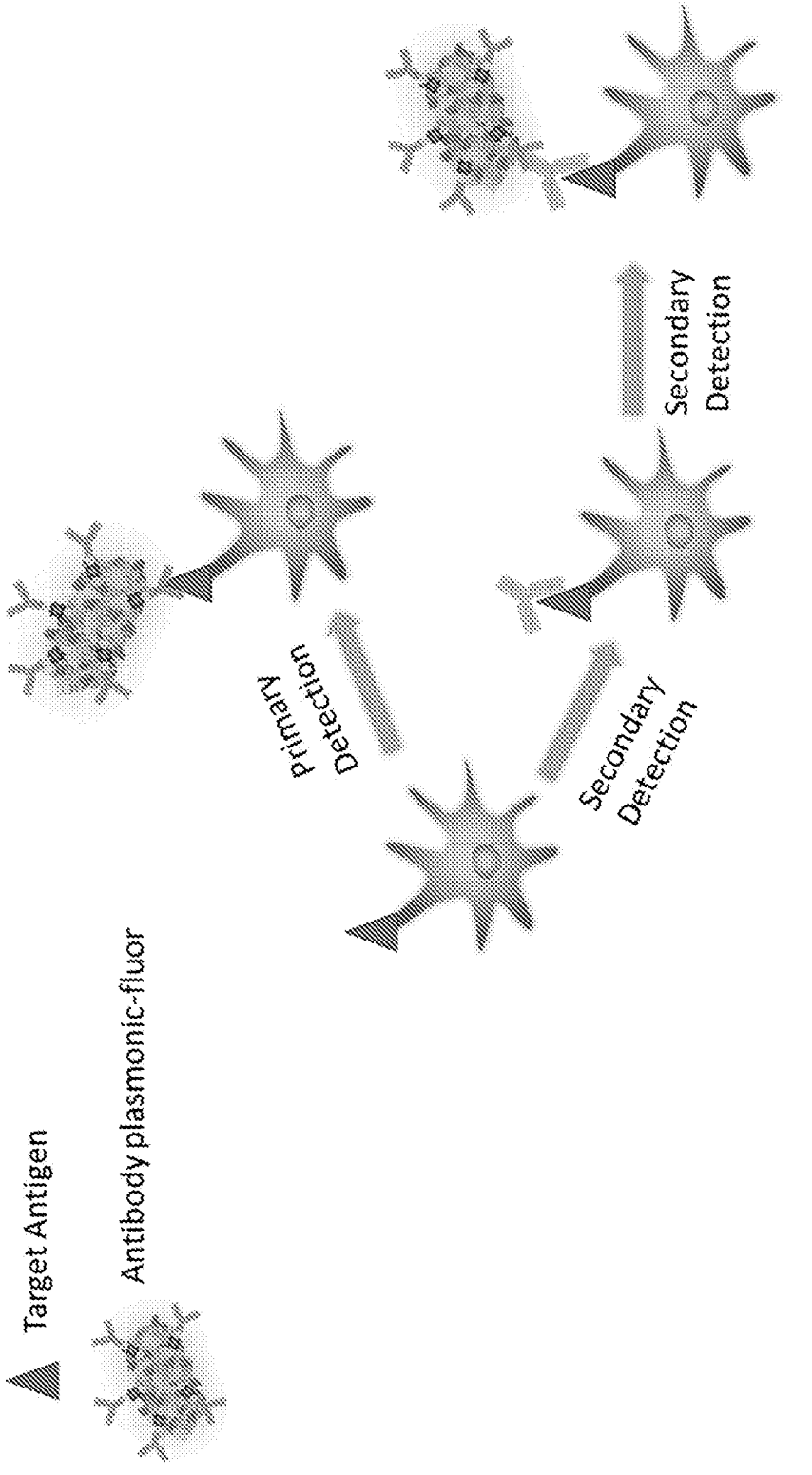
FIG. 92 is an exemplary embodiment of an exemplary embodiment of two schemes for using antibody-labeled plasmonic-fluors in labeling a target antigen on a cell in accordance with the present disclosure.

To further validate the performance of plasmonic-fluors in delineating cell populations with small differences in surface receptor expression levels, bone marrow-derived dendritic cells (BMDCs) were employed as a model system in which the surface expression of receptors can be modulated using immunogenic stimulus. Dendritic cells after exposure to an immunogenic stimulus undergo activation and maturation, which leads to cytokine secretion and upregulation of maturation markers such as CD40, CD80, CD86, MHC I, and MHC II. Here, BMDCs were isolated from 6-8 weeks old C57BL/6 mice and lipopolysaccharide (LPS) was employed as immunogenic stimulus to trigger the upregulation of CD80 and cytokine release in a dose-dependent manner. Subsequently, the cells were fixed and treated with biotinylated CD80 antibody. Finally, BMDCs were probed by conventional fluorophore (680LT) followed by plasmonic-fluor-680LT, and the fluorescence levels were compared using flow cytometer (FIG. 91). FIG. 91 is a schematic illustration showing bone marrow derived dendritic cells (BMDCs) treated with the immuno-stimulant (lipopolysaccharide (LPS)). The small changes of maturation markers (CD80) expression after stimulation are detected by immunofluorescence staining followed by addition of plasmonic-fluor-680LT. FIG. 92 shows two schemes for using antibody-labeled plasmonic-fluors in labeling a target antigen on a cell.

Figure 93:
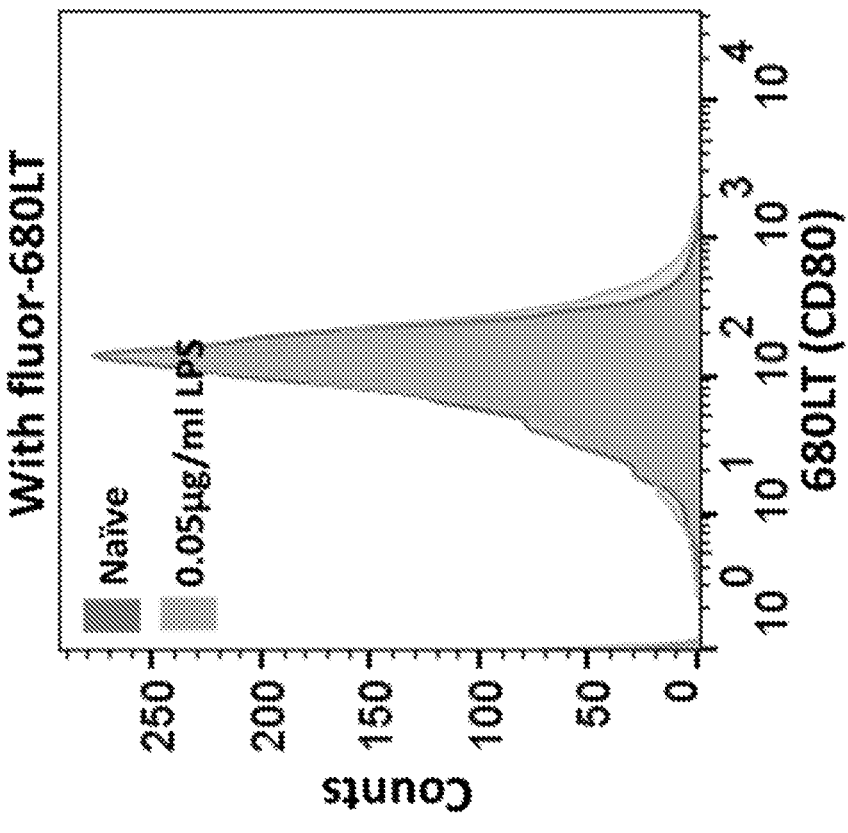
FIG. 93 is an exemplary embodiment of fluorescence intensity distribution corresponding to naïve (control) and LPS-stimulated BMDCs obtained using conventional fluors (680LT) in accordance with the present disclosure.
Figure 94:
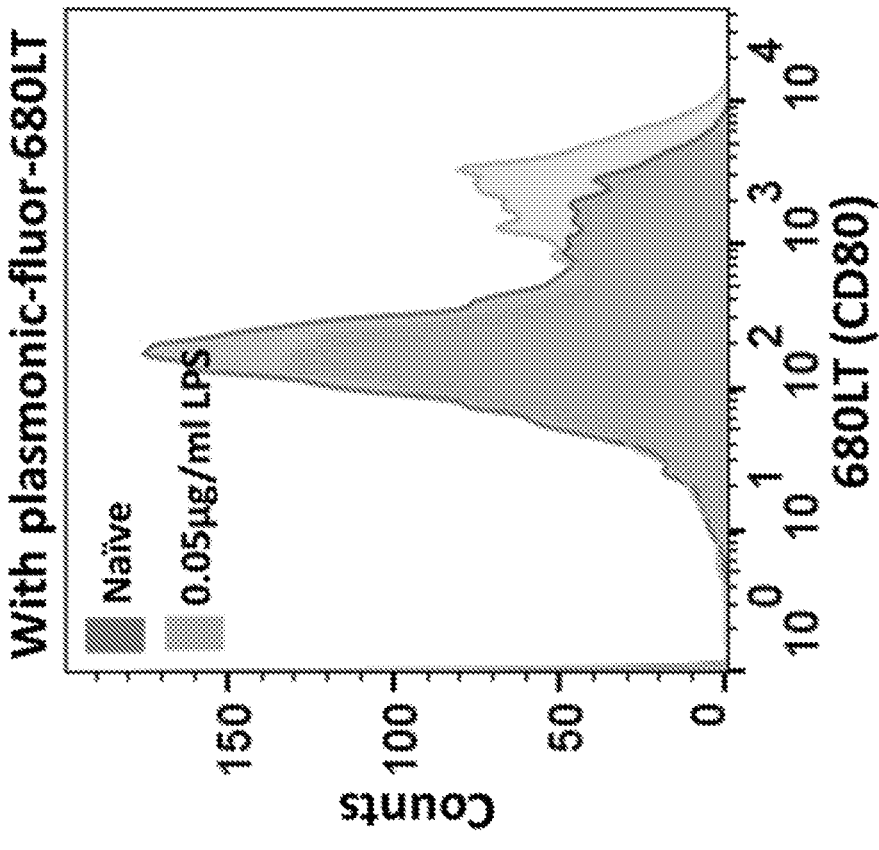
FIG. 94 is an exemplary embodiment of fluorescence intensity distribution corresponding to naïve (control) and LPS-stimulated BMDCs obtained using plasmonic-fluor-680LT in accordance with the present disclosure.
Figures 95A, 95B:
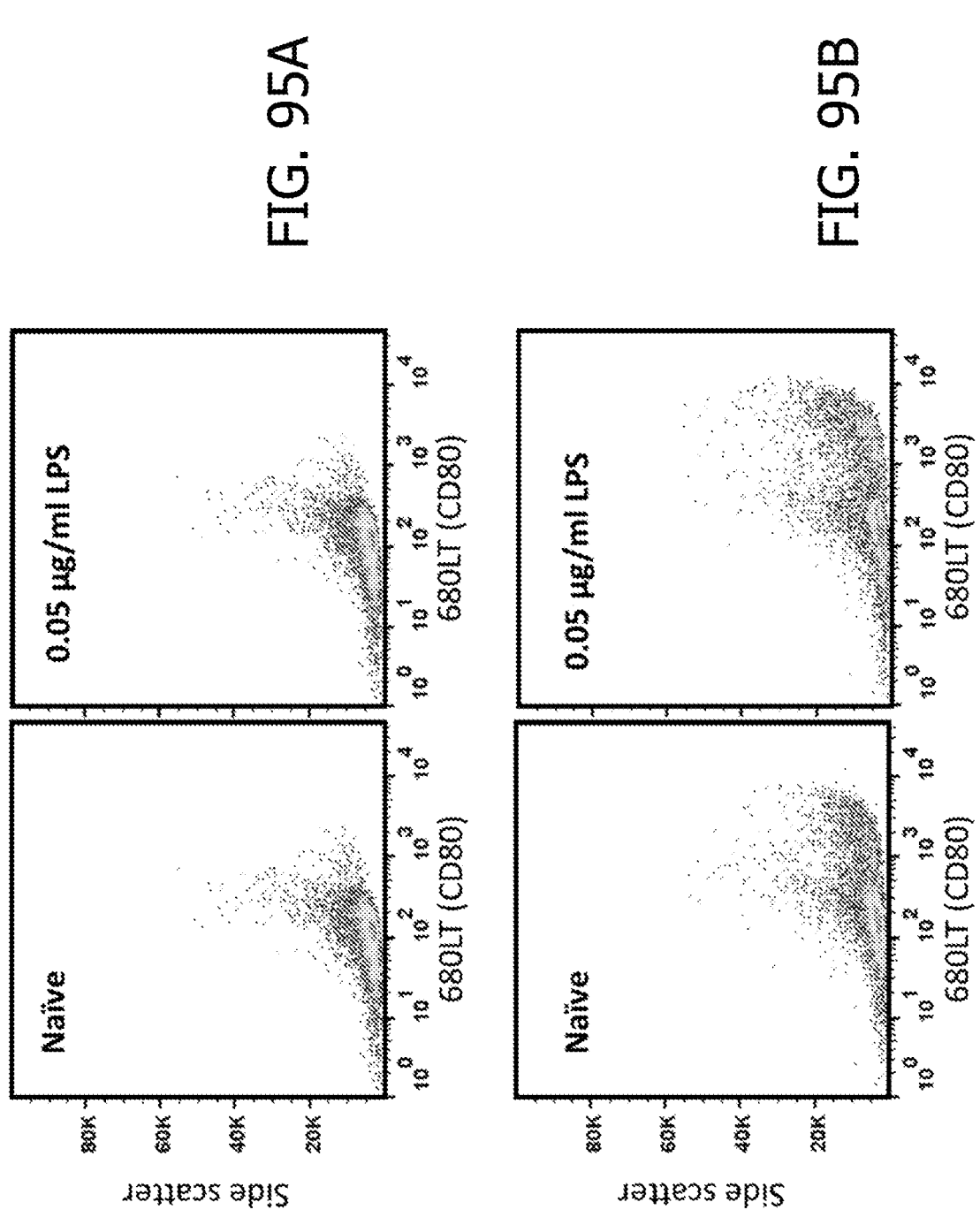
FIG. 95A is an exemplary embodiment of pseudocolor plots showing the side scatter vs. CD80 fluorescence of BMDC population without LPS stimulation (left: naïve) and after being treated with 0.05 μg/ml LPS (right) using conventional immunofluorescence staining in accordance with the present disclosure.
FIG. 95B is an exemplary embodiment of pseudocolor plots showing the side scatter vs. CD80 fluorescence of BMDC population without LPS stimulation (left: naïve) and after being treated with 0.05 μg/ml LPS (right) using plasmonic-fluor-680LT in accordance with the present disclosure.
Figure 96:
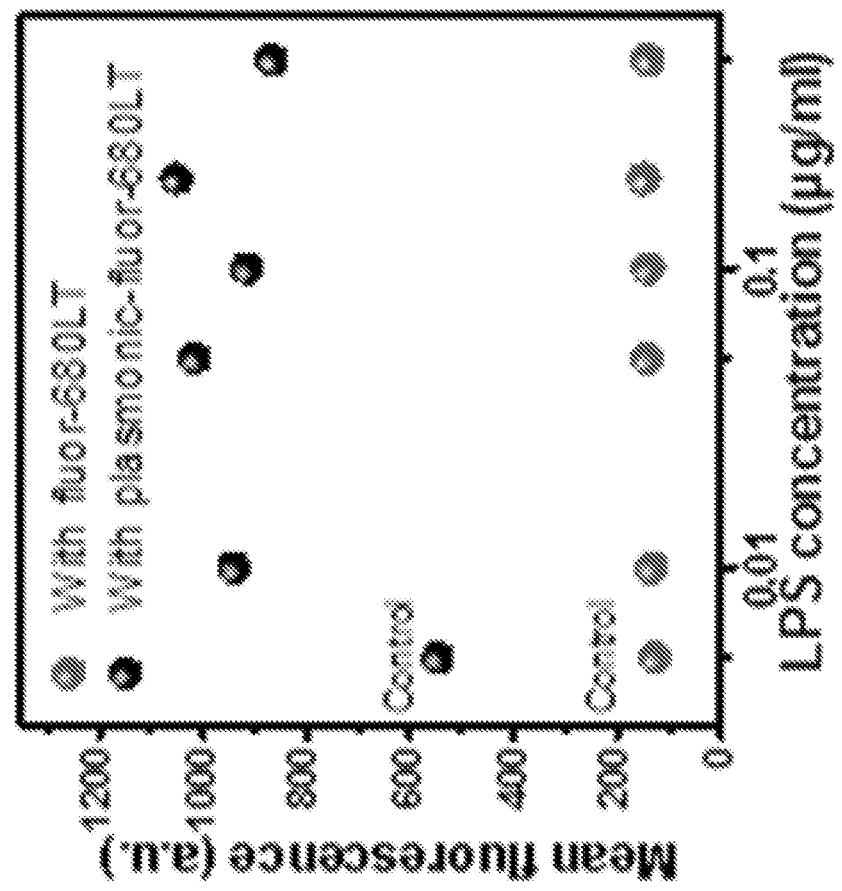
FIG. 96 is an exemplary embodiment of a plot showing mean fluorescence intensity of BMDCs (corresponding to the expression level of CD80) after stimulation with different amounts of LPS in accordance with the present disclosure.
Figures 97A, 97B:
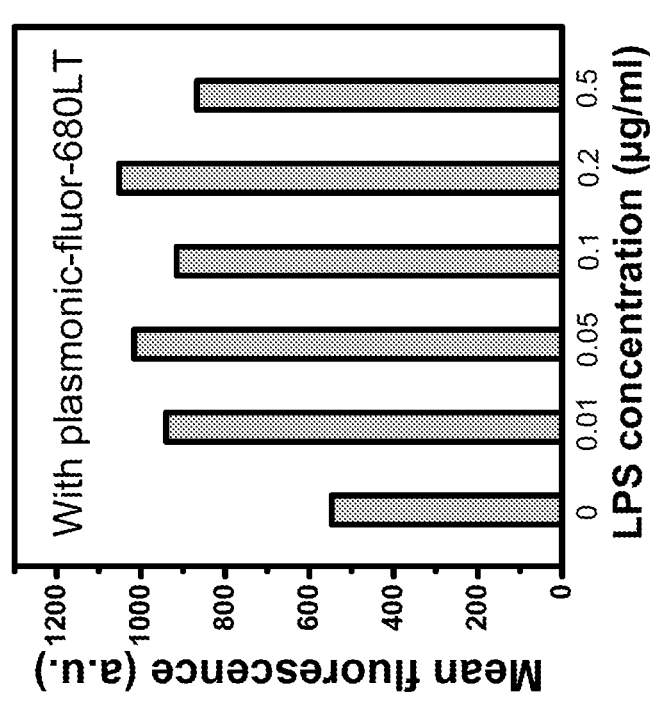
FIG. 97A is an exemplary embodiment of a plot showing mean fluorescence of BMDCs (corresponding to the expression level of CD80) probed using conventional immunofluorescence staining after being stimulated with different amounts of LPS in accordance with the present disclosure.
FIG. 97B is an exemplary embodiment of a plot showing mean fluorescence of BMDCs (corresponding to the expression level of CD80) probed using plasmonic-fluor-680LT after being stimulated with different amounts of LPS in accordance with the present disclosure.
Figure 98:
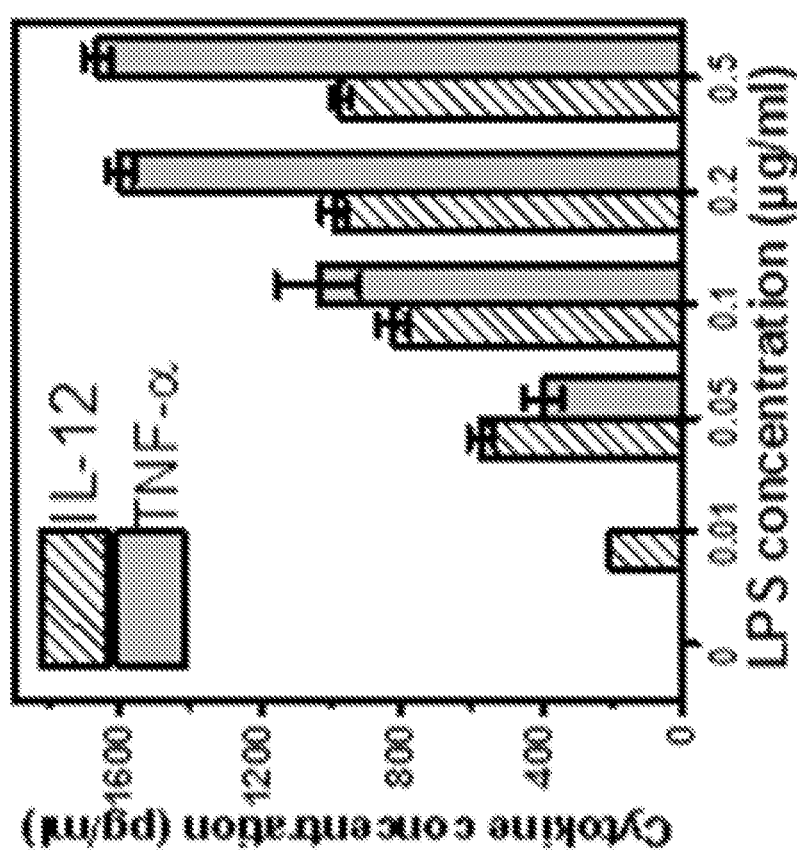
FIG. 98 is an exemplary embodiment of secretion levels of pro-inflammatory cytokines (TNF-α and IL-12) in accordance with the present disclosure.

Fluorescence intensity distribution histograms corresponding to naïve (control) and LPS (0.05 µg/ml)-stimulated BMDCs obtained using conventional fluors (680LT) and plasmonic-fluor-680LT are shown in FIG. 93, and FIG. 94, respectively. Clearly, plasmonic-fluor stained BMDCs exhibited a significant fluorescence difference between activated (blue) and naïve (red) cell populations (FIG. 93, FIG. 94, and FIG. 95(A-B)). FIG. 95(A-B) show pseudocolor plots showing the side scatter vs. CD80 fluorescence of BMDC population without LPS stimulation (left: naïve) and after being treated with 0.05 µg/ml LPS (right) using conventional immunofluorescence staining (FIG. 95A) and plasmonic-fluor-680LT (FIG. 95B). LPS dose-dependent (0 to 0.05 µg/ml) stimulation of BMDCs was further investigated, where a steep increase in the mean fluorescence intensity was observed using plasmonic-fluor-680LT followed by plateau at higher LPS dose (FIG. 96, FIG. 97(A-B)), indicating an increase in the expression of CD80. FIG. 96 is a plot showing mean fluorescence intensity of BMDCs (corresponding to the expression level of CD80) after stimulation with different amounts of LPS. BMDCs stained with conventional fluorophore, however, exhibited a shallow fluorescence increase with LPS dose, which was obscured by the high fluorescence background (FIG. 96, and FIG. 97(A-B)). FIG. 97(A-B) shows plots of mean fluorescence of BMDCs (corresponding to the expression level of CD80) after being stimulated with different amounts of LPS. The BMDCs were probed using conventional immunofluorescence staining (FIG. 97A) and followed by plasmonic-fluor-680LT (FIG. 97B). Moreover, the secretion levels of pro-inflammatory cytokines (TNF-α and IL-12) exhibited an increasing trend with the increase of LPS concentration (FIG. 98, FIG. 99). FIG. 98 shows secretion levels of pro-inflammatory cytokines (TNF-α and IL-12), which confirmed the dose-dependent activation and maturation of BMDCs. FIG. 99 shows individual data points (absorbance and concentration), mean concentration, and standard deviation of ELISA results corresponding to the secreted inflammatory cytokines after LPS stimulation. This further confirmed the dose-dependent activation and maturation of BMDCs as well as the specificity and accuracy of plasmonic-fluor in differentiating the minute changes in the cell surface maturation markers.

Example 19—Synthesis of AuNR for Enhancement of 800CW and 680LT

AuNR-760 (LSPR wavelength ~760 nm), which is suitable for enhancing 800CW, was prepared by a seed-mediated method. Au seed was synthesized by adding 0.6 ml of ice-cold NaBH$_4$ solution (10 mM) (Sigma-Aldrich, 71321) into a solution containing 0.25 ml HAuCl$_4$ (10 mM) (Sigma-Aldrich, 520918) and 9.75 ml CTAB (0.1 M) (Sigma-Aldrich, H5882) under vigorous stirring at room temperature for 10 min. The color of the solution changed from yellow to brown indicating the formation of Au seed. For the synthesis of AuNR, the growth solution was prepared by the sequential addition of aqueous HAuCl$_4$ (0.01 M, 2 ml), CTAB (0.1 M, 38 ml), AgNO$_3$ (0.01 M, 0.5 ml, Sigma-Aldrich, 204390), HCl (1M, 0.8 ml, Sigma-Aldrich, H9892) and ascorbic acid (0.1 M, 0.22 ml, Sigma-Aldrich, A92902) followed by gentle inversion to homogenize the solution. The AgNO3 and HCl volume ratio may vary to obtain the right wavelength. Subsequently, 5 µl of the seed solution was added into the growth solution and left undisturbed in the dark for 24 hours. AuNR solution was centrifuged at 7000 rpm for 40 minutes to remove the supernatant and the AuNR was re-dispersed into nanopure water to achieve a final peak extinction ~2.0. For AuNR-647 (LSPR wavelength ~647 nm) which is suitable for enhancing 680LT, the growth solution contained HAuCl$_4$ (0.01 M, 2 ml), CTAB (0.1M, 38 ml), AgNO$_3$ (0.01 M, 0.2 ml, this value may vary), and ascorbic acid (0.1 M, 0.32 ml).

Example 20—Synthesis of AuNR@Ag for Cy3

AuNR with LSPR wavelength around 711 nm was employed as the core for the synthesis of AuNR@Ag nanostructures. Specifically, 3 ml of 711 nm AuNR (peak extinction ~4) was incubated with 8 ml of CTAC (20 mM) at 60° C. for 20 minutes under stirring. Then, 8 ml of AgNO$_3$ (4 mM), 4 ml of CTAC (20 mM), and 0.8 ml of ascorbic acid (0.1M) were added sequentially and the mixture was incubated at 60° C. for 4 h under magnetic stirring to form AuNR@Ag nanocuboids. Finally, AuNR@Ag nanocuboids solution was centrifuged at 6000 rpm and the nanocuboids were redispersed in nanopure water.

Example 21—Conjugation Procedure for Fluorescently-Labeled Functional Layer Plasmonic Fluors Biotin and 800CW were sequentially conjugated to BSA through EDC/NHS chemistry. In pH 7-9 buffers, NHS esters react efficiently with primary amino groups (—NH$_2$) by nucleophilic attack, forming an amide bond and releasing the NHS. Specifically, 2 mg of NHS activated biotin (NHS-PEG4-Biotin, Thermo Scientific, Prod #: 21329) was added to 2.2 ml of BSA (Sigma-Aldrich, A7030) solution (5 mg/ml in 1×PBS). The mixture was incubated at room temperate (~22° C.) for 1 hour to complete the reaction. Excess NHS-PEG4-Biotin was removed from the solution using a desalting column (5 mL, 7000 MWCO, Thermo Scientific, Prod #: 21329) pre-equilibrated with 1×PBS. Next, 800CW was conjugated to BSA-biotin. 0.1 ml of 1M potassium phosphate buffer (K$_2$HPO$_4$, pH=9) was added into 1 ml of purified BSA-biotin solution to raise the pH. Next, 25 µl of 4 mg/ml NHS-800CW (LI-COR, 929-70020) was added to the mixture and the solution was incubated at 23° C. for 2.5 hours. Free NHS-800CW was then separated from the conjugate using a Zeba desalting column pre-equilibrated with nanopure water. BSA-biotin-680LT and BSA-biotin-Cy3 were prepared using a similar method, except for changing the fluorophore.

Example 22—Synthesis of Fluorescently-Labeled Functional Layer-Based Plasmonic-Fluor To fabricate plasmonic-fluor with high fluorescence enhancement efficacy, it is extremely important to choose an "on-resonant" plasmonic nanostructure for a given fluorophore. For 800CW, AuNR-760 (length and diameter of 83 and 24 nm, respectively) was employed as the nanostructure. 1 µl of MPTMS (Sigma Aldrich, 175617) was added to 1 ml AuNR with extinction ~2.0 and the mixtures was shaken for 1 hour allowing the formation of an interfacial layer on the AuNR. MPTMS-modified AuNR was further mixed with different volumes of APTMS (Sigma Aldrich, 281778) and TMPS (Sigma Aldrich, 662275) (from 0.5 µl to 2 µl) to form the polymer spacer layer on AuNR. Finally, AuNR/polymer solution was centrifuged twice each at 6000 rpm for 10 minutes to remove the free monomer. After second centrifugation, AuNR/polymer was concentrated into a final volume of 10 µl.

Next, BSA-biotin-800CW conjugate was coated around AuNR/polymer. Specifically, 1 µl of 20 mg/ml citric acid (Alfa Aesar, 36664) was added into 100 µl of BSA-biotin-800CW (~4 mg/ml) to lower the pH. Concentrated AuNR/polymer solution was subsequently added into this mixture and sonicated for 20 minutes under dark condition. The nanostructures were then collected using mild centrifugation (5000 rpm for 3 minutes). Subsequently, the AuNRs were incubated with 0.5 ml BSA-biotin-800CW (~0.4 mg/ml, pH=10) for 3 days under dark condition in 4° C. Finally, the nanostructures were washed four times using nanopure water (pH=10) by centrifugation at 6000 rpm. After the last washing step, the particles were re-dispersed into 1% BSA (buffered with 1×PBS).

Material characterization: Transmission electron microscopy (TEM) images were obtained using a JEOL JEM-2100F field emission (FE) instrument. A drop of aqueous solution was dried on a carbon-coated grid, which had been made hydrophilic by glow discharge. SEM images were obtained using a FEI Nova 2300 field-emission scanning electron microscope at an acceleration voltage of 10 kV. AFM imaging was performed on a Dimension 3000 using silicon cantilevers with a nominal spring constant of 40 N/m in light tapping mode. The extinction spectra of plasmonic nanostructures were obtained using a Shimadzu UV-1800 spectrophotometer. Fluorescence lifetime was measured using time correlated single photon counting (TCSPC implemented in Fluorolog-3, Horiba Jobin Yvon) with a 740 nm excitation source NanoLed® (impulse repetition rate 1 MHz) at 90° to the PMT R928P detector (Hamamatsu Photonics, Japan). Unless otherwise stated, most of the fluorescence mappings were recorded using LI-COR Odyssey CLx imaging system. Luminex 200 system was employed to read the fluorescence signal from the microbeads. Cell imaging was performed using Olympus FV1000 LSM confocal laser scanning microscopy (785 nm excitation laser) under 40× water-immersion objective. Guava easyCyte was employed to acquire the flow cytometry data.

Calculation of the protein/biotin ratio: BSA/biotin ratio was calculated through 4-Hydroxyazobenzene-2-carboxylic acid (HABA) assay. Specifically, biotinylated BSA (0.4 mg/ml×100 µl) was added to a mixture of HABA (Thermo Scientific, 1854180) and avidin solution (900 Thermo Scientific, 21121). Due to its higher affinity to avidin, biotin replaced HABA from avidin and the absorbance at 500 nm decreased proportionally. The change in the absorbance was calculated using the following equation:

$$\Delta A_{500} = (0.9 \times A_{500}) \sim A_{500}B, \tag{1}$$

where $A_{500}$ and $A_{500}B$ represent the absorbance of HABA/avidin before and after the addition of biotinylated BSA, respectively. A correction factor (0.9) was employed to adjust for the dilution of HABA/avidin solution by adding biotinylated BSA. The concentration of the sample can be calculated using Beer's Law:

$$A_\lambda = \varepsilon_\lambda bC, \tag{2}$$

where $A_\lambda$ is the absorbance of the sample at wavelength $\lambda$ nm ($\Delta A_{500}$), $\varepsilon_\lambda$ represents the extinction coefficient at wavelength $\lambda$ nm (34,000 $M^{-1}cm^{-1}$), b is the cell path length (1 cm using quartz cuvette), and C is the concentration of the sample. Using this equation, biotin concentration was calculated to be:

$$C\left(\frac{mmol}{ml}\right) = \frac{\Delta A_{500}}{34,000 \times b} = \frac{0.1765}{34,000} = 5.19 \times 10^{-6} mmol/ml \tag{3}$$

BSA concentration was $6 \times 10^{-7}$ mmol/ml. On an average, 8.7 biotin molecules were conjugated to BSA molecule. Similarly, dye to protein ratio was calculated using the following equation:

$$\left(\frac{A_{780}}{\varepsilon_{Dye}}\right) / \left(\frac{A_{280} - 0.03 \times A_{780}}{\varepsilon_{protein}}\right), \tag{4}$$

where 0.03 is the correction factor for the absorbance of 800CW at 280 nm, $\varepsilon_{Dye}$ (270,000 $M^{-1}cm^{-1}$) and $\varepsilon_{protein}$ (43,824 $M^{-1}cm^{-1}$) are the extinction coefficients for 800CW and BSA respectively, and $A_{780} = 0.3$ and $A_{280} = 0.05$ are the absorbance of BSA-800CW at 780 nm and 280 nm, respectively. The final dye to protein ratio was therefore calculated to be 1.2.

Fluorescence lifetime measurements: Fluorescence lifetimes (FLT) were measured using Time-Correlated Single Photon Counting (TCSPC, implemented in Fluorolog-3, Horiba Jobin Yvon) with a 740 nm excitation source NanoLed® (impulse repetition rate 1 MHz) at 90° to the PMT R928P detector (Hamamatsu Photonics, Japan). The detector was set to 800 nm with a 20 nm bandpass and data were collected until the peak signal reached 2,000 counts. The details of the system have been published in previous studies. The instrument response function was obtained using a Rayleigh scatter of Ludox-40 (0.05% in MQ water; Sigma-Aldrich) in an acrylic transparent cuvette at 740 nm emission. Lifetime values were obtained by fitting the decay curve using Decay analysis software (DAS6 v6.8; Horiba), based on $$I(t) = \sum_{i=1}^{n} I(0) * \exp\left(\frac{-t}{\tau}\right) \tag{5}$$

where I represents the fluorescence intensity, t represents decay time and $\tau$ represents lifetime. The quality of fit was judged by $\chi^2$ values, Durbin-Watson parameters, as well as visual observations of fitted line, residuals, and autocorrelation functions. The fitting (bi-exponential fitting) provided two values of the fluorescence lifetime: $\tau_1$ and $\tau_2$ as listed in the table below (Table 8). Since $\tau_2$ is extremely large compared to that of common fluorophore and showed insignificant contribution (<5%), this value is regarded as background noise. The reason to use bi-exponential fitting is to fit the environment photons out (usually have longer lifetime) to get a cleaner 1st exponential value for the real fluorescence lifetime.

57

TABLE 8

| Fluorescence lifetimes and $\chi^2$ obtained using bi-exponential fit | | | |
|---|---|---|---|
| Samples | $\tau_1$ | $\tau_2$ (background) | $\chi^2$ |
| 800CW-BSA | 0.722 ns (95.42%) | 4.81 ns (4.58%) | 1.014 |
| Plasmonic-fluor-800CW | 0.178 ns (93.12%) | 4.77 ns (4.41%) | 1.107 |

Calculation of quantum yield: The radiative and nonradiative decay rate can be calculated from the measured lifetime and quantum yield of 800CW (conjugated to BSA):

$$\Gamma = \frac{Q_0}{\tau_0} = 0.15ns^{-1} \tag{6}$$

$$k_{nr} = \frac{1}{\tau_0} - \Gamma = 1.2ns^{-1} \tag{7}$$

where $\Gamma$ and $k_{nr}$ represent radiative and non-radiative decay rate of 800CW. $Q_0$ (11%) and $\tau_0$ (0.74 ns) represent the measured quantum yield and lifetime of 800CW. It is assumed that $K_{nr}$ remains unaltered after conjugating the fluorophore to AuNR (due to minimal quenching observed). Therefore, the radiative rate enhancement of 800CW ($\Gamma_{AuNR}$) and improved quantum yield induced by AuNR ($Q_{AuNR}$) can be calculated as:

$$\Gamma_{AuNR} = \frac{1}{\tau_{AuNR}} - k_{nr} = 4.4ns^{-1} \tag{8}$$

$$Q_{AuNR} = \Gamma_{AuNR} * \tau_{AuNR} = 0.79 \tag{9}$$

where $\tau_{AuNR}$ (0.179 ns) represents the lifetime of 800CW after its conjugation to AuNR. The result shows that the fluorophore quantum yield is improved by 7-fold (from 11% to 79%) upon conjugation to AuNR with optimal optical properties and spacer layer.

Estimation of the amount of 800CW absorbed on an example plasmonic-fluor-800CW: To estimate the amount of fluorophore on AuNR, the amount of BSA (-conjugate) using the bicinchoninic acid assay (BCA assay) was first estimated. From the amount of BSA, 800CW concentration can be calculated as the dye to protein ratio has been determined to be 1.2 (described above). Micro BCA protein assay kit (Thermo Scientific, product number 23235, lot number QG218473A) was employed for the test. Specifically, BCA working reagent was prepared by mixing 2.5 ml of reagent MA, 2.4 ml of reagent MB, and 0.1 ml of reagent MC. 150 µl of BSA standards (from 0 to 40 µg/ml) or plasmonic-fluor-800CW (extinction ~4.6) was mixed with 150 µl of the working reagent and the mixture was incubated in 60° C. for 1 hour. The absorbance at 562 nm was measured by a plate reader and a BSA standard curve was obtained. The concentration of BSA absorbed around plasmonic-fluor-800CW was calculated to be 6.2 µg/ml based on the standard curve. Therefore, plasmonic-fluor-800CW with extinction ~0.63 is comprised of ~0.9 µg/ml of BSA (~13.5 nM) and ~16.2 nM of 800CW.

The extinction coefficient of AuNR (length-83 nm and diameter-24 nm) was calculated to be $\varepsilon \approx 8.27 \times 10^9$ (L M$^{-1}$ cm$^{-1}$). Molar concentration of the AuNR corresponding to optical extinction of 0.63 can be derived from Beer's Law, which is calculated to be 76.2 pM. Therefore, the number of 800CW (n) on a single AuNR can be calculated based on:

$$n = \frac{c_{800CW}}{c_{AuNR}} = 210 \tag{10}$$

where $C_{800CW}$ (16 nM) and $C_{AuNR}$ (76.2 pM) represent the molar concentration of 800CW and AuNR, respectively. This version of the plasmonic-fluor, wherein the dye is conjugated to the BSA which is then adhered to a spacer-coated nanostructure, showed a fluorescence brightness that was 6500-times that of the free 800CW.

Example 23—Exemplary Conditions for Fluorescence Enhancement of 800CW-Streptavidin Using AuNR-Plasmonic-Fluor-800CW and AuNP-Plasmonic-Fluor-800CW Experimental procedure employed for this test (the results of which are disclosed herein elsewhere) is illustrated in FIG. 34 and the data in shown in FIG. 5(A-B). Specifically, BSA-biotin was first immobilized on the bottom of plastic 96-well plate by incubating the well with 50 ng/ml BSA-biotin (in 1×PBS) at room temperature for 15 minutes. The plate was washed three times using PBST (0.05% Tween 20 in 1×PBS) and then blocked using Odyssey® Blocking Buffer (PBS) (LI-COR, P/N 927-40100). Wells coated with BSA-biotin were subsequently incubated with 1 µg/ml streptavidin-800CW (in Odyssey® Blocking Buffer) for 10 minutes to allow specific binding of streptavidin to biotin. Next, the plate was washed three times using PBST and then incubated with ~76 pM plasmonic-fluor-800CW (in 1% BSA). The plate was washed three more times using PBST to remove free plasmonic-fluor. Finally, 200 µl of PBST was added into each well and the fluorescence signal before and after the addition of plasmonic-fluor was recorded using the LI-COR CLx fluorescence imager with the following scanning parameters: laser power ~L2; resolution ~169 µm; channel: 800; height: 4 mm. The experiment was repeated four times independently and the fluorescence intensities before and after adding plasmonic-fluor-800CW were compared. The data is statistically significant, and the P value was calculated to be 0.0044, **P<0.01 by two-tailed unpaired t-test with Welch's correction.

Example 24—Exemplary Conditions for Human IL-6 ELISA

Human IL-6 DuoSet ELISA kit (R&D, catalog #DY206, lot #P173353) was employed, the results of which are disclosed herein elsewhere. Specifically, 96-well plates were first coated with capture antibodies (2 µg/ml in PBS) through overnight incubation at room temperature, followed by blocking with 300 µl reagent diluent (1×PBS containing 3% BSA, 0.2 µm filtered). After three times washing with PBST, 100 µl of serial diluted standard samples as well as patients' serum samples (10-fold dilution using reagent diluent) were added into different wells and the plate was incubated at room temperature for 2 hours. The plate was washed subsequently and incubated with biotinylated detection antibodies (PART #840114, 50 ng/ml in reagent diluent) for 2 hours, washed again with PBST, and incubated with HRP-labeled streptavidin (PART #893975, 200-fold dilution using reagent diluent) for 20 mins. 100 µl of substrate solution (1:1 mixture of Color Reagent A (H$_2$O$_2$) and Color Reagent B (tetramethylbenzidine) (R&D Systems, Catalog #DY999)) was added to each well and the reaction was stopped by adding 50 µl of $H_2SO_4$ (2 N) (R&D Systems, Catalog #DY994) after 20 mins. Optical density of each well was determined immediately using a microplate reader set to 450 nm.

Example 25—Human IL-6 FLISA and p-FLISA

Figure 100A:
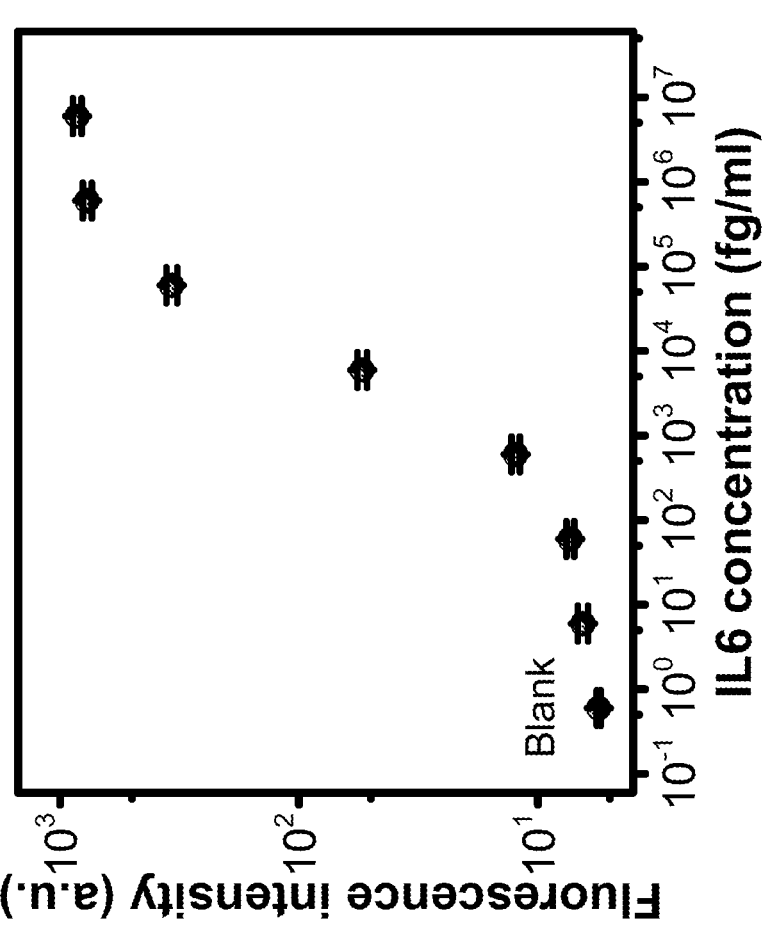
FIG. 100A, FIG. 100B, and FIG. 100C are illustrative of experiments performed independently on different days with different batches of plasmonic-fluor-800CW FIG. 101(A-B) is an exemplary embodiment of bead-based mouse TNF-α standard curves obtained after applying plasmonic-fluor-Cy3 in accordance with the present disclosure.
Figure 100B:
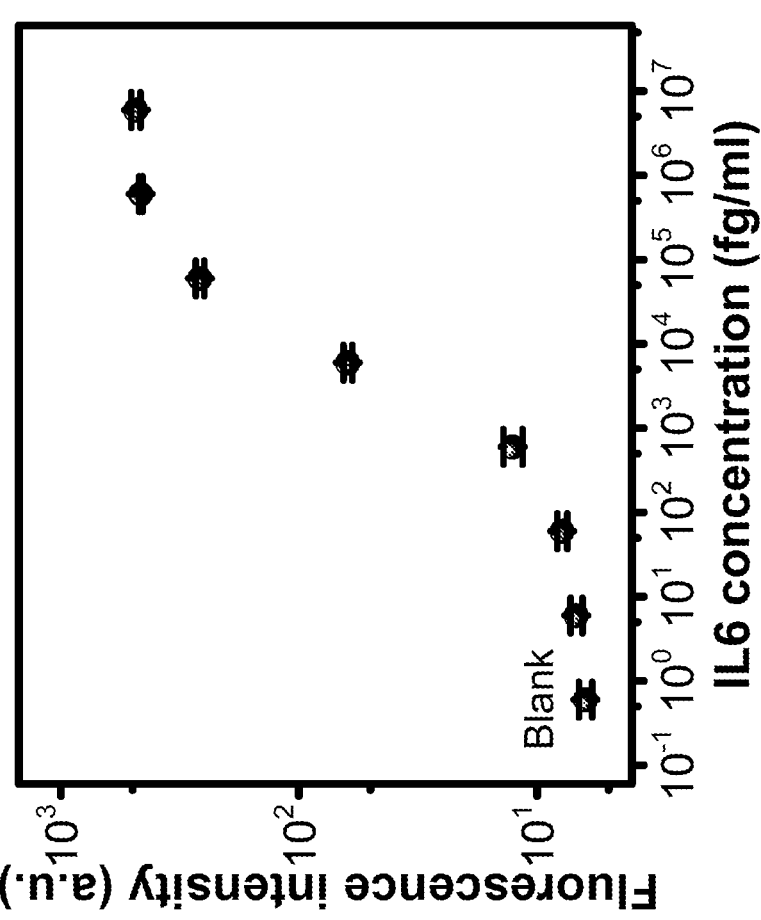
Figure 100C:
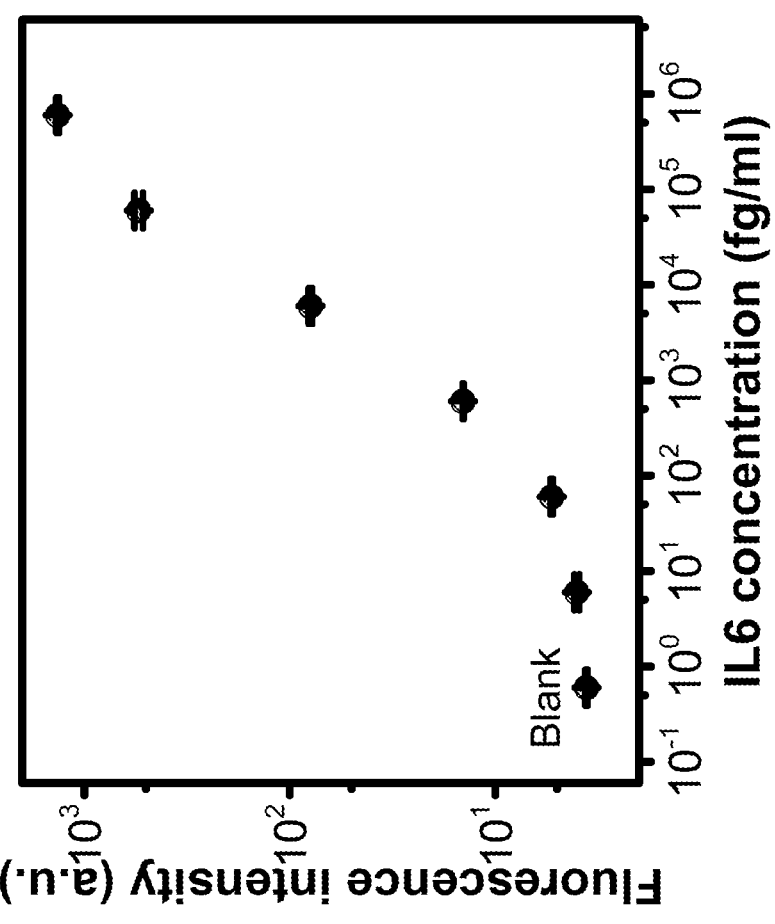

Human IL-6 FLISA was implemented adopting the similar approach as the ELISA described above, expect that HRP-labeled streptavidin was replaced by 800CW-labeled streptavidin (LI-COR P/N 926-32230, 50 ng/ml for 20 minutes). The plate was washed three times using PBST followed by washing with nanopure water. In p-FLISA, plasmonic-fluor-800CW was added subsequently (extinction ~1), incubated for 1 hour, and the plate was washed 3 times each with reagent diluent followed by PBST. The plate was imaged using LI-COR CLx fluorescence imager with the following scanning parameters: laser power ~L2; resolution ~169 µm; channel: 800; height: 4 mm. The results from independent experiment are shown in FIG. 47 and FIG. 49, as well as in FIG. 100(A-C). FIG. 100(A-C) shows plots of the IL-6 dose-dependent fluorescence intensity from p-FLISA. In FIG. 100A, FIG. 100B, and FIG. 100C, the data represents experiments that were performed independently on different days with different batches of plasmonic-fluor-800CW. Error bar represents s.d. (n≥2 repeated tests).

Example 26—Plasmonic-Fluor Enhanced Luminex Bead-Based Assay

Figure 101A:
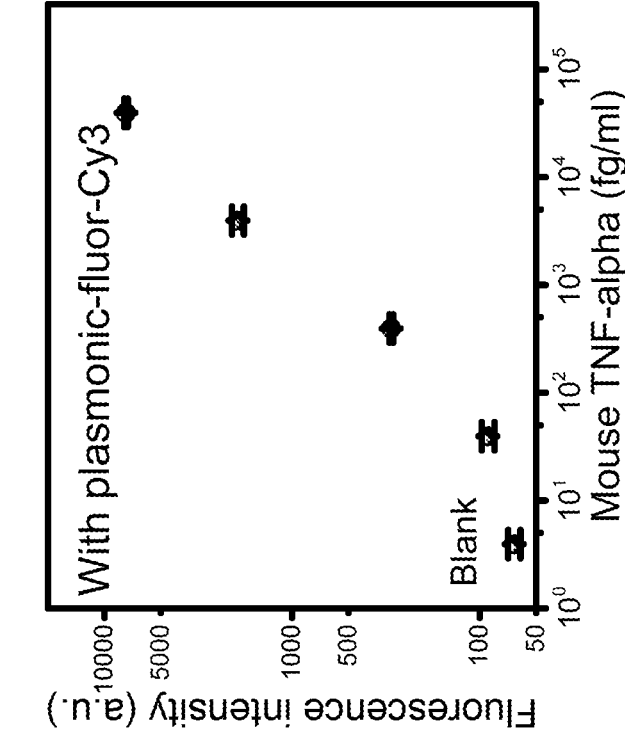
FIG. 101A and FIG. 101B illustrate experiments performed independently for different batches of plasmonic-fluor-Cy3.
Figure 101B:
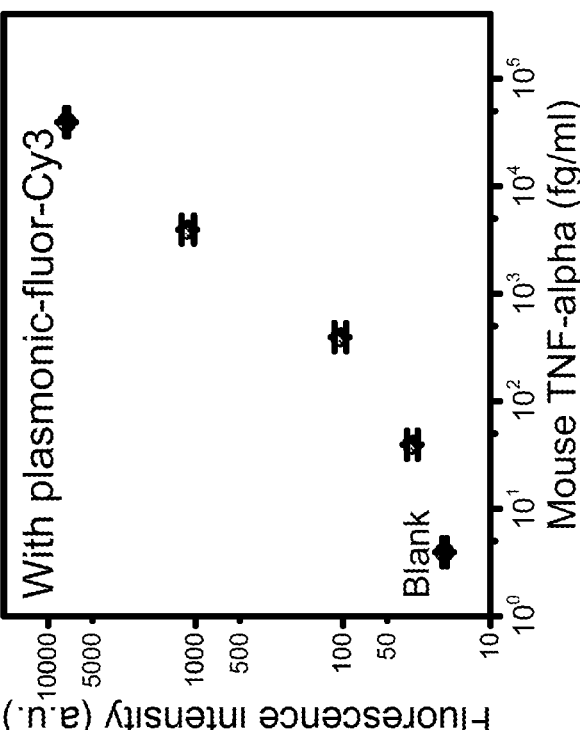
Figure 102B:
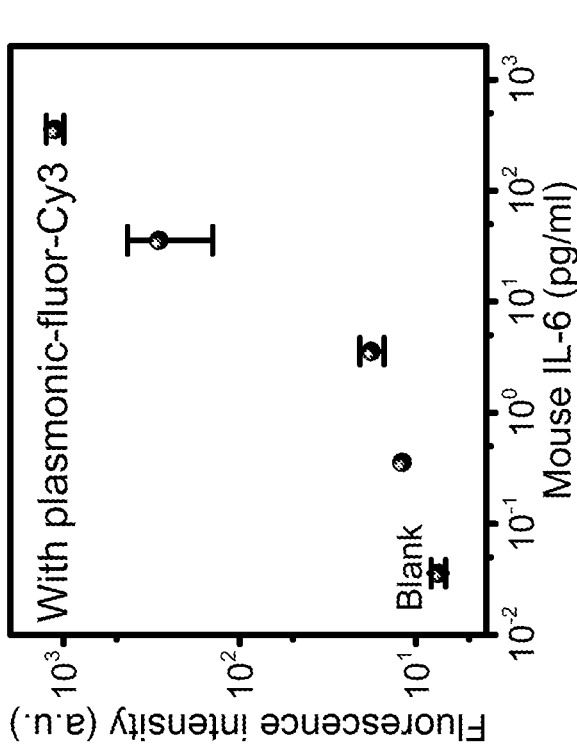
FIG. 102A and FIG. 102B illustrate experiments performed independently for different batches of plasmonic-fluor-Cy3.
Figure 102A:
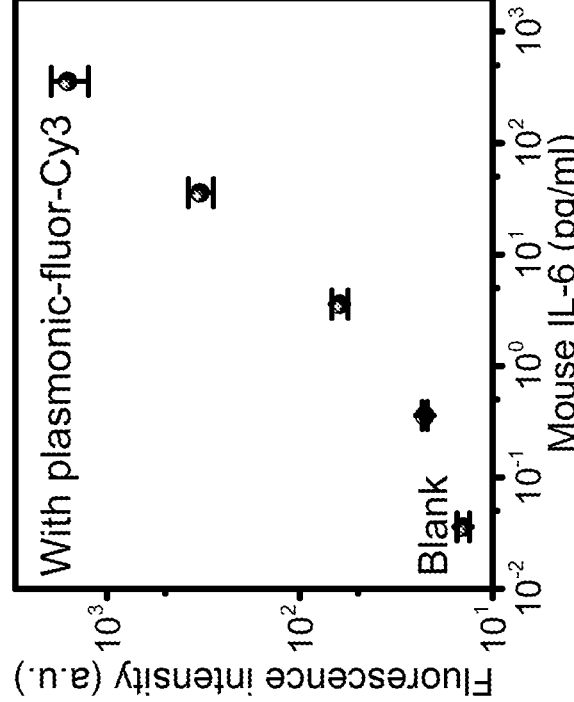

Mouse magnetic Luminex assay was purchased from R&D systems (catalog number: LXSAMSM-03, lot #L126064), which was customized to simultaneously detect mouse TNF-α and mouse IL-6. To begin with, 50 µl of standards that contain different concentrations of TNF-α and IL-6 (PART #984658) were mixed with 50 µl of diluted microbead cocktail (PART #894724) in 96-well plate. The mixture was homogenized by shaking horizontally using a microplate orbital shaker (0.12" orbit) set at 800 rpm for 2 hours. Microbeads were subsequently collected using a magnetic device (Millipore Sigma 40-285) designed to accommodate the microplate and were washed by removing the liquid and filling with wash buffer (PART #895003). The washing step was repeated by three times. Next, 50 µl of diluted biotin-antibody cocktail (PART #894666) was introduced to each well and incubated for 1 hour on the shaker at 800 rpm. The microbeads were washed three times again and then incubated with 100 ng/ml Cy3-streptavidin (in 3% BSA buffered with 1×PBS) for 30 minutes at 800 rpm. After three-time washing, the microbeads were incubated with 50 µl plasmonic-fluor-Cy3 (extinction ~5 at the LSPR maximum) for 1 hour at 800 rpm and washed 3 times each with 3% BSA and washing buffer. Finally, the microbeads were resuspended in 100 µl washing buffer and incubated for 2 minutes at 800 rpm prior to reading. Luminex 200 instrument was employed for fluorescence readout. Dual mode fluorescence of the microbead was observed on a Confocor II LSM system (Carl Zeiss-Evotec, Jena, Germany) using a ×40 water-immersion objective. The results from independent experiment are shown in FIG. 61 and FIG. 62, as well as in FIG. 101(A-B) and FIG. 102(A-B). FIG. 101(A-B) shows bead-based mouse TNF-α standard curves obtained after applying plasmonic-fluor-Cy3. In FIG. 101A and FIG. 101B, the data represents experiments that were performed independently for three times on different days with different batches of plasmonic-fluor-Cy3. Error bar represents s.d. (n=2 repeated tests). FIG. 102(A-B) show bead-based mouse IL-6 standard curves obtained after applying plasmonic-fluor-Cy3. In FIG. 102A and FIG. 102B, the data represents experiments that were performed independently for three times on different days with different batches of plasmonic-fluor-Cy3. Error bar represents s.d. (n=2 repeated tests).

Example 27—Plasmonic-Fluor Enhanced Human Kidney Biomarker Array

Figure 103A:
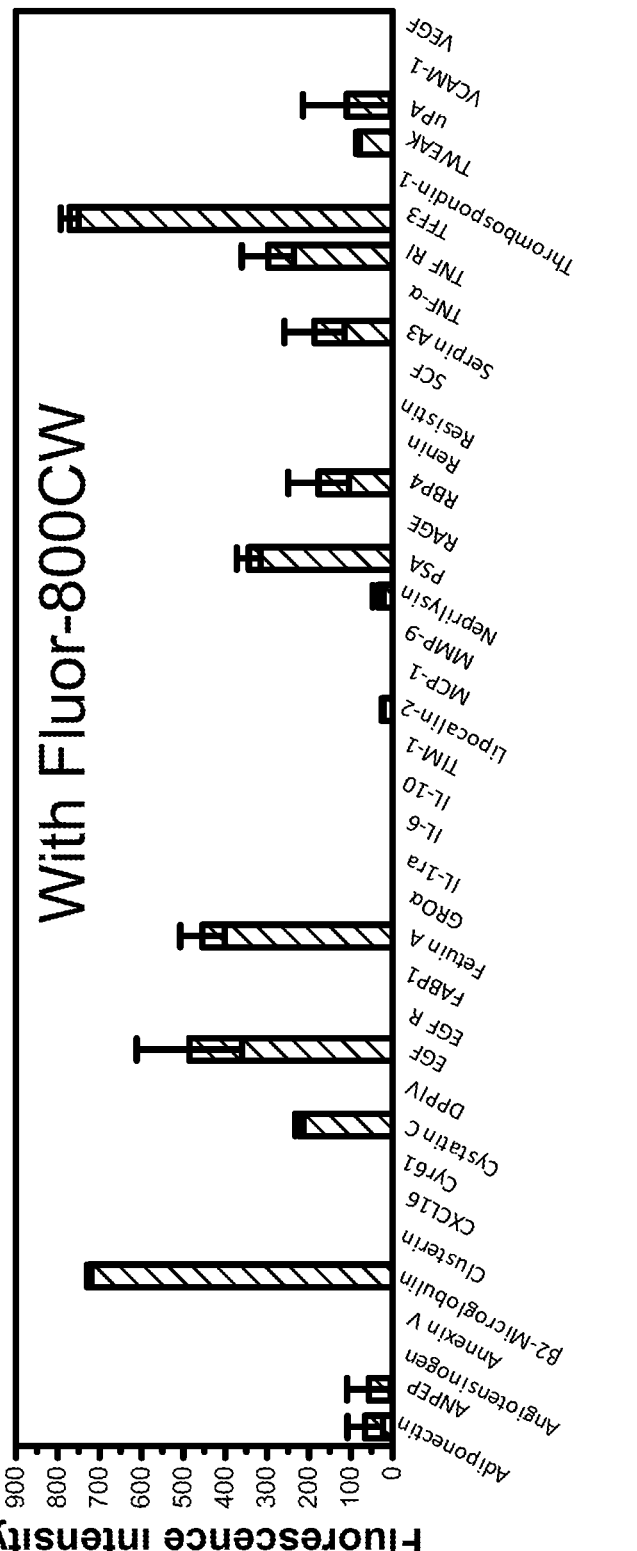
FIG. 103A is another exemplary embodiment of fluorescence intensity corresponding to the concentrations of various urinary biomarkers before (typical assay using conventional fluorophore) the addition of plasmonic-fluor-800CW in accordance with the present disclosure.
Figure 103B:
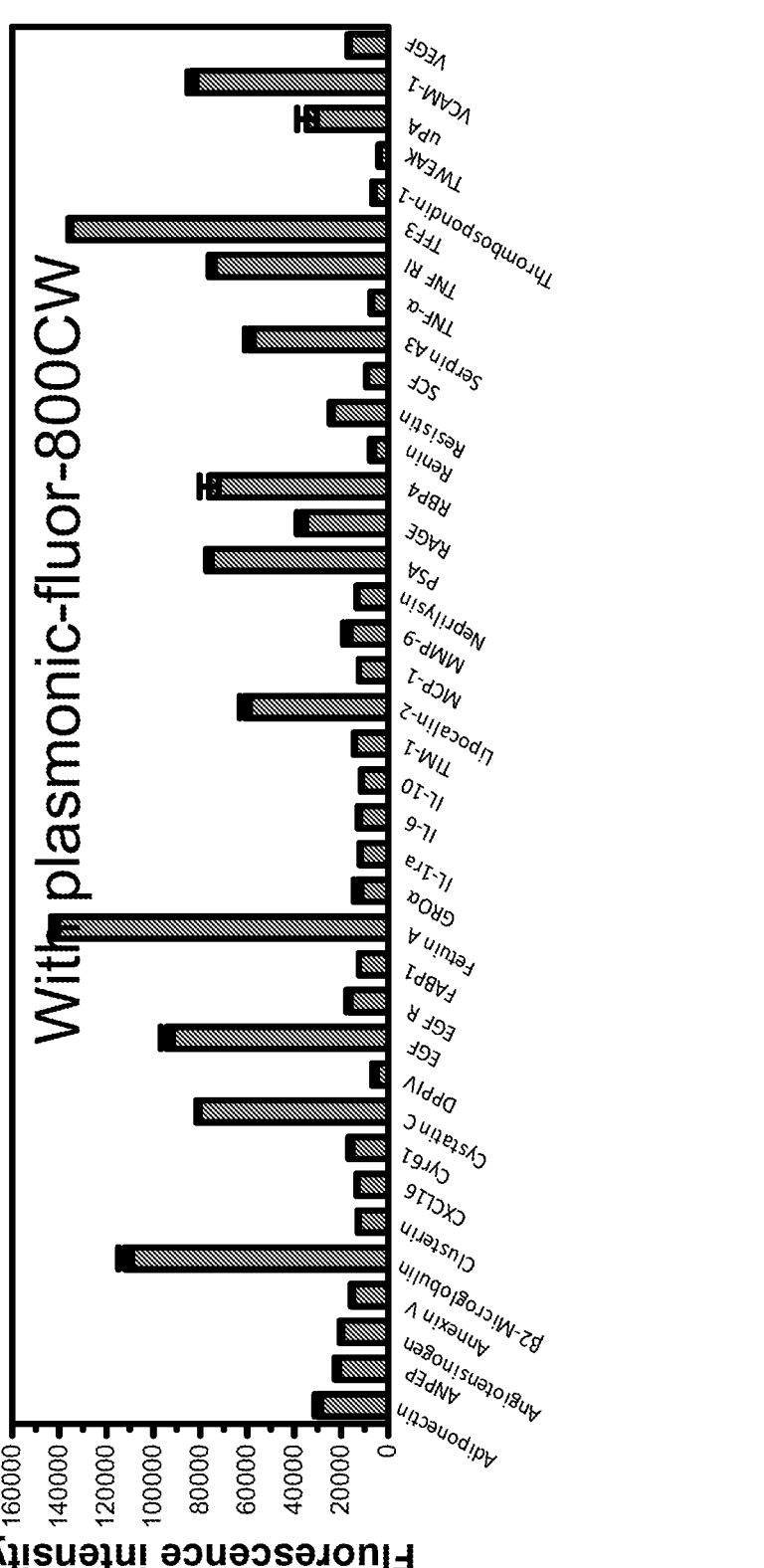
FIG. 103B is another exemplary embodiment of fluorescence intensity corresponding to the concentrations of various urinary biomarkers (typical assay using conventional fluorophore) after the addition of plasmonic-fluor-800CW in accordance with the present disclosure.

Human kidney biomarker array kit was purchased from R&D system (catalog #ARY019, lot #1311110). Urine sample from kidney disease patient (ID #25, age 61, male) was employed for this study. The study was approved by Washington University IRB 201601082 "Nanotech Biomarkers for Renal Cancer Intervention: Clinical Validation and Utility". Informed consent was obtained from the participants. The nitrocellulose membrane (PART #893967) was blocked by incubation with 2 ml of blocking buffer (PART #893573) in the 4-well multi-dish for 1.5 hour under gentle rocking. During blocking process, kidney disease patient (ID #25) urine sample (150 µl) was diluted with 500 µl of blocking buffer and 850 µl of array buffer (PART #895876), resulting in a total 10-fold dilution. The diluted urine sample was mixed with 15 µl of reconstituted detection antibody cocktail (PART #893966) and the mixture was incubated at room temperature for 1 hour. The nitrocellulose membrane was taken out from the blocking solution and incubated with the mixture of urinary sample and biotinylated detection antibodies for overnight at 4° C. The membrane was subsequently washed with 20 ml of 1× washing buffer (PART #895003) for 10 minutes under gentle rocking, and the washing process was repeated for two more times. Next, the membrane was incubated with 800CW-streptavidin (50 ng/ml in 1% BSA) for 30 minutes under gentle rocking, washed three times, and incubated with plasmonic-fluor-800CW (extinction ~0.5) for one more hour. Finally, the membrane was scanned using The membrane was then imaged using the LI-COR CLx imager at L2 laser power, with focusing height at 0.5 mm and resolution of 169 µm. The photograph of the protein array was acquired using the iPhone6 camera and the image was analyzed using Image Studio Lite software to measure the median intensity of each spot (background subtracted). The results from independent experiment are shown in FIG. 103(A-B). FIG. 103(A-B) shows the second independent experiment of kidney biomarker array. Fluorescence intensity corresponding to the concentrations of various urinary biomarkers (typical assay using conventional fluorophore) before (FIG. 103A) and after (FIG. 103B) the addition of plasmonic-fluor-800CW. Error bar represents s.d. (n=2 repeated tests).

Example 28—Exemplary Conditions for Plasmonic-Fluor Enhanced Human Cytokine Microarray Forty-plex human cytokine microarray (RayBiotech, catalog #: QAH-CYT-4) was employed to further test the efficacy of plasmonic-fluor, and the results of which are disclosed herein elsewhere. To begin, the glass substrate of the microarray was blocked with 100 µl sample diluent (catalog #: QA-SDB) followed by incubation with sample standard (catalog #: QAH-CYT-4-STD) at room temperature for 2 hours with gentle rocking. The microarray was washed by five times using 1× wash buffer I (catalog #: AA-WB1-

30ML) followed by twice washing with 1× wash buffer II (catalog #: AA-WB2-30ML). Next, 80 µl of reconstituted detection antibody cocktail was added into each well and incubated for another 2 hours under gentle rocking. Following the incubation, washing process was repeated again as described above. Subsequently, 80 µl of 800CW-streptavidin (50 ng/ml in 1% BSA) was added to the array slide and incubated for 20 minutes, washed, and immersed with plasmonic-fluor-800CW (extinction ~1) for one hour. The slide was scanned using LI-COR CLx scanner with the following parameters: laser power ~3.5; resolution ~21 µm; channel: 800; height: 1.8 mm.

Example 29—Plasmonic-Fluor Enhanced Immunocytochemistry/Immunofluorescence (ICC/IF)

Figure 104A:
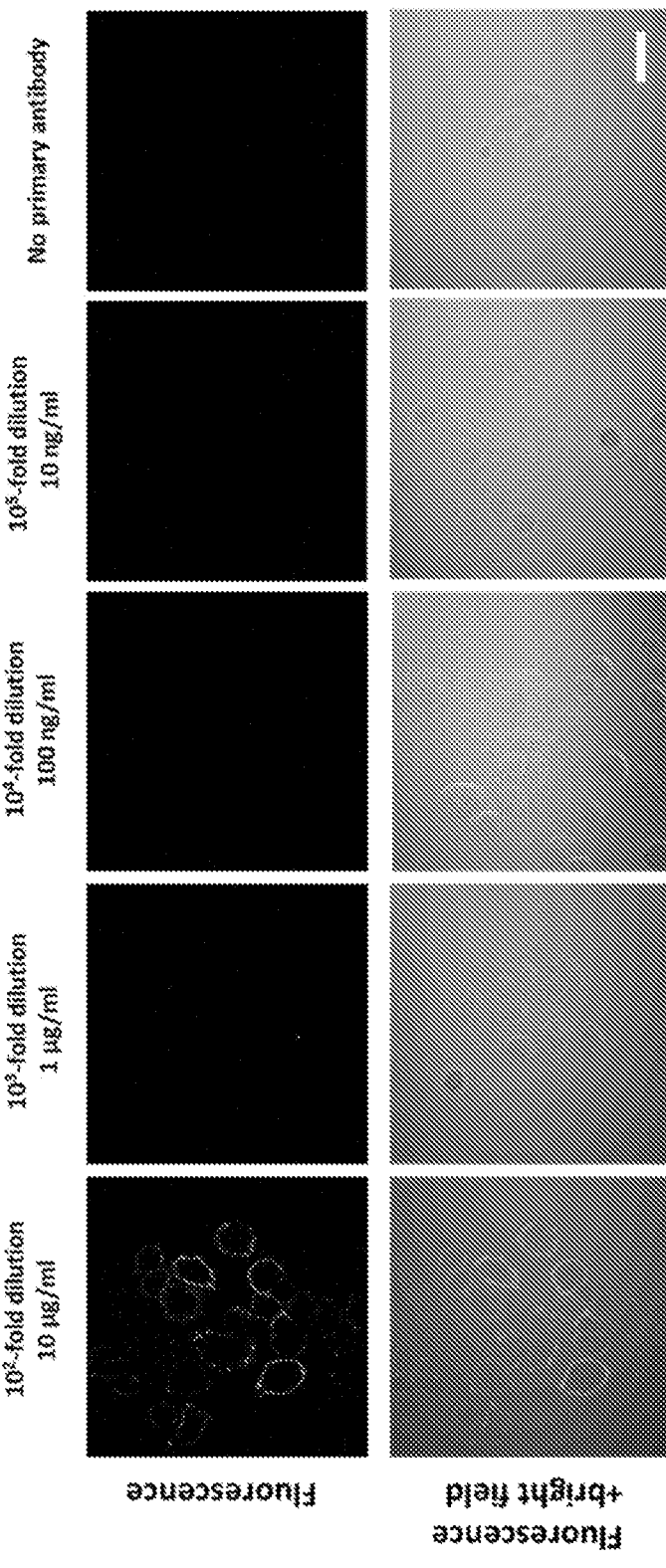
FIG. 104A is another exemplary embodiment of confocal laser scanning microscopy (CLSM) images of ErbB2 stained breast cancer cells (SK-BR-3) obtained using conventional immunocytochemistry procedure (cells are labelled with biotinylated primary antibody and streptavidin-fluor (800CW) sequentially) at different dilutions of ERbB2 primary antibody in accordance with the present disclosure.
Figure 104B:
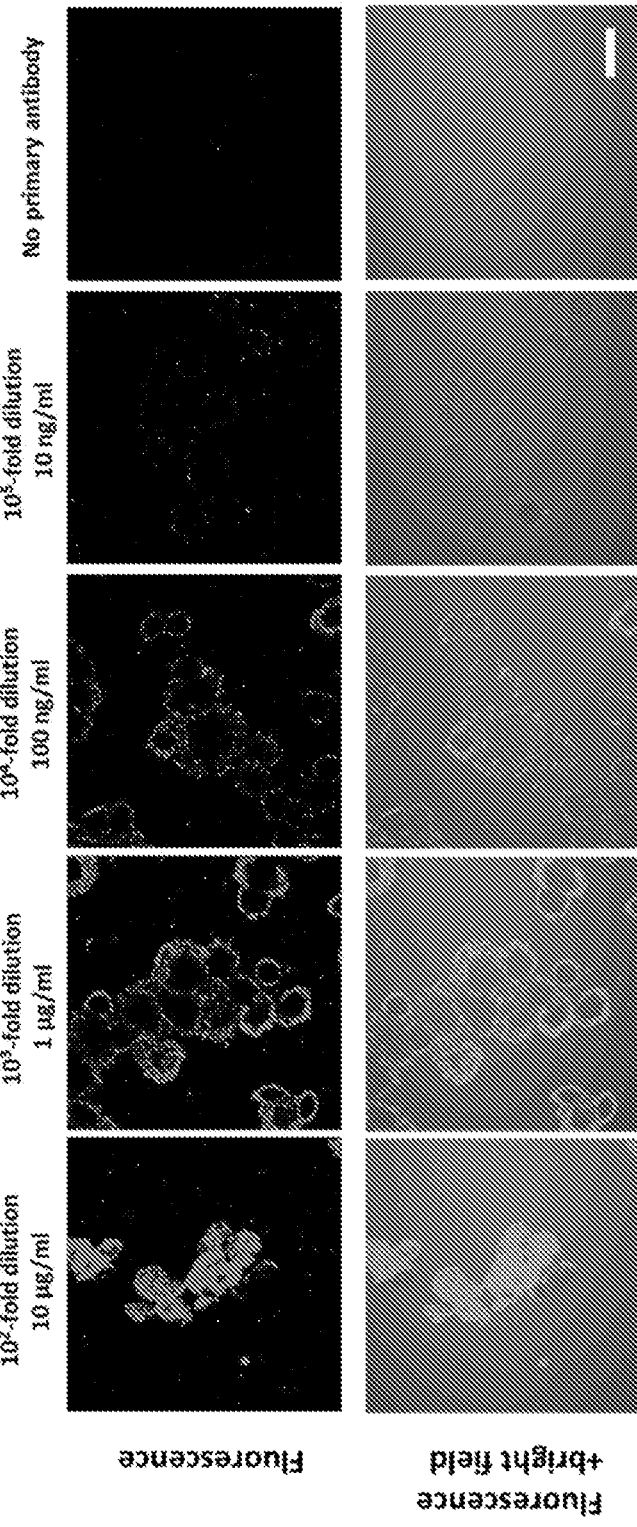
FIG. 104B is another exemplary embodiment of confocal laser scanning microscopy (CLSM) images of ErbB2 stained breast cancer cells (SK-BR-3) after the addition of plasmonic-fluor-800CW at different dilutions of ERbB2 primary antibody in accordance with the present disclosure.
Figure 105A:
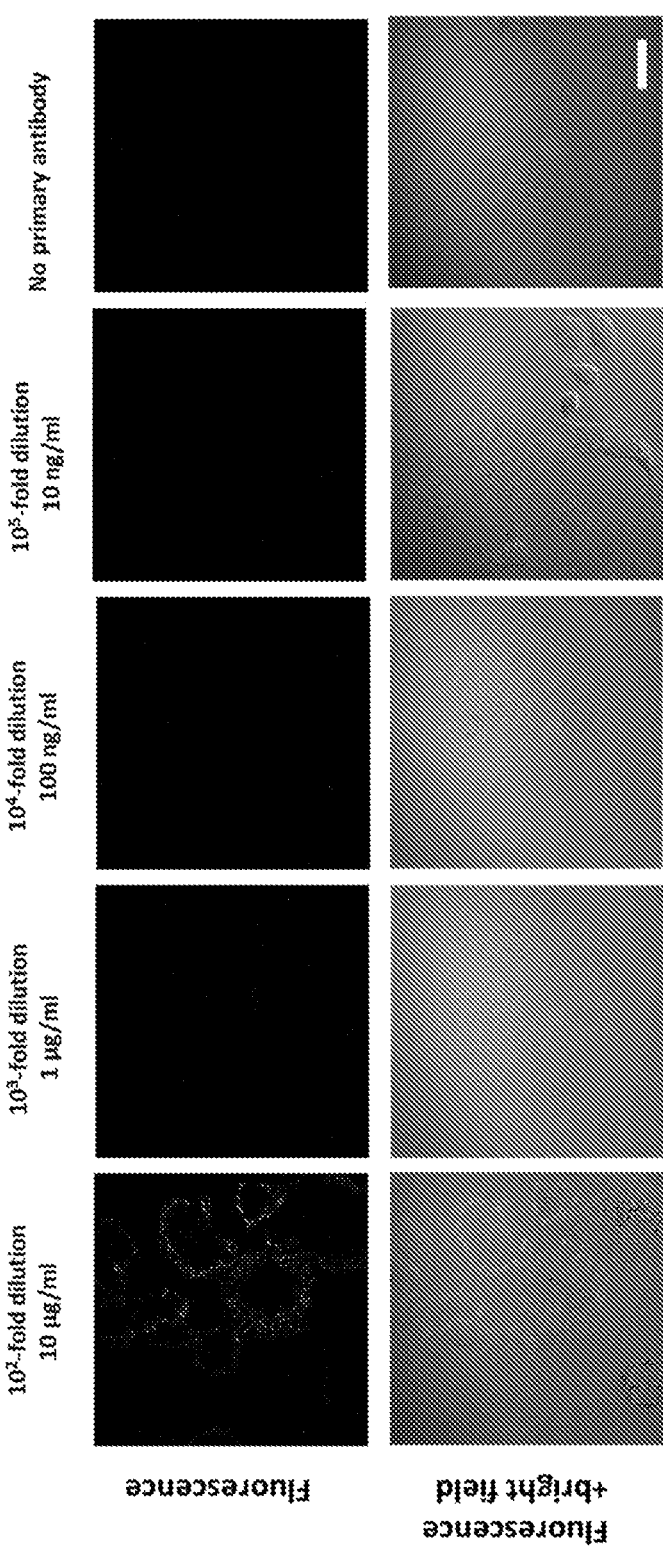
FIG. 105A is yet another exemplary embodiment of confocal laser scanning microscopy (CLSM) images of ErbB2 stained breast cancer cells (SK-BR-3) obtained using conventional immunocytochemistry procedure (cells are labelled with biotinylated primary antibody and streptavidin-fluor (800CW) sequentially) at different dilutions of ERbB2 primary antibody in accordance with the present disclosure.
Figure 105B:
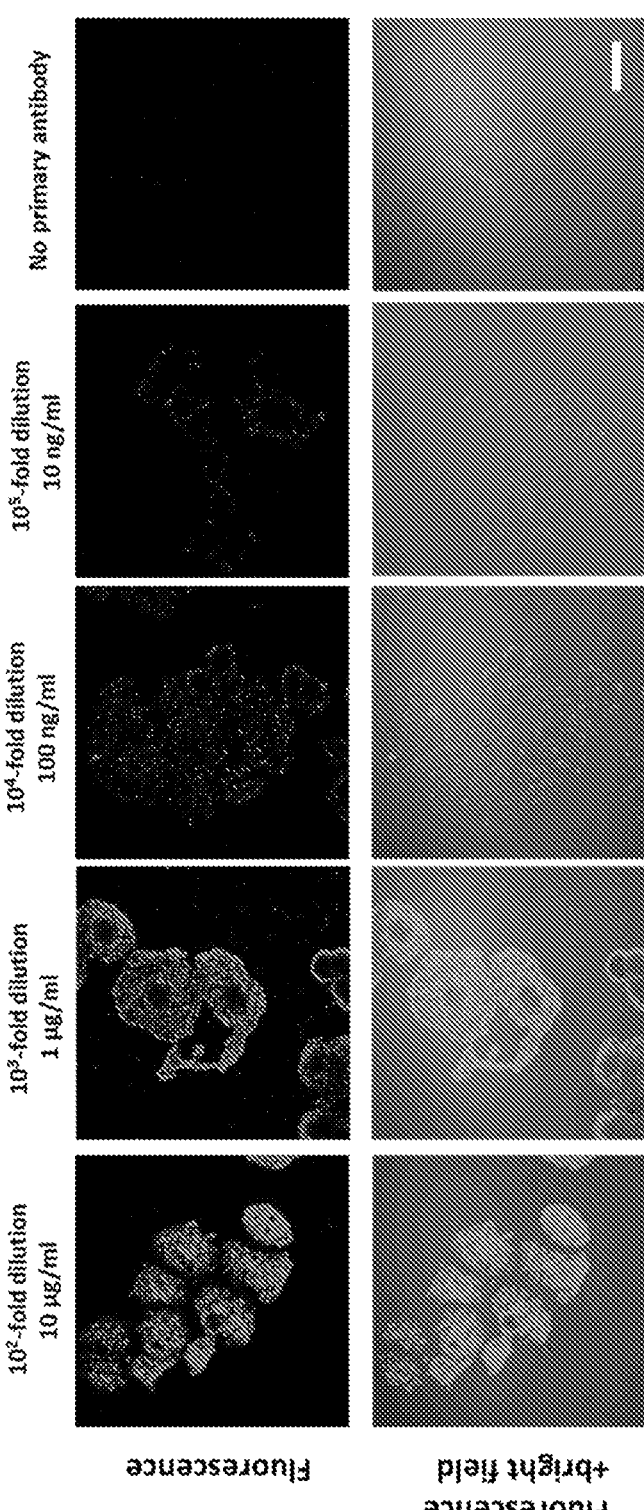
FIG. 105B is yet another exemplary embodiment of confocal laser scanning microscopy (CLSM) images of ErbB2 stained breast cancer cells (SK-BR-3) after the addition of plasmonic-fluor-800CW at different dilutions of ERbB2 primary antibody in accordance with the present disclosure.

Human epithelial breast cancer cells SK-BR-3 [SKBR3] (ATCC® HTB30™) were purchased from ATCC (Manassas, Va.) and sub-cultured in McCoy's 5A medium with 10% fetal bovine serum (FBS) and antibiotics (100 µg/ml penicillin and 100 µg/ml streptomycin) (Sigma, St. Louis, Mo.). Cells were grown in water jacketed incubator at 37° C. with 5% $CO_2$-humidified atmosphere in T-25 tissue culture flasks. Once the cells reached to 90% confluence, they were washed with PBS and detached from the flask bottom using a scraper. After centrifugation, cells were re-dispersed in culture medium and seeded on 6-well plate for overnight to allow attachment to the plate bottom. Cells were subsequently fixed using 3.7% formaldehyde (in 1×PBS) for 30 minutes, washed three times with 1×PBS, and blocked with 3% BSA for 1 hour. Next, ErbB2 primary antibody (anti-human HER-2/biotin, eBioscience, clone 2G11, REF #BMS120BT, lot #186281000) was diluted using 1% BSA and incubated with SK-BR-3 cells for 1.5 hours. The cells were subsequently washed three times, incubated with 800CW-streptavidin (1 µg/ml in 1% BSA) for 30 minutes, washed for another three times, and probed with plasmonic-fluor-800CW (extinction ~0.3). The cells were finally imaged using Olympus FV1000 LSM confocal laser scanning microscopy (785 nm excitation laser) under 40× water-immersion objective. The results from independent experiments are shown in FIG. 78 as well as in FIG. 104(A-B), FIG. 105(A-B). FIG. 104(A-B) shows the second independent immunocytochemistry experiment. Confocal laser scanning microscopy (CLSM) images of ErbB2 stained breast cancer cells (SK-BR-3) obtained using conventional immunocytochemistry procedure (cells are labelled with biotinylated primary antibody and streptavidin-fluor (800CW) sequentially, see FIG. 104A), followed by the addition of plasmonic-fluor-800CW (FIG. 104B), at different dilutions of ERbB2 primary antibody. Scale bar represents 15 µm. FIG. 105(A-B) shows the third independent immunocytochemistry experiment. Confocal laser scanning microscopy (CLSM) images of ErbB2 stained breast cancer cells (SK-BR-3) obtained using conventional immunocytochemistry procedure (cells are labelled with biotinylated primary antibody and streptavidin-fluor (800CW) sequentially, see FIG. 105A), followed by the addition of plasmonic-fluor-800CW (FIG. 105B), at different dilutions of ERbB2 primary antibody. Scale bar represents 15 µm.

Example 30—SK-BR-3 Flow Cytometry Measurements

Figure 106A:
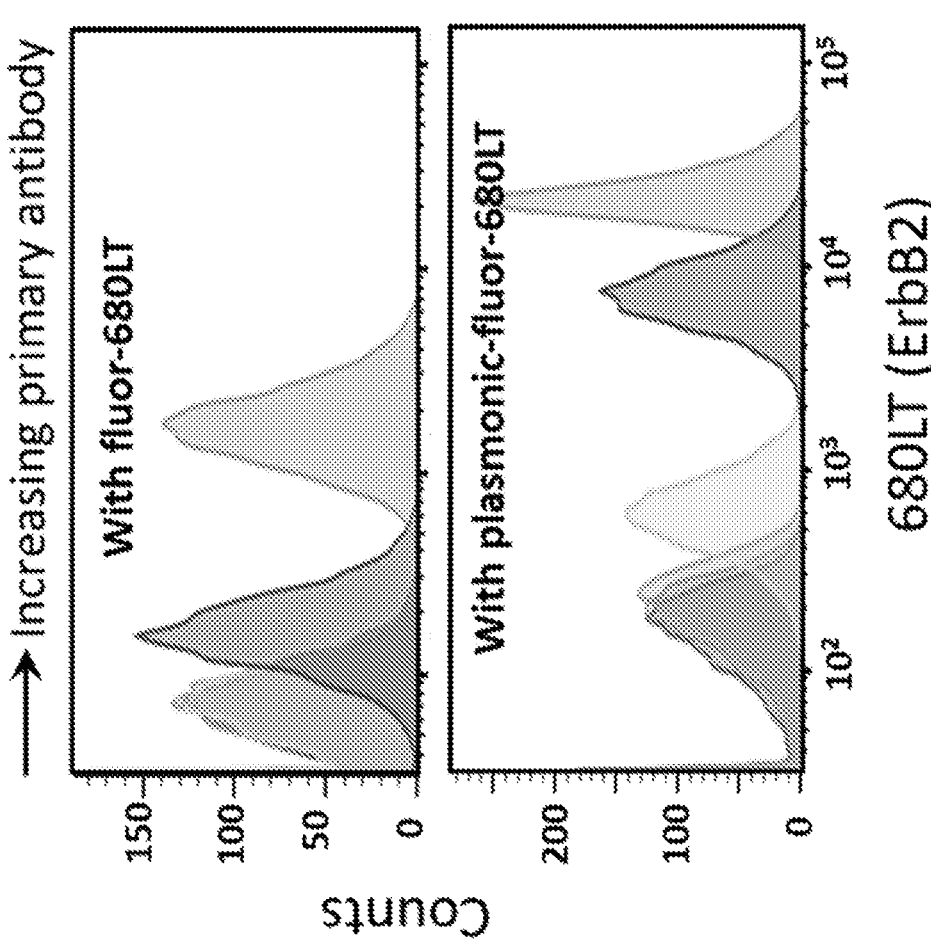
FIG. 106A is another exemplary embodiment of a histogram showing fluorescence of SK-BR-3 cells before (top) and after (bottom) the addition of plasmonic-fluor-680LT in accordance with the present disclosure.
Figure 106B:
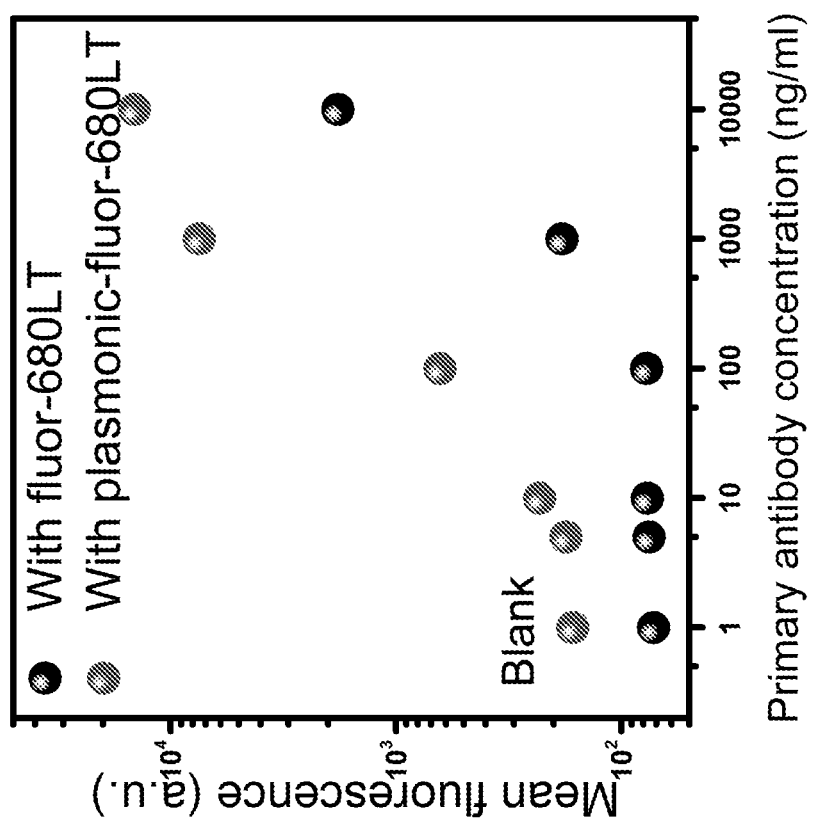
FIG. 106B is another exemplary embodiment of a plot showing the mean fluorescence intensity obtained from flow cytometry at different primary antibody concentrations in accordance with the present disclosure.
Figure 107A:
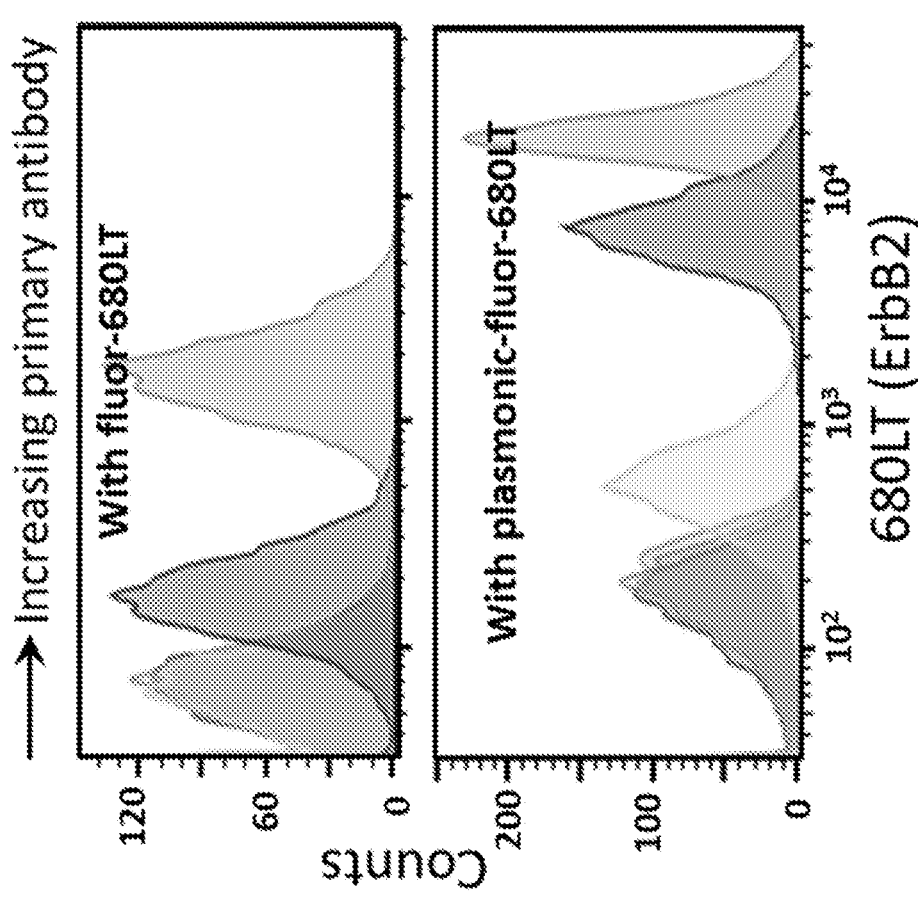
FIG. 107A is yet another exemplary embodiment of a histogram showing fluorescence of SK-BR-3 cells before (top) and after (bottom) the addition of plasmonic-fluor- 680LT in accordance with the present disclosure.
Figure 107B:
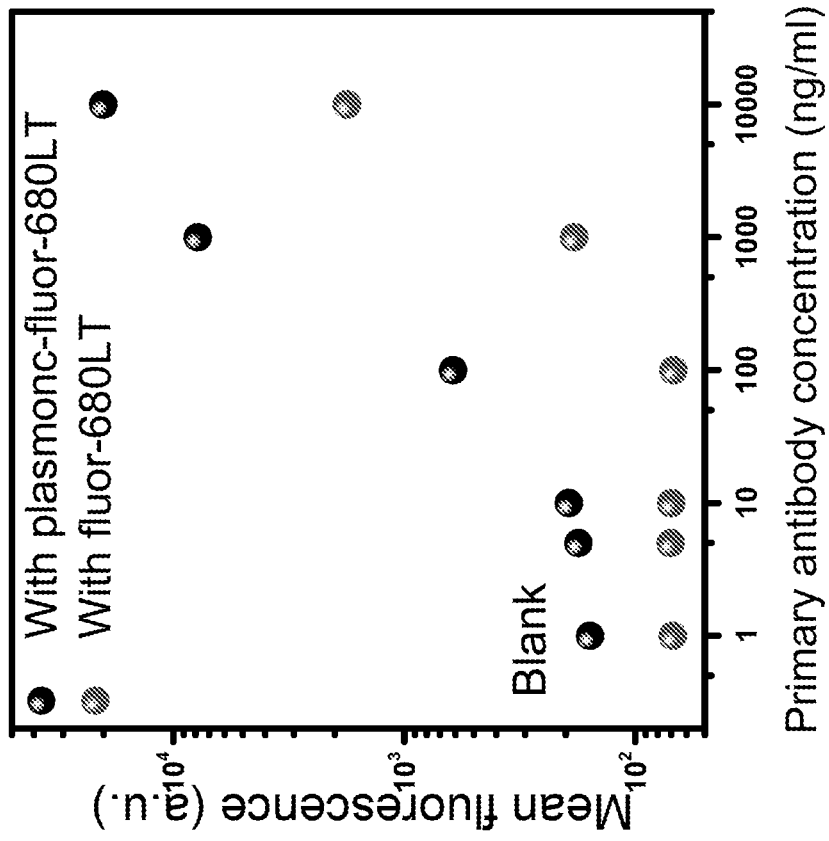
FIG. 107B is yet another exemplary embodiment of a plot showing the mean fluorescence intensity obtained from flow cytometry at different primary antibody concentrations in accordance with the present disclosure.

SK-BR-3 cells were grown and harvested using the method described above. The cells were centrifuged at 1000 rpm for 10 minutes to remove the culture medium and were subsequently fixed using 3.7% formaldehyde in 1×PBS for 30 minutes. The cell suspension was centrifuged again to remove the free formaldehyde and the cells were subsequently blocked with 3% BSA for overnight. Next, different amounts of ErbB2 primary antibody were added into the cell suspension and the mixture was incubated for 1 hour under gentle shaking. The cells were centrifuged at 1000 rpm and washed once with 1×PBS to remove the free antibody, incubated with streptavidin-680LT (LI-COR: P/N 926-6803; 1 pg/ml in 1% BSA) for 1 hour, washed two more times, and incubated with plasmonic-fluor-680LT (extinction ~2.0) for 1 hour. Finally, 5000 cells were analyzed by Guava easyCyte to acquire the fluorescence signal (RED-R channel (excitation laser: 642 nm; filter: 662/15 nm)) in combination with forward scatter (FSC) and side scatter (SSC). The results from independent experiment are shown in FIG. 89 and FIG. 90, as well as in FIG. 106(A-B) and FIG. 107(A-B). FIG. 106(A-B) shows the second independent SK-BR-3 flow cytometry experiment. FIG. 106A is a histogram showing fluorescence of SK-BR-3 cells before (top) and after (bottom) the addition of plasmonic-fluor-680LT. Red: no primary antibody; blue: $2\times10^5$-fold dilution; orange: $10^5$-fold dilution; light green: $10^4$-fold dilution; green: $10^3$-fold dilution; rose: $10^2$-fold dilution of the stock solution provided by the vendor (1 mg/ml). FIG. 106B is a plot showing the mean fluorescence intensity obtained from flow cytometry at different primary antibody concentrations. FIG. 107(A-B) show the third independent SK-BR-3 flow cytometry experiment. FIG. 107A is a histogram showing fluorescence of SK-BR-3 cells before (top) and after (bottom) the addition of plasmonic-fluor-680LT. Red: no primary antibody; blue: $2\times10^5$-fold dilution; orange: $10^5$-fold dilution; light green: $10^4$-fold dilution; green: $10^3$-fold dilution; rose: $10^2$-fold dilution of the stock solution provided by the vendor (1 mg/ml). FIG. 107B is a plot showing the mean fluorescence intensity obtained from flow cytometry at different primary antibody concentrations.

Example 31—BMDC Isolation and Flow Cytometry Measurement

Female C57BL/6 (H-2b) mice that were 5 to 6 weeks of age were purchased from Jackson Labs (Bar Harbor, Me., USA). The mice were maintained under pathogen-free conditions. All experiments employing mice were performed in accordance with laboratory animal protocol approved by the School of Medicine Animal Studies Committee of Washington University in St. Louis. Mice were euthanized using $CO_2$ asphyxiation and cervical dislocation. The euthanized mouse was kept in 70% (v/v) ethanol for 1 min. Both the femurs and tibiae were isolated, and the muscle attachments were carefully removed using gauze pads. Both ends of the bones were cut with scissors and the marrow was centrifuged in an adapted centrifuge tube (0.6 ml tube with a hole inserted in 1.5 ml tube) at 1000 rpm for 10 seconds. The pellet was resuspended by vigorous pipetting in RPMI 1640 media. The cells were passed through a 70 µm cell strainer to prepare a single cell suspension. After one washing (1200 rpm, 5 min), red blood cells were depleted with RBC lysis buffer (Sigma-Aldrich). The bone marrow cells were collected and cultured in 100-mm Petri dishes containing 10 mL RPMI medium supplemented with 10% heat-inactivated FBS, 50 IU $mL^{-1}$ penicillin, 50 µg $mL^{-1}$ streptomycin, and 20 ng mL-1 mouse recombinant granulocyte-macrophage colony-stimulating factor (GM-CSF, R&D Systems, MN, USA). $1\times10^6$ BMDCs were cultured in 6 well plates and were stimulated by adding 1 ml of different concentrations of LPS (0.5 μg/ml, 0.2 μg/ml, 0.1 μg/ml, 0.05 μg/ml, 0.01 μg/ml, and 0 μg/ml) for 24 hours. Cells were harvested using a cell scraper for further staining and flow cytometry analysis.

Figures 108A, 108B:
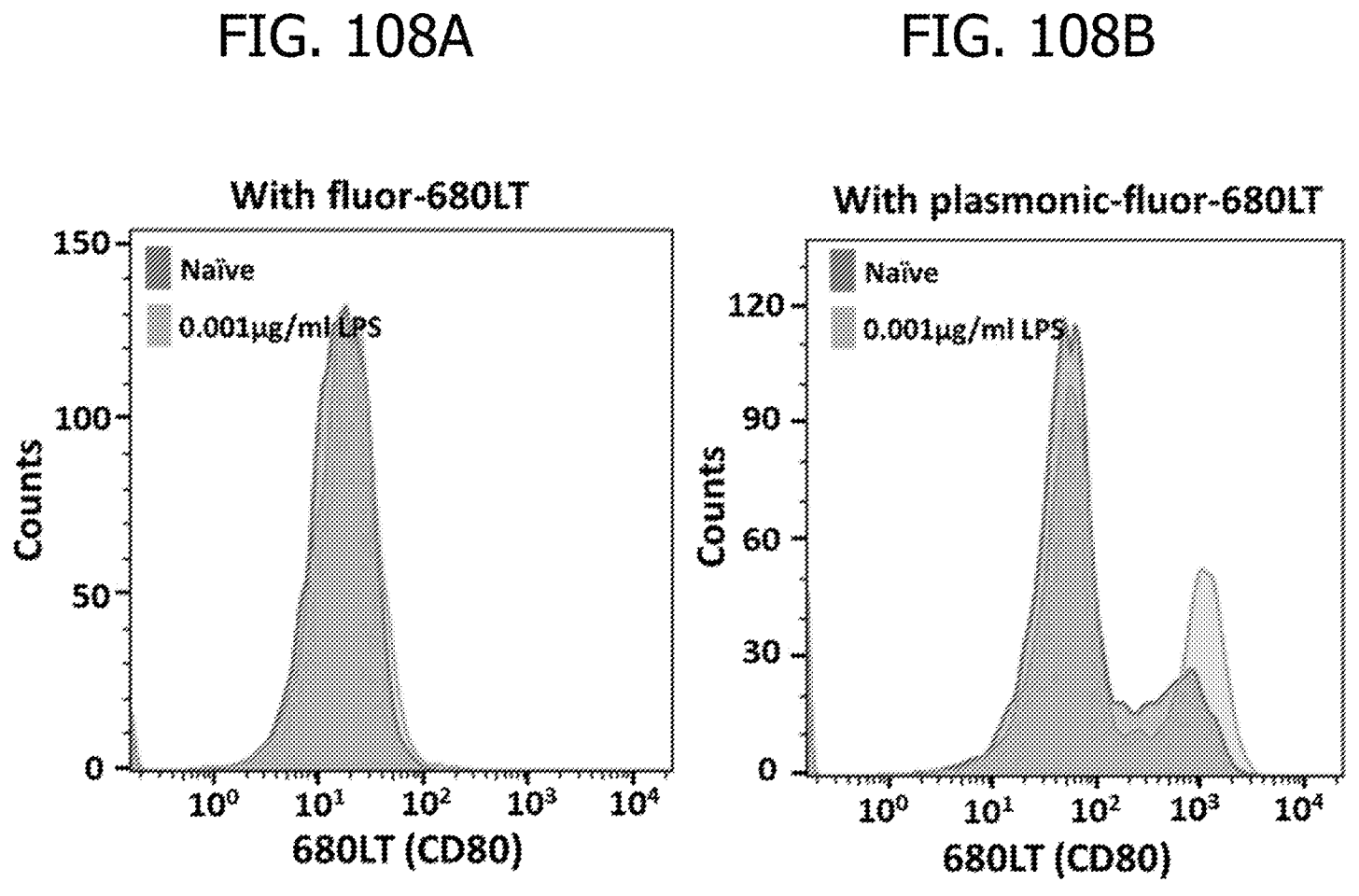
Figure 108C:
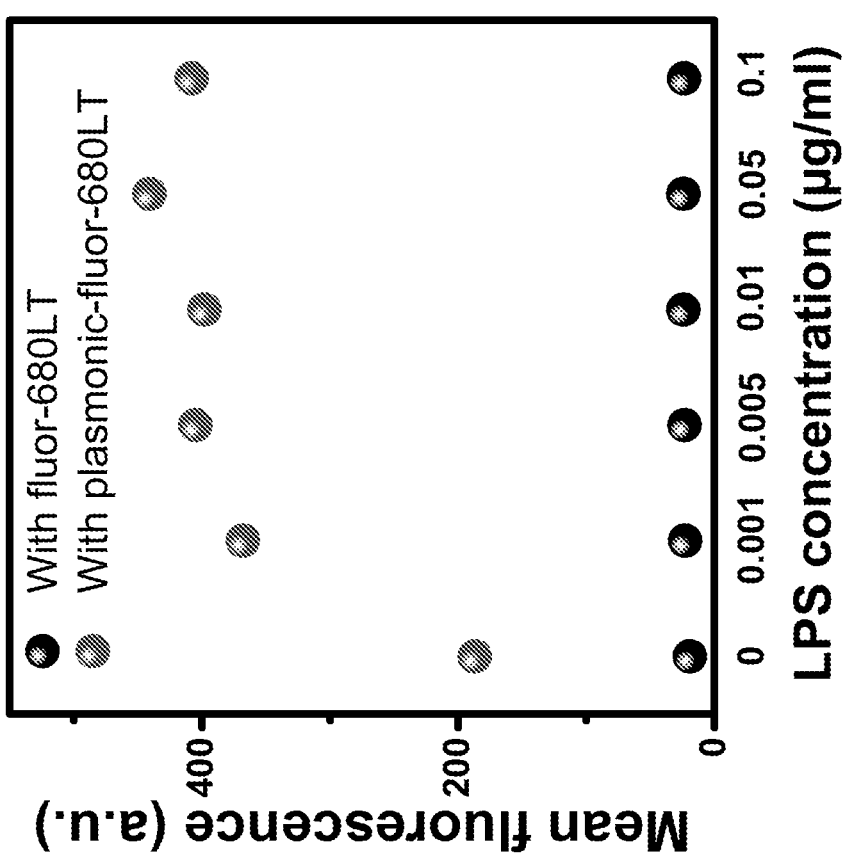
FIG. 108C is another exemplary embodiment of a plot showing mean fluorescence intensity of BMDCs (corresponding to the expression level of CD80) after stimulation with different amounts of LPS in accordance with the present disclosure.
Figures 109A, 109B:
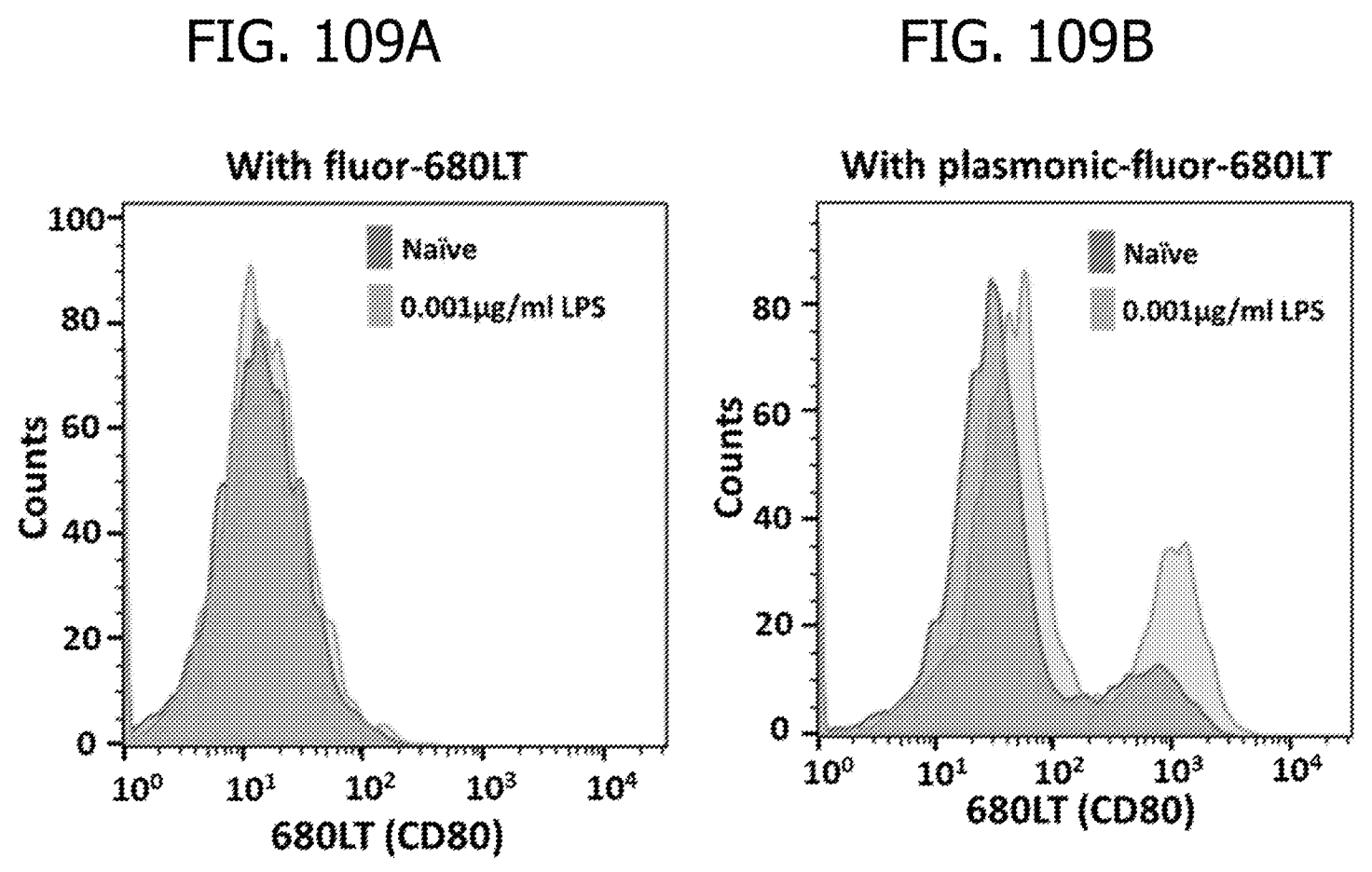
Figure 109C:
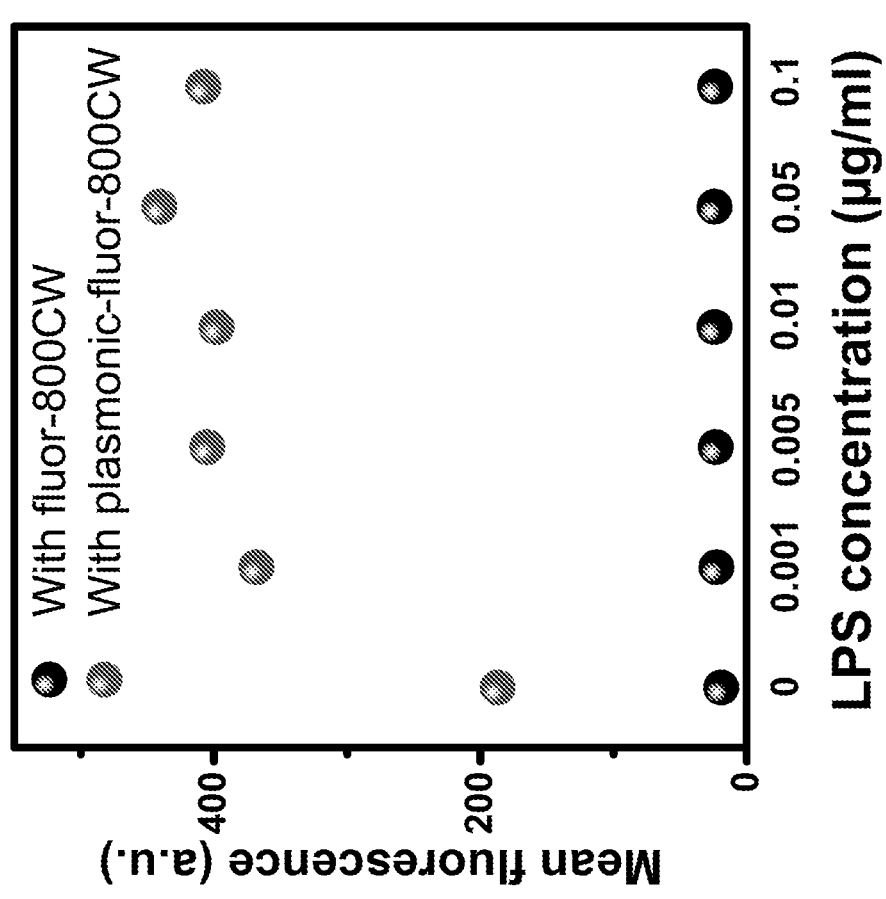
FIG. 109C is yet another exemplary embodiment of a plot showing mean fluorescence intensity of BMDCs (corresponding to the expression level of CD80) after stimulation with different amounts of LPS in accordance with the present disclosure.

CD80 overexpressed on the cell surface was probed using conventional fluorophore followed with plasmonic-fluor-680LT. Specifically, stimulated BMDCs were washed once with 1×PBS to remove the culture medium (centrifugation at 2000 rpms for 5 mins) and fixed using 10% neutral buffered formalin for 20 minutes. The cells were then washed (2000 rpms for 5 mins) and blocked with 3% BSA for overnight at 4° C. Next, biotinylated CD80 primary antibody (anti-Mo CD80/biotin (Invitrogen, REF #13-0801-82, Clone 16-10A1, lot #1934784)) was added into the BMDC suspension to achieve a final antibody concentration of 100 ng/ml and the mixture was incubated for 1 hour. The BMDCs were washed once (2000 rpms for 5 mins) and were subsequently incubated with 1 μg/ml streptavidin-680LT (in 1% BSA) for 40 minutes. Finally, the cells were washed two more times and incubated with plasmonic-fluor-680LT (extinction ~2) for 1 hour, followed by once more washing to remove unbound plasmonic-fluor-680LT. 10,000 cells were analyzed by Guava easyCyte to acquire the fluorescence signal (RED-R channel (excitation laser: 642 nm; filter: 662/15 nm)) in combination with forward scatter (FSC) and side scatter (SSC). The results from independent experiments are shown in FIG. 108(A-C) and FIG. 109(A-C). FIG. 108(A-C) show the second independent flow cytometry measurement of BMDC maturation maker probed by plasmonic-fluor-680LT. Fluorescence intensity distribution corresponding to naïve (control) and LPS-stimulated BMDCs obtained using conventional fluors (680LT) (FIG. 108A) and plasmonic-fluor-680LT (FIG. 108B). (FIG. 108C) Plot showing mean fluorescence intensity of BMDCs (corresponding to the expression level of CD80) after stimulation with different amounts of LPS. FIG. 109(A-C) shows the third independent flow cytometry measurement of BMDC maturation maker probed by plasmonic-fluor-680LT. Fluorescence intensity distribution corresponding to naïve (control) and LPS-stimulated BMDCs obtained using conventional fluors (680LT) (FIG. 109A) and plasmonic-fluor-680LT (FIG. 109B). FIG. 109C is a plot showing mean fluorescence intensity of BMDCs (corresponding to the expression level of CD80) after stimulation with different amounts of LPS.

Statistics: For analyzing the statistical difference between two groups, unpaired two-tailed t-test with Welch's correction was used. For analyzing the statistical difference between more than two groups, one-way ANOVA with post-hoc Tukey's honest significance test was used. Statistical significance of the data was calculated at 95% ($p<0.05$) CIs. All values are expressed as mean±standard deviation. GraphPad Prism 6 (San Diego, Calif., USA) was used for all statistical analysis. Four-parameter logistic (4PL) or polynomial fit was employed to calculate the limit-of-detection in the standard curves of bioassays. The limit-of-detection is defined as the analyte concentration corresponding to the mean fluorescence intensity of blank plus three times of its standard deviation (mean+3σ). Origin 2016 (Northampton, Mass., USA) was employed for calculating the limit-of-detection.

What is claimed is:

1. A fluorescent nanoconstruct comprising:
   a plasmonic nanostructure having at least one localized surface plasmon resonance wavelength (ALSPR) between 400 nm and 1000 nm;

at least one spacer coating;
   at least one fluorescent agent having a maximum excitation wavelength (XEX);
   at least one functional layer wherein functional layer comprises bovine serum albumin (BSA); and
   at least one biorecognition element;
   wherein the plasmonic nanostructure is coated with the at least one spacer coating;
   wherein the at least one spacer coatings is coated with the at least one functional layer;
   wherein the at least one of the spacer coating and the at least one of the functional layer is conjugated with the at least one fluorescent agent;
   wherein the plasmonic nanostructure comprises gold or a silver coated gold;
   wherein the spacer coating comprises a siloxane network;
   wherein the spacer coating is on the nanostructure and has a thickness of about 0.5 nm to about 20 nm;
   wherein the at least one biorecognition element is conjugated with the at least one spacer coating or the at least one functional layer;
   wherein the fluorescent nanoconstruct has a fluorescent intensity that is at least 500 times greater than a fluorescent intensity of the at least one fluorescent agent alone; and
   wherein a wavelength difference between the at least one ALSPR and the AEX is less than 75 nm.

2. The fluorescent nanoconstruct according to claim 1, wherein the at least one fluorescent agent comprises at least about 5 fluorescent agents.

3. The fluorescent nanoconstruct according claim 1, wherein the plasmonic nanostructure is selected from the group consisting of: nanorods, nanocubes, nanospheres, bimetallic nanostructures, gold core silver shell nanocuboids, nanotubes, gold nanorods, silver nanocubes, silver nanospheres, gold nanorod core-silver shell (AuNR@Ag) nanocuboids, nanostructures with sharp tips, nanostars, nanoraspberries, and combinations thereof.

4. The fluorescent nanoconstruct according to claim 1, wherein the spacer coating comprises a dielectric material selected from the group consisting of:
   APTMS/APTES, TMPS, MPTMS, Silanes and mixtures of silanes, and combinations thereof.

5. The fluorescent nanoconstruct according to claim 1, wherein the spacer coating comprises at least one polymer coating selected from the group consisting of mercaptosilanes, aminopropyl silanes, trimethoxypropyl silanes, and combinations thereof.

6. The fluorescent nanoconstruct according to claim 1, wherein the spacer coating comprises an initiation layer of mercaptosilane attached to the plasmonic nanostructure and further comprises a siloxane network added to the initiation layer selected from the group comprising aminopropyl silanes, trimethoxypropyl silanes, and combinations thereof.

7. The fluorescent nanoconstruct according to claim 1, wherein the at least one biorecognition element is selected from the group consisting of streptavidin, biotin, antibodies, nucleic acids, and combinations thereof.

8. The fluorescent nanoconstruct according to claim 1, wherein the functional layer comprises at least one reactive group to which the at least one biorecognition element is covalently attached.

9. The fluorescent nanoconstruct according to claim 1, wherein the functional layer comprises a mixture of BSA that is attached to at least one biotin (biotinylated-BSA) and a BSA that is not attached to biotin (native-BSA), and further wherein the percentage of biotinylated-BSA relative to native-BSA is between 0% and 100%.

10. The fluorescent nanoconstruct according to claim 1, wherein the fluorescent agent is maintained within about 0.5 nm to about 10 nm from a surface of the plasmonic nanostructure.

11. The fluorescent nanoconstruct according to claim 1, wherein the spacer coating is between about 0.5 nm and about 15 nm thick.

12. The fluorescent nanoconstruct according to claim 1, wherein the at least one biorecognition element is attached to a flexible linker.

13. The fluorescent nanoconstruct according to claim 1, wherein the functional layer substantially covers the at least one spacer coating or wherein the functional layer encapsulates the at least one spacer coating.

14. The fluorescent nanoconstruct according to claim 1, wherein the spacer coating substantially covers the plasmonic nanostructure or wherein the spacer coating encapsulates the plasmonic nanostructure.

\* \* \* \* \*